United States Patent
Miyoshi et al.

(10) Patent No.: US 9,458,249 B2
(45) Date of Patent: Oct. 4, 2016

(54) CELLULOSE ETHER CONTAINING CATIONIC GROUP

(71) Applicant: KAO CORPORATION, Tokyo (JP)

(72) Inventors: Eisuke Miyoshi, Wakayama (JP); Naoyuki Yamazaki, Tokyo (JP); Yumi Yamaguchi, Wakayama (JP); Ryosuke Fujii, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/433,827

(22) PCT Filed: Dec. 2, 2013

(86) PCT No.: PCT/JP2013/082355
§ 371 (c)(1),
(2) Date: Apr. 6, 2015

(87) PCT Pub. No.: WO2014/087968
PCT Pub. Date: Jun. 12, 2014

(65) Prior Publication Data
US 2015/0239993 A1    Aug. 27, 2015

(30) Foreign Application Priority Data

Dec. 3, 2012 (JP) .................. 2012-264636
Dec. 3, 2012 (JP) .................. 2012-264640
Dec. 3, 2012 (JP) .................. 2012-264641
Dec. 3, 2012 (JP) .................. 2012-264643
Mar. 1, 2013 (JP) .................. 2013-040818

(51) Int. Cl.
| | | |
|---|---|---|
| *A61K 8/73* | (2006.01) | |
| *C08B 11/145* | (2006.01) | |
| *A61Q 19/10* | (2006.01) | |
| *A61Q 5/02* | (2006.01) | |
| *C08B 11/193* | (2006.01) | |
| *A61Q 5/00* | (2006.01) | |
| *A61Q 5/04* | (2006.01) | |
| *A61Q 5/12* | (2006.01) | |
| *A61Q 5/06* | (2006.01) | |
| *A61Q 5/08* | (2006.01) | |
| *A61Q 5/10* | (2006.01) | |

(52) U.S. Cl.
CPC ............. *C08B 11/193* (2013.01); *A61K 8/731* (2013.01); *A61Q 5/004* (2013.01); *A61Q 5/02* (2013.01); *A61Q 5/04* (2013.01); *A61Q 5/06* (2013.01); *A61Q 5/065* (2013.01); *A61Q 5/08* (2013.01); *A61Q 5/10* (2013.01); *A61Q 5/12* (2013.01); *A61Q 19/10* (2013.01); *C08B 11/145* (2013.01); *A61K 2800/4324* (2013.01); *A61K 2800/5426* (2013.01)

(58) Field of Classification Search
None
See application file for complete search history.

(56) References Cited

U.S. PATENT DOCUMENTS

| 4,663,159 A | 5/1987 | Brode, II et al. |
| 2007/0031362 A1 | 2/2007 | Kreeger et al. |
| 2013/0296212 A1 | 11/2013 | Fujii et al. |

FOREIGN PATENT DOCUMENTS

| DE | 3301667 A1 | 7/1984 |
| JP | 61-181801 A | 8/1986 |
| JP | 2006-527785 A | 12/2006 |
| JP | 2012-140576 A | 7/2012 |
| WO | WO 2012/091072 A1 | 7/2012 |
| WO | WO 2013/137474 A1 | 9/2013 |

OTHER PUBLICATIONS

International Search Report, issued in PCT/JP2013/082355, dated Feb. 18, 2014.
U.S. Appl. No. 14/384,915, filed Sep. 12, 2014.

*Primary Examiner* — H. Sarah Park
(74) *Attorney, Agent, or Firm* — Birch, Stewart, Kolasch & Birch, LLP

(57) ABSTRACT

Provided is a cationic group-containing cellulose ether which, when incorporated in a hair wash, is able to give an excellent smoothness property and its sustained feeling, finger combability and coated feeling in rinsing, and which, when incorporated in a skin cleanser, is able to give an excellent moist feeling to the skin after washing, and also provided are a surfactant composition, a hair wash composition, a skin cleanser composition, a hair conditioner composition and a hair treatment composition containing the cationic group-containing cellulose ether.

20 Claims, No Drawings

CELLULOSE ETHER CONTAINING CATIONIC GROUP

FIELD OF THE INVENTION

The present invention relates to a cationic group-containing cellulose ether, and to a surfactant composition, a hair wash composition, a skin cleanser composition, a hair conditioner composition and a hair treatment composition containing the cationic group-containing cellulose ether.

BACKGROUND OF THE INVENTION

Hair is damaged by living environments (UV and heat from sunlight, drying), daily hair-care actions (hair washing, brushing, heat by drier) and chemical treatments (coloring, perming, etc.), and hair is kept in friction with each other while wetted, the surface thereof receives a great frictional force so that, while in hair washing, hair would generate a feeling of squeakiness and a feeling of entanglement. In a hair-care composition, in general, a cationic polymer such as typically a cationized hydroxyethyl cellulose is incorporated for the purpose of securing good finger-combability, smoothness and good slip retention in rinsing, in addition to securing the basic function thereof of washing away the dirt from hair as a conditioner composition.

For example, PTL 1 discloses hydrophobe-substituted water-soluble cationic polysaccharides, and in Examples therein, there are exemplified water-soluble cationic polysaccharides that are produced by reacting a cellulose-type starting substance with glycidol followed by quaternizing/alkylating it. The literature further says that aqueous solutions of the cationic polysaccharides enable powerful viscosity increase and foaming, and are therefore useful as hair-care compositions such as shampoos, hair conditioners, etc.

PTL 2 discloses a cellulose ether substituted with a substituent containing an alkyl or arylalkyl group with from 8 to 24 carbon atoms and a quaternary nitrogen-containing substituent, in a ratio of from 0.0003 to 0.08 mol per mol of the anhydroglucose unit therein, and a hair-care composition such as shampoo and the like containing the cellulose ether, further illustrating that the hair-care composition can better the combability of hair in wet and in dry. PTL 3 illustrates a hair-care composition containing a cationized glycerolated cellulose in which the mean addition molar number of the cationic group is from 0.2 to 0.5 and the mean addition molar number of the glycerol group is from 1 to 2.58, saying that the composition can better the combability of hair in hair washing.

CITATION LIST

Patent Literature

[PTL 1] JP-A 61-181801
[PTL 2] JP-T 2006-527785
[PTL 3] German Patent 3301667

SUMMARY OF THE INVENTION

The present invention provides the following [1] to [10].
[1] A cationic group-containing cellulose ether, which has a main chain derived from an anhydroglucose represented by the following general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a hydrocarbon group and has from 3 to 7 carbon atoms and is represented by any of the following general formulae (6) to (8) is from 0.0001 to 0.2:

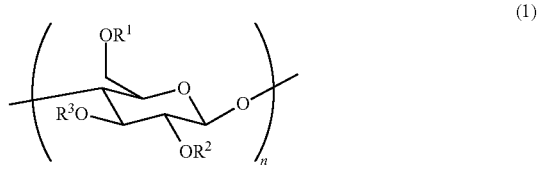

(In the formula, $R^2$ and $R^3$ each independently represent a substituent comprising at least one structural unit selected from a group consisting of the following formulae (2) to (8), or a hydrogen atom. n indicates a mean degree of polymerization of the anhydroglucose-derived main chain, and is a number of from 100 to 12000.)

(In these formulae, the structural unit represented by the formula (2) or (3) is a cationized oxyalkylene group; the structural unit represented by the formula (4) or (5) is a glycerol group; and the structural unit represented by any of the formulae (6) to (8) is a group that contains a hydrocarbon group and has from 3 to 7 carbon atoms. $R^4$ to $R^9$ each independently represent a linear or branched alkyl group having from 1 to 3 carbon atoms; $X^-$ and $Y^-$ each represent an anion; and r and s each indicate an integer of from 0 to 3. $R^{19}$ and $R^{11}$ each independently represent a linear or branched alkyl group having from 1 to 5 carbon atoms, or a linear or branched alkenyl group having from 2 to 5 carbon atoms. $R^{12}$ represents, an alkyl group, an alkenyl group, an aralkyl group or a phenyl group optionally substituted with a methyl group which each have 3 to 7 carbon atoms; and p indicates an integer of 0 or 1. In the structural unit represented by any of the formulae (2) to (7), the oxygen atom bonds to a hydrogen atom or to the carbon atom of the above-mentioned structural unit.)

[2] A surfactant composition containing the cationic group-containing cellulose ether of the above [1], a surfactant and water.

[3] A hair wash composition containing the cationic group-containing cellulose ether of the above [1], a surfactant and water.

[4] A skin cleanser composition containing the cationic group-containing cellulose ether of the above [1], a surfactant and water.

[5] A hair conditioner composition containing the cationic group-containing cellulose ether of the above [1], a surfactant, an oily agent and water.

[6] A hair treatment composition containing the cationic group-containing cellulose ether of the above [1], as well as at least one treatment agent selected from a hair-coloring dye, an oxidizing agent, an alkali agent, and a keratin-reducing agent.

[7] A method of washing hair, including washing hair with the hair wash composition of the above [3], then rinsing and drying the hair.

[8] A method of cleansing a skin, including washing a skin with the skin cleanser composition of the above [4], then rinsing and drying the skin.

[9] A method of conditioning hair, including washing hair with a detergent, and then applying the hair conditioner composition of the above [5] to the hair.

[10] A method of treating hair, including treating hair by contact with the hair treatment composition of the above [6], then rinsing and drying the hair.

DETAILED DESCRIPTION OF THE INVENTION

The present invention relates to a cationic group-containing cellulose ether, which has a main chain derived from an anhydroglucose represented by the above-mentioned general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a hydrocarbon group and has from 3 to 7 carbon atoms and is represented by any of the above-mentioned general formulae (6) to (8) is from 0.001 to 0.2, and to a surfactant composition, a hair wash composition, a skin cleanser composition, a hair conditioner composition and a hair treatment composition containing the cationic group-containing cellulose ether.

The present invention is to provide a cationic group-containing cellulose ether which, when incorporated in a hair wash composition, is able to give an excellent smoothness property and its sustained feeling, an excellent finger-combability, softness and a good coated feeling in rinsing, and which, when incorporated in a skin cleanser composition, is able to give an excellent moist feeling to the skin after drying, and to provide a surfactant composition, a hair wash composition, a skin cleanser composition, a hair conditioner composition and a hair treatment composition containing the cellulose ether.

The present inventors have found that the specific cationic group-containing cellulose ether can solve the above-mentioned problems.

The cationic group-containing cellulose that is provided by the present invention can give, when incorporated in a hair wash composition, foam softness, good finger-combability of hair and hair softness in hair washing, can give an excellent smoothness property and its sustained feeling a hair softness, a good finger-combability and a coated feeling in rinsing, and can give a moist feeling and uniformity after drying.

The cationic group-containing cellulose that is provided by the present invention can give, when incorporated in a skin cleanser composition, an excellent moist feeling to the skin washed with the composition and dried.

The cationic group-containing cellulose that is provided by the present invention can give, when incorporated in a hair conditioner composition, an excellent presence in application of the composition to hair, can give an excellent smoothness property as well as softness in rinsing, and can give an excellent coated feeling after drying.

The cationic group-containing cellulose that is provided by the present invention can give, when incorporated in a hair treatment composition, a smoothness property, a good coated feeling and softness to hair in rinsing after treated with the composition, and can further give a smoothness property, a good coated feeling and softness to hair in rinsing after treated with a conditioner. Hereinafter these effects are referred to as the effects of the present invention.

Further according to the present invention, there are provided the hair wash composition excellent in foam softness, good finger-combability of hair and hair softness in hair washing, capable of giving an excellent smoothness property and its sustained feeling as well as softness and a coated feeling in rinsing, and capable of giving an excellent moist feeling and uniformity after drying; a skin cleanser composition capable of giving an excellent moist feeling to the skin washed with the composition and dried; a hair conditioner composition capable of giving an excellent presence in application of the composition to hair, capable of giving an excellent smoothness property as well as softness in rinsing, and capable of giving an excellent coated feeling after drying; and a hair treatment composition capable of giving a smoothness property, a good coat feeling and softness to hair in rinsing after treated with the composition, and can further capable of giving a smoothness property, a good coat feeling and softness to hair in rinsing after treated with a conditioner.

[Cationic Group-Containing Cellulose Ether]

The cationic group-containing cellulose ether (hereinafter this may be referred to as "CCE") of the present invention has a main chain derived from an anhydroglucose represented by the following general formula (1), in which the degree of substitution with a cationized oxyalkylene group per the anhydroglucose unit is from 0.01 to 1.0, the degree of substitution with a glycerol group is from 0.5 to 5.0, and the degree of substitution with a group containing a hydrocarbon group, having from 3 to 7 carbon atoms and being represented by any of the following general formulae (6) to (8) is from 0.0001 to 0.2.

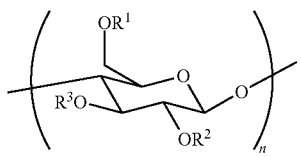
(1)

In the general formula (1), $R^1$, $R^2$ and $R^3$ each independently represent a substituent comprising at least one structural unit selected from a group consisting of the following formulae (2) to (8), or a hydrogen atom. n indicates a mean degree of polymerization of the anhydroglucose-derived main chain, and is a number of from 100 to 12000.

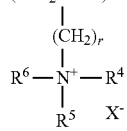
(2)

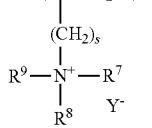
(3)

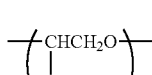
(4)

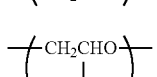
(5)

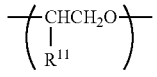
(6)

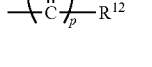
(7)

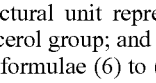
(8)

In these formulae, the structural unit represented by the formula (2) or (3) is a cationized oxyalkylene group; the structural unit represented by the formula (4) or (5) is a glycerol group; and the structural unit represented by any of the formulae (6) to (8) is a group containing a hydrocarbon group and having from 3 to 7 carbon atoms. $R^4$ to $R^9$ each independently represent a linear or branched alkyl group having from 1 to 3 carbon atoms; $X^-$ and $Y^-$ each represent an anion; and r and s each indicate an integer of from 0 to 3. $R^{10}$ and $R^{11}$ each independently represent a linear or branched alkyl group having from 1 to 5 carbon atoms, or a linear or branched alkenyl group having from 2 to 5 carbon atoms. $R^{12}$ represents, an alkyl group, an alkenyl group, an aralkyl group or a phenyl group optionally substituted with a methyl group, which each have from 3 to 7 carbon atoms; and p indicates an integer of 0 or 1. In the structural unit represented by any of the formulae (2) to (7), the oxygen atom bonds to a hydrogen atom or to the carbon atom of the above-mentioned structural unit.

Though not clear, the reason why CCE of the present invention could exhibit the effects of the present invention would be considered as follows:

CCE of the present invention has a predetermined amount of a group containing a hydrocarbon group and having from 3 to 7 carbon atoms (hereinafter "group containing a hydrocarbon group" may also be referred to as "hydrocarbon group-containing group"), and therefore, as compared with a case having a hydrocarbon group-containing group with 8 or more carbon atoms, the hydrophobicity thereof could increase suitably. Consequently, CCE of the present invention that has such a hydrocarbon group-containing group having from 3 to 7 carbon atoms could readily precipitate and could suitably adhere to hair and skin. As a result, when CCE of the present invention is incorporated in a hair wash composition, then the composition can provide an excellent smoothness property and its sustained feeling as well as softness and a coated feeling in rinsing, and can provide an excellent moist feeling and uniformity after drying; and when incorporated in a skin cleanser composition, then the composition can provide an excellent moist feeling to the skin washed with the composition and dried. When incorporated in a hair conditioner composition, then the composition can provide an excellent presence in application of the composition to hair, can provide an excellent smoothness property and softness in rinsing, and can provide an excellent coated feeling after drying; and when incorporated in a hair treatment composition, then the composition can provide excellent effects of giving a smoothness property, a good coated feeling and softness to hair in rinsing.

(Substituents $R^1$, $R^2$ and $R^3$)

In the above-mentioned general formula (1), when the substituent $R^1$ is a substituent comprising at least one structural unit selected from the formulae (2) to (8), then the substituent $R^1$ may be a substituent comprising multiple structural units selected from the formulae (2) to (8), or may be a substituent of only one structural unit selected from the formulae (2) to (8) of such that a hydrogen atom bonds to the oxygen atom of the structural unit.

When the substituent $R^1$ is a substituent comprising multiple structural units selected from the formulae (2) to (7), then the structural units bond to each other via the oxygen atom of one structural unit and the carbon atom of the other structural unit, and in the case, the oxygen atom not bonding to the carbon atom of the other structural unit, for example, the oxygen atom positioned at the terminal of the substituent bonds to a hydrogen atom.

The combination of the structural units is not specifically defined. Multiple structural units of one and the same formula selected from formulae (2) to (8) may bond together, or from 2 to 7 different types of structural units selected from the formulae (2) to (8) may bond together. In the general formula (1), in case where $R^1$ is a substituent having two or more different groups selected from a group containing any of a cationized oxyalkylene group, a glycerol group and a hydrocarbon group-containing group having from 3 to 7 carbon atoms, the bonding mode may be any of block bonding, random bonding, or alternate bonding. From the viewpoint of easiness in production, preferred is block bonding.

In case where the substituent $R^1$ is a substituent that contains at least one structural unit selected from the formulae (2) to (8), the terminal carbon atom bonds to the oxygen atom of the hydroxyl group in the anhydroglucose-derived main chain.

In case where the substituent $R^2$ is a substituent that comprises at least one structural unit selected from the formulae (2) to (8), the embodiments of the substituent are the same as the embodiments of the case where the above-mentioned substituent $R^1$ is a substituent that comprises at least one structural unit selected from the formulae (2) to (8).

In case where the substituent $R^3$ is a substituent that comprises at least one structural unit selected from the formulae (2) to (8), the embodiments of the substituent are the same as the embodiments of the case where the above-mentioned substituent $R^1$ is a substituent that comprises at least one structural unit selected from the formulae (2) to (8).

The substituents $R^1$, $R^2$ and $R^3$ are independent of each other, and may be the same or different.

Within a range not detracting from the effects of the present invention, the substituent $R^1$ may contain any other structural unit than the structural units of the formulae (2) to (8).

(Cationized Oxyalkylene Group Represented by Formula (2) or (3))

In the above-mentioned formula (2) or (3), $R^4$ to $R^9$ each independently represent a linear or branched alkyl group having from 1 to 3 carbon atoms. Specific examples of the group include a methyl group, an ethyl group, an n-propyl group and an isopropyl group. Of those, preferred are a methyl group and an ethyl group from the viewpoint of the availability of the reactants; and more preferred is a methyl group.

In the formulae (2) and (3), $X^-$ and $Y^-$ each represent an anion that is a counter ion to the quaternary ammonium ion. Not specifically defined, $X^-$ and $Y^-$ may be any anion, and as specific examples thereof, there may be mentioned at least one selected from an alkylsulfate ion having from 1 to 3 carbon atoms, a sulfate ion, a phosphate ion, a fatty acid ion having from 1 to 3 carbon atoms and a halide ion.

Of those, preferred are an alkylsulfate ion having from 1 to 3 carbon atoms, a sulfate ion and a halide ion, from the viewpoint of the easiness in production; and more preferred is a halide ion. As the halide ion, there may be mentioned at least one selected from a fluoride ion, a chloride ion, a bromide ion and an iodide ion. From the viewpoint of the water-solubility and the chemical stability of CCE, preferred is at least one selected from a chloride ion and a bromide ion; and more preferred is a chloride ion.

r and s each indicate an integer of from 0 to 3. From the viewpoint of the availability of the starting materials, r and s each are preferably 1.

(Group Containing Hydrocarbon Group and Having from 3 to 7 Carbon Atoms)

In the present invention, the group containing a hydrocarbon group and having from 3 to 7 carbon atoms is the structural unit represented by any of the above-mentioned general formulae (6) to (8). CCE of the present invention has the above-mentioned structural unit and therefore can exhibit the advantageous effects of the present invention, and in particular, when incorporated in a hair wash composition, that CCE can give an excellent smoothness property and its sustained feeling and, in addition thereto, an excellent finger-combability, softness and coated feeling in rinsing. The coated feeling means that the surface of the hair has a feeling that is likely coated with a gel-like lubricant substance, and when the washed hair could have an excellent coated feeling, then the hair could enjoy more strongly the effects of the present invention, smoothness property and its sustained feeling.

The group containing a hydrocarbon group and having from 3 to 7 carbon atoms preferably comprises one or more structural units selected from the structural units represented by the above-mentioned general formulae (6) and (7) especially from the viewpoint of the capability of giving a coated feeling when the compound is used in a hair wash composition.

In the above-mentioned formulae (6) and (7), $R^{10}$ and $R^{11}$ each independently represent a linear or branched alkyl group having from 1 to 5 carbon atoms, or a linear or branched alkenyl group having from 2 to 5 carbon atoms. Accordingly, the formulae (6) and (7) each contain a hydrocarbon group having from 3 to 7 carbon atoms. Specific examples of $R^{10}$ and $R^{11}$ include a methyl group, an ethyl group, an n-propyl group, an isopropyl group, an n-butyl group, an isobutyl group, a tert-butyl group, an n-pentyl group, an isopentyl group, a neopentyl group, a vinyl group, a 1-propenyl group, a 2-propenyl group, a 1-butenyl group, a 2-butenyl group, a 1-pentenyl group, a 2-pentenyl group, etc. Of those, from the viewpoint of the solubility in water of CCE, from the viewpoint of expressing the advantageous effects of the present invention and especially from the viewpoint of expressing a coated feeling in use in a hair wash composition, preferred is an alkyl group having from 1 to 4 carbon atoms or an alkenyl group having from 2 to 4 carbon atoms, more preferred is an alkyl group having from 1 to 4 carbon atoms, even more preferred is a methyl group or an ethyl group, and still further preferred is an ethyl group.

In the formula (8), $R^{12}$ represents, having from 3 to 7 carbon atoms, an alkyl group, an alkenyl group, an aralkyl group or a phenyl group optionally substituted with a methyl group, and specific examples thereof include an n-propyl group, an isopropyl group, an n-butyl group, an isobutyl group, a tert-butyl group, an n-pentyl group, an isopentyl group, a neopentyl group, an n-hexyl group, an n-heptyl group, a 1-propenyl group, a 2-propenyl group, a 1-butenyl group, a 2-butenyl group, a 1-pentenyl group, a 2-pentenyl group, a 1-hexenyl group, a 2-hexenyl group, a 1-heptenyl group, a 2-heptenyl group, a phenyl group, a methylphenyl group, a benzyl group, etc. Of those, from the above-mentioned viewpoints, preferred are one or more selected from an alkyl group, an alkenyl group and a phenyl group each having from 3 to 6 carbon atoms, more preferred are one or more selected from an alkyl group and an alkenyl group having from 3 to 6 carbon atoms, and even more preferred is an alkyl group having from 3 to 6 carbon atoms.

(Degree of Substitution with Cationized Oxyalkylene Group)

In the present invention, the degree of substitution with a cationized oxyalkylene group (hereinafter this may be referred to as "MS(N+)") means a mean value of the number of the cationized oxyalkylene groups existing in the molecule of CCE per one anhydroglucose unit that constitutes the main chain of the molecule. MS(N+) may be measured and calculated according to the method described in the section of Examples to be given hereinunder.

MS(N+) in CCE of the present invention is from 0.01 to 1.0. When MS(N+) falls within the range, then the present invention can provide the effects of the invention. From this viewpoint, MS(N+) is preferably at least 0.04, more preferably at least 0.05, even more preferably at least 0.07, still more preferably at least 0.09, still further more preferably at least 0.10, further more preferably at least 0.12, further more preferably at least 0.15, further more preferably at least 0.17, further more preferably at least 0.18, and is preferably at most 0.90, more preferably at most 0.75, even more preferably at most 0.65, still more preferably at most 0.60, further preferably at most 0.50, and further more preferably at most 0.35, and is, from the viewpoint of realizing good smoothness property and its sustained feeling in rinsing, still further more preferably at most 0.30, further more preferably at most 0.22, and further more preferably at most 0.20.

In addition, from the viewpoint of realizing good smoothness property and its sustained feeling, good finger-combability, softness, coated feeling and moist feeling in rinsing with the hair wash composition, MS(N+) preferably falls within a range of from 0.04 to 0.60, more preferably from 0.07 to 0.30, even more preferably from 0.09 to 0.20, still more preferably from 0.17 to 0.20.

Further, from the viewpoint of realizing softness in rinsing with the hair wash composition, MS(N+) preferably falls within a range of from 0.15 to 0.75, more preferably from 0.35 to 0.75, even more preferably from 0.40 to 0.65.

(Degree of Substitution with Glycerol Group)

In the present invention, the degree of substitution with a glycerol group (hereinafter this may be referred to as "MS(Gly)") means a mean value of the number of the glycerol groups existing in the CCE molecule per one anhydroglucose unit that constitutes the main chain of the molecule. MS(Gly) may be measured and calculated according to the method described in the section of Examples to be given hereinunder.

MS(Gly) in CCE of the present invention is from 0.5 to 5.0. When MS(Gly) falls within the range, then the present invention can provide the effects of the invention. In addition when MS(Gly) falls within the range, then the solubility of CCE in a surfactant composition is high, and therefore CCE could be readily incorporated in the composition. From these viewpoints, MS(Gly) is preferably at least 0.6, more preferably at least 0.7, even more preferably at least 0.8, still more preferably at least 1.0, further preferably at least 1.2, further more preferably at least 1.3, further more preferably at least 1.8, further more preferably at least 2.1. From the above-mentioned viewpoints and from the viewpoint of the cost of CCE of the present invention, MS(Gly) is preferably at most 4.0, more preferably at most 3.8, even more preferably at most 3.0, still more preferably at most 2.3.

In addition, from the viewpoint of realizing good smoothness property and its sustained feeling, good finger-combability, softness, coated feeling and moist feeling in rinsing with the hair wash composition, and from the viewpoint of easiness in formulation of the composition, MS(Gly) is preferably within a range of from 0.5 to 4.0, more preferably from 0.5 to 3.8, even more preferably from 0.6 to 2.3, still more preferably from 1.0 to 2.3, and further more preferably from 1.8 to 2.3.

(Degree of Substitution with Hydrocarbon Group-Containing Group Having from 3 to 7 Carbon Atoms)

In the present invention, the degree of substitution with a group containing a hydrocarbon group and having from 3 to 7 carbon atoms (hereinafter this may be referred to as "MS(HC)") means a mean value of the number of the groups each containing a hydrocarbon group and having from 3 to 7 carbon atoms and represented by any of the above-mentioned formulae (6) to (8) and exist in the CCE molecule per one anhydroglucose unit that constitutes the main chain of the molecule. MS(HC) may be measured and calculated according to the method described in the section of Examples to be given hereinunder.

MS(HC) in CCE of the present invention is from 0.0001 to 0.2. When MS(HC) falls within the range, then the present invention can provide the effects of the invention. From these viewpoints, MS(HC) is preferably at least 0.0005, more preferably at least 0.005, even more preferably at least 0.01, still more preferably at least 0.02, further more preferably at least 0.03. From the above-mentioned viewpoints and from the viewpoint of the production cost of CCE of the present invention, MS(HC) is preferably at most 0.15, more preferably at most 0.10, even more preferably at most 0.06, further preferably at most 0.05, and further more preferably at most 0.04.

In addition, from the above-mentioned viewpoints and from the viewpoint of the production cost of CCE of the present invention, MS(HC) preferably falls within a range of from 0.0005 to 0.2, more preferably from 0.005 to 0.15, even more preferably from 0.005 to 0.10, still more preferably from 0.02 to 0.05, and further more preferably from 0.03 to 0.04.

In the present invention, MS(N+), MS(Gly) and MS(HC) of CCE may be measured according to the methods described in the section of Examples to be given hereinunder.

(Cation Charge Density)

The cation charge density of CCE of the present invention is preferably at least 0.05 mmol/g, more preferably at least 0.15 mmol/g, even more preferably at least 0.2 mmol/g from the viewpoint of attaining the effects of the present invention, and is even more preferably at least 0.3 mmol/g from the viewpoint of attaining the above-mentioned good smoothness property and its sustained feeling. From the viewpoint of attaining the above-mentioned good smoothness property and its sustained feeling, good finger-combability, softness, coated feeling and moist feeling, the cation charge density is preferably at most 2.0 mmol/g, more preferably at most 1.6 mmol/g, even more preferably at most 1.5 mmol/g, still more preferably at most 1.2 mmol/g; but from the viewpoint of attaining the above-mentioned good smoothness property and its sustained feeling, the cationic charge density is further more preferably at most 0.9 mmol/g.

In addition, from the viewpoint of attaining the above-mentioned effects of the present invention, the cation charge density is preferably from 0.05 to 2.0 mmol/g, more preferably from 0.15 to 1.5 mmol/g, even more preferably from 0.2 to 1.2 mmol/g, still more preferably from 0.3 to 0.9 mmol/g.

Further, from the viewpoint of the softness in rinsing with the hair wash composition of the present invention, the cation charge density is preferably from 0.6 to 2.0 mmol/g, more preferably from 1.1 to 1.6 mmol/g, even more preferably from 1.2 to 1.6 mmol/g, still more preferably from 1.35 to 1.6 mmol/g.

In case where CCE of the present invention is used in a hair wash composition and where the composition contains a silicone oil such as dimethylpolysiloxane (dimethicone) as the oily agent (C) to be mentioned below, the cation charge density of CCE is preferably higher since the residual amount of the silicone oil such as dimethicone or the like after hair treatment could increase. Increasing the residual amount of the silicone oil such as dimethicone or the like in hair enhances moist feeling. From the viewpoint of increase in the residual amount of silicone oil such as dimethicone or the like in hair and from the viewpoint of improvement of moist feeling, the cation charge density of CCE is preferably at least 0.4 mmol/g, more preferably at least 0.8 mmol/g, even more preferably at least 1.0 mmol/g, still more preferably at least 1.2 mmol/g, and further more preferably at least 1.3 mmol/g. In addition, from the viewpoint of realizing good smoothness property and its sustained feeling in rinsing hair, the cation charge density is preferably at most 2.0 mmol/g. From these viewpoints, the cation charge density of CCE is preferably from 0.4 to 2.0 mmol/g, more preferably from 0.8 to 2.0 mmol/g, even more preferably from 1.0 to 2.0 mmol/g, still more preferably from 1.2 to 2.0 mmol/g, and further more preferably from 1.3 to 2.0 mmol/g.

The amount of silicone oil such as dimethicone or the like to remain in hair can be determined concretely according to the method described in the section of Examples.

In the present invention, the cation charge density means the molar number of the cationic groups contained in 1 g of CCE, and is calculated according to the following math formula.

$$\text{Cation Charge Density (mmol/g)} = \text{MS(N+)}/(74.1 \times \text{MS(Gly)} + a \times \text{MS(HC)} + b \times \text{MS(N+)} + 162.1) \times 1000$$

(In the formula, a indicates the molecular weight of the group that the hydrocarbon group contains, b indicates the molecular weight of the cationized oxyalkylene group.)

(Mean Degree of Polymerization of CCE)

In CCE of the present invention, the mean degree of polymerization of the anhydroglucose-derived main chain, n, is the viscosity-average degree of polymerization to be measured according to the copper-ammonia method described in the section of Examples. In case where etherification is carried out in an inert gas such as nitrogen or the like, depolymerization of cellulose does not occur, and therefore the mean degree of polymerization of the starting cellulose could be considered to be the same as that of CCE. In the present invention, the mean degree of polymerization of cellulose that is the starting material for CCE is considered to be the same as the mean degree of polymerization, n, of CCE. In the present invention, the mean degree of polymerization of cellulose means the viscosity-average degree of polymerization of cellulose, and concretely, it may be measured according to the method described in the section of Examples.

The mean degree of polymerization, n is at least 100, but preferably at least 200, more preferably at least 500, even more preferably at least 1000 from the viewpoint of securing the effects of the present invention. In addition, from that viewpoint and from the other viewpoint of the handleability of CCE of the present invention and that of the composition to which CCE has been incorporated, the mean degree of polymerization, n is at most 12000, but preferably at most 10000, more preferably at most 5000, even more preferably at most 2500.

From the above-mentioned viewpoints, the mean degree of polymerization, n, is preferably within a range of from 200 to 10000, more preferably from 500 to 5000, even more preferably from 1000 to 2500.

[Production of CCE]

CCE of the present invention may be produced by reacting cellulose with a cationizing agent that corresponds to the cationized oxyalkylene group in CCE of the present invention (hereinafter this may be simply referred to as "cationizing agent"), a glycerolating agent, and a reagent for introducing a group containing a hydrocarbon group and having from 3 to 7 carbon atoms (hereinafter this may be simply referred to as "hydrocarbon group-containing group). Here the order of the cationization reaction, the glycerolation reaction and the hydrocarbon group-containing group introduction reaction is not specifically defined, and any of these may be carried out first, or all of these may be carried out at a time, or may be repeated in any desired order. In case where the introduction of the cationized oxyalkylene group or the hydrocarbon group-containing group into cellulose is carried out first, then it is desirable that the glycerolation reaction is first carried out and thereafter the cationization reaction and the hydrocarbon group-containing introduction reaction are carried since the yield of glycerolation reaction based on the glycerolating agent may readily lower.

In general, cellulose has a high crystallinity, and is therefore poorly reactive. Accordingly, it is desirable that the crystallinity of cellulose is lowered before reaction, or that is, cellulose is preferably pre-treated for reactivity increase. For producing such CCE, for example, there are mentioned the following methods (i) to Method (i):

This is an activation method of generally so-called alcelization or mercerization, in which starting cellulose is mixed with a large amount of water and with a large excessive amount of an alkali metal hydroxide to give an alkali cellulose, and thereafter this is reacted with a glycerolating agent, a cationizing agent, and a hydrocarbon group-containing group-introducing agent.

Method (ii):

Using a solvent capable of dissolving cellulose, such as tetrabutylammonium fluoride-containing dimethyl sulfoxide, paraformaldehyde-containing dimethyl sulfoxide, lithium chloride-containing dimethylacetamide or the like, as in "Cellulose Dictionary", edited by the Cellulose Society of Japan, published by Asakura Publishing, "Macromol. Chem. Phys. 201", 627-631 (2000) or the like, the starting cellulose is dissolved therein, and thereafter the starting cellulose is reacted with a glycerolating agent, a cationizing agent, and a hydrocarbon group-containing group-introducing agent. Method (iii);

Any excess alkali or specific solvent for dissolving cellulose, as in the above-mentioned methods (i) and (ii), are not used. A powdery or floc-like starting cellulose is reacted with a glycerolating agent, a cationizing agent and a hydrocarbon group-containing group-introducing agent in the presence of an alkali.

The details of the cellulose, the glycerolating agent, the cationizing agent and the hydrocarbon group-containing group-introducing agent that are used as the materials for producing CCE of the present invention are described below.

<Starting Cellulose>

Cellulose that is used as the starting material for CCE of the present invention (hereinafter this may be referred to as "starting cellulose") is not specifically defined in point of the type thereof but from the viewpoint of the cellulose purity, the degree of polymerization and the availability, preferred are various types of wood chips; pulps such as wood pulp produced from wood, cotton linter pulp obtained from fibers around cotton seeds, etc.

From the viewpoint of securing the effects of the present invention, the mean degree of polymerization of the starting cellulose is preferably at least 100, more preferably at least 200, even more preferably at least 500, still more preferably at least 1000; and from the same viewpoints as above, the mean degree of polymerization is preferably at most 12000, more preferably at most 10000, even more preferably at most 5000, still more preferably at most 2500.

From the above-mentioned viewpoints, the mean degree of polymerization of the starting cellulose is preferably within a range of from 100 to 12000, more preferably from 200 to 10000, even more preferably from 500 to 5000, still more preferably from 1000 to 2500.

The mean degree of polymerization of the starting cellulose means the viscosity-average mean degree of polymerization thereof measured according to the copper-ammonia method described in the section of Examples or the like.

The shape of the starting cellulose is not specifically defined so far as not interfering with the introduction thereof into a production apparatus, but from the viewpoint of handleability thereof, preferred is use of sheet-like, pellet-like, chip-like, floc-like or powder one. More preferred is a chip-like, floc-like or powdery cellulose, and even more preferred is a floc-like or powdery cellulose. A chip-like cellulose can be prepared, for example, by cutting a starting cellulose. A floc-like or powdery cellulose can be prepared, for example, by cutting a starting cellulose, then optionally drying it, and thereafter grinding it.

(Cutting Treatment)

Depending on the type and the shape of the starting cellulose, cutting treatment is preferably carried out as the pretreatment prior to grinding treatment. The method of cutting a starting cellulose may be suitably selected depending on the type and the shape of the starting cellulose. For example, there may be mentioned a method of using one or more different types of cutting machines selected from a shredder, a slitter cutter and a rotary cutter.

In case where a sheet-like starting cellulose is used here, preferably used is a shredder or a slitter cutter as the cutting machine; and from the viewpoint of the producibility, more preferred is use of a slitter cutter.

A slitter cutter is a cutting machine that cuts a sheet longitudinally in the machine direction parallel to the lengthwise direction of the sheet with a roll cutter, thereby giving thin and long strips, in which the thus-cut slips are thereafter further cut laterally into short strips in the width direction thereof with a fixed blade and a rotary blade. Using such a slitter cutter, the starting cellulose can be chopped into fine pellets. As the slitter cutter, preferably used is a sheet pelletizer manufactured by Horai Co., Ltd. Using the apparatus, a sheet-like starting cellulose can be cut into pellets of from about 1 to 20 mm square.

In case where wood materials such as timber from forest thinning, pruned branches, scrap wood in building or the like, or any other cellulose materials than sheet-like ones are cut, preferred is use of a rotary cutter. A rotary cutter comprises a rotary blade and a screen. Using such a rotary cutter, a starting cellulose that has been cut with the rotary blade into a size not larger than the screen mesh can be readily obtained. If desired, a fixed blade may be arranged in the cutter, in which materials may be cut with both the rotary blade and the fixed blade.

In case where a rotary cutter is used, the size of the roughly cut material to be obtained may be controlled by changing the screen mesh. The screen mesh is preferably from 1 to 70 mm, more preferably from 2 to 50 mm, even more preferably from 3 to 40 mm. When the screen mesh is at least 1 mm, then a roughly ground product having a suitable bulkiness can be obtained and the handleability thereof is thereby improved. When the screen mesh is at most 70 mm, then the roughly ground product can have a suitable size as the source material to be further ground in the subsequent grinding treatment, and the load can be thereby reduced.

The size of the starting cellulose to be obtained after the cutting treatment is preferably at least 1 mm square, more preferably at least 2 mm square from the viewpoint of the producibility; but from the viewpoint of reducing the load in grinding in the subsequent grinding treatment and from the viewpoint of more efficiently carrying out the subsequent drying treatment to be mentioned below, the size is preferably at most 70 mm square, more preferably at most 50 mm square.

(Drying Treatment)

The water content of the starting cellulose to be ground is preferably smaller. The lower limit of the water content during grinding treatment could be 0% by mass relative to the starting cellulose; however, from the viewpoint of the producibility, the water content is preferably at least 0.01% by mass, more preferably at least 0.05% by mass, even more preferably at least 0.1% by mass. On the other hand, from the viewpoint of the starting cellulose grinding efficiency, the water content is preferably at most 10% by mass, more preferably at most 7% by mass, even more preferably at most 4% by mass, still more preferably at most 2% by mass.

In general, a starting cellulose of commercially-available pulps, as well as paper materials which are utilized as a biomass resource, wood materials, plant stems and leaves, plant shells and the like contains water in an amount of more than 5% by mass, and generally contains water in an amount of from 5 to 30% by mass. Accordingly, by drying such a starting cellulose, preferably a starting cellulose obtained after cutting treatment, it is desirable to control the water content of the starting cellulose for use herein.

As the drying method, any known drying means may be suitably selected, and for example, there may be mentioned a hot air heat-receiving drying method, a conductive heat-receiving drying method, a dehumidified air drying method, a cold air drying method, a microwave drying method, an IR drying method, a solar drying method, a vacuum drying method, a freeze drying method, etc.

In the above-mentioned drying method, any known drier may be suitably selected and used. For example, various driers usable herein are described in "Introduction to Powder Technology" (edited by the Society of Powder Technology, Japan, published by the Information Center of Particle Technology, Japan, 1995), page 176.

One alone or two or more different types of such drying methods and driers may be used here either singly or as combined. The drying treatment may be in any mode of batch treatment or continuous treatment, but from the viewpoint of the producibility, continuous treatment is preferred.

As a continuous drier, preferred is a conductive heat-receiving, horizontal stirring drier from the viewpoint of the heat conductivity efficiency. Further, from the viewpoint that fine powder hardly forms and from the viewpoint of the stability in continuous discharge, also preferred is a double-screw horizontal stirring drier. As such a double-screw horizontal stirring drier, Nara Machinery's Double-Screw Paddle Drier is preferably used here.

The temperature in the drying treatment could not be indiscriminately defined as varying depending on the drying means, the drying time and others, but is preferably not lower than 10° C., more preferably not lower than 25° C., even more preferably not lower than 50° C. Also preferably, the temperature is not higher than 250° C., more preferably not higher than 180° C., even more preferably not higher than 150° C. The treatment time is preferably nor shorter than 0.01 hours, more preferably not shorter than 0.02 hours, and is preferably not longer than 2 hours, more preferably not longer than 1 hour. If desired, the drying treatment may be carried out under reduced pressure, and the pressure is preferably not lower than 1 kPa, more preferably not lower than 50 kPa, and is preferably not higher than 120 kPa, more preferably not higher than 105 kPa.

(Grinding Treatment)

The grinder for use for grinding treatment is not specifically defined, and may be any and every device capable of powdering or flocculating the starting cellulose.

Specific examples of the grinder include a roll mill such as a high-pressure compression roll mill, a roll tumbling mill, etc.; a vertical roller mill such as a ring roller mill, a roller-race mill, a ball-race mill, etc.; a vessel-driving medium mill such as a tumbling ball mill, a shaking ball mill, a shaking rod mill, a shaking tube mill, a planetary ball mill, a centrifugal fluidization mill, etc.; a medium stirring mill such as a tower grinder, a stirring tank mill, a circulation tank mill, an annular mill, etc.; a consolidation shear mill such as a fast centrifugal roller mill, an angmill, etc.; as well as a mortar, a stone mill, a mass-colloider, a fret mill, an edge runner mill, a knife mill, a pin mill, a cutter mill, etc.

Of those, preferred are a vessel-driving medium mill and a medium stirring mill, from the viewpoint of the cellulose grinding efficiency, the producibility and the efficiency of the subsequent glycerolation or the like introducing agent efficiency; and more preferred is a vessel-driving medium mill. Further preferred is a shaking mill such as a shaking ball mill, a shaking rod mill or a shaking tube mill; and still further preferred is a shaking rod mill. The grinding method may be in any mode of batch treatment or continuous treatment.

The material of the apparatus and the material of the media to be used for the grinding treatment are not specifically defined, including, for example, iron, stainless, alumina, zirconia, silicon carbide, silicon nitride, glass, etc. From the viewpoint of the starting cellulose grinding efficiency, preferred are iron, stainless, zirconia, silicon carbide and silicon nitride; and from the viewpoint of the industrial applicability, especially preferred are iron and stainless.

In case where the apparatus to be used is a shaking mill and the media are rods, the diameter of the rods is preferably not less than 0.1 mm and more preferably not less than 0.5 mm from the viewpoint of the starting cellulose grinding efficiency; and from the same viewpoints, the diameter is preferably not more than 100 mm, more preferably not more than 50 mm.

A preferred range of the rods packing ratio varies depending on the type of the shaking mill. From the viewpoint of the cellulose grinding efficiency and the producibility, the ratio is preferably not less than 10%, more preferably not less than 15%, even more preferably not less than 50%, and is preferably not more than 97%, more preferably not more than 95%. From the same viewpoints, the range of the rods packing ratio is preferably from 10 to 97%, more preferably from 15 to 97%, even more preferably from 50 to 95%.

When the packing ratio falls within the range, then the contact frequency between cellulose and rods could increase and the grinding efficiency could be improved not interfering with the movement of the media. Here the packing ratio means the apparent volume of the rods relative to the capacity of the stirring site of the shaking mill.

The temperature during the grinding treatment is not specifically defined. From the viewpoint of preventing cellulose decomposition and from the viewpoint of the operation cost, the temperature is preferably not lower than −100° C., more preferably not lower than 0° C., even more preferably not lower than 10° C., and is, from the same viewpoints, preferably not higher than 200° C., more preferably not higher than 100° C., even more preferably not higher than 70° C. Also from the same viewpoints, the temperature during the grinding treatment is preferably from −100 to 200° C., more preferably from 0 to 100° C., even more preferably from 10 to 70° C.

The grinding treatment time may be suitably controlled so that the starting cellulose could be powdered or flocculated. The grinding treatment time may vary depending on the grinder to be used, the necessary energy amount and others, but may be generally from 10 seconds to 12 hours. From the viewpoint of sufficiently powdering or flocculating the starting cellulose, the grinding treatment time is preferably not shorter than 15 seconds, more preferably not shorter than 20 seconds; and from the viewpoint of the producibility, the grinding treatment time is preferably not longer than 3 hours, more preferably not longer than 1 hour, even more preferably not longer than 20 minutes. From the same viewpoints, the grinding treatment time is preferably from 15 seconds to 3 hours, more preferably from 15 seconds to 1 hour, even more preferably from 20 seconds to 20 minutes.

<Glycerolating Agent>

The glycerolating agent for use in producing CCE of the present invention may be at least one selected from glycidol; 3-halo-1,2-propanediols such as 3-chloro-1,2-propanediol, 3-bromo-1,2-propanediol, etc.; glycerin; glycerin carbonates. Of those, preferred is glycidol from the viewpoint of the property thereof not producing any salt and from the viewpoint of the reactivity thereof.

One alone or two or more different types of such glycerolating agents may be used here either singly or as combined.

The amount of the glycerolating agent to be used may be suitably selected in consideration of the desired MS(Gly). From the viewpoint of the solubility in water of CCE and of the object of securing the effects of the present invention, the amount is preferably at least 0.2 mols relative to one mol of the anhydroglucose unit (hereinafter this may be referred to as "AGU") in the starting cellulose, more preferably at least 1 mol, even more preferably at least 3 mols, still more preferably at least 4 mols, further more preferably at least 5 mols; and from the above viewpoint and additionally from the viewpoint of the production cost of CCE, the amount is preferably at most 60 mols, more preferably at most 50 mols, even more preferably at most 45 mols, still more preferably at most 40 mols. From the above-mentioned viewpoints, the amount of the glycerolating agent to be used is preferably from 0.2 to 60 mols relative to one mol of AGU in the starting cellulose, more preferably from 1 to 50 mols, even more preferably from 3 to 45 mols, further more preferably from 4 to 40 mols, and still further preferably from 5 to 40 mols. From the viewpoint of softness, and from the viewpoint of increasing the residual amount of silicone oil such as dimethicone or the like in hair and of improving moist feeling, the amount of the glycerolating agent to be used is preferably from 10 to 60 mols relative to one mol of AGU in the starting cellulose, more preferably from 10 to 50 mols.

Regarding the mode of addition thereof, the glycerolating agent may be added to the system all at a time, or intermittently or continuously. From the viewpoint of increasing the reaction yield of the starting cellulose with the glycerolating agent, continuous addition is preferred.

<Cationizing Agent>

The cationizing agent for use in producing CCE of the present invention includes compounds represented by the following general formula (9) or (10), etc.

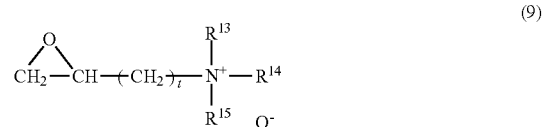

(9)

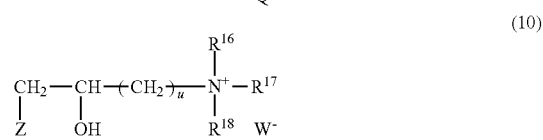

(10)

In the general formulae (9) and (10), $R^{13}$ to $R^{18}$ and preferred embodiments thereof are the same as $R^4$ to $R^9$ in the above-mentioned general formulae (2) and (3). t and u and preferred embodiments thereof are also the same as r in the formula (2) and s in the formula (3). $Q^-$ and $W^-$ and preferred embodiments thereof are the same as $X^-$ in the formula (2) and $Y^-$ in the formula (3). Z represents a halogen atom. $R^{13}$ to $R^{18}$ may be the same or different.

Specific examples of the compounds represented by the above-mentioned general formulae (9) and (10) include glycidyltrimethylammonium, glycidyltriethylammonium and glycidyltripropylammonium chlorides, bromides and iodides; 3-chloro-2-hydroxypropyltrimethylammonium, 3-chloro-2-hydroxypropyltriethylammonium and 3-chloro-2-hydroxytripropylammonium chlorides; 3-bromo-2-hydroxypropyltrimethylammonium, 3-bromo-2-hydroxypropyltriethylammonium and 3-bromo-2-hydroxypropyltripropylammonium bromides; 3-iodo-2-hydroxypropyltrimethylammonium, 3-iodo-2-hydroxypropyltriethylammonium and 3-iodo-2-hydroxypropyltripropylammonium iodides.

Of those, from the viewpoint of the availability of the starting materials and of the chemical stability of the compound, preferred is at least one selected from glycidyltrimethylammonium or glycidyltriethylammonium chlorides or bromides; 3-chloro-2-hydroxypropyltrimethylammonium or 3-chloro-2-hydroxypropyltriethylammonium chlorides; and 3-bromo-2-hydroxypropyltrimethylammonium or 3-bromo-2-hydroxypropyltriethylammonium bromides. More preferred is at least one selected from glycidyltrimethylammonium chloride and 3-chloro-2-hydroxypropyltrimethylammonium chloride; and even more preferred is glycidyltrimethylammonium chloride.

One alone or two or more different types of these cationizing agents may be used here either singly or as combined.

The amount of the cationizing agent to be used may be suitably selected in consideration of the desired MS(N+) and the reaction yield. From the viewpoint of the solubility in water of CCE and of the object of securing the effects of the present invention, the amount is preferably at least 0.01 mols relative to one mol of AGU in the starting cellulose, more preferably at least 0.03 mols, even more preferably at least 0.05 mols; and from the same viewpoints, the amount is preferably at most 60 mols, more preferably at most 35 mols, even more preferably at most 10 mols, still more preferably at most 5 mols. From the same viewpoints, the amount of the cationizing agent to be used is preferably from 0.01 to 60 mols, more preferably from 0.01 to 35 mols, even more preferably from 0.03 to 10 mols, still more preferably from 0.05 to 5 mols. From the viewpoint of softness, and from the viewpoint of increasing the residual amount of silicone oil such as dimethicone or the like in hair and of improving moist feeling, the amount of the cationizing agent to be used is preferably from 5 to 60 mols relative to one mol of AGU in the starting cellulose, more preferably from 10 to 60 mols, even more preferably from 20 to 60 mols.

Regarding the mode of addition thereof, the cationizing agent may be added to the system all at a time, or intermittently or continuously.

<Hydrocarbon Group-Containing Group-Introducing Agent>

The hydrocarbon group-containing group-introducing agent for use in producing CCE of the present invention may be any one capable of introducing the structural unit represented by any of the above-mentioned general formulae (6) to (8).

The introducing agent for introducing the structural unit represented by the general formula (6) or (7) includes compounds represented by the following general formula (11) or (12), etc.

In the general formulae (11) and (12), $R^{19}$ and $R^{20}$ and preferred embodiments thereof are the same as $R^{10}$ in the above-mentioned general formula (6) and $R^{11}$ in the general formula (7). A represents a halogen atom.

Specific examples of the compounds represented by the general formula (11) include propylene oxide, 1,2-butylene oxide, 1,2-epoxypentane, 1,2-epoxyhexane, and 1,2-epoxyheptane. Specific examples of the compounds represented by the general formula (12) include 1-halo-2-alkanols having from 3 to 7 carbon atoms such as 1-chloro-2-propanol, 1-chloro-2-butanol, 1-chloro-hexanol, 1-bromo-2-butanol, etc.

Of those, preferred are the compounds represented by the general formula (11) from the viewpoint of no salt generation during reaction, and from the viewpoint of the availability of the starting materials and the chemical stability of the compounds. From the viewpoint of the solubility of CCE in water and of securing the effects of the present invention, preferred are one or more selected from propylene oxide, 1,2-butylene oxide, 1,2-epoxypentane and 1,2-epoxyhexane, more preferred are one or more selected from propylene oxide and 1,2-butylene oxide; and even more preferred is 1,2-butylene oxide.

One alone or two or more different types of those compounds may be used here either singly or as combined.

The introducing agent capable of introducing the structural unit represented by the general formula (8) includes compounds represented by the following formula (13), (14) or (15), etc.

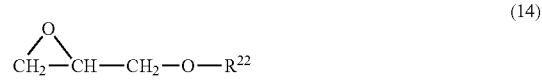

In the general formulae (13), (14) and (15), $R^{21}$, $R^{22}$, $R^{23}$ and $R^{24}$ and preferred embodiments thereof are the same as $R^{12}$ in the above-mentioned general formula (8). q and preferred embodiments thereof are the same as p in the general formula (8). B represents a halogen atom. In the general formula (15), $R^{23}$ and $R^{24}$ may be the same or different, but are preferably the same. When the compound represented by the general formula (14) is used, a glycerol group represented by the general formula (4) or (5) and a structural unit represented by the general formula (8) (in which p is 0) may be introduced at the same time.

Specific examples of the compounds represented by the general formula (13) include halides of alkanes, alkenes or arylalkanes having from 3 to 7 carbon atoms such as 1-chloro-propane, 1-bromo-propane, 1-chloro-butane, 1-bromo-butane, 1-chloro-pentane, 1-bromo-pentane, 1-chloro-hexane, 1-bromo-hexane, 1-chloro-heptane, 1-bromo-heptane, 1-chloro-3-butene, benzyl chloride, etc.; carboxylic acid halides having from 4 to 8 carbon atoms such as butanoic acid chloride, hexanoic acid chloride, etc. Of those, preferred is use of alkane halides having from 3 to 7 carbon atoms.

Specific examples of the compounds represented by the general formula (14) include glycidyl ethers having an alkyl group with from 3 to 7 carbon atoms, such as propyl glycidyl ether, butyl glycidyl ether, pentyl glycidyl ether, hexyl glycidyl ether, heptyl glycidyl ether, etc.; glycidyl ether having an alkenyl group with from 3 to 7 carbon atoms; phenyl glycidyl ether, tolyl glycidyl ether, benzyl glycidyl ether, etc.

Specific examples of the compounds represented by the general formula (15) include carboxylic acid anhydrides having an alkyl group with from 3 to 7 carbon atoms, such as butanoic acid anhydride, hexanoic acid anhydride, etc.

Of those, preferred are the compounds represented by the general formula (13) or (14), from the viewpoint of the availability of the starting materials and of the chemical stability of CCE; but from the viewpoint of the solubility in water of CCE and the object of securing the effects of the present invention, preferred are one or more selected from alkane halides having from 3 to 7 carbon atoms and glycidyl ethers having an alkyl group with from 3 to 7 carbon atoms, more preferred are glycidyl ethers having an alkyl group with from 3 to 7 carbon atoms, even more preferred are one or more selected from propyl glycidyl ether, butyl glycidyl ether, pentyl glycidyl ether and hexyl glycidyl ether, and still more preferred are one or more selected from propyl glycidyl ether and butyl glycidyl ether.

One alone or two or more different types of these may be used here either singly or as combined.

The amount of the hydrocarbon group-containing group-introducing agent to be used here may be suitably selected in consideration of the desired MS(HC) and the reaction yield. From the viewpoint of the solubility in water of CCE and of the object of securing the effects of the present invention, the amount is preferably at least 0.01 mols relative to 1 mol of AGU in the starting cellulose, more preferably at least 0.03 mols, even more preferably at least 0.1 mols; and from the same viewpoints, the amount is preferably at most 5 mols, more preferably at most 3 mols, even more preferably at most 2 mols. From the same viewpoints, the amount of the hydrocarbon group-containing group-introducing agent to be used is preferably from 0.01 to 5 mols relative to one mol of AGU in the starting cellulose, more preferably from 0.03 to 3 mols, even more preferably from 0.1 to 2 mols.

Regarding the mode of addition thereof, the hydrocarbon group-containing group-introducing agent may be added to the system all at a time, or intermittently or continuously.

<Alkali Compound>

CCE of the present invention can be obtained by reacting a powdery cellulose or a flock-like cellulose that has been prepared preferably through the above-mentioned grinding treatment, with the above-mentioned glycerolating agent, the cationizing agent and the hydrocarbon group-containing group-introducing agent, thereby attaining the glycerolation reaction, the cationization reaction and the hydrocarbon group-containing group introduction reaction to give CCE.

These reactions are all carried out in the presence of an alkali compound. The alkali compound for use in these reactions includes alkali metal hydroxides such as sodium hydroxide, potassium hydroxide, lithium hydroxide, etc.; alkaline earth metal hydroxides such as magnesium hydroxide, calcium hydroxide, etc.; tertiary amines such as trimethylamine, triethylamine, etc. Of those, from the viewpoint of the reaction speed in the glycerolation reaction, the cationization reaction and the hydrocarbon group-containing group introduction reaction, preferred are alkali metal hydroxides and alkaline earth metal hydroxides, more preferred are alkali metal hydroxides, and even more preferred are sodium hydroxide and potassium hydroxide. One alone or two or more different types of these alkali metal compounds may be used here either singly or as combined.

Regarding the mode of addition thereof, the alkali compound may be added to the system all at a time, or intermittently or continuously. The alkali compound may be added thereto in a solid state or may be added as an aqueous solution thereof.

Except in the case of the above-mentioned method (i), the amount of the alkali compound to be used in the glycerolation reaction is, when the alkali compound is a monohydric basic compound such as an alkali metal hydroxide or a compound having one tertiary amine in the molecule or the like, preferably at least 0.2 mols relative to 1 mol of AGU in the starting cellulose, from the viewpoint of improving the cellulose reactivity and of the reaction selectivity of the glycerolation reaction agent, more preferably at least 0.7 mols, even more preferably at least 0.8 mols; and from the same viewpoints, the amount is preferably at most 2.0 mols, more preferably at most 1.3 mols, even more preferably at most 1.2 mols. Also from the same viewpoints, the amount of the alkali compound to be used in the glycerolation reaction is preferably from 0.2 to 2.0 mols relative to one mol of AGU in the starting cellulose, more preferably from 0.7 to 1.3 mols, even more preferably from 0.8 to 1.2 mols.

Except in the case of the above-mentioned method (i), the amount of the alkali compound to be used in the cationization reaction and in the hydrocarbon group-containing group introduction reaction is, when the alkali compound is a monohydric basic compound, preferably at least 0.01 mols relative to 1 mol of AGU in the starting cellulose, from the viewpoint of the reaction selectivity of the reactant, more preferably at least 0.05 mols, even more preferably at least 0.1 mols; and from the same viewpoints, the amount is preferably at most 1.0 mol, more preferably at most 0.8 mols, even more preferably at most 0.5 mols. Also from the same viewpoints, the amount of the alkali compound to be used in the cationization reaction and in the hydrocarbon group-containing group introduction reaction is preferably from 0.01 to 1.0 mol relative to one mol of AGU in the starting cellulose in the case where the alkali compound is a monohydric base compound, more preferably from 0.05 to 0.8 mols, even more preferably from 0.1 to 0.5 mols.

The preferred amount of the alkali compound to be used in the case where the cationization reaction and the hydrocarbon group-containing group introduction reaction are carried out simultaneously is the same as the amount of the alkali compound to be used in the case where the cationization reaction and the hydrocarbon group-containing group introduction reaction are carried out separately.

In case where the alkali compound for use in the glycerolation reaction, the cationization reaction or the hydrocarbon group-containing group introduction reaction is a polyhydric base such as an alkaline earth hydroxide or the like, the preferred range of the amount of the alkali compound to be used falls within the range obtained by dividing the range of the preferred amount of the alkali compound to be used in each reaction by the valence of the polyhydric base. For example, when the alkali compound to be used is calcium hydroxide (dihydric base), then the amount of calcium hydroxide to be used in the glycerolation reaction is, except in the case of the method (i), preferably at least 0.1 mols relative to 1 mol of AGU in the starting cellulose, from the viewpoint of improving the cellulose reaction activity and of the reaction selectivity of the glycerolation reaction agent, more preferably at least 0.35 mols, even more preferably at least 0.4 mols; and from the same viewpoints, the amount is preferably at most 1.0 mol, more preferably at most 0.65 mols, even more preferably at most 0.6 mols. Also from the same viewpoints, in the case where the alkali compound is a polyhydric base, the amount of the alkali compound to be used in the glycerolation reaction is preferably from 0.1 to 1.0 mol relative to one mol of AGU in the starting cellulose, more preferably from 0.35 to 0.65 mols, even more preferably from 0.4 to 0.6 mols.

CCE of the present invention can be obtained by reacting a powdery cellulose or a flock-like cellulose that has been prepared preferably through the above-mentioned grinding treatment, with the above-mentioned glycerolating agent, the cationizing agent and the hydrocarbon group-containing group-introducing agent, thereby attaining the glycerolation reaction, the cationization reaction and the hydrocarbon group-containing group introduction reaction. Hereinunder the glycerolation reaction, the cationization reaction and the hydrocarbon group-containing group introduction reaction may be referred to as a collective term "reaction in CCE production".

In each reaction in CCE production, the mode of addition of the glycerolating agent, the cationizing agent and the hydrocarbon group-containing group-introducing agent is not specifically defined. In case where the glycerolating agent, the cationizing agent and the hydrocarbon group-containing group-introducing agent each are in a liquid state, they may be used directly as they are, or may be diluted with a good solvent for the glycerolating agent or the cationizing agent, such as water, a nonaqueous solvent or the like, and may be used in the form of a diluted solution thereof.

The nonaqueous solvent to be used for dilution may be any one to be used generally in the art, including secondary or tertiary lower alcohols having from 3 to 4 carbon atoms, such as isopropanol, tert-butanol, etc.; ketones having from 3 to 6 carbon atoms such as acetone, methyl ethyl ketone, methyl isobutyl ketone, etc.; ethers such as tetrahydrofuran, 1,4-dioxane, ethylene glycol dimethyl ether, diethylene glycol dimethyl ether, etc.; other aprotic polar solvents such as dimethyl sulfoxide, etc.

Each reaction in CCE production in the above-mentioned method (ii), a solvent capable of dissolving cellulose is used and the starting cellulose is dissolved therein, and also in the methods (i) and the reaction may be carried out in the presence of a nonaqueous solvent from the viewpoint of the reaction yield with the glycerolating agent, the cationizing agent and the hydrocarbon group-containing group-introducing agent. As the nonaqueous solvent, usable is any of the above-mentioned nonaqueous solvents.

The amount of the nonaqueous solvent to be used is preferably at least 100% by mass relative to the starting cellulose, from the viewpoint of the addition effect of the nonaqueous solvent, more preferably at least 1000% by mass, even more preferably at least 5000% by mass, but from the viewpoint of the producibility and the reaction yield, the amount is preferably at most 100000% by mass, more preferably at most 50000% by mass, even more preferably at most 20000% by mass. Also from the same viewpoints, the amount of the nonaqueous solvent to be used is preferably from 100 to 100000% by mass relative to the starting cellulose, more preferably from 1000 to 50000% by mass, even more preferably from 5000 to 20000% by mass.

As the apparatus for use for each reaction in CCE production mentioned above, there are mentioned mixing machines, for example, a mixer such as a stirrable Ledige mixer, etc.; and a so-called kneader for use for kneading powders, high-viscosity substances, resins, etc.

The temperature in each reaction in CCE production is preferably not lower than 0° C., from the viewpoint of the reaction speed, more preferably not lower than 20° C., even more preferably not lower than 30° C. From the viewpoint of preventing decomposition of the glycerolating agent, the cationizing agent and the hydrocarbon group-containing group-introducing agent used, the temperature is preferably nit higher than 200° C., more preferably not higher than 100° C., even more preferably not higher than 80° C. Also from the same viewpoints, the temperature in each reaction is preferably from 0 to 200° C., more preferably from 20 to 100° C., even more preferably from 30 to 80° C.

The reaction time for each reaction in CCE production may be suitably controlled, depending on the reaction speed of the glycerolating agent, the cationizing agent and the hydrocarbon group-containing group-introducing agent used. In general, the reaction time is from 0.1 hours to 72 hours, but from the viewpoint of the reaction yield and the producibility, the time is preferably not shorter than 0.2 hours, more preferably not shorter than 0.5 hours, even more preferably not shorter than 1 hour, still more preferably not shorter than 3 hours. Also preferably, the time is not longer than 36 hours, more preferably not longer than 18 hours, even more preferably not longer than 12 hours, still more preferably not longer than 8 hours. Also from the same viewpoints, the reaction time is preferably from 0.2 to 36 hours, more preferably from 0.5 to 18 hours, even more preferably from 1 to 12 hours, still more preferably from 3 to 8 hours.

Each reaction in CCE production may be carried out, if desired, in an inert gas atmosphere such as nitrogen or the like, from the viewpoint of preventing discoloration of the products and preventing reduction in the molecular weight of the anhydroglucose-derived main chain in the products.

After the reaction, the alkali may be neutralized with an acid. In case where the glycerolation reaction, the cationization reaction and the hydrocarbon group-containing group introduction reaction are carried out separately, the compound may be neutralized in each reaction; however, from the viewpoint of preventing the formation of neutralized salts, it is desirable that the neutralization is carried out after all the reactions. As the acid, usable is an inorganic acid such as sulfuric acid, hydrochloric acid, phosphoric acid, etc., or an organic acid such as acetic acid, lactic acid, etc.

Before use, CCE obtained after all those reactions in CCE production may be, if desired, fractionated through filtration or the like, or may be washed with hot water, water-containing isopropyl alcohol, water-containing acetone or the like solvent to thereby remove the unreacted cationizing agent, glycerolating agent, hydrocarbon group-containing group-introducing agent, as well as side products derived from those reactants, and salts formed as side products through neutralization or the like. In addition, as the purification methods, also usable are ordinary purification methods of reprecipitating purification, centrifugation, dialysis, etc.

CCE of the present invention may be formulated in a surfactant composition containing CCE of the present invention (hereinafter this may be referred to also as a component (A)), a surfactant (hereinafter this may be referred to also as a component (B)) and water, and may be applied to a hair wash composition, a skin cleanser composition, a hair conditioner composition or a hair treatment composition. When CCE of the present invention is applied to a hair wash composition, then the hair wash composition can give foam softness, good finger-combability of hair and hair softness in hair washing, can give an excellent smoothness property and its sustained feeling as well as softness and a coated feeling in rinsing, and can give a moist feeling and uniformity after drying. When CCE of the present invention is applied to a skin cleanser composition, the skin cleanser composition can give an excellent moist feeling to the skin washed with the composition and dried. When CCE of the present invention is applied to a hair conditioner composition, the hair conditioner composition can give an excellent presence in application of the composition to hair, can give an excellent smoothness property and its sustained feeling as well as softness in rinsing, and can give an excellent coated feeling after drying.

In the present invention, the coated feeling after drying means that the hair coated with the conditioning component could take an almost healthy hair feeling with no damage.

In addition, CCE of the present invention is applicable to various hair treatment compositions such as a hair color composition, a hair bleach composition, a perm wave composition, a straight perm composition, a sustainable hair styling composition, a hair relaxer composition, etc. When CCE of the present invention is applied to such a hair treatment composition, the hair treatment composition can give a smoothness property, a good coated feeling and softness to hair in rinsing after treated with the composition, and can further give a smoothness property, a good coated feeling and softness to hair in rinsing after treated with a conditioner.

[Surfactant Composition]

The surfactant composition of the present invention comprises CCE of the present invention, a surfactant and water.

<CCE>

The CCE content in the surfactant composition of the present invention is preferably at least 0.01% by mass, from the viewpoint of providing the effects of the present invention, more preferably at least 0.05% by mass, even more preferably at least 0.1% by mass. On the other hand, from the viewpoint of the handleability of the surfactant composition, the content is preferably at most 10% by mass, more preferably at most 5% by mass, even more preferably at most 1% by mass. From these viewpoints, the CCE content in the surfactant composition is preferably from 0.01 to 10% by mass, more preferably from 0.05 to 5% by mass, even more preferably from 0.1 to 1% by mass.

From the viewpoint of providing the effects of the present invention, CCE contained in the surfactant composition in the present invention preferably has MS(N+) of from 0.04 to 0.6, MS(Gly) of from 0.5 to 4.0 and MS(HC) of from 0.005 to 0.15.

<Surfactant>

The surfactant composition in the present invention contains one or more surfactants.

The surfactant may be any and every surfactant capable of being generally used in drugs, quasi-drugs, cosmetics, toiletry goods, sundries, etc. Concretely, there are mentioned alone or in a combination of two or more kinds selected from anionic surfactants, nonionic surfactants, cationic surfactants and ampholytic surfactants.

(Anionic Surfactant)

As the anionic surfactant, preferred is at least one selected from sulfate ester salts, sulfonate salts, carboxylate salts, phosphate ester salts and amino acid salts having a hydrophobic site.

Concretely, there are mentioned sulfate ester salts having a hydrophobic site, such as alkylsulfate salts, alkenylsulfate salts, polyoxyalkylene alkyl ether sulfate salts, polyoxyalkylene alkenyl ether sulfate salts, polyoxyalkylene alkylphenyl ether sulfate salts, etc.; sulfonate salts having a hydrophobic site, such as alkyl sulfosuccinate salts, alkyl polyoxyalkylenesulfosuccinate salts, alkanesulfonate salts, acylisethionates, acylmethyl taurates, internal olefinsulfonate salts having from 12 to 24 carbon atoms to be mentioned below, etc.; carboxylic acid salts having a hydrophobic site, such as higher fatty acid salts having from 8 to 16 carbon atoms, alkyl ether acetate salts represented by the following general formula (I), etc.; phosphate ester salts having a hydrophobic site, such as alkylphosphate salts, polyoxyalkylene alkyl ether phosphate salts, etc.; amino acid salts having a hydrophobic site, such as acylglutamate salts, alanine derivatives, glycine derivatives, arginine derivatives, etc.

$$R-O-(CH_2CH_2O)_a-CH_2-COOM \qquad (I)$$

(In the formula, R represents an alkyl group having from 4 to 22 carbon atoms, a indicates a number of from 4 to 16, M represents a hydrogen atom, an alkali metal, an alkaline earth metal (½ atom), an ammonium or an organic ammonium.)

Except the above-mentioned internal olefinsulfonate salts having from 12 to 24 carbon atoms, the above-mentioned anion surfactants preferably have, as the hydrophobic site therein, an alkyl group or alkenyl group having from 8 to 20 carbon atoms, from the viewpoint of the washing performance, the foaming performance and the foam quality of the surfactant composition and from the viewpoint of securing the effects of the present invention. The alkyl group or alkenyl group more preferably has at least 10 carbon atoms and more preferably has at most 16 carbon atoms.

Of the above-mentioned anionic surfactants, more preferred is at least one selected from alkylsulfate salts such as sodium lauryl sulfate, etc.; polyoxyethylene alkyl ether sulfate salts such as polyoxyethylene lauryl ether sulfate salts (ammonium laureth-(1) sulfate, sodium laureth-(1) sulfate, sodium laureth-(2) sulfate, sodium laureth-(3) sulfate), etc.; higher fatty acid salts having from 8 to 16 carbon atoms, such as potassium laurate, sodium laurate, sodium myristate, potassium myristate, potassium palmitate, etc.; alkyl ether acetate salts represented by the above-mentioned general formula (I), such as sodium laureth-(4.5) acetate, sodium laureth-(10) acetate, etc.; alkyl sulfosuccinate salts such as sodium laureth-2 sulfosuccinate, etc.; acylglutamate salts such as sodium N-acyl-L-glutamate (sodium cocoyl-glutamate), etc.; glycine derivatives such as sodium N-lauroylsarcosine, etc.; olefin sulfonate salts such as α-olefin sulfonates having from 14 to 16 carbon atoms, internal olefin sulfonate salts having from 12 to 24 carbon atoms, etc.

[Internal Olefinsulfonate Salts]

The surfactant composition of the present invention may contain, as a anion surfactant therein, an internal olefinsulfonate salt having from 12 to 24 carbon atoms (hereinafter this may be simply referred to as "internal olefinsulfonate salt"), from the viewpoint of the stability of the composition to the environment and the mildness thereof, from the viewpoint of improving the washing performance of the composition, improving the foam quality thereof, improving the foaming property, improving the good foam sustainability and improving the rinsing performance thereof, and in washing hair, improving the finger-combability of the composition, in rinsing hair, improving the good smoothness property and its sustained feeling thereof in rinsing hair, and after drying, giving a good moist feeling, uniformity and manageability to the hair, and further from the viewpoint of giving a good moist feeling and a good moisturizing feeling to the skin after drying.

In the present invention, the internal olefinsulfonate salt is a sulfonate salt obtained by sulfonating a starting internal olefin (olefin having a double bond inside the olefin chain), followed by neutralizing and hydrolyzing it. In the broad sense thereof, such an internal olefin includes a case that contains a minor amount of a so-called α-olefin in which the double bond is positioned at the 1-position of the carbon chain. In other words, when such an internal olefin is sulfonated, then a β-sultone is quantitatively formed, and a part of the β-sultone is changed into a γ-sultone and an olefinsulfonic acid, and further, these are converted into a hydroxyalkanesulfonate salt and an olefinsulfonate salt in the neutralization/hydrolysis step (for example, J. Am. Oil Chem. Soc., 69, 39 (1992)). The hydroxyl group in the hydroxyalkanesulfonate salt obtained here exists inside the alkane chain, and the double bond of the olefinsulfonate salt exists inside the olefin chain. The obtained product is mainly a mixture of these, and in a part thereof, there may be contained a minor amount of a hydroxyalkanesulfonate salt having a hydroxy group at the terminal of the carbon chain therein, or an olefinsulfonate salt having a double bond at the terminal of the carbon chain therein. In this specification, these products and their mixtures are referred to as a collective term of an internal olefinsulfonate salt. In addition, a hydroxyalkanesulfonate salt may be referred to as a hydroxy form of an internal olefinsulfonate salt (hereinafter this may also be referred to as HAS), and an olefinsulfonate salt may be referred to as an olefin form of an internal olefinsulfonate salt (hereinafter this may be also referred to as IOS).

The carbon number of the internal olefinsulfonate salt is preferably at least 12, from the viewpoint of improving the foamability, the foaming sustainability and the rinsing performance of the surfactant composition, and therefore improving the smoothness property in rinsing, the uniformity and the manageability of hair after drying, and the moist feeling and the moisturizing feeling of skin after drying, more preferably at least 14, even more preferably at least 16. In addition, from the viewpoint of improving the finger-combing performance in hair washing, the smoothness property and its sustained feeling in hair rinsing, the moist feeling, uniformity and manageability after drying, and the moist feeling and moisturizing feeling of skin after drying, the carbon number is preferably at most 24, more preferably at most 20, even more preferably at most 18. Various types of those hydroxy forms and olefin forms each having a different carbon number are derived from the internal olefins used as the starting material, and the surfactant for use herein may contain any other hydroxy forms and olefin forms of which the carbon number differs from that of the above-mentioned ones.

One alone or two or more different types of such internal olefinsulfonate salts may be used here either singly or as combined.

In case where two or more different types of internal olefinsulfonate salts are used as combined, preferred is use of a combination of an internal olefinsulfonate salt having 16 carbon atoms and an internal olefinsulfonate salt having 18 carbon atoms, from the viewpoint of improving the foaming sustainability and the rinsing performance, improving the finger-combability in hair washing, improving the smoothness property and its sustained feeling in rinsing, improving the moist feeling, uniformity and manageability after drying, and improving the moist feeling and moisturizing feeling of the skin after drying.

In this case, in the surfactant composition of the present invention, the ratio by mass of the content of the internal olefinsulfonate salt having 16 carbon atoms to the content of the internal olefinsulfonate salt having 18 carbon atoms (internal olefinsulfonate salt having 16 carbon atoms/internal olefinsulfonate salt having 18 carbon atoms) is preferably from 50/50 to 99/1, from the above-mentioned viewpoints, more preferably from 60/40 to 95/5, even more preferably from 70/30 to 90/10, still more preferably from 75/25 to 90/10, further more preferably from 75/25 to 85/15, still further more preferably from 78/22 to 85/15.

The ratio by mass may be determined through high-performance liquid chromatography-mass spectrometry (hereinafter this is abbreviated as "HPLC-MS"). Concretely, from the internal olefinsulfonate salt or the obtained surfactant composition to be analyzed, the internal olefinsulfonate salt having 16 carbon atoms and the internal olefinsulfonate salt having 18 carbon atoms are separated through HPLC, and the two are further analyzed through MS for identification. From the HPLC-MS peak area, the intended mass ratio may be determined.

The content of the internal olefinsulfonate salts in which the sulfonate group exists at the 2-position to the total amount of the internal olefinsulfonate salts in the surfactant composition of the present invention is preferably at most 25% by mass, from the viewpoint of improving the foaming performance, the foam quality and the rinsing performance, improving the finger-combability in hair washing, improving the smoothness property and its sustained feeling in hair rinsing, improving the moist feeling, uniformity and manageability after drying and improving the moist feeling and moisturizing feeling of the skin after drying, more preferably at most 23% by mass; but from the viewpoint of reducing the production cost, increasing the producibility and improving the foaming sustainability and the finger-combability in hair washing, the content is preferably at least 5% by mass, more preferably at least 8% by mass.

The content of the internal olefinsulfonate salts in which the sulfonate group exists at the 2-position therein may be determined according to the method of nuclear magnetic resonance spectrometry. Concretely, the content may be determined according to the method of gas chromatography described in the section of Examples given hereinunder.

Preferably, the internal olefinsulfonate salt is a mixture of the hydroxy form and the olefin form thereof. The ratio by mass of the content of the hydroxy form of the internal olefinsulfonate salt to the content of the olefin form of the internal olefinsulfonate salt (hydroxy form/olefin form) in the surfactant composition is preferably from 50/50 to 100/0, from the viewpoint of improving the producibility and reducing impurities, more preferably from 70/30 to 100/0, even more preferably from 75/25 to 95/5.

The ratio by mass of the content of the hydroxy form of the internal olefinsulfonate salt to the content of the olefin form of the internal olefinsulfonate salt in the surfactant composition of the present invention may be determined by separating the hydroxy form and the olefin form from the internal olefinsulfonate salt or the surfactant composition containing the salt through HPLC and quantifying them according to the method described in the section of Examples.

The internal olefinsulfonate salt may be obtained by sulfonating a starting internal olefin having from 12 to 24 carbon atoms followed by neutralizing and hydrolyzing it. The conditions of sulfonation, neutralization and hydrolysis are not specifically defined. For example, herein referred to are the conditions described in Japanese Patent 1633184 and 2625150, and Tenside Surf. Det. 31 (5) 299 (1994).

In the present invention, the starting internal olefin means an olefin substantially having a double bond inside the olefin chain thereof, as described above. The carbon number of the starting internal olefin is preferably at least 12, from the viewpoint of improving the foamability, the foaming sustainability and the rinsing performance of the surfactant composition and therefore improving the smoothness performance in rinsing, the uniformity and the manageability of hair after drying, and the moist feeling and moisturizing feeling of skin, more preferably at least 14, even more preferably at least 16. In addition, from the viewpoint of improving the finger-combing performance in hair washing, the smoothness property and its sustained feeling in rinsing, the moist feeling, uniformity and manageability after drying, and the moist feeling and moisturizing feeling of skin after drying, the carbon number is preferably at most 24, more preferably at most 20, even more preferably at most 18. One alone or two or more different types of the starting olefins may be used here either singly or as combined.

The content of the internal olefin in which the double bond exists in the 2-position therein in the starting internal olefin is preferably at most 40% by mass, from the viewpoint of improving the foamability, the foaming sustainability and the rinsing performance and therefore improving the finger-combability in hair washing, the smoothness property and its sustained feeling in hair rinsing, the moist feeling, the uniformity and the manageability after drying, and the moist feeling and moisturizing feeling of skin, more preferably at most 35% by mass; and from the viewpoint of reducing the production cost and improving the producibility and from the viewpoint of imparting to the composition a good finger-combing feeling in hair washing, the content is preferably at most 5% by mass, more preferably at most 9% by mass, even more preferably at most 15% by mass.

The double bond distribution in the starting internal olefin may be analyzed, for example, through gas chromatography-mass spectrometry (hereinafter abbreviated as "GC-MS"). Concretely, using a gas chromatography analyzer (hereinafter abbreviated as "GC"), the components differing from each other in point of the carbon chain length and the double bond position are accurately separated from each other, and each component is subjected to mass spectrometry (hereinafter abbreviated as "MS") to thereby identify the double bond position therein. From the GC peak area, the proportion of each component may be determined.

The sulfonation reaction may be attained by reacting one mol of a starting internal olefin with from 1.0 to 1.2 mols of sulfur trioxide gas. The reaction temperature is preferably from 20 to 40° C.

For the neutralization, an aqueous alkali solution of sodium hydroxide, ammonia, 2-aminoethanol or the like is reacted with the sulfonated product in an amount of from 1.0 to 1.5 molar times relative to the theoretical amount of the sulfonate group in the product.

The hydrolysis may be carried out at from 90 to 200° C. for 30 minutes to 3 hours in the presence of water. These reactions may be carried out continuously. After the reaction, the product may be purified through extraction, washing, etc.

In producing the internal olefinsulfonate salt, a starting internal olefin having a carbon number distribution of from 12 to 24 may be used for sulfonation, neutralization and hydrolysis; or a starting internal olefin having a single carbon number may be used for sulfonation, neutralization and hydrolysis; and if desired, different types of internal olefinsulfonate salts each having a different carbon number and having been produced separately may be mixed.

(Nonionic Surfactant)

The nonionic surfactant for use herein includes polyethylene glycol-type nonionic surfactants such as polyoxyethylene sorbitan fatty acid esters, polyoxyethylene sorbitol fatty acid esters, polyoxyethylene glycerin fatty acid esters, polyoxyethylene fatty acid esters, polyoxyethylene alkyl ethers, polyoxyethylene alkylphenyl ethers, polyoxyalkylene (hardened) castor oil, etc.; polyalcohol-type nonionic surfactants such as sucrose fatty acid esters, polyglycerin alkyl ethers, polyglycerin fatty acid esters, alkyl glycosides, etc.; and fatty acid alkanolamides.

From the viewpoint of providing the effects of the present invention, the nonionic surfactant preferably has, as the hydrophobic site therein, an alkyl group or alkenyl group having from 8 to 20 carbon atoms.

Of those, preferred is at least one selected from polyoxyethylene alkyl ethers such as polyoxyethylene lauryl ether (laureth-3), etc., polyoxyethylene hardened castor oil, fatty acid alkanolamides such as coconut oil fatty acid monoethanolamide, coconut oil fatty acid N-methylmonoethanolamide, etc., alkyl glucosides such as lauryl glucoside, etc.; more preferred is at least one selected from polyoxyalkylene alkyl ethers and fatty acid alkanolamides; and even more preferred is at least one selected from polyoxyethylene alkyl ethers and fatty acid monoalkanolamides; and still more preferred is at least one selected from polyoxyethylene lauryl ether and coconut oil fatty acid monoethanolamide.

(Ampholytic Surfactant)

The ampholytic surfactant includes betaine-type surfactants such as imidazoline betaines, alkyldimethylaminoacetate betaines, fatty acid amide propylbetaines, sulfobetaines, etc.; and amine oxide-type surfactants such as alkyldimethylamine oxides, etc.

Of those, from the effect of providing the effects of the present invention, preferred is at least one selected from imidazoline betaines, alkyldimethylaminoacetate betaines, fatty acid amide propylbetaines, and alkylhydroxysulfobetaines; concretely preferred is at least one selected from laurylcarboxymethylhydroxyimidazolium betaine, lauryldimethylaminoacetate betaine, coconut oil fatty acid amide propylbetaine, and laurylhydroxysulfobetaine.

(Cationic Surfactant)

The cationic surfactant includes quaternary ammonium salts having a hydrocarbon group having from 12 to 28 carbon atoms and optionally interrupted by an amide group, an ester group or an ether group, pyridinium salts, as well as tertiary amine salts with mineral acids or organic acids. Concretely, there are mentioned mono-long chain alkyltrimethylammonium salts such as cetyltrimethylammonium salts, stearyltrimethylammonium salts, behenyltrimethylammonium salts, octadecyloxypropyltrimethylammonium salts, etc.; di-long chain alkyldimethylammonium salts such as distearyldimethylammonium salts, diisotetradecyldimethylammonium salts, etc.; mono-long chain alkyldimethylamine salts such as stearyldimethylamine, behenyldimethylamine, octadecyloxypropyldimethylamine, dimethylaminopropylstearamide hydrochloride, citrate or lactate, etc.

Of those, from the viewpoint of providing the effects of the present invention, preferred are mono-long chain alkyltrimethylammonium salts such as behenyltrimethylammonium chloride, cetyltrimethylammonium chloride, etc.

(Content of Surfactant)

The content of the surfactant in the surfactant composition of the present invention is, from the viewpoint of providing the effects of the present invention, preferably at least 0.1% by mass, more preferably at least 1% by mass, even more preferably at least 5% by mass; and from the same viewpoints, the content is preferably at most 80% by mass, more preferably at most 50% by mass, even more preferably at most 36% by mass. Accordingly from the viewpoints as above, the content of the surfactant is preferably within a range of from 0.1 to 80% by mass, preferably from 1 to 80% by mass, even more preferably from 5 to 50% by mass, still more preferably from 5 to 36% by mass.

(Ratio by Mass of CCE to Surfactant)

In the surfactant composition of the present invention, the ratio by mass of CCE to the surfactant [CCE/surfactant] is, from the viewpoint of providing the effects of the present invention, preferably at least 0.0002, more preferably at least 0.001, even more preferably at least 0.003, and is, from the same viewpoints, preferably at most 10, more preferably at most 5, even more preferably at most 2.

<Water>

The content of water in the surfactant composition of the present invention is, from the viewpoint of providing the effects of the present invention, preferably at least 10% by mass in the surfactant composition, more preferably at least 40% by mass, and is preferably at most 99.5% by mass.

<Cationic Polymer Except CCE>

The surfactant composition of the present invention may additionally contain any other cationic polymer than CCE (hereinafter this may also be referred to as a component (D)), from the viewpoint of, in application thereof to a hair wash composition, the foam softness and the good finger-combing feeling and the softness in washing hair, and the smoothness property, its sustained feeling, the softness, and the coated feeling in hair rinsing, and, in application thereof to a skin cleanser composition, from the viewpoint of further improving the moist feeling after drying. The cationic polymer as referred to in the present invention means a polymer that has a substituent capable of being a cation (cationic group) under the condition where the surfactant composition of the present invention is used. The cationic group includes, for example, quaternary ammonium groups, and primary to tertiary amino groups.

As the other cationic polymer than CCE, there may be mentioned at least one selected from cationic galactomannans, cationized hydroxyalkyl celluloses, cationized starches, and cationic synthetic polymers produced through radical polymerization.

The cationic galactomannan is a polymer prepared by introducing a cationic group into a galactomannan polysaccharide, and is preferably a cationic polymer prepared by introducing a quaternary nitrogen-containing group thereinto. The cationic galactomannan may be produced by reacting a galactomannan polysaccharide with a cationizing agent.

The cationic galactomannan includes cationized tara gum (*Caesalpinia* gum) such as Catinal CTR-100 (by Toho Chemical), etc.; cationized locust bean gum such as Catinal CLB-100 (by Toho Chemical), etc.; cationized fenugreek gum such as Catinal CG-100 (by Toho Chemical), etc.; cationized guar gum such as Jaguar C-13S, Jaguar C-14S, Jaguar C-17, Jaguar C-500, Jaguar C-162 and Jaguar EXCEL sold by Rhodia, N-Hance BF17, N-Hance 3215, N-Hance CCG450, N-Hance 3196, N-Hance BF13, N-Hance CG13, N-Hance CCG45, N-Hance 3000, AquaCat PF618, AquaCat CG518 and N-Hance HPCG1000 sold by Ashland, etc.; cationized *cassia* gum such as Sensomer CT-250 polymer and Sensomer CT-400 polymer sold by Lubrizol, etc.; cationized fenugreek gum; cationized honey locust gum; and cationized Chinese parasol-tree gum, etc.

Of those, from the viewpoint of the foam softness, the finger-combability and the softness of hair in hair washing, and the smoothness property, its sustained feeling, the softness, and the coated feeling in hair rinsing in application of the surfactant composition of the present invention to a hair wash composition, and from the viewpoint of the moist feeling of skin after dried in application of the composition to a skin cleanser composition, preferred are cationized tara gum, cationized locust bean bum, cationized fenugreek gum, cationized guar gum, and cationized *cassia* gum.

The cationized hydroxyalkyl cellulose includes a cationized hydroxyethyl cellulose (hereinafter this may be referred to as "C-HEC"), a cationized hydroxypropyl cellulose (hereinafter this may be referred to as "C-HPC"), etc. The cationized hydroxyalkyl cellulose may be obtained by adding a cationic group and an alkyleneoxy group to cellulose. The cationic group is preferably a quaternary ammonium group.

Examples of commercial products of C-HEC include UCARE JR125, UCARE JR400, UCARE JR30M, UCARE LR400, UCARE LR30M, SOFTCAT SL-5, SOFTCAT SL-30, SOFTCAT SL-60, SOFTCAT SL-100, SOFTCAT SX-400X, SOFTCAT SX-1300H, SOFTCAT SX-1300X, SOFTCAT SK-H and SOFTCAT SK-MH sold by Dow Chemical, etc.

The cationized hydroxypropyl cellulose may be produced by reacting cellulose with a cationizing agent and propylene oxide, and for the details of the production method, for example, referred to is WO2012/091072.

The cationized starch is a starch derivative prepared by introducing a quaternary nitrogen-containing group into starch. The cationized starch may be produced by reacting starch with a cationizing agent. The cationic group is preferably a quaternary ammonium group. Commercial products of the cationized starch include Sensomer CI-50 sold by Lubrizol, etc.

The cationic synthetic polymer produced through radical polymerization includes, for example, methacryloxyalkyl quaternary ammonium salt-acrylamide copolymers such as Merquat 5 (by Lubrizol), etc.; diallyl quaternary ammonium salts-acrylamide copolymers such as Merquat 550, Merquat 740, Merquat 2200 and Merquat S (all by Lubrizol), etc.; diallyl quaternary ammonium-acrylic acid copolymers such as Merquat 280 and Merquat 295 (both by Lubrizol), etc.; diallyl quaternary ammonium salt-acrylamide-acrylic acid copolymers such as Merquat 3330DRY (by Lubrizol), etc.; methacrylamide alkyl quaternary ammonium salt-acrylic acid-acrylate copolymers such as Merquat 2001 (by Lubrizol), etc.; methacrylamide alkyl quaternary ammonium salt-acrylic acid-acrylamide copolymers such as Merquat 2003 (by Lubrizol), etc.; diallyl quaternary ammonium salt-vinylpyrrolidone-vinylimidazole copolymers such as Luviquat Sensation (by BASF), etc.; and crosslinked copolymers of cationic synthetic polymers produced through radical polymerization as mentioned above, such as Sofcare KG-301W (by Kao), Sofcare KG-101W (by Kao), etc.

Of the above, as the cationic polymer except CCE, from the viewpoint of the foam softness, the finger-combability and the softness of hair in hair washing, and the smoothness property, its sustained feeling, the softness and the coated feeling in hair rinsing in application of the surfactant composition of the present invention to a hair wash composition, preferred is at least one selected from cationic galactomannans, cationized hydroxyalkyl celluloses, cationized starch, and cationic synthetic polymers produced through radical polymerization.

One alone or two or more different types of such other cationic polymers than CCE may be used here either singly or as combined.

The content of the other cationic polymer than CCE in the surfactant composition of the present invention is, from the viewpoint of the foam softness, the finger-combability and the softness of hair in hair washing, and the smoothness property, its sustained feeling, the softness, and the coated feeling in hair rinsing in application of the surfactant composition of the present invention to a hair wash composition, and from the viewpoint of the moist feeling after drying in application of the composition to a skin cleanser composition, preferably at least 0.01% by mass in the surfactant composition, more preferably at least 0.05% by mass, even more preferably at least 0.10% by mass, still more preferably at least 0.2% by mass, further more preferably at least 0.3% by mass, and is preferably at most 5% by mass, more preferably at most 2% by mass, even more preferably at most 1.0% by mass, still more preferably at most 0.5% by mass.

The ratio by mass of CCE to the other cationic polymer than CCE [CCE/other cationic polymer than CCE] in the surfactant composition of the present invention is, from the viewpoint of the foam softness, the finger-combability and the softness of hair in hair washing, and the smoothness property, the softness, its sustained feeling and the coated feeling in hair rinsing in application of the surfactant composition of the present invention to a hair wash composition, and from the viewpoint of the moist feeling after skin washing in application of the composition to a skin cleanser composition, preferably at least 0.05, more preferably at least 0.1, even more preferably at least 0.3, still more preferably at least 0.5, and is preferably at most 10, more preferably at most 5, even more preferably at most 2, still more preferably at most 1.

<Oily Agent>

Within a range not detracting from the effects of the present invention, the surfactant composition of the present invention may contain an oily agent (hereinafter this may be referred to as a component (C)).

The oily agent is an oily component generally used in drugs, quasi-drugs, cosmetics, toiletry goods, sundries and the like, and usable here is any and every hardly water-soluble or water-insoluble oily agent of which the amount of dissolution in 100 g of water at 20° C. is from 0 g to 1 g. The oily agent is, from the viewpoint of providing the effects of the present invention, especially providing an excellent moist feeling, good uniformity and excellent moisturizing feeling after drying in use of the surfactant composition of the present invention, preferably such that the amount of dissolution thereof in 100 g of water at 20° C. is at most 0.5 g, more preferably at most 0.1 g.

From the above-mentioned viewpoints, the oily agent for use herein is preferably at least one selected from (i) ester oils, (ii) silicone oils, (iii) ether oils, (iv) hydrocarbon oils, (v) higher alcohols, and (vi) carboxylic acids having a hydrocarbon group optionally substituted with a hydroxyl group and having from 17 to 23 carbon atoms.

((i) Ester Oil)

As the ester oil, from the viewpoint of providing the effects of the present invention, especially providing an excellent moist feeling, good uniformity and excellent moisturizing feeling after drying in use of the surfactant composition of the present invention, preferred are ester oils represented by the following general formula (16), (17) or (19), hydrophobic carboxylate esters of dipentaerythritol, and dialkyl carbonate compounds represented by the following general formula (20).

[Ester Oil Represented by General Formula (16)]

$$R^{25}\text{—COO—}R^{26} \qquad (16)$$

(In the formula, $R^{25}$ represents a linear or branched alkyl group having from 7 to 22 carbon atoms, $R^{26}$ represents a linear or branched alkyl or alkenyl group having from 1 to 22 carbon atoms.)

The carbon number of $R^{25}$ in the general formula (16) is, from the viewpoint of the excellent moist feeling, uniformity and moisturizing feeling after drying in use of the surfactant composition of the present invention, preferably at least 10, more preferably at least 12, and is preferably at most 20, more preferably at most 18.

The carbon number of $R^{26}$ is, from the above-mentioned viewpoints, preferably at most 20, more preferably at most 18. More preferably, $R^{26}$ is a linear or branched alkyl or alkenyl group having from 1 to 18 carbon atoms and optionally interrupted by a phenyl group.

Specific examples of the ester oils represented by the general formula (16) include bees wax, lanolin, lanolin hydrogenated, lanolin fatty acid octyl dodecyl ester, caprylyl eicosenoate, myristyl 2-ethylhexanoate, cetyl 2-ethylhexanoate, stearyl 2-ethylhexanoate, octyl octanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, 2-ethylhexyl hydroxystearate, oleyl erucate, etc.

Of the ester oils represented by the general formula (16), more preferred from the viewpoint of the excellent moist feeling, the uniformity and the moisturizing feeling after drying in use of the surfactant composition of the present invention, is at least one selected from octyl laurate, isopropyl myristate, octyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate, isotridecyl stearate and 2-ethylhexyl hydroxystearate; and even more preferred is at least one selected myristyl myristate, isopropyl palmitate, cetyl palmitate and stearyl stearate.

[Ester Oil Represented by General Formula (17)]

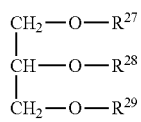  (17)

(In the formula, $R^{27}$, $R^{28}$ and $R^{29}$ each independently represent a hydrogen atom, or a group represented by the following general formula (18), and all of these are not hydrogens at the same time.)

  (18)

(In the formula, $R^{30}$ represents a linear or branched alkyl or alkenyl group having from 8 to 22 carbon atoms, optionally substituted with a hydroxyl group and optionally interrupted by a carboxylate ester group.)

In the general formula (18), the carbon number of $R^{30}$ is, from the viewpoint of the excellent moist feeling, the uniformity and the moisturizing feeling after drying in use of the surfactant composition of the present invention, preferably from 8 to 20, more preferably from 8 to 18.

Specific examples of the ester oils represented by the general formula (17) include castor oil, cacao oil, mink oil, avocado oil, olive oil, sunflower oil, camellia oil, apricot kernel oil, almond oil, wheat germ oil, *Theobroma grandiflorum* seed butter, grape seed oil, babassu oil, jojoba oil, macadamia nut oil, *Camellia Oleifera* seed oil, shea butter, *Camellia reticulata* seed oil, meadowfoam oil, glyceryl tribehanate, triisostearin, etc.

Among the ester oils represented by the general formula (17), from the viewpoint of the excellent moist feeling, the uniformity and the moisturizing feeling after drying in use of the surfactant composition of the present invention, preferred is at least one selected from sunflower oil, avocado oil, camellia oil, macadamia nut oil and shea butter, and more preferred is at least one selected from sunflower oil, avocado oil and macadamia nut oil.

[Ester Oil Represented by General Formula (19)]

$$R^{31}O\text{-}(AO)_m\text{-}COR^{32} \qquad (19)$$

(In the formula, $R^{31}$ represents a substituted or unsubstituted hydrocarbon group containing at least one aromatic group and having from 6 to 20 carbon atoms, $R^{32}$ represents a linear or branched alkyl or alkenyl group having from 1 to 25 carbon atoms. AO represents an oxyalkylene group having from 2 to 4 carbon atoms, m indicates a number of from 1 to 50. When m is 2 or more, m's AO groups may be the same or different.)

$R^{31}$ in the general formula (19) is, from the viewpoint of the moist feeling, the uniformity and the moisturizing feeling after drying in use of the surfactant composition of the present invention, preferably an aromatic hydrocarbon having from 6 to 12 carbon atoms, more preferably an aromatic hydrocarbon group having from 6 to 10 carbon atoms, even more preferably a benzyl group.

$R^{32}$ is, from the above-mentioned viewpoints, preferably an alkyl group having at least 7 carbon atoms, more preferably an alkyl group having at least 11 carbon atoms, and is preferably an alkyl group having at most 21 carbon atoms, more preferably at most 15 carbon atoms.

The AO group is, from the above-mentioned viewpoints, preferably a propyleneoxy group, and m is preferably from 1 to 10, more preferably from 1 to 5.

Preferred examples of the ester oils represented by the general formula (19) include an ester of myristic acid with benzyl alcohol propylene oxide (3 mols) adduct (Croda's trade name, Crodamol STS), an ester of 2-ethylhexyl acid with benzyl alcohol propylene oxide (3 mols) adduct (Croda's trade name, Crodamol SFX), etc. Preferred is an ester of benzyl alcohol/propylene oxide 3-mol adduct and myristic acid.

[Hydrophobic Carboxylate of Dipentaerythritol]

The hydrophobic carboxylate of dipentaerythritol is a compound produced through dehydrating condensation of dipentaerythritol and one or more hydrophobic carboxylic acids, in which the hydrophobic carboxylic acid is a carboxylic acid that has a hydrocarbon group having from 15 to 23 carbon atoms and optionally having a hydroxyl group. Specific examples of the hydrophobic carboxylic acid include palmitic acid, stearic acid, oleic acid, isostearic acid, hydroxystearic acid, rosin acid, etc.

From the viewpoint of availability, preferred is an ester of a mixed acid of hydroxystearic acid, stearic acid and rosin acid with pentaerythritol.

[Dialkyl Carbonate Compound Represented by General Formula (20)]

$$R^{33}\text{—O—}(CH_2CH_2O)_v\text{—CO—}(OCH_2CH_2)_w\text{—OR}^{34} \qquad (20)$$

(In the formula, $R^{33}$ and $R^{34}$ each represent a linear or branched alkyl group and/or alkenyl group each having from 6 to 22 carbon atoms, v and w each indicate 0 or a number of from 1 to 50.)

$R^{33}$ and $R^{34}$ in the general formula (20) is, from the viewpoint of the moist feeling, the uniformity and the moisturizing feeling after drying in use of the surfactant composition of the present invention, preferably an alkyl group having at least 8 carbon atoms, more preferably an alkyl group having at most 18 carbon atoms, even more preferably an alkyl group having at most 12 carbon atoms.

Also from the above-mentioned viewpoints, preferably, v and w each indicate 0 or a number of from 1 to 5, more preferably 0.

The dialkyl carbonate compound represented by the general formula (20) is preferably dioctyl carbonate (Cognis' Cetiol CC), etc.

The other ester oils than the above include, for example, an ester of a polycarboxylic acid with an alcohol, an ester of a polyalcohol except glycerin, dipentaerythritol and saccharides with a fatty acid, an ester of a saccharide and a fatty acid, etc. Their specific examples include diisopropyl dimer acid ester, propanediol dicaprate, diisopropyl adipate, dimethoxyethyl succinate, 2-ethylhexyl succinate, poly-soybean fatty acid sucrose, polysucrose behenate, sucrose tetraisostearate, hydroxyalkyl (C16-18) hydroxydimer dilinoleyl ether, pentaerythrityl tetrastearate, glycol distearate, etc. Preferred is sucrose tetraisostearate.

((ii) Silicone Oil)

As the silicone oil, from the viewpoint of the excellent moist feeling, the uniformity and the moisturizing feeling after drying in use of the surfactant composition of the present invention, preferred is at least one selected from dimethylpolysiloxane, dimethiconol (dimethylpolysiloxane having a hydroxyl group at the terminal thereof), and amino-modified silicone (dimethylpolysiloxane having an amino group in the molecule), polyether-modified silicone, glyceryl-modified silicone, amino derivative silicone, silicone wax and silicone elastomer; and more preferred are high-polymerized dimethylpolysiloxane, dimethiconol, amino-modified silicone, and polyether-modified silicone.

The viscosity of the silicone oil (at 25° C.) is preferably from 10 mm$^2$/sec to 15,000,000 mm$^2$/sec from the above-mentioned viewpoint and from the viewpoint of the dispersibility in preparing the surfactant composition.

((iii) Ether Oil)

As the ether oil, from the viewpoint of the excellent moist feeling, the uniformity and the moisturizing feeling after drying in use of the surfactant composition of the present invention, preferred are dialkyl ether compounds represented by the following general formula (21) or polyoxyalkylene alkyl ether compounds represented by the following general formula (22).

[Dialkyl Ether Compound Represented by General Formula (21)]

$$R^{35}\text{—O—}R^{36} \quad (21)$$

(In the formula, $R^{35}$ and $R^{36}$ each represent a linear or branched alkyl and/or alkenyl group each having from 6 to 22 carbon atoms.)

$R^{35}$ and $R^{36}$ in the general formula (21) each are, from the viewpoint of the moist feeling, the uniformity and the moisturizing feeling after drying in use of the surfactant composition of the present invention, preferably an alkyl group having at least 8 carbon atoms, and is preferably an alkyl group having at most 18 carbon atoms, more preferably an alkyl group having at most 12 carbon atoms.

The dialkyl ether compound represented by the general formula (21) is preferably dioctyl ether (Cognis' CETIOL OE).

[Polyoxyalkylene Alkyl Ether Compound Represented by General Formula (22)]

$$R^{37}\text{—O—}(PO)_r(EO)_s\text{—H} \quad (22)$$

(In the formula, $R^{37}$ represents a linear or branched alkyl or alkenyl group having from 6 to 22 carbon atoms. PO represents an oxypropylene group, and EO represents an oxyethylene group. The mean addition molar number of PO, r is a number of from 0.1 to 15, and the mean addition molar number of EO, s is a number of from 0 to 10. When s is not 0, the addition mode of PO and EO may be in a random mode or a block mode, and the addition sequence of PO and EO is not specifically defined.)

In the general formula (22), from the viewpoint of the excellent moist feeling, the uniformity and the moisturizing feeling after drying in use of the surfactant composition of the invention, the carbon number of $R^{37}$ is preferably at least 8. Also preferably the carbon number of $R^{37}$ is at most 20, more preferably at most 18, even more preferably at most 12.

The mean addition molar number r is, from the above-mentioned viewpoints, preferably at least 1, more preferably at least 2, even more preferably at least 3. The mean addition molar number r is preferably at most 13, more preferably at most 10.

The mean addition molar number s is, from the above-mentioned viewpoints, preferably at most 5, more preferably at most 1, even more preferably 0.

Specific examples of the polyoxyalkylene alkyl ether compounds represented by the general formula (22) include polyoxypropylene hexyl ether, polyoxypropylene octyl ether, polyoxypropylene 2-ethylhexyl ether, polyoxypropylene decyl ether, polyoxypropylene isodecyl ether, polyoxypropylene lauryl ether, polyoxypropylene myristyl ether, polyoxypropylene palmityl ether, polyoxypropylene cetyl ether, polyoxypropylene stearyl ether, polyoxypropylene isostearyl ether, polyoxypropylene octyldecyl ether, polyoxypropylene eicosyl ether and polyoxypropylene behenyl ether, in which the mean addition molar number r of oxypropylene groups is from 1 to 15.

Of those, from the above-mentioned viewpoints, preferred is at least one selected from polyoxypropylene octyl ether, polyoxypropylene decyl ether and polyoxypropylene lauryl ether in which the mean addition molar number r of oxypropylene groups is from 3 to 10.

((iv) Hydrocarbon Oil)

The hydrocarbon oil is, from the viewpoint of the excellent moist feeling, the uniformity and the moisturizing feeling after drying in use of the surfactant composition of the present invention, preferably a saturated or unsaturated hydrocarbon having at least 20 carbon atoms.

Specific examples of the hydrocarbon oil include squalene, squalane, liquid paraffin, liquid isoparaffin, heavy liquid isoparaffin, α-olefin oligomer, cycloparaffin, polybutene, vaseline, paraffin wax, microcrystalline wax, polyethylene wax, and ceresin. Preferred is at least one selected from squalane, liquid paraffin, vaseline and paraffin wax; and more preferred is at least one selected from squalane, liquid paraffin and paraffin wax.

((v) Higher Alcohol)

The higher alcohol is, from the viewpoint of the excellent moist feeling, the uniformity and the moisturizing feeling after drying in use of the surfactant composition of the present invention, preferably an alcohol having a linear or branched alkyl or alkenyl group having from 6 to 22 carbon atoms. More preferably, the carbon number of the alkyl or alkenyl group is at least 8, even more preferably at least 12, and is more preferably at most 20, even more preferably at most 18.

Specific examples of the higher alcohols include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyldodecanol, eicosyl alcohol, behenyl alcohol.

Of those, from the above-mentioned viewpoints, preferred is at least one selected from lauryl alcohol, myristyl alcohol, cetyl alcohol, stearyl alcohol and behenyl alcohol; and more preferred is at least one selected from myristyl alcohol, cetyl alcohol and stearyl alcohol.

((vi) Carboxylic Acid Having Hydrocarbon Group with from 17 to 23 Carbon Atoms Optionally Substituted with Hydroxyl Group)

The hydrocarbon group in the carboxylic acid having a hydrocarbon group with from 17 to 23 carbon atoms optionally substituted with a hydroxyl group is, from the viewpoint of the excellent moist feeling, the uniformity and the moisturizing feeling after drying in use of the surfactant composition of the present invention, preferably a linear or branched alkyl or alkenyl group having from 17 to 23 carbon atoms.

Specific examples of the carboxylic acid having a hydrocarbon group with from 17 to 23 carbon atoms optionally substituted with a hydroxyl group include stearic acid, oleic acid, isostearic acid, hydroxystearic acid, behenic acid, rosin acid, etc. Of those, from the above-mentioned viewpoints, preferred is at least one selected from stearic acid, oleic acid, isostearic acid, hydroxystearic acid, and behenic acid, and more preferred is at least one selected from stearic acid, oleic acid and isostearic acid.

One or more of the above-mentioned oily agents may be used here either singly or as combined.

(Content of Oily Agent)

The content of the oily agent in the surfactant composition of the present invention is, from the viewpoint of the effects of the invention, especially from the viewpoint of the excellent moist feeling, the uniformity and the moisturizing feeling particularly after drying in use of the surfactant composition of the present invention, preferably at least 0.01% by mass, more preferably at least 0.05% by mass, even more preferably at least 0.1% by mass, still more preferably at least 0.5% by mass, further more preferably at least 1.0% by mass. From the viewpoint of preventing the sticky feeling after use of the surfactant of the present invention, the content of the oily agent in the surfactant composition is preferably at most 30% by mass, more preferably at most 20% by mass, even more preferably at most 10% by mass, still more preferably at most 5% by mass, further more preferably at most 3% by mass.

(Ratio by Mass of CCE to Oily Agent)

The ratio by mass of CCE to the oily agent in the surfactant composition [CCE/oily agent] is, from the viewpoint of the effects of the present invention, especially from the viewpoint of the excellent moist feeling, the uniformity and the moisturizing feeling particularly after drying in use of the surfactant composition of the present invention, preferably at least 0.001, more preferably at least 0.005, even more preferably at least 0.01, still more preferably at least 0.03, and is preferably at most 5, more preferably at most 1, even more preferably at most 0.6.

<Other Components>

Further, if desired, glycerin, moisturizers, polysaccharides, polypeptides, pearl agents, solvents, dyes, fragrances, propellants, chelating agents such as edetic acid acetate, citrates and the like, pH regulators, preservatives, anti-dandruff agents such as zinc pyrithione, piroctone olamine and the like, hair-coloring dyes, oxidizing agents, alkali agents, keratin reducing agents and others that may be generally incorporated in hair wash compositions, skin cleanser compositions, hair conditioner compositions or hair treatment compositions may be suitably incorporated in the surfactant composition of the present invention.

<Method for Producing Surfactant Composition>

The method for producing the surfactant composition of the present invention is not specifically defined, and the composition may be produced in any ordinary method. Concretely, for example, water and a surfactant are mixed under heat, then the dissolution thereof is confirmed, and thereafter CCE is added and mixed therein. The addition sequence of CCE and surfactant may be reversed.

If desired, CCE may be previously dispersed or dissolved and then added to the system.

If desired, moisturizers such as oils, cationic polymers, glycerin and the like, as well as pearl agents, pH regulators, fragrances, dyes and other components may be added to the mixture, but the addition time thereof is no specifically defined. They may be added before or after mixing of the surfactant and CCE, or may be added simultaneously with the mixing.

The forms of the surfactant composition of the present invention are not specifically defined. The composition may be in any form of liquid, foam, paste, cream, solid, powder, etc. Preferred is liquid, paste or cream, and more preferred is liquid. In case where the composition is formed as a liquid, preferably used is water as well as polyethylene glycol, ethanol and the like as a liquid medium.

The surfactant composition of the present invention can be used as hair wash compositions, skin cleanser compositions, hair conditioner compositions and hair treatment compositions, exhibiting excellent effects therein.

[Hair Wash Composition]

The surfactant of the present invention can be used as a hair wash composition.

The hair wash composition of the present invention contains CCE of the present invention, a surfactant and water.

<CCE>

The preferred range of the content of CCE in the hair wash composition of the present invention is the same as the preferred range of the content of CCE in the above-mentioned surfactant composition.

From the viewpoint of giving an excellent smoothness property and its sustained feeling as well as a coated feeling, good finger-combability and softness in hair rinsing, CCE in the hair wash composition of the present invention is preferably CCE having a degree of substitution with cationized oxyalkylene group per anhydroglucose unit (MS(N+)) of from 0.04 to 0.60, a degree of substitution with glycerol group (MS(Gly)) of from 0.5 to 4.0, and a degree of substitution with hydrocarbon group-containing group having 3 to 7 carbon atoms (MS(HC)) of from 0.005 to 0.15, more preferably CCE having MS(N+) of from 0.07 to 0.30, MS(Gly) of from 0.5 to 3.8 and MS(HC) of from 0.005 to 0.10, even more preferably CCE having MS(N+) of from 0.09 to 0.20, MS(Gly) of from 0.6 to 2.3 and MS(HC) of from 0.005 to 0.10, still more preferably CCE having MS(N+) of from 0.17 to 0.20, MS(Gly) of from 1.8 to 2.3 and MS(HC) of from 0.03 to 0.04.

From the viewpoint of the softness in rinsing after hair treatment, CCE to be contained in the hair wash composition of the present invention is preferably CCE having MS(N+) of from 0.15 to 0.75, MS(Gly) of from 0.6 to 2.3 and MS(HC) of from 0.005 to 0.10, more preferably CCE having MS(N+) of from 0.35 to 0.75, MS(Gly) of from 1.0 to 2.3 and MS(HC) of from 0.03 to 0.04, even more preferably CCE having MS(N+) of from 0.40 to 0.65, MS(Gly) of from 1.8 to 2.3 and MS(HC) of from 0.03 to 0.04, still more preferably CCE having MS(N+) of from 0.55 to 0.65, MS(Gly) of from 1.8 to 2.3 and MS(HC) of from 0.03 to 0.04.

In case where the hair wash composition contains an oily agent, CCE therein is, from the viewpoint of the excellent finger-combing feeling in hair washing, the excellent smoothness property and its sustained feeling in hair rinsing, and the moist feeling and the uniformity after drying, preferably CCE having MS(N+) of from 0.04 to 0.60, MS(Gly) of from 0.5 to 4.0 and MS(HC) of from 0.01 to 0.10, more preferably CCE having MS(N+) of from 0.07 to 0.50, MS(Gly) of from 0.7 to 3.8 and MS(HC) of from 0.01 to 0.06, even more preferably CCE having MS(N+) of from 0.09 to 0.35, MS(Gly) of from 1.0 to 3.8 and MS(HC) of from 0.01 to 0.06, still more preferably CCE having MS(N+) of from 0.10 to 0.20, MS(Gly) of from 1.0 to 2.3 and MS(HC) of from 0.02 to 0.06, further more preferably CCE having MS(N+) of from 0.12 to 0.20, MS(Gly) of from 1.3 to 2.3 and MS(HC) of from 0.02 to 0.06, and further more preferably CCE having MS(N+) of from 0.18 to 0.20, MS(Gly) of from 2.1 to 2.3 and MS(HC) of from 0.02 to 0.04.

In case where the oily agent contains a silicone oil such as dimethylpolysiloxane (dimethicone) or the like, CCE therein is, from the viewpoint of increasing the residual amount of silicone oil in hair and of improving moist feeling, preferably CCE having MS(N+) of from 0.40 to 0.90, MS(Gly) of from 0.6 to 3.0 and MS(HC) of from 0.01 to 0.06, more preferably CCE having MS(N+) of from 0.45 to 0.80, MS(Gly) of from 0.7 to 2.5 and MS(HC) of from 0.02 to 0.05, and even more preferably CCE having MS(N+) of from 0.50 to 0.75, MS(Gly) of from 0.8 to 2.3 and MS(HC) of from 0.03 to 0.04.

In case where the hair wash composition contains any other cationic polymer than CCE, then CCE therein is, from the viewpoint of foam softness, excellent finger-combing feeling and softness in hair washing, as well as good smoothness property and its sustained feeling, softness of hair and a coated feeling in rinsing, preferably CCE having MS(N+) of from 0.04 to 0.60, MS(Gly) of from 0.5 to 4.0 and MS(HC) of from 0.01 to 0.10, more preferably CCE having MS(N+) of from 0.09 to 0.60, MS(Gly) of from 0.6 to 3.8 and MS(HC) of from 0.01 to 0.10, even more preferably CCE having MS(N+) of from 0.09 to 0.50, MS(Gly) of from 1.0 to 3.8 and MS(HC) of from 0.01 to 0.10, still more preferably CCE having MS(N+) of from 0.15 to 0.30, MS(Gly) of from 1.2 to 3.0 and MS(HC) of from 0.02 to 0.06, and further more preferably CCE having MS(N+) of from 0.17 to 0.21, MS(Gly) of from 2.1 to 2.3 and MS(HC) of from 0.02 to 0.04, <Surfactant>

The surfactant to be in the hair wash composition of the present invention may be any and every surfactant capable of being generally used in drugs, quasi-drugs, cosmetics, toiletry goods, sundries, etc. Their preferred embodiments are the same as the preferred embodiments of the surfactant described in the section of the surfactant composition mentioned above. From the viewpoint of foam softness, excellent finger-combability of hair and hair softness in hair washing, good smoothness property and its sustained feeling as well as softness, good finger-combability and coated feeling in rinsing, and moist feeling and uniformity after drying in use of the hair wash composition of the present invention, the surfactant to be used in the hair wash composition is more preferably at least one, or a combination of two or three selected from the anionic surfactants, nonionic surfactants and ampholytic surfactants described in the section of the surfactant composition given above. The preferred embodiments of the anionic surfactants, the nonionic surfactants and the ampholytic surfactants are the same as those described in the section of the surfactant composition.

(Content of Surfactant)

The preferred embodiment of the content of the surfactant in the hair wash composition of the present invention is the same as that of the content of the surfactant described in the section of the surfactant composition mentioned above. From the viewpoint of foam softness, smooth finger-combability and softness of hair, excellent smoothness property and its sustained feeling as well as softness, good finger-combability and coated feeling in rinsing, and good moist feeling and uniformity after drying in use of the hair wash composition of the present invention, the surfactant content is more preferably at most 30% by mass, even more preferably at most 25% by mass, still more preferably at most 20% by mass, and is more preferably at least 8% by mass, and even more preferably at least 10% by mass.

(Ratio by Mass of CCE to Surfactant)

In the hair wash composition of the present invention, the preferred embodiment of the ratio by mass of CCE to the surfactant [CCE/surfactant] is the same as the preferred embodiment of the ratio by mass of CCE to the surfactant in the section of the surfactant mentioned above. From the viewpoint of foam softness, smooth finger-combability and softness of hair in hair washing, excellent smoothness property and its sustained feeling as well as softness, good finger-combability and coated feeling in hair rinsing, and good moist feeling and uniformity after drying in use of the hair wash composition of the present invention, the ratio by mass of CCE to the surfactant is more preferably at most 0.5, even more preferably at most 0.2, still more preferably at most 0.1, and is more preferably at least 0.005, even more preferably at least 0.010, and still more preferably at least 0.015.

<Water>

The preferred embodiment of the water content in the hair wash composition of the present invention is the same as the preferred embodiment thereof described in the section of the surfactant composition mentioned above. From the viewpoint of excellent finger-combability of hair, hair softness and foam softness in hair washing, excellent smoothness property and its sustained feeling as well as softness and coated feeling in hair rinsing, and excellent moist feeling and uniformity after drying in use of the hair wash composition of the present invention, the water content is more preferably at least 60% by mass, even more preferably at least 70% by mass, and is more preferably at most 95% by mass, even more preferably at most 90% by mass.

<Cationic Polymer except CCE>

From the viewpoint of foam softness, smooth finger-combability of hair and softness in hair washing, excellent smoothness property and its sustained feeling as well as hair softness and coated feeling in hair rinsing in use of the hair wash composition of the present invention, the hair wash composition of the present invention may contain any other cationic polymer than CCE. The preferred embodiments of the other cationic polymer than CCE are the same as the preferred embodiments of the other cationic polymer than CCE described in the section of the surfactant composition mentioned above. One alone or two or more different types of such other cationic polymers than CCE may be used here either singly or as combined.

The preferred embodiments of the content of the other cationic polymer than CCE in the hair wash composition of the present invention and the ratio by mass of CCE to the other cationic polymer than CCE therein [CCE/other cationic polymer than CCE] are the same as the preferred embodiments of the content of the other cationic polymer than CCE and the ratio by mass of CCE to the other cationic polymer than CCE described in the section of the surfactant composition given hereinabove.

<Oily Agent>

From the viewpoint of giving a smooth finger-combability of hair in hair washing, an excellent smoothness property and its sustained feeling in rinsing, and an excellent moist feeling, uniformity and a moisturizing performance after drying, the hair wash composition of the invention may contain an oily agent added thereto. The uniformity as referred to herein means that the feeling from the hair root to the hair tip of hair tresses is uniform.

The preferred embodiments of the oily agent are the same as the preferred embodiments thereof described in the section of the surfactant composition mentioned above. One alone or two or more different types of oily agents may be used here either singly or as combined.

The preferred embodiments of the content of the oily agent in the hair wash composition of the present invention and the ratio by mass of CCE to the oily agent [CCE/oily agent] therein are the same as the preferred embodiments of the content of oily agent and the ratio by mass of CCE to the oily agent described in the section of the surfactant composition given hereinabove.

<Other Components>

Further, if desired, glycerin, moisturizers, polysaccharides, polypeptides, pearl agents, solvents, dyes, fragrances, chelating agents such as edetic acid acetate, citrates and the like, pH regulators, preservatives, and anti-dandruff agents such as zinc pyrithione, piroctone olamine and the like that may be generally incorporated in hair wash compositions may be suitably incorporated in the hair wash composition of the present invention.

The pH of the hair wash composition of the present invention is preferably from pH 2 to 12, more preferably from pH 3 to 10, from the viewpoint of providing the effects of the present invention.

The forms of the hair wash composition of the present invention are not specifically defined. The composition may be in any form of liquid, foam, paste, cream, solid, powder, etc. Preferred is liquid, paste or cream, and more preferred is liquid.

[Hair Washing Method]

The present invention also provides a hair washing method that comprises washing hair with the hair wash composition of the present invention, then rinsing and drying the hair.

The hair washing method is not specifically defined, to which any known method is applicable here.

[Skin Cleanser Composition]

The surfactant composition of the present invention is usable as a skin cleanser composition.

The skin cleanser composition of the present invention contains CCE of the present invention, a surfactant and water.

<CCE>

The preferred range of the content of CCE in the skin cleanser composition of the present invention is the same as the preferred range of the content of CCE in the above-mentioned surfactant composition.

From the viewpoint of giving an excellent moisturizing feeling after drying, CCE in the skin cleanser composition of the present invention is preferably CCE having MS(N+) of from 0.04 to 0.60, MS(Gly) of from 0.5 to 4.0 and MS(HC) of from 0.0005 to 0.15, more preferably CCE having MS(N+) of from 0.07 to 0.50, MS(Gly) of from 0.7 to 3.8 and MS(HC) of from 0.005 to 0.10, and even more preferably CCE having MS(N+) of from 0.10 to 0.50, MS(Gly) of from 1.0 to 3.0 and MS(HC) of from 0.01 to 0.10.

<Surfactant>

The surfactant to be in the skin cleanser composition of the present invention may be any and every surfactant capable of being generally used in drugs, quasi-drugs, cosmetics, toiletry goods, sundries, etc. Their preferred embodiments are the same as the preferred embodiments of the surfactant described in the section of the surfactant composition mentioned above. From the viewpoint of giving an excellent moisturizing feeling after drying in use of the skin cleanser composition of the present invention, preferred is at least one selected from the anionic surfactants, the nonionic surfactants and the ampholytic surfactants described in the section of the surfactant composition mentioned above. The preferred embodiments of the anionic surfactants, the nonionic surfactants and the ampholytic surfactants are the same as those described in the section of the surfactant composition. Preferred is at least one selected from anionic surfactants of polyoxyethylene alkyl ether sulfates; higher fatty acids or their salts having from 8 to 16 carbon atoms; hydrophobic site-having sulfonate salts such as acyl isethionate, acylmethyl taurate, etc.; hydrophobic site-having amino acid salts such as acylglycine, acylsarcosine, etc.; nonionic surfactants of fatty acid monoalkanolamides, etc.; and ampholytic surfactants of fatty acid amide propylbetaine, imidazoline-type betaine, etc. More preferred is at least one selected from polyoxyethylene alkyl ether sulfate salts such as sodium laureth-(2) sulfate, etc.; higher fatty acid salts having from 8 to 16 carbon atoms such as laurate salts, myristate salts, palmitate salts, etc.; acylisethionates such as sodium cocoylisethionate, etc.; acylmethyltaurates such as sodium cocoylmethyltaurine, etc.; acylglycines such as acylmethyl taurate, sodium cocoylglycine, etc.; acylsarcosines such as potassium lauroylsarcosine, etc.; fatty acid amide propylbetaines such as coconut oil fatty acid amide propylbetaine, etc.; and imidazoline-type betaines such as sodium cocoamphoacetate, etc.

(Content of Surfactant)

The preferred embodiment of the content of the surfactant in the skin cleanser composition of the present invention is the same as that of the content of the surfactant described in the section of the surfactant composition mentioned above. From the viewpoint of giving an excellent moisturizing feeling after drying in use of the skin cleanser composition of the present invention, the surfactant content is more preferably at least 8% by mass, even more preferably at least 10% by mass, and is more preferably at most 36% by mass.

(Ratio by Mass of CCE to Surfactant)

In the skin cleanser composition of the present invention, the preferred embodiment of the ratio by mass of CCE to the surfactant [CCE/surfactant] is the same as the preferred embodiment of the ratio by mass of CCE to the surfactant in the section of the surfactant composition mentioned above. From the viewpoint of the moisturizing feeling after skin washing with the skin cleanser composition of the present invention and after drying, the ratio is more preferably at least 0.005 and more preferably at most 0.3, even more preferably at most 0.1 and still more preferably at most 0.05.

<Water>

The preferred embodiment of the water content in the skin cleanser composition of the present invention is the same as the preferred embodiment thereof described in the section of the surfactant composition mentioned above. From the viewpoint of giving a moisturizing feeling after skin washing with the skin cleanser composition of the present invention and after drying, the water content is more preferably at least 40% by mass and more preferably at most 95% by mass, even more preferably at most 90% by mass.

<Cationic Polymer except CCE>

From the viewpoint of further improving the moisturizing feeling after washing with the skin cleanser composition of the present invention and after drying, the skin cleanser composition of the present invention may contain any other cationic polymer than CCE. The preferred embodiment of the other cationic polymer than CCE is the same as the preferred embodiment of the other cationic polymer than CCE described in the section of the surfactant composition mentioned above. From the viewpoint of further improving the moisturizing feeling after washing with the skin cleanser composition of the present invention and drying, the cationic polymer except CCE is more preferably a cationized guar gum or a cationic synthetic polymer. One alone or two or more different types of such other cationic polymers than CCE may be used here either singly or as combined.

The preferred embodiments of the content of the other cationic polymer than CCE in the skin cleanser composition of the present invention and the ratio by mass of CCE to the other cationic polymer than CCE therein [CCE/other cationic polymer than CCE] are the same as those of the content of the other cationic polymer than CCE in the surfactant composition of the present invention and the ratio by mass of CCE to the other cationic polymer than CCE therein described in the section of the surfactant composition mentioned above.

<Oily Agent>

From the viewpoint of giving a moist feeling and a moisturizing feeling after washing, the skin cleanser composition of the invention may contain an oily agent. The preferred embodiment of the oily agent is the same as the preferred embodiment thereof described in the section of the surfactant composition mentioned above. From the viewpoint of giving a moist feeling and a moisturizing performance after washing with the skin cleanser composition of the present invention, the oily agent is preferably at least one selected from ester oils and hydrocarbon oils; and more preferred is at least one selected from sunflower oil and vaseline.

(Content of Oily Agent)

The preferred embodiment of the content of the oily agent in the skin cleanser composition of the present invention is the same as the preferred embodiment of the content of the oily agent in the surfactant composition mentioned above. From the viewpoint of giving excellent moist feeling and moisturizing performance after washing, the content of the oily agent is preferably at least 3% by mass, more preferably at least 5% by mass, and is preferably at most 20% by mass, more preferably at most 15% by mass.

(Ratio by Mass of CCE to Oily Agent)

In the skin cleanser composition of the present invention, the preferred embodiment of the ratio by mass of CCE to the oily agent [CCE/oily agent] is the same as that of the ratio by mass of CCE to the oily agent in the surfactant composition. From the viewpoint of giving an excellent moist feeling and moisturizing performance after washing, the ratio by mass of CCE to the oily agent is more preferably at least 0.01 and is more preferably at most 0.3, even more preferably at most 0.1.

<Other Components>

Further, if desired, glycerin, moisturizers, polysaccharides, polypeptides, pearl agents, solvents, dyes, fragrances, chelating agents such as edetic acid acetate, citrates and the like, pH regulators, preservatives and others that may be generally incorporated in skin cleanser compositions may be suitably incorporated in the skin cleanser composition of the present invention.

The pH of the skin cleanser composition of the present invention is preferably from pH 2 to 12, more preferably from pH 3 to 10, from the viewpoint of providing the effects of the present invention.

The forms of the skin cleanser composition of the present invention are not specifically defined. The composition may be in any form of liquid, foam, paste, cream, solid, powder, etc. Preferred is liquid, paste or cream, and more preferred is liquid.

[Skin Washing Method]

The present invention also provides a skin washing method that comprises washing skin with the skin cleanser composition of the present invention, then rinsing and drying the skin.

The skin washing method is not specifically defined, to which any known method is applicable here.

Specific examples of the skin cleanser composition of the present invention include body shampoo, hand wash, face wash, and makeup remover. In consideration of the effects of the present invention, the composition is preferably used as body shampoo, hand wash or face wash.

[Hair Conditioner Composition]

The surfactant composition of the present invention is usable as a hair conditioner composition.

The hair conditioner composition of the present invention contains CCE of the present invention, a surfactant, an oily agent and water.

<CCE>

The preferred range of the content of CCE in the hair conditioner composition of the present invention is the same as the preferred range of the content of CCE in the above-mentioned surfactant composition. From the viewpoint of giving a good presence in application of the hair conditioner composition to hair, giving an excellent smoothness property and softness in rinsing, and giving an excellent coated feeling after drying, the content of CCE in the hair conditioner composition is preferably at least 0.05% by mass, more preferably at least 0.1% by mass, even more preferably at least 0.2% by mass, still more preferably at least 0.3% by mass, and is preferably at most 3% by mass, more preferably at most 2% by mass, even more preferably at most 1% by mass, still more preferably at most 0.5% by mass.

From the viewpoint of giving a good presence in application of the hair conditioner composition to hair, giving an excellent smoothness property and softness in rinsing, and giving an excellent coated feeling after drying, CCE in the hair conditioner composition of the present invention is preferably CCE having MS(N+) of from 0.04 to 0.60, MS(Gly) of from 0.5 to 4.0 and MS(HC) of from 0.01 to 0.10, more preferably CCE having MS(N+) of from 0.17 to 0.60, MS(Gly) of from 0.8 to 3.8 and MS(HC) of from 0.02 to 0.06, even more preferably CCE having MS(N+) of from 0.17 to 0.30, MS(Gly) of from 2.0 to 3.8 and MS(HC) of from 0.02 to 0.06, still more preferably CCE having MS(N+) of from 0.18 to 0.22, MS(Gly) of from 2.1 to 2.3 and MS(HC) of from 0.02 to 0.04.

In the present invention, the coated feeling after drying means a feeling of the surface of hair likely coated with a filmy substance.

<Surfactant>

The surfactant to be in the hair conditioner composition of the present invention may be any and every surfactant capable of being generally used in drugs, quasi-drugs, cosmetics, toiletry goods, sundries, etc. Their preferred embodiments are the same as the preferred embodiments of the surfactant described in the section of the surfactant composition mentioned above. From the viewpoint of the good presence in application of the hair conditioner composition of the present invention to hair, the excellent smoothness property and softness in rinsing, and the excellent coated feeling after drying, preferred are the cationic surfactants described in the section of the surfactant composition mentioned above. A cationic surfactant and a nonionic surfactant may be combined for use herein. The preferred embodiments of the cationic surfactants are the same as those described in the section of the surfactant composition. Further, preferred is at least one selected from behenyltrimethylammonium salts, stearyltrimethylammonium salts, stearoxypropyltrimethylammonium salts, cetyltrimethylammonium salts, distearyldimethylammonium salts, stearamidopropyldimethylamine and behanamidopropyldimethylamine.

(Content of Surfactant)

The preferred embodiment of the content of the surfactant in the hair conditioner composition of the present invention is the same as that of the content of the surfactant described in the section of the surfactant composition mentioned above. From the viewpoint of the good presence in application of the hair conditioner composition of the present invention to hair, the excellent smoothness property and softness in rinsing, and the excellent coated feeling after drying, the content of the surfactant in the hair conditioner composition is preferably at least 0.2% by mass, more preferably at least 0.5% by mass, even more preferably at least 1.0% by mass, still more preferably at least 1.5% by mass, and is preferably at most 20% by mass, more preferably at most 10% by mass, even more preferably at most 5% by mass, still more preferably at most 3% by mass.

(Ratio by Mass of CCE to Surfactant)

In the hair conditioner composition of the present invention, the preferred embodiment of the ratio by mass of CCE to the surfactant [CCE/surfactant] is the same as the preferred embodiment of the ratio by mass of CCE to the surfactant in the section of the surfactant composition mentioned above. From the viewpoint of the good presence in application of the hair conditioner composition of the present invention to hair, the excellent smoothness property and softness in rinsing, and the excellent coated feeling after drying, the ratio is preferably at least 0.05, more preferably at least 0.10, even more preferably at least 0.15, and is preferably at most 1.5, more preferably at most 1.0, even more preferably at most 0.5, and further more preferably at most 0.35.

<Water>

The preferred embodiment of the water content in the hair conditioner composition of the present invention is the same as the preferred embodiment thereof described in the section of the surfactant composition mentioned above. From the viewpoint of the good presence in application of the hair conditioner composition of the present invention to hair, the excellent smoothness property and softness in rinsing, and the excellent coat feeling after drying, the water content is preferably at least 70% by mass, more preferably at least 80% by mass, even more preferably at least 88% by mass, and is preferably at most 95% by mass, more preferably at most 93% by mass.

<Oily Agent>

From the viewpoint of giving a moist feeling, uniformity and a moisturizing performance to hair after drying, the hair conditioner composition of the present invention contains an oily agent. The preferred embodiments of the oily agent are the same as the preferred embodiments thereof described in the section of the surfactant composition mentioned above. From the viewpoint of giving a moist feeling and a moisturizing performance to hair after drying, the oily agent is preferably a combination of at least one selected from ester oils, silicone oils, ether oils and hydrocarbon oils, and a higher alcohol. More preferred is a combination of at least one selected from ester oils, silicone oils, ether oils and hydrocarbon oils, and cetyl alcohol and stearyl alcohol.

(Content of Oily Agent)

The preferred embodiment of the content of the oily agent in the hair conditioner composition of the present invention is the same as the preferred embodiment of the content of the oily agent in the surfactant composition mentioned above. From the viewpoint of giving a moist feeling, uniformity and a moisturizing feeling to hair after drying, the content of the oily agent in the hair conditioner composition is preferably at least 2% by mass, more preferably at least 4% by mass, even more preferably at least 5% by mass, and is preferably at most 15% by mass, more preferably at most 12% by mass.

(Ratio by Mass of CCE to Oily Agent)

In the hair conditioner composition of the present invention, the preferred embodiment of the ratio by mass of CCE to the oily agent [CCE/oily agent] is the same as that of the ratio by mass of CCE to the oily agent in the surfactant composition. From the viewpoint of the good presence in application of the hair conditioner composition of the present invention to hair, the excellent smoothness property and softness in rinsing, the excellent coat feeling after drying, and the excellent moist feeling, uniformity and moisturizing performance after drying, the ratio by mass of CCE to the oily agent is preferably at least 0.01, more preferably at least 0.02, even more preferably at least 0.025, and is preferably at most 0.3, more preferably at most 0.10, even more preferably at most 0.06.

<Other Components>

Further, if desired, glycerin, moisturizers, polysaccharides, polypeptides, pearl agents, solvents, dyes, fragrances, chelating agents such as edetic acid acetate, citrates and the like, pH regulators, preservatives and others that may be generally incorporated in skin cleanser compositions may be suitably incorporated in the skin cleanser composition of the present invention.

<pH>

From the viewpoint of the presence in application of the composition to hair, the smoothness property and softness in rinsing, the coat feeling after drying, and the stability of the conditioner, the pH of the hair conditioner composition of the present invention is preferably at least pH 1, more preferably at least pH 2, even more preferably at least pH 3, and is preferably at most pH 10, more preferably at most pH 8, and even more preferably at most pH 6. Accordingly from the above-mentioned viewpoints, the pH of the hair conditioner composition of the present invention is preferably from 1 to 10, more preferably from 2 to 8, even more preferably from 3 to 6.

The forms of the hair conditioner composition of the present invention are not specifically defined. The composition may be in any form of liquid, foam, paste, cream, solid, powder, etc. Preferred is liquid, paste or cream, and more preferred is liquid.

[Hair Conditioning Method]

The hair conditioning method with the hair conditioner composition of the present invention is not specifically defined, to which any known method is applicable here. For example, hair is washed with a detergent, and then the conditioner composition of the present invention may be applied to the washed hair. As the detergent, usable is any known hair wash as well as the hair wash composition of the present invention.

Specific examples of the hair conditioner composition of the present invention include hair rinse, treatment, hair conditioner, leave-in hair conditioner, hair cream, conditioner gel, conditioner foam, etc.

[Hair Treatment Composition]

The hair treatment composition of the present invention is meant to indicate a treatment composition in the broad sense of the term, including a hair color composition, a hair bleach composition, a perm wave composition, a straight perm composition, a sustainable hair styling composition, a hair relaxer composition, etc.

The hair treatment composition of the present invention contains CCE, as well as at least one treatment agent selected from hair-coloring dyes, oxidizing agents, alkali agents and keratin-reducing agents (hereinafter this may be referred to as a component (E)).

Containing CCE, the hair treatment composition of the present invention gives a good smoothness property, a good coat feeling and softness to hair in rinsing.

Typical embodiments of the hair treatment composition of the present invention include a hair color composition and a perm composition. "Hair color composition" is a concept including both a colorant-containing hair color composition and a colorant-free hair breach composition, further including a composition that bleaches and colors hair. "Perm composition" is a concept including a perm wave composition, a straight perm composition and a hair relaxer composition.

<CCE>

CCE in the hair treatment composition of the present invention is, from the viewpoint of giving a smoothness property, a good coat feeling and softness to hair in rinsing after treatment when the treatment agent is used as a hair color composition, preferably CCE having MS(N+) of from 0.04 to 0.60, MS(Gly) of from 0.5 to 4.0 and MS(HC) of from 0.01 to 0.10, more preferably CCE having MS(N+) of from 0.04 to 0.22, MS(Gly) of from 1.0 to 3.0 and MS(HC) of from 0.01 to 0.10, and even more preferably CCE having MS(N+) of from 0.12 to 0.22, MS(Gly) of from 2.1 to 2.3 and MS(HC) of from 0.02 to 0.06.

The CCE content in the hair treatment composition of the present invention is, from the viewpoint of giving a good smoothness property, a good coat feeling and softness to hair in rinsing after treatment, for example, when the treatment composition is sued as a hair color composition, preferably at least 0.01% by mass, more preferably at least 0.05% by mass, even more preferably at least 0.1% by mass, and from the viewpoint of the handleability of the hair treatment composition, the CCE content is preferably at most 10% by mass, more preferably at most 5% by mass, even more preferably at most 2% by mass, still more preferably at most 1% by mass.

In case where the hair treatment composition is a multi-pack composition in which two or more packs are mixed before use, it is desirable that CCE is incorporated in the first pack from the viewpoint of giving a good smoothness property, a good coat feeling and softness to hair in rinsing after treatment.

From the viewpoint of expressing the function of the hair treatment composition of the present invention, the content of the treatment agent (E) in the composition is preferably at least 0.1% by mass, more preferably at least 0.5% by mass, even more preferably at least 1% by mass, and is preferably at most 20% by mass, more preferably at most 15% by mass, and even more preferably at most 10% by mass.

From the viewpoint of giving a good smoothness property, a good coat feeling and softness to hair in rinsing after treated with the hair treatment composition of the present invention, the ratio by mass of CCE to the treatment agent [CCE/treatment agent] in the hair treatment composition of the present invention is preferably at least 0.005, more preferably at least 0.01, even more preferably at least 0.02, and is preferably at most 3, more preferably at most 1 even more preferably at most 0.5, still more preferably at most 0.2.

<Hair-Coloring Dye>

A hair-coloring dye may be incorporated in the hair treatment composition such as a hair color composition, etc.

The hair-coloring dye includes a direct dye and an oxidation dye intermediate.

Not specifically defined, the direct dye for use herein may be any and every one generally used in cosmetics and the like, including nitro dyes, anthraquinone dyes, acidic dyes, oil-soluble dyes, basic dyes, etc.

Specific examples of those dyes are described in WO2011/040632. One or more those direct dyes may be used here either singly or as combined.

The content of the direct dye in the hair treatment composition is, from the viewpoint of the dye stainability on hair, preferably at least 0.005% by mass in the hair treatment composition, more preferably at least 0.01% by mass, even more preferably at least 0.1% by mass, and is preferably at most 10% by mass, more preferably at most 5% by mass, even more preferably at most 2% by mass.

As the oxidation dye intermediate, usable here are known precursors and couplers generally used in hair colors.

Specific examples of precursors and couplers are described in WO2011/040632. One alone or two or more different types of those oxidation dye intermediates may be used here either singly or as combined.

The content of the oxidation dye intermediate is, from the viewpoint of the dye stainability on hair, preferably at least 0.01% by mass in the hair treatment composition, more preferably at least 0.05% by mass, even more preferably at least 0.1% by mass, still more preferably at least 0.2% by mass, and is preferably at most 10% by mass, more preferably at most 5% by mass, even more preferably at most 3% by mass, and still more preferably at most 2% by mass.

<Oxidizing Agent>

An oxidizing agent may be incorporated in the hair treatment composition such as a hair color composition, a perm composition, etc.

The oxidizing agent to be used in the hair color composition includes hydrogen peroxide, as well as a generator to generate hydrogen peroxide or oxygen, such as urea peroxide, melamine peroxide, sodium perborate, potassium perborate, sodium percarbonate, potassium carbonate, etc. One alone or two or more of these may be used here either singly or as combined. From the viewpoint of the dye stainability on hair, preferred is hydrogen peroxide.

In the permanent wave composition, the oxidizing agent is incorporated into the second permanent wave pack to be combined with the first permanent wave pack. The oxidizing agent to be used in the second permanent wave pack includes potassium bromate, sodium bromate, sodium perborate, hydrogen peroxide, etc.

One alone or two or more of these oxidizing agents may be used here either singly or as combined.

The content of the oxidizing agent in the hair treatment composition is, from the viewpoint of the hair-coloring performance and the hair-bleaching performance when used in a hair color composition and from the viewpoint of the capability of efficiently recombining the broken disulfide bonds in the hair keratin when used in a perm composition, preferably at least 0.1% by mass, more preferably at least 0.5% by mass, even more preferably at least 2% by mass, still more preferably at least 3% by mass. On the other hand, from the viewpoint of reducing hair damage and scalp irritation, the content of the oxidizing agent is preferably at most 20% by mass, more preferably at most 12% by mass, even more preferably at most 9% by mass, still more preferably at most 6% by mass.

<Alkali Agent>

An alkali agent may be incorporated in the hair treatment composition such as a hair color composition, a perm composition, etc.

The alkali agent includes sodium hydroxide, ammonia and its salts; alkanolamines and their salts such as monoethanolamine, isopropanolamine, 2-amino-2-methyl-propanol, 2-aminobutanol, etc.; alkanediamines and their salts such as 1,3-propanediamine, etc.; carbonates such as guanidine carbonate, sodium carbonate, potassium carbonate, sodium hydrogencarbonate, potassium hydrogencarbonate, etc. From the viewpoint of the hair-coloring performance and the hair-bleaching performance when the hair treatment composition is used as a hair color composition, and from the viewpoint the improved keratin-reducing performance when used as a perm composition, the alkali agent is preferably at least one selected from ammonia and its salts, alkanolamines and their salts and sodium hydrogencarbonate.

From the viewpoint of the hair-coloring performance and the hair-bleaching performance when the hair treatment composition is used as a hair color composition, from the viewpoint the improved keratin-reducing performance when used as a perm composition, from the viewpoint of the curling sustainability after treatment and from the viewpoint of reducing hair damage and scalp irritation, the content of the alkali agent is preferably from 0.1% by mass to 10% by mass.

<Keratin-Reducing Agent>

A keratin-reducing agent may be incorporated in the hair treatment composition such as a perm composition, etc. The keratin-reducing agent can cleave the disulfide bonds in keratin that constitute hair. The hair treatment composition that contains the keratin-reducing agent of the type is preferably used as the first perm wave agent in the perm composition.

The keratin-reducing agent includes thioglycolic acid and its derivatives, thiolactic acid and its derivatives, cysteine and its derivatives, as well as their salts, and thioglyceryl alkyl ethers and their salts of the following formula (23), mercaptoalkylamides of the following formula (24), and their salts.

$$R^{38}OCH_2CH(OH)CH_2SH \qquad (23)$$

(In the formula, $R^{38}$ represents a hydrogen atom, a lower alkyl group or a lower alkoxy-lower alkyl group.)

$$H-(CHOH)_x-(CH_2)_y-CONH(CH_2)_z-SH \qquad (24)$$

(In the formula, x indicates a number of from 0 to 5, y indicates a number of from 0 to 3, z indicates a number of from 2 to 5; however, y and z are not 0 at the same time.)

Specific examples of the keratin-reducing agent include thioglycolic acid, ammonium thioglycolate, glycerin thioglycolate ester, L-cysteine, D-cysteine, N-acetylcysteine, ammonium salts of those cysteines; ethanolamine salts such as monoethanolamine, diethanolamine, triethanolamine or the like of those cysteines; thioglyceryl alkyl ethers such as ethoxyhydroxypropanethiol, methoxyethoxyhydroxypropanethiol, isopropoxyethoxyhydroxypropanethiol, etc.; mercaptoethylpropanamide, mercaptoethylgluconamide, etc.

One alone or two or more different types of those keratin-reducing agents may be used here either singly or as combined.

From the viewpoint of cleaving the disulfide bonds in hair-constituting keratin and from the viewpoint of securing good perming performance in finish, the content of the keratin-reducing agent is preferably at least 0.1% by mass in the hair treatment composition, more preferably at least 1% by mass, even more preferably at least 3% by mass. Also from the same viewpoint as above, the content of the keratin-reducing agent is preferably at most 20% by mass in the hair treatment composition, more preferably at most 15% by mass, even more preferably at most 10% by mass, and still more preferably at most 8% by mass.

<Water>

The hair treatment composition of the present invention contains CCE and preferably water as the solvent or the dispersant for the treatment agent therein. The water content in the hair treatment composition is preferably at least 50% by mass, more preferably at least 70% by mass, and is preferably at most 95% by mass, more preferably at most 90% by mass.

<Surfactant>

The hair treatment composition of the present invention may contain a surfactant from the viewpoint of improving the smoothness property, the coat feeling and the softness of hair in rinsing after treatment. The concrete type of the surfactant, the content of the surfactant and the preferred embodiments thereof are the same as those described in the section of the surfactant composition given hereinabove.

From the viewpoint of the smoothness property, the coat feeling and the softness of hair in rinsing after treatment, the content of the surfactant in the hair treatment composition of the present invention is preferably at least 0.3% by mass, more preferably at least 0.5% by mass, even more preferably at least 1% by mass, and is preferably at most 20% by mass, more preferably at most 10% by mass, even more preferably at most 5% by mass.

From the above-mentioned viewpoints, the surfactant is preferably a nonionic surfactant such as polyoxyethylene alkyl ether, polyoxyethylene hardened castor oil, etc.; an anionic surfactant such as polyoxyethylene alkyl ether sulfate salt, higher fatty acid salt, etc.; a cationic surfactant such as mono-long chain alkyltrimethylammonium salt, etc.

<Oily Agent>

The hair treatment composition of the present invention may contain an oily agent from the viewpoint of improving the smoothness property, the coat feeling and the softness of hair in rinsing after treatment. The concrete type of the oily agent, the content of the oily agent and the preferred embodiments thereof are the same as those described in the section of the surfactant composition given hereinabove.

From the viewpoint of the smoothness property, the coat feeling and the softness in ringing after treatment and form the viewpoint of the moist feeling and the moisturizing performance after treatment and drying, the content of the oily agent in the hair treatment composition of the present invention is preferably at least 1% by mass, more preferably at least 3% by mass, even more preferably at least 5% by mass, and is preferably at most 30% by mass, more preferably at most 20% by mass, and even more preferably at most 15% by mass.

Also from the above-mentioned viewpoints, the oily agent is preferably a higher alcohol such as cetyl alcohol, stearyl alcohol, etc.

In case where the hair treatment composition is a multi-pack composition in which two or more packs are mixed before use, the preferred content of CCE, the treatment agent, the surfactant or the oily agent therein means the preferred content of CCE, the treatment agent, the surfactant or the oily agent relative to the total amount of each agent in all packs constituting the composition.

<Other Components>

Further, if desired, glycerin, moisturizers, polysaccharides, polypeptides, pearl agents, solvents, dyes, fragrances, propellants, chelating agents such as edetic acid acetate, citrates and the like, pH regulators, preservatives, anti-dandruff agents such as zinc pyrithione, piroctone olamine and the like that may be generally incorporated in hair treatment compositions may be suitably incorporated in the hair treatment composition of the present invention.

<Method for Producing Hair Treatment Composition>

The method for producing the hair treatment composition of the present invention is not specifically defined, and the composition may be produced according to an ordinary method. Concretely, for example, water, CCE and treatment agents except oxidizing agent and alkali agent, and other components are mixed and uniformly dissolved under heat. After the dissolution has been confirmed, oxidizing agent and alkali agents are added and further mixed.

If desired, CCE may be previously dispersed or dissolved in water before added to the composition. Further if desired, a pearl agent, a pH regulator, a fragrance, a dye and the like may be added to the composition.

The forms of the hair treatment composition of the present invention are not specifically defined. The composition may be in any form of liquid, foam, paste, cream, solid, powder, etc. Preferred is liquid, paste or cream, and more preferred is liquid.

[Hair Treatment Method]

The hair treatment method with the hair treatment composition of the present invention is not specifically defined, to which any known method is applicable here. For example, the hair treatment composition of the present invention may be brought into contact with hair to treat the hair, and then the hair may be rinsed and dried for the intended treatment.

<Hair Color Composition>

In case where the hair treatment composition of the present invention is a hair color composition, the hair color composition contains CCE, and at least one or more treatment agents selected from a hair-coloring dye, an oxidizing agent and an alkali agent. Embodiments of the hair treatment composition of the present invention as a hair color composition are described below.

The hair color composition includes, for example, a one-pack hair color composition of the following (a) and (b), and a multi-pack hair color composition of the following (c) and (d).

(a) One-pack hair color composition containing a hair-coloring dye and optionally an oxidizing agent.

(b) One-pack hair color composition not containing a hair-coloring dye but containing an oxidizing agent.

(c) Two-pack hair color composition composed of a first pack containing an alkali agent and/or a hair-coloring dye, and a second pack containing an oxidizing agent.

(d) Three-pack hair color composition composed of a first pack containing an alkali agent and/or a hair-coloring dye, a second pack containing an oxidizing agent, and a third pack containing an oxidation promoter.

In the above two-pack hair color composition (c), the content ratio (by mass) of the first pack to the second [first pack/second pack] is preferably from 2/8 to 6/4, more preferably from 3/7 to 5/5, even more preferably from 3.5/6.5 to 4.5/5.5.

The hair color composition may be applicable to any form of one to be used at room temperature or one to be used under heat.

(CCE)

In case where the hair treatment composition of the present invention is a hair color composition, the preferred range of the content of CCE is the same as the preferred range of the content of CCE for use in the above-mentioned hair treatment composition.

In case where the hair treatment composition is a hair color composition, the ratio by mass of CCE to the treatment agent [CCE/treatment agent] is the same as the ratio by mass of CCE to the treatment agent in the above-mentioned hair treatment agent.

(Hair-Coloring Dye)

The preferred embodiments of the type and the content of the hair-coloring dye to be in the hair color composition are the same as the preferred embodiments of the type and the content of the hair-coloring dye to be in the hair treatment composition mentioned above.

In case where the hair color composition is for bleaching hair, the hair color composition may not contain a hair-coloring dye.

(Oxidizing Agent)

The preferred embodiments of the type and the content of the oxidizing agent for use in the hair color composition are the same as the preferred embodiments of the type and the content of the oxidizing agent for use in the above-mentioned hair treatment composition.

(Alkali Agent)

The preferred embodiments of the type and the content of the alkali agent for use in the hair color composition of the present invention are the same as the preferred embodiments of the type and the content of the alkali agent for use in the above-mentioned hair treatment composition.

(Water)

In case where the hair treatment composition of the present invention is a hair color composition, it is also desirable that the composition contains water. The preferred embodiment of the water content is the same as the preferred embodiment of the water content in the above-mentioned hair treatment composition.

(Surfactant)

In case where the hair color composition contains a surfactant, the preferred embodiments of the type and the content of the surfactant are the same as the preferred embodiments of the type and the content of the surfactant, if any, in the above-mentioned hair treatment agent.

(Oily Agent)

In case where the hair color composition contains an oily agent, the preferred embodiments of the type and the content of the oily agent are the same as the preferred embodiments of the type and the content of the oily agent, if any, in the above-mentioned hair treatment agent.

(pH)

The pH of the hair color composition of the invention is, when the composition is a one-pack composition, preferably from pH 3 to 9 for the purpose of preventing skin and hair damage. In case where the composition is a two-pack hair color composition, the pH of the first pack is preferably from pH 8 to 13, and the pH of the second pack is preferably from pH 2 to 5. In case where the composition is a three-pack hair color composition, the pH of the first pack is preferably from pH 8 to 13, and the pH of the second pack is preferably from pH 2 to 5. The pH control may be attained by the use of a known pH regulator.

(Other Components)

The hair color composition may contain any other component as described in the section of the other components for the above-mentioned hair treatment composition.

<Perm Composition>

In case where the hair treatment composition of the present invention is a perm composition, the perm composition contains CCE and contains a keratin-reducing agent, an oxidizing agent and an alkali agent as treatment agents. Embodiments of the hair treatment composition of the present invention as a perm composition are described below.

The perm composition is a two-pack composition composed of a first pack that contains a keratin-reducing agent, and a second pack that contains an oxidizing agent.

In the perm composition, the ratio (by mass) to be used of the first pack to the second pack [first pack/second pack] is preferably from 3/7 to 7/3, more preferably from 4/6 to 6/4, even more preferably from 4.5/5.5 to 5.5/4.5.

The perm composition is applicable to any form of one to be used at room temperature, one to be used under heat, one to be used for wave formation, one to be used for hair relaxation, etc.

(CCE)

The preferred embodiment of the content of CCE in the perm composition is the same as the preferred embodiment of the content of CCE to be used in the above-mentioned hair treatment composition.

From the viewpoint of imparting a good smoothness property, a coat feeling and softness to hair in rinsing after treatment, CCE is preferably incorporated in the first pack.

(Keratin-Reducing Agent)

The preferred embodiments of the type and the content of the keratin-reducing agent for use in the perm composition are the same as the preferred embodiments of the type and the content of the keratin-reducing agent in the above-mentioned hair treatment composition.

(Oxidizing Agent)

In the perm composition, the oxidizing agent is incorporated in the second pack. The preferred embodiments of the type and the content of the oxidizing agent for use in the perm composition are the same as the preferred embodiments of the type and the content of the oxidizing agent in the above-mentioned hair treatment composition.

(Alkali Agent)

The preferred embodiments of the type and the content of the alkali agent for use in the perm composition are the same as the preferred embodiments of the type and the content of the alkali agent in the above-mentioned hair treatment composition.

(pH)

For reducing skin and hair damage, the pH of the first pack of the perm composition is preferably from pH 6 to 12, and the pH of the second pack thereof is preferably from pH 3 to 9. The pH control may be attained by the use of a known pH regulator.

(Water)

In case where the hair treatment composition of the present invention is a perm composition, it is also desirable that the composition contains water. The preferred embodiment of the water content is the same as the preferred embodiment of the water content in the above-mentioned hair treatment composition.

(Surfactant)

In case where the perm composition contains a surfactant, the preferred embodiments of the type and the content of the surfactant therein are the same as the preferred embodiments of the type and the content of the surfactant, if any, in the above-mentioned hair treatment composition.

(Other Components)

The perm composition may contain, in addition to the oily agent therein, any other component such as those described in the section of the other components for the above-mentioned hair treatment composition.

Relating to the above-mentioned embodiments thereof, the present invention discloses a cationic group-containing cellulose ether, and a surfactant composition, a hair wash composition, a skin cleanser composition, a hair conditioner composition and a hair treatment composition containing the cellulose ether, which are described below.

<1> A cationic group-containing cellulose ether, which has a main chain derived from an anhydroglucose represented by the following general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group containing a hydrocarbon group, having from 3 to 7 carbon atoms and represented by any of the following general formulae (6) to (8) is from 0.0001 to 0.2:

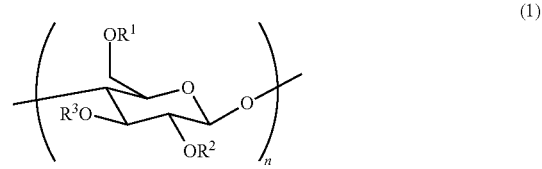

(In the formula, $R^1$, $R^2$ and $R^3$ each independently represent a substituent comprising at least one structural unit selected from a group consisting of the following formulae (2) to (8), or a hydrogen atom. n indicates a mean degree of polymerization of the anhydroglucose-derived main chain, and is a number of from 100 to 12000.)

(In these formulae, the structural unit represented by the formula (2) or (3) is a cationized oxyalkylene group; the structural unit represented by the formula (4) or (5) is a glycerol group; and the structural unit represented by any of the formulae (6) to (8) is a group containing a hydrocarbon group and having from 3 to 7 carbon atoms. $R^4$ to $R^9$ each independently represent a linear or branched alkyl group having from 1 to 3 carbon atoms; $X^-$ and $Y^-$ each represent an anion; and r and s each indicate an integer of from 0 to 3. $R^{10}$ and $R^{11}$ each independently represent a linear or branched alkyl group having from 1 to 5 carbon atoms, or a linear or branched alkenyl group having from 2 to 5 carbon atoms. $R^{12}$ represents, having from 3 to 7 carbon atoms, an alkyl group, an alkenyl group, an aralkyl group, or a phenyl group optionally substituted with a methyl group; and p indicates an integer of 0 or 1. In the structural unit represented by any of the formulae (2) to (7), the oxygen atom bonds to a hydrogen atom or to the carbon atom of the above-mentioned structural unit.)

<2> The cationic group-containing cellulose ether according to the above <1>, of which the cation charge density is at least 0.05 mmol/g, preferably at least 0.15 mmol/g, more preferably at least 0.2 mmol/g, even more preferably at least 0.3 mmol/g, and is at most 2.0 mmol/g, preferably at most 1.6 mmol/g, more preferably at most 1.5 mmol/g, even more preferably at most 1.2 mmol/g, further more preferably at most 0.9 mmol/g, and is from 0.05 to 2.0 mmol/g, preferably from 0.15 to 1.5 mmol/g, more preferably from 0.2 to 1.2 mmol/g, even more preferably from 0.3 to 0.9 mmol/g.

<3> The cationic group-containing cellulose ether according to the above <1>, of which the cation charge density is preferably from 0.6 to 2.0 mmol/g, more preferably from 1.1 to 1.6 mmol/g, even more preferably from 1.2 to 1.6 mmol/g, and still more preferably from 1.35 to 1.6 mmol/g.

<4> The cationic group-containing cellulose ether according to the above <1>, of which the cation charge density is preferably at least 0.4 mmol/g, more preferably at least 0.8 mmol/g, even more preferably at least 1.0 mmol/g, further more preferably at least 1.2 mmol/g, still more preferably at least 1.3 mmol/g, and is preferably at most 2.0 mmol/g, and is preferably from 0.4 to 2.0 mmol/g, more preferably from 0.8 to 2.0 mmol/g, even more preferably from 1.0 to 2.0 mmol/g, still more preferably from 1.2 to 2.0 mmol/g, further more preferably from 1.3 to 2.0 mmol/g.

<5> The cationic group-containing cellulose ether according to any of the above <1> to <4>, wherein the degree of substitution with a cationized oxyalkylene group per the anhydroglucose unit (MS(N+)) is at least 0.04, preferably at least 0.05, more preferably at least 0.07, even more preferably at least 0.09, further more preferably at least 0.10, still further more preferably at least 0.12, still further more preferably at least 0.15, still further more preferably at least 0.17, still further more preferably at least 0.18, and is at most 0.90, preferably at most 0.75, more preferably at most 0.65, even more preferably at most 0.60, further more preferably at most 0.50, still further more preferably at most 0.35, still further more preferably at most 0.30, still further more preferably at most 0.22, still further more preferably at most 0.20, and is within a range of from 0.04 to 0.60, preferably within a range of from 0.07 to 0.30, more preferably within a range of from 0.09 to 0.20, even more preferably within a range of from 0.17 to 0.20.

<6> The cationic group-containing cellulose ether according to any of the above <1> to <5>, wherein the degree of substitution with a cationized oxyalkylene group per the anhydroglucose unit (MS(N+)) is preferably within a range of from 0.15 to 0.75, more preferably within a range of from 0.35 to 0.75, even more preferably within a range of from 0.40 to 0.65.

<7> The cationic group-containing cellulose ether according to any of the above <1> to <6>, wherein the degree of substitution with a glycerol group per the anhydroglucose unit (MS(Gly)) is at least 0.6, more preferably at least 0.7, even more preferably at least 0.8, still more preferably at least 1.0, further more preferably at least 1.2, still further more preferably at least 1.3, still further more preferably at least 1.8, still further more preferably at least 2.1, and is at most 4.0, preferably at most 3.8, more preferably at most 3.0, even more preferably at most 2.3, and is within a range of from 0.5 to 4.0, preferably within a range of from 0.5 to 3.8, more preferably within a range of from 0.6 to 2.3, even more preferably within a range of from 1.0 to 2.3, and still more preferably within a range of from 1.8 to 2.3.

<8> The cationic group-containing cellulose ether according to any of the above <1> to <7>, wherein the degree of substitution with a hydrocarbon group-containing group having from 3 to 7 carbon atoms per the anhydroglucose unit (MS(HC)) is at least 0.0005, preferably at least 0.005, more preferably at east 0.01, even more preferably at least 0.02, still more preferably at least 0.03, and is preferably at most 0.15, more preferably at most 0.10, even more preferably at most 0.06, still more preferably at most 0.05, still further more preferably at most 0.04, and is within a range of from 0.0005 to 0.2, preferably within a range of from 0.005 to 0.15, more preferably within a range of from 0.005 to 0.10, even more preferably within a range of from 0.02 to 0.05, and still more preferably within a range of from 0.03 to 0.04.

<9> The cationic group-containing cellulose ether according to any of the above <1> to <8>, of which the mean degree of polymerization, n is at least 200, preferably at least 500, more preferably at least 1000, and is at most 10000, preferably at most 5000, more preferably at most 2500, and is within a range of from 200 to 10000, preferably within a range of from 500 to 5000, more preferably within a range of from 1000 to 2500.

<10> The cationic group-containing cellulose ether according to any of the above <1> to <9>, wherein in the formulae (2) and (3), $R^4$ to $R^9$ each are a methyl group, an ethyl group, an n-propyl group or an isopropyl group, preferably a methyl group or an ethyl group, more preferably a methyl group.

<11> The cationic group-containing cellulose ether according to any of the above <1> to <10>, wherein in the formulae (2) and (3), $X^-$ and $Y^-$ each are at least one selected from an alkyl sulfate ion having from 1 to 3 carbon atoms, a sulfate ion, and a halide ion, preferably at least one selected from a halide ion, more preferably at least one selected from a chloride ion and a bromide ion, even more preferably a chloride ion.

<12> The cationic group-containing cellulose ether according to any of the above <1> to <11>, wherein the group containing a hydrocarbon group and having from 3 to 7 carbon atoms is at least one structural unit selected from the structural units represented by the above-mentioned general formulae (6) and (7).

<13> The cationic group-containing cellulose ether according to any of the above <1> to <12>, wherein in the formulae (6) and (7), $R^{19}$ and $R^{11}$ each are an alkyl group having from 1 to 4 carbon atoms or an alkenyl group having from 2 to 4 carbon atoms, preferably an alkyl group having from 1 to 4 carbon atoms, more preferably a methyl group or an ethyl group, even more preferably an ethyl group.

<14> The cationic group-containing cellulose ether according to any of the above <1> to <11> or <13>, wherein in the formula (8), $R^{12}$ is at least one selected from an alkyl group, an alkenyl group and a phenyl group having from 3 to 6 carbon atoms, preferably at least one selected from an alkyl group and an alkenyl group having from 3 to 6 carbon atoms, more preferably an alkyl group having from 3 to 6 carbon atoms.

<15> A method for producing a cationic group-containing cellulose ether of any of the above <1> to <14>, which includes reacting a starting cellulose with a glycerolating agent, a cationizing agent and a reagent for introducing a group containing a hydrocarbon group and having from 3 to 7 carbon atoms, and in which, preferably, the glycerolation reaction is first and followed by the cationization reaction and the reaction of introducing the group that contains a hydrocarbon group and has from 3 to 7 carbon atoms in that order.

<16> The method for producing a cationic group-containing cellulose ether according to the above <15>, which is any of the following methods (i) to Method (i): A method in which a starting cellulose is mixed with a large amount of water and with a large excessive amount of an alkali metal hydroxide to give an alkali cellulose, and thereafter this is reacted with a glycerolating agent, a cationizing agent, and a reagent for introducing a group that contains a hydrocarbon group and has from 3 to 7 carbon atoms.

Method (ii): A method in which a starting cellulose is dissolved in a solvent capable of dissolving cellulose and selected from tetrabutylammonium fluoride-containing dimethyl sulfoxide, paraformaldehyde-containing dimethyl sulfoxide, and lithium chloride-containing dimethylacetamide or the like, and thereafter the starting cellulose is reacted with a glycerolating agent, a cationizing agent and a reagent for introducing a group that contains a hydrocarbon group and has from 3 to 7 carbon atoms.

Method (iii): A method not using any excess alkali or specific solvent capable of dissolving cellulose, in which a powdery or floc-like starting cellulose is reacted with a glycerolating agent, a cationizing agent and a reagent for introducing a group that contains a hydrocarbon group and has from 3 to 7 carbon atoms, in the presence of an alkali.

<17> The method for producing a cationic group-containing cellulose ether according to the above <15> or <16>, wherein the glycerolating agent is at least one selected from glycidol, 3-halo-1,2-propanediol, glycerin and glycerin carbonate, preferably glycidol.

<18> The method for producing a cationic group-containing cellulose ether according to any of the above <15> to <17>, wherein the amount of the glycerolating agent to be used is at least 0.2 mols relative to one mol of the anhydroglucose unit in the starting cellulose, preferably at least 1 mol, more preferably at least 3 mols, even more preferably at least 4 mols, still more preferably at least 5 mols, and is at most 60 mols, preferably at most 50 mols, more preferably at most 45 mols, even more preferably at most 40 mols, and is preferably from 0.2 to 60 mols, more preferably from 1 to 50 mols, even more preferably from 3 to 45 mols, still more preferably from 4 to 40 mols, further more preferably from 5 to 40 mols.

<19> The method for producing a cationic group-containing cellulose ether according to any of the above <15> to <17>, wherein the amount of the glycerolating agent to be used is preferably from 10 to 60 mols, more preferably from 10 to 50 mols relative to 1 mol of the anhydroglucose unit in the starting cellulose.

<20> The method for producing a cationic group-containing cellulose ether according to any of the above <15> to <19>, wherein the cationizing agent is at least one selected from the compounds by the above-mentioned general formulae (9) and (10), preferably at least one selected from glycidyltrimethylammonium or glycidyltriethylammonium chlorides or bromides, 3-chloro-2-hydroxypropyltrimethylammonium or 3-chloro-2-hydroxypropyltriethylammonium chlorides, 3-bromo-2-hydroxypropyltrimethylammonium or 3-bromo-2-hydroxypropyltriethylammonium bromides, more preferably at least one selected from glycidyltrimethylammonium chloride and 3-chloro-2-hydroxypropyltrimethylammonium chloride, even more preferably glycidyltrimethylammonium chloride.

<21> The method for producing a cationic group-containing cellulose ether according to any of the above <15> to <20>, wherein the amount of the cationizing agent to be used is at least 0.01 mols relative to 1 mol of AGU in the starting cellulose, preferably at least 0.03 mols, more preferably at least 0.05 mols, and is at most 60 mols, preferably at most 35 mols, more preferably at most 10 mols, even more preferably at most 5 mols, and is from 0.01 to 60 mols, preferably from 0.01 to 35 mols, preferably from 0.03 to 10 mols, more preferably from 0.05 to 5 mols.

<22> The method for producing a cationic group-containing cellulose ether according to any of the above <15> to <20>, wherein the amount of the cationizing agent to be used is preferably from 5 to 60 mols relative to 1 mol of AGU in the starting cellulose, more preferably from 10 to 60 mols, even more preferably from 20 to 60 mols.

<23> The method for producing a cationic group-containing cellulose ether according to any of the above <15> to <22>, wherein the reagent for introducing a group containing a hydrocarbon group and having from 3 to 7 carbon atoms is at least one selected from the compounds represented by the above-mentioned general formulae (11) and (12), preferably a compound represented by the general formula (11), more preferably at least one selected from propylene oxide, 1,2-butylene oxide, 1,2-epoxypentane and 1,2-epoxyhexane, even more preferably at least one selected from propylene oxide and 1,2-butylene oxide, still more preferably 1,2-butylene oxide.

<24> The method for producing a cationic group-containing cellulose ether according to any of the above <15> to <22>, wherein the reagent for introducing a group containing a hydrocarbon group and having from 3 to 7 carbon atoms is at least one selected from the compounds represented by the above-mentioned general formulae (13), (14) and (15), preferably a compound represented by the general formula (13) or (14), more preferably at least one selected from alkane halides having from 3 to 7 carbon atoms and glycidyl ethers having an alkyl group with from 3 to 7 carbon atoms, even more preferably a glycidyl ether having an alkyl group with from 3 to 7 carbon atoms, still more preferably at least one selected from propyl glycidyl ether, butyl glycidyl ether, pentyl glycidyl ether, and hexyl glycidyl ether, still more preferably at least one selected from propyl glycidyl ether and butyl glycidyl ether.

<25> The method for producing a cationic group-containing cellulose ether according to any of the above <15> to <24>, wherein the amount of the reagent for introducing a group that contains a hydrocarbon group and has from 3 to 7 carbon atoms is at least 0.01 mols relative to 1 mol of AGU in the starting cellulose, preferably at least 0.03 mols, more preferably at least 0.1 mols, and is at most 5 mols, preferably at most 3 mols, more preferably at most 2 mols, and is from 0.01 to 5 mols, preferably from 0.03 to 3 mols, more preferably from 0.1 to 2 mols.

<26> A surfactant composition containing the cationic group-containing cellulose ether of any of the above <1> to <14>, a surfactant and water.

<27> The surfactant composition according to the above <26>, wherein the content of the cationic group-containing cellulose ether is, in the surfactant composition, at least 0.01% by mass, preferably at least 0.05% by mass, more preferably at least 0.1% by mass, and is at most 10% by mass, preferably at most 5% by mass, more preferably at most 1% by mass, and is from 0.01 to 10% by mass, preferably from 0.05 to 5% by mass, even more preferably from 0.1 to 1% by mass.

<28> The surfactant composition according to the above <26> or <27>, wherein the cationic group-containing cellulose ether is preferably a cationic group-containing cellulose ether having a degree of substitution with a cationized oxyalkylene group per the anhydroglucose unit (MS(N+)) of from 0.04 to 0.6, a degree of substitution with a glycerol group (MS(Gly)) of from 0.5 to 4.0 and a degree of substitution with a hydrocarbon group-containing group having from 3 to 7 carbon atoms (MS(HC)) of from 0.005 to 0.15.

<29> The surfactant composition according to any of the above <26> to <28>, wherein the surfactant is alone or in a combination of two or more kinds selected from anionic surfactants, nonionic surfactants, cationic surfactants and ampholytic surfactants.

<30> The surfactant composition according to any of the above <26> to <29>, wherein the content of the surfactant is, in the surfactant composition, preferably at least 0.1% by mass, more preferably at least 1% by mass, even more preferably at least 5% by mass, and is preferably at most 80% by mass, more preferably at most 50% by mass, even more preferably at most 36% by mass, and is preferably from 0.1 to 80% by mass, more preferably from 1 to 80% by mass, even more preferably from 5 to 50% by mass, still more preferably from 5 to 36% by mass.

<31> The surfactant composition according to any of the above <26> to <30>, wherein the ratio by mass of the cationic group-containing cellulose ether to the surfactant is at least 0.0002, preferably at least 0.001, more preferably at least 0.003, and is at most 10, preferably at most 5, more preferably at most 2.

<32> The surfactant composition according to any of the above <26> to <31>, wherein the water content is, in the surfactant composition, preferably at least 10% by mass, more preferably at least 40% by mass, and is preferably at most 99.5% by mass.

<33> The surfactant composition according to any of the above <26> to <32>, which further contains any other cationic polymer than the cationic group-containing cellulose ether.

<34> The surfactant composition according to the above <33>, wherein the other cationic polymer than the cationic group-containing cellulose ether is preferably at least one selected from cationic galactomannan, cationized hydroxyalkyl cellulose, cationized starch, and cationic synthetic polymer produced through radical polymerization.

<35> The surfactant composition according to the above <33> or <34>, wherein the content of the other cationic polymer than the cationic group-containing cellulose ether is, in the surfactant composition, preferably at least 0.01% by mass, more preferably at least 0.05% by mass, even more preferably at least 0.10% by mass, still more preferably at least 0.2% by mass, further more preferably at least 0.3% by mass, and is preferably at most 5% by mass, more preferably at most 2% by mass, even more preferably at most 1.0% by mass, and still more preferably at most 0.5% by mass.

<36> The surfactant composition according to any of the above <33> to <35>, wherein the ratio by mass of the cationic group-containing cellulose ether to the other cationic polymer than the cationic group-containing cellulose ether [cationic group-containing cellulose ether/other cationic polymer than cationic group-containing cellulose ether] is preferably at least 0.05, more preferably at least 0.1, even more preferably at least 0.3, still more preferably at least 0.5, and is preferably at most 10, more preferably at most 5, even more preferably at most 2, and still more preferably at most 1.

<37> The surfactant composition according to any of the above <26> to <36>, which further contains an oily agent.

<38> The surfactant composition according to the above <37>, wherein the amount of dissolution of the oily agent in 100 g of water at 20° C. is preferably at least 0 g and preferably at most 1 g, more preferably at most 0.5 g, and even more preferably at most 0.1 g.

<39> The surfactant composition according to the above <37> or <38>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group.

<40> The surfactant composition according to any of the above <37> to <39>, wherein the content of the oily agent is, in the surfactant composition, preferably at least 0.01% by mass, more preferably at least 0.05% by mass, even more preferably at least 0.1% by mass, still more preferably at least 0.5% by mass, further more preferably at least 1.0% by mass, and is preferably at most 30% by mass, more preferably at most 20% by mass, even more preferably at most 10% by mass, still more preferably at most 5% by mass, further more preferably at most 3% by mass.

<41> The surfactant composition according to any of the above <37> to <40>, wherein the ratio by mass of the cationic group-containing cellulose ether to the oily agent [cationic group-containing cellulose ether/oily agent] is preferably at least 0.001, more preferably at least 0.005, even more preferably at least 0.01, still more preferably at least 0.03, and is preferably at most 5, more preferably at most 1, and even more preferably at most 0.6.

<42> The surfactant composition according to any of the above <26> to <41>, which is used as a hair wash composition, a skin cleanser composition, a hair conditioner composition or a hair treatment composition.

<43> A hair wash composition containing the cationic group-containing cellulose ether of any of the above <1> to <14>, a surfactant and water.

<44> The hair wash composition according to the above <43>, wherein the content of the cationic group-containing cellulose ether is, in the hair wash composition, at least 0.01% by mass, preferably at least 0.05% by mass, more preferably at least 0.1% by mass, and is at most 10% by mass, preferably at most 5% by mass, more preferably at most 1% by mass, and is from 0.01 to 10% by mass, preferably from 0.05 to 5% by mass, more preferably from 0.1 to 1% by mass.

<45> The hair wash composition according to any of the above <43> or <44>, wherein the cationic group-containing cellulose ether is preferably a cationic group-containing cellulose ether having MS(N+) of from 0.04 to 0.60, MS(Gly) of from 0.5 to 4.0 and MS(HC) of from 0.005 to 0.15, more preferably a cationic group-containing cellulose ether having MS(N+) of from 0.07 to 0.30, MS(Gly) of from 0.5 to 3.8 and MS(HC) of from 0.005 to 0.10, even more preferably a cationic group-containing cellulose ether having MS(N+) of from 0.09 to 0.20, MS(Gly) of from 0.6 to 2.3 and MS(HC) of from 0.005 to 0.10, and still more preferably a cationic group-containing cellulose ether having MS(N+) of from 0.17 to 0.20, MS(Gly) of from 1.8 to 2.3 and MS(HC) of from 0.03 to 0.04.

<46> The hair wash composition according to any of the above <43> or <44>, wherein the cationic group-containing cellulose ether is preferably a cationic group-containing cellulose ether having MS(N+) of from 0.15 to 0.75, MS(Gly) of from 0.6 to 2.3 and MS(HC) of from 0.005 to 0.10, more preferably a cationic group-containing cellulose ether having MS(N+) of from 0.35 to 0.75, MS(Gly) of from 1.0 to 2.3 and MS(HC) of from 0.03 to 0.04, even more preferably a cationic group-containing cellulose ether having MS(N+) of from 0.40 to 0.65, MS(Gly) of from 1.8 to 2.3 and MS(HC) of from 0.03 to 0.04, and still more preferably a cationic group-containing cellulose ether having MS(N+) of from 0.55 to 0.65, MS(Gly) of from 1.8 to 2.3 and MS(HC) of from 0.03 to 0.04.

<47> The hair wash composition according to any of the above <43> to <46> wherein the content of the surfactant is, in the hair wash composition, preferably at least 0.1% by mass, more preferably at least 1% by mass, even more preferably at least 5% by mass, still more preferably at least 8% by mass, further more preferably at least 10% by mass, and is preferably at most 80% by mass, more preferably at most 50% by mass, even more preferably at most 36% by mass, still more preferably at most 30% by mass, further more preferably at most 25% by mass, and still further more preferably at most 20% by mass.

<48> The hair wash composition according to any of the above <43> to <47> wherein the ratio by mass of the cationic group-containing cellulose ether to the surfactant [cationic group-containing cellulose ether/surfactant] is preferably at most 0.5, more preferably at most 0.2, even more preferably at most 0.1, and is preferably at least 0.005, more preferably at least 0.010, and even more preferably at least 0.015.

<49> The hair wash composition according to any of the above <43> to <48> wherein the surfactant is at least one selected from anionic surfactants, nonionic surfactants, cationic surfactants and ampholytic surfactants, preferably at least one selected from anionic surfactants, nonionic surfactants and ampholytic surfactants, and is more preferably a combination of two or three of those surfactants.

<50> The hair wash composition according to the above <49>, wherein the anionic surfactant is preferably at least one selected from alkylsulfate salts, polyoxyalkylene alkyl ether sulfate salts, higher fatty acid salts having from 8 to 16 carbon atoms, alkyl ether acetate salts represented by the following general formula (I), alkyl sulfosuccinate salts, acylglutamate salts, glycine derivatives, α-olefin sulfonates having from 14 to 16 carbon atoms, and internal olefin sulfonate salts having from 12 to 24 carbon atoms.

R—O—(CH$_2$CH$_2$O)$_a$—CH$_2$—COOM  (I)

(In the formula, R represents an alkyl group having from 4 to 22 carbon atoms, a indicates a number of from 4 to 16, M represents a hydrogen atom, an alkali metal, an alkaline earth metal (½ atom), an ammonium or an organic ammonium.)

<51> The hair wash composition according to the above <49>, wherein the nonionic surfactant is preferably at least one selected from polyethylene glycol-type nonionic surfactants, polyalcohol-type nonionic surfactants and fatty acid alkanolamides, more preferably at least one selected from polyoxyalkylene alkyl ethers, polyoxyethylene hardened castor oil, fatty acid alkanolamides, and alkyl glycosides, even more preferably at least one selected from polyoxyalkylene alkyl ethers and fatty acid alkanolamides, still more preferably at least one selected from polyoxyethylene alkyl ethers and fatty acid monoalkanolamides.

<52> The hair wash composition according to the above <49>, wherein the ampholytic surfactant is preferably at least one selected from betaine-type surfactants and amine oxide-type surfactants, more preferably at least one selected from imidazoline-type betaines, alkyldimethylamine acetate betaines, fatty acid amide propylbetaines, and alkylhydroxysulfobetaines, even more preferably at least one selected from laurylcarboxymethylhydroxyimidazolium betaine, lauryldimethylaminoacetate betaine, coconut oil fatty acid amide propylbetaine and laurylhydroxysulfobetaine.

<53> The hair wash composition according to the above <49>, wherein the cationic surfactant is preferably at least one selected from quaternary ammonium salts having a hydrocarbon group having from 12 to 28 carbon atoms and optionally interrupted by an amide group, an ester group or an ether group, pyridinium salts, and tertiary amine salts with mineral acids or organic acids, and more preferably at least one selected from mono-long chain alkyltrimethylammonium salts, di-long chain alkyldimethylammonium salts, mono-long chain alkyldimethylamine salts.

<54> The hair wash composition according to any of the above <43> to <53>, wherein the water content is, in the hair wash composition, preferably at least 60% by mass, more preferably at least 70% by mass, and is preferably at most 95% by mass, more preferably at most 90% by mass.

<55> The hair wash composition according to any of the above <43> to <54>, which further contains any other cationic polymer than the cationic group-containing cellulose ether.

<56> The hair wash composition according to the above <55>, wherein the cationic group-containing cellulose ether is preferably a cationic group-containing cellulose ether having MS(N+) of from 0.04 to 0.60, MS(Gly) of from 0.5 to 4.0 and MS(HC) of from 0.01 to 0.10, more preferably a cationic group-containing cellulose ether having MS(N+) of from 0.09 to 0.60, MS(Gly) of from 0.6 to 3.8 and MS(HC) of from 0.01 to 0.10, even more preferably a cationic group-containing cellulose ether having MS(N+) of from 0.09 to 0.50, MS(Gly) of from 1.0 to 3.8 and MS(HC) of from 0.01 to 0.10, still more preferably a cationic group-containing cellulose ether having MS(N+) of from 0.15 to 0.30, MS(Gly) of from 1.2 to 3.0 and MS(HC) of from 0.02 to 0.06, and further more preferably a cationic group-containing cellulose ether having MS(N+) of from 0.17 to 0.21, MS(Gly) of from 2.1 to 2.3 and MS(HC) of from 0.02 to 0.04.

<57> The hair wash composition according to the above <55> or <56>, wherein the other cationic polymer than the cationic group-containing cellulose ether is preferably at least one selected from cationic galactomannan, cationized hydroxyalkyl cellulose, cationized starch, and cationic synthetic polymer produced through radical polymerization.

<58> The hair wash composition according to any of the above <55> to <57>, wherein the content of the other cationic polymer than the cationic group-containing cellulose ether is, in the hair wash composition, preferably at least 0.01% by mass, more preferably at least 0.05% by mass, even more preferably at least 0.10% by mass, still more preferably at least 0.2% by mass, further more preferably at least 0.3% by mass, and is preferably at most 5% by mass, more preferably at most 2% by mass, even more preferably at most 1.0% by mass, and still more preferably at most 0.5% by mass.

<59> The hair wash composition according to any of the above <55> to <58>, wherein the ratio by mass of the cationic group-containing cellulose ether to the other cationic polymer than the cationic group-containing cellulose ether [cationic group-containing cellulose ether/other cationic polymer than cationic group-containing cellulose ether] is preferably at least 0.05, more preferably at least 0.1, even more preferably at least 0.3, still more preferably at least 0.5, and is preferably at most 10, more preferably at most 5, even more preferably at most 2, and still more preferably at most 1.

<60> The hair wash composition according to any of the above <43> to <59>, which further contains an oily agent.

<61> The hair wash composition according to the above <60>, wherein the cationic group-containing cellulose ether is preferably a cationic group-containing cellulose ether having MS(N+) of from 0.04 to 0.60, MS(Gly) of from 0.5 to 4.0 and MS(HC) of from 0.01 to 0.10, more preferably a cationic group-containing cellulose ether having MS(N+) of from 0.07 to 0.50, MS(Gly) of from 0.7 to 3.8 and MS(HC) of from 0.01 to 0.06, even more preferably a cationic group-containing cellulose ether having MS(N+) of from 0.09 to 0.35, MS(Gly) of from 1.0 to 3.8 and MS(HC) of from 0.01 to 0.06, still more preferably a cationic group-containing cellulose ether having MS(N+) of from 0.10 to 0.20, MS(Gly) of from 1.0 to 2.3 and MS(HC) of from 0.02 to 0.06, further more preferably a cationic group-containing cellulose ether having MS(N+) of from 0.12 to 0.20, MS(Gly) of from 1.3 to 2.3 and MS(HC) of from 0.02 to 0.06, and further more preferably a cationic group-containing cellulose ether having MS(N+) of from 0.18 to 0.20, MS(Gly) of from 2.1 to 2.3 and MS(HC) of from 0.02 to 0.04.

<62> The hair wash composition according to the above <60>, wherein the cationic group-containing cellulose ether is preferably a cationic group-containing cellulose ether having MS(N+) of from 0.40 to 0.90, MS(Gly) of from 0.6 to 3.0 and MS(HC) of from 0.01 to 0.06, more preferably a cationic group-containing cellulose ether having MS(N+) of from 0.45 to 0.80, MS(Gly) of from 0.7 to 2.5 and MS(HC) of from 0.02 to 0.05, and even more preferably a cationic group-containing cellulose ether having MS(N+) of from 0.50 to 0.75, MS(Gly) of from 0.8 to 2.3 and MS(HC) of from 0.03 to 0.04.

<63> The hair wash composition according to any of the above <60> to <62>, wherein the amount of dissolution of the oily agent in 100 g of water at 20° C. is preferably at least 0 g and preferably at most 1 g, more preferably at most 0.5 g, and even more preferably at most 0.1 g.

<64> The hair wash composition according to any of the above <60> to <63>, wherein the oily agent is preferably at least one selected from (i) ester oils, (ii) silicone oils, (iii) ether oils, (iv) hydrocarbon oils, (v) higher alcohols and (vi) carboxylic acids having a hydrocarbon group having from 17 to 23 carbon atoms and optionally substituted with a hydroxyl group.

<65> The hair wash composition according to any of the above <60> to <64>, wherein the content of the oily agent is, in the hair wash composition, preferably at least 0.01% by mass, more preferably at least 0.05% by mass, even more preferably at least 0.1% by mass, still more preferably at least 0.5% by mass, further more preferably at least 1.0% by mass, and is preferably at most 30% by mass, more preferably at most 20% by mass, even more preferably at most 10% by mass, still more preferably at most 5% by mass, and further more preferably at most 3% by mass.

<66> The hair wash composition according to any of the above <60> to <65>, wherein the ratio by mass of the cationic group-containing cellulose ether to the oily agent [cationic group-containing cellulose ether/oily agent] is preferably at least 0.001, more preferably at least 0.005, even more preferably at least 0.01, still more preferably at least 0.03, and is preferably at most 5, more preferably at most 1, and even more preferably at most 0.6.

<67> A skin cleanser composition containing the cationic group-containing cellulose ether of any of the above <1> to <14>, a surfactant and water.

<68> The skin cleanser composition according to the above <67>, wherein the content of the cationic group-containing cellulose ether is, in the skin cleanser composition, at least 0.01% by mass, preferably at least 0.05% by mass, more preferably at least 0.1% by mass, and is at most 10% by mass, preferably at most 5% by mass, more preferably at most 1% by mass, and is from 0.01 to 10% by mass, preferably from 0.05 to 5% by mass, more preferably from 0.1 to 1% by mass.

<69> The skin cleanser composition according to the above <67> or <68>, wherein the cationic group-containing cellulose ether is preferably a cationic group-containing cellulose ether having MS(N+) of from 0.04 to 0.60, MS(Gly) of from 0.5 to 4.0 and MS(HC) of from 0.0005 to 0.15, more preferably a cationic group-containing cellulose ether having MS(N+) of from 0.07 to 0.50, MS(Gly) of from 0.7 to 3.8 and MS(HC) of from 0.005 to 0.10, and even more preferably a cationic group-containing cellulose ether having MS(N+) of from 0.10 to 0.50, MS(Gly) of from 1.0 to 3.0 and MS(HC) of from 0.01 to 0.10.

<70> The skin cleanser composition according to any of the above <67> to <69>, wherein the content of the surfactant is, in the skin cleanser composition, preferably at least 8% by mass, more preferably at least 10% by mass, and is preferably at most 36% by mass.

<71> The skin cleanser composition according to any of the above <67> to <70>, wherein the ratio by mass of the cationic group-containing cellulose ether to the surfactant [cationic group-containing cellulose ether/surfactant] is preferably at least 0.005, more preferably at most 0.3, even more preferably at most 0.1, and is preferably at most 0.05.

<72> The skin cleanser composition according to any of the above <67> to <71>, wherein the surfactant is preferably at least one selected from polyoxyethylene alkyl ether sulfate salts, higher fatty acids or their salts having from 8 to 16 carbon atoms, acylisethionates, acylmethyltaurates, acylglycine, acylsarcosine, fatty acid monoalkanolamides, fatty acid amide propylbetaines and imidazoline-type betaines, more preferably at least one selected from sodium laureth-(2) sulfate, laurate salts, myristate salts, palmitate salts, sodium cocoylisethionate, sodium cocoylmethyltaurine, sodium cocoylglycine, potassium lauroylsarcosine, coconut oil fatty acid amide propylbetaine and sodium cocoamphoacetate.

<73> The skin cleanser composition according to any of the above <67> to <72>, wherein the water content in the skin cleanser composition is preferably at least 40% by mass and is preferably at most 95% by mass, more preferably at most 90% by mass.

<74> The skin cleanser composition according to any of the above <67> to <73>, which further contains any other cationic polymer than the cationic group-containing cellulose ether.

<75> The skin cleanser composition according to the above <74>, wherein the other cationic polymer than the cationic group-containing cellulose ether. is preferably at least one selected from cationized guar gum and cationic synthetic polymer produced through radical polymerization.

<76> The skin cleanser composition according to the above <74> or <75>, wherein the content of the other cationic polymer than the cationic group-containing cellulose ether is, in the skin cleanser composition, preferably at least 0.01% by mass, more preferably at least 0.05% by mass, even more preferably at least 0.10% by mass, still more preferably at least 0.2% by mass, further more preferably at least 0.3% by mass, and is preferably at most 5% by mass, more preferably at most 2% by mass, even more preferably at most 1.0% by mass, and still more preferably at most 0.5% by mass.

<77> The skin cleanser composition according to any of the above <74> to <76>, wherein the ratio by mass of the cationic group-containing cellulose ether to the other cationic polymer than the cationic group-containing cellulose ether [cationic group-containing cellulose ether/other cationic polymer than cationic group-containing cellulose ether] is preferably at least 0.05, more preferably at least 0.1, even more preferably at least 0.3, still more preferably at least 0.5, and is preferably at most 10, more preferably at most 5, even more preferably at most 2, and still more preferably at most 1.

<78> The skin cleanser composition according to any of the above <67> to <77>, which further contains an oily agent.

<79> The skin cleanser composition according to the above <78>, wherein the amount of dissolution of the oily agent in 100 g of water at 20° C. is preferably at least 0 g and preferably at most 1 g, more preferably at most 0.5 g, and even more preferably at most 0.1 g.

<80> The skin cleanser composition according to the above <78> or <79>, wherein the oily agent is preferably at least one selected from ester oils and hydrocarbon oils, and more preferably at least one selected from sunflower oil and vaseline.

<81> The skin cleanser composition according to any of the above <78> to <80>, wherein the content of the oily agent is, in the skin cleanser composition, preferably at least 3% by mass, more preferably at least 5% by mass, and is preferably at most 20% by mass, more preferably at most 15% by mass.

<82> The skin cleanser composition according to any of the above <78> to <81>, wherein the ratio by mass of the cationic group-containing cellulose ether to the oily agent [cationic group-containing cellulose ether/oily agent] is preferably at least 0.01 and is preferably at most 0.3, more preferably at most 0.1.

<83> The skin cleanser composition according to any of the above <67> to <82>, which is at least one selected from body shampoo, hand wash, face wash and makeup remover, preferably at least one selected from body shampoo, hand wash and face wash.

<84> A hair conditioner composition containing the cationic group-containing cellulose ether of any of the above <1> to <14>, a surfactant, an oily agent and water.

<85> The hair conditioner composition according to the above <84>, wherein the content of the cationic group-containing cellulose ether is, in the hair conditioner composition, preferably at least 0.05% by mass, more preferably at least 0.1% by mass, even more preferably at least 0.2% by mass, still more preferably at least 0.3% by mass, and is preferably at most 3% by mass, more preferably at most 2% by mass, even more preferably at most 1% by mass, and still more preferably at most 0.5% by mass.

<86> The hair conditioner composition according to the above <84> or <85>, wherein the cationic group-containing cellulose ether is preferably a cationic group-containing cellulose ether having MS(N+) of from 0.04 to 0.60, MS(Gly) of from 0.5 to 4.0 and MS(HC) of from 0.01 to 0.10, more preferably a cationic group-containing cellulose ether having MS(N+) of from 0.17 to 0.60, MS(Gly) of from 0.8 to 3.8 and MS(HC) of from 0.02 to 0.06, even more preferably a cationic group-containing cellulose ether having MS(N+) of from 0.17 to 0.30, MS(Gly) of from 2.0 to 3.8 and MS(HC) of from 0.02 to 0.06, still more preferably a cationic group-containing cellulose ether having MS(N+) of from 0.18 to 0.22, MS(Gly) of from 2.1 to 2.3 and MS(HC) of from 0.02 to 0.04.

<87> The hair conditioner composition according to any of the above <84> to <86>, wherein the content of the surfactant is, in the hair conditioner composition, preferably at least 0.2% by mass, more preferably at least 0.5% by mass, even more preferably at least 1.0% by mass, still more preferably at least 1.5% by mass, and is preferably at most 20% by mass, more preferably at most 10% by mass, even more preferably at most 5% by mass, and still more preferably at most 3% by mass.

<88> The hair conditioner composition according to any of the above <84> to <87>, wherein the ratio by mass of the cationic group-containing cellulose ether to the surfactant [cationic group-containing cellulose ether/surfactant] is preferably at least 0.05, more preferably at least 0.10, even more preferably at least 0.15, and is preferably at most 1.5, more preferably at most 1.0, even more preferably at most 0.5, and still more preferably at most 0.35.

<89> The hair conditioner composition according to any of the above <84> to <88>, wherein the surfactant is preferably a cationic surfactant, more preferably a combination of a cationic surfactant and a nonionic surfactant.

<90> The hair conditioner composition according to any of the above <84> to <89>, wherein the cationic surfactant is preferably at least one selected from behenyltrimethylammonium salts, stearyltrimethylammonium salts, stearoxypropyltrimethylammonium salts, cetyltrimethylammonium salts, distearyldimethylammonium salts, and stearamidopropyldimethylamine, behanamidopropyldimethylamine.

<91> The hair conditioner composition according to any of the above <84> to <90>, wherein the water content is, in the hair conditioner composition, preferably at least 70% by mass, more preferably at least 80% by mass, even more preferably at least 88% by mass, and is preferably at most 95% by mass, and more preferably at most 93% by mass.

<92> The hair conditioner composition according to any of the above <84> to <91>, wherein the amount of dissolution of the oily agent in 100 g of water at 20° C. is preferably at least 0 g and preferably at most 1 g, more preferably at most 0.5 g, and even more preferably at most 0.1 g.

<93> The hair conditioner composition according to any of the above <84> to <92>, wherein the oily agent is preferably a combination of at least one selected from ester oils, silicone oils, ether oils and hydrocarbon oils, and a higher alcohol, more preferably a combination of at least one selected from ester oils, silicone oils, ether oils and hydrocarbon oils, and cetyl alcohol and stearyl alcohol.

<94> The hair conditioner composition according to any of the above <84> to <93>, wherein the content of the oily agent is, in the hair conditioner composition, preferably at least 2% by mass, more preferably at least 4% by mass, even more preferably at least 5% by mass, and is preferably at most 15% by mass, and more preferably at most 12% by mass.

<95> The hair conditioner composition according to any of the above <84> to <94>, wherein the ratio by mass of the cationic group-containing cellulose ether to the oily agent [cationic group-containing cellulose ether/oily agent] is preferably at least 0.01, more preferably at least 0.02, even more preferably at least 0.025, and is preferably at most 0.3, more preferably at most 0.10, and even more preferably at most 0.06.

<96> The hair conditioner composition according to any of the above <84> to <95>, of which the pH is preferably at least 1, more preferably at least 2, even more preferably at least 3, and is preferably at most 10, more preferably at most 8, even more preferably at most 6.

<97> The hair conditioner composition according to any of the above <84> to <96>, which is hair rinse, treatment, hair conditioner, leave-in hair conditioner, hair cream, conditioner gel, or conditioner foam.

<98> A hair treatment composition containing the cationic group-containing cellulose ether of any of the above <1> to <14>, and containing at least one treatment agent selected from a hair-coloring dye, an oxidizing agent, an alkali agent and a keratin-reducing agent.

<99> The hair treatment composition according to the above <98>, which is a hair color composition or a perm composition, and wherein the hair color composition is a hair color composition containing a dye, a hair bleach composition not containing a dye, and a composition which bleaches and dyes hair, and wherein the perm composition is a permanent wave composition, a straight perm composition or a hair relaxer composition.

<100> The hair treatment composition according to the above <98> or <99>, wherein the cationic group-containing cellulose ester is preferably a cationic group-containing cellulose ether having MS(N+) of from 0.04 to 0.60, MS(Gly) of from 0.5 to 4.0 and MS(HC) of from 0.01 to 0.10, more preferably a cationic group-containing cellulose ether having MS(N+) of from 0.04 to 0.22, MS(Gly) of from 1.0 to 3.0 and MS(HC) of from 0.01 to 0.10, and even more preferably a cationic group-containing cellulose ether having MS(N+) of from 0.12 to 0.22, MS(Gly) of from 2.1 to 2.3 and MS(HC) of from 0.02 to 0.06.

<101> The hair treatment composition according to any of the above <98> to <100>, wherein the content of the cationic group-containing cellulose ether is, in the hair treatment composition, preferably at least 0.01% by mass, more preferably at least 0.05% by mass, even more preferably at least 0.1% by mass, and is preferably at most 10% by mass, more preferably at most 5% by mass, even more preferably at most 2% by mass, and still more preferably at most 1% by mass.

<102> The hair treatment composition according to any of the above <98> to <101>, which is preferably a multi-pack composition to be used by mixing two packs or more and in which the cationic group-containing cellulose ether is incorporated in the first pack.

<103> The hair treatment composition according to any of the above <98> to <102>, wherein the content of the treatment agent is, in the hair treatment composition, preferably at least 0.1% by mass, more preferably at least 0.5% by mass, even more preferably at least 1% by mass, and is preferably at most 20% by mass, more preferably at most 15% by mass, and even more preferably at most 10% by mass.

<104> The hair treatment composition according to any of the above <98> to <103>, wherein the ratio by mass of the cationic group-containing cellulose ether to the treatment agent [cationic group-containing cellulose ether/treatment agent] is preferably at least 0.005, more preferably at least 0.01, even more preferably at least 0.02, and is preferably at most 3, more preferably at most 1, even more preferably at most 0.5, and still more preferably at most 0.2.

<105> The hair treatment composition according to any of the above <98> to <104>, wherein the hair-coloring dye is at least one selected from direct dyes and oxidation dye intermediates.

<106> The hair treatment composition according to the above <105>, wherein the direct dye is at least one selected from nitro dyes, anthraquinone dyes, acidic dyes, oil-soluble dyes and basic dyes.

<107> The hair treatment composition according to the above <105> or <106>, wherein the content of the direct dye is, in the hair treatment composition, preferably at least 0.005% by mass, more preferably at least 0.01% by mass, even more preferably at least 0.1% by mass, and is preferably at most 10% by mass, more preferably at most 5% by mass, and even more preferably at most 2% by mass.

<108> The hair treatment composition according to any of the above <105> to <107>, wherein the oxidation dye intermediate is at least one selected from precursors and couplers.

<109> The hair treatment composition according to any of the above <105> to <108>, wherein the content of the oxidation dye intermediate is, in the hair treatment composition, preferably at least 0.01% by mass, more preferably at least 0.05% by mass, even more preferably at least 0.1% by mass, still more preferably at least 0.2% by mass, and is preferably at most 10% by mass, more preferably at most 5% by mass, even more preferably at most 3% by mass, and still more preferably at most 2% by mass.

<110> The hair treatment composition according to any of the above <98> to <109>, wherein the oxidizing agent to be used in the hair color composition is preferably at least one selected from hydrogen peroxide, urea peroxide, melamine peroxide, sodium perborate, potassium perborate, sodium percarbonate and potassium percarbonate, and more preferably hydrogen peroxide.

<111> The hair treatment composition according to any of the above <98> to <109>, wherein the oxidizing agent to be used in the permanent wave agent is incorporated in the permanent wave second pack and is at least one selected from potassium bromate, sodium bromate, sodium perborate and hydrogen peroxide.

<112> The hair treatment composition according to any of the above <98> to <111>, wherein the content of the oxidizing agent is, in the hair treatment composition, preferably at least 0.1% by mass, more preferably at least 0.5% by mass, even more preferably at least 2% by mass, still more preferably at least 3% by mass, and is preferably at most 20% by mass, more preferably at most 12% by mass, even more preferably at most 9% by mass, and still more preferably at most 6% by mass.

<113> The hair treatment composition according to any of the above <98> to <112>, wherein the alkali agent is preferably at least one selected from sodium hydroxide, ammonia and its salts, alkanolamine and its salts, alkanediamine and its salt, as well as carbonates, more preferably at least one selected from ammonia and its salts, alkanolamine and its salts, and sodium hydrogencarbonate.

<114> The hair treatment composition according to any of the above <98> to <113>, wherein the content of the alkali agent is preferably at least 0.1% by mass and is at most 10% by mass.

<115> The hair treatment composition according to any of the above <98> to <114>, wherein the keratin-reducing agent is preferably at least one selected from thioglycolic acid and its derivatives, thiolactic acid and its derivatives, cysteine and its derivatives, and their salts, thioglyceryl alkyl ethers represented by the above-mentioned formula (23) and their salts, and mercaptoalkylamides represented by the above-mentioned formula (24) and their salts, and is more preferably at least one selected from thioglycolic acid, ammonium thioglycolate, glycerin thioglycolate, L-cysteine, D-cysteine, N-acetylcysteine, ammonium salts and ethanolamine salts of those cysteines, thioglyceryl alkyl ethers, mercaptoethylpropanamide, and mercaptoethylgluconamide.

<116> The hair treatment composition according to any of the above <98> to <115>, wherein the content of the keratin-reducing agent is, in the hair treatment composition, preferably at least 0.1% by mass, more preferably at least 1% by mass, even more preferably at least 3% by mass, and is preferably at most 20% by mass, more preferably at most 15% by mass, even more preferably at most 10% by mass, and still more preferably at most 8% by mass.

<117> The hair treatment composition according to any of the above <98> to <116>, which further contains water and in which the content of water is, in the hair treatment composition, preferably at least 50% by mass, more preferably at least 70% by mass, and is preferably at most 95% by mass, more preferably at most 90% by mass.

<118> The hair treatment composition according to any of the above <98> to <117>, which further contains a surfactant and in which the content of the surfactant is, in the hair treatment composition, preferably at least 0.3% by mass, more preferably at least 0.5% by mass, even more preferably at least 1% by mass, and is preferably at most 20% by mass, more preferably at most 10% by mass, even more preferably at most 5% by mass.

<119> The hair treatment composition according to the above <118>, wherein the surfactant is at least one selected from polyoxyethylene alkyl ethers, polyoxyethylene hardened castor oils, polyoxyethylene alkyl ether sulfate salts, higher fatty acids, and mono-long chain alkyltrimethylammonium salts.

<120> The hair treatment composition according to any of the above <98> to <119>, which further contains an oily agent and in which the oily agent is preferably a higher alcohol, more preferably at least one selected from cetyl alcohol and stearyl alcohol.

<121> The hair treatment composition according to the above <120>, wherein the content of the oil agent is, in the hair treatment composition, preferably at least 1% by mass, more preferably at least 3% by mass, even more preferably at least 5% by mass, and is preferably at most 30% by mass, more preferably at most 20% by mass, even more preferably at most 15% by mass.

<122> The hair treatment composition according to the above <120> or <121>, wherein the ratio by mass of the cationic group-containing cellulose ether to the oily agent [cationic group-containing cellulose ether/oily agent] is at least 0.001, more preferably at least 0.005, even more preferably at least 0.01, still more preferably at least 0.03, and is preferably at most 5, more preferably at most 1, and even more preferably at most 0.6.

<123> The hair treatment composition according to any of the above <99> to <122>, wherein the hair color composition contains the cationic group-containing cellulose ether, and at least one treatment agent selected from a hair-coloring dye, an oxidizing agent and an alkali agent.

<124> The hair treatment composition according to the above <99> or <122>, wherein the hair color composition is preferably at least one selected from one-pack hair color compositions (a) and (b) mentioned below, and multi-pack hair color composition of (c) and (d) mentioned below.

(a) One-pack hair color composition containing a hair-coloring dye and optionally an oxidizing agent.

(b) One-pack hair color composition not containing a hair-coloring dye but containing an oxidizing agent.

(c) Two-pack hair color composition composed of a first pack containing an alkali agent and/or a hair-coloring dye, and a second pack containing an oxidizing agent.

(d) Three-pack hair color composition composed of a first pack containing an alkali agent and/or a hair-coloring dye, a second pack containing an oxidizing agent, and a third pack containing an oxidation promoter.

<125> The hair treatment composition according to the above <124>, wherein the content ratio (by mass) of the first pack to the second pack [first pack/second pack] in the above two-pack hair color composition (c) is preferably from 2/8 to 6/4, more preferably from 3/7 to 5/5, even more preferably from 3.5/6.5 to 4.5/5.5.

<126> The hair treatment composition according to any of the above <122> to <124>, wherein the pH of the hair color composition is such that the pH of a one-pack color composition is from 3 to 9, the pH of the first pack of a two-pack color composition is from 8 to 13 and the second pack thereof is from 2 to 5, and the pH of the first pack of a three-pack color composition is from 8 to 13 and the pH of the second pack thereof is from 2 to 5.

<127> The hair treatment composition according to any of the above <99> to <122>, wherein the perm composition contains the cationic group-containing cellulose ether and, as treatment agents, a keratin-reducing agent, an oxidizing agent and an alkali agent.

<128> The hair treatment composition according to the above <127>, wherein the perm composition is a two-pack composition composed of a first pack that contains a keratin-reducing agent and a second pack that contains an oxidizing agent, and the usage ratio (by mass) of the first pack to the second pack [first pack/second pack] is preferably from 3/7 to 7/3, more preferably from 4/6 to 6/4, even more preferably from 4.5/5.5 to 5.5/4.5.

<129> The hair treatment composition according to the above <127> or <128>, wherein the pH of the perm composition is preferably such that the first pack has a pH of from 6 to 12 and the second pack has a pH of from 3 to 9.

<130> A hair washing method, including washing hair with the hair wash composition of any of the above <43> to <66>, then rinsing and drying the hair.

<131> A skin cleaning method, including washing a skin with the skin cleanser composition of any of the above <67> to <83>, then rinsing and drying the skin.

<132> A hair conditioning method, including washing hair with a detergent, and then applying the hair conditioner composition of any of the above <84> to <97> to the hair.

<133> A hair treating method, including treating hair with the hair treatment composition of any of the above <98> to <129> through contact therewith, then rinsing and drying the hair.

<134> Use of a composition that contains the cationic group-containing cellulose ether of any of the above <1> to <14>, a surfactant and water as a hair wash composition.

<135> Use as a hair wash composition according to the above <134>, wherein the composition further contains an oily agent.

<136> Use as a hair wash composition according to the above <134> or <135>, wherein the composition further contains any other cationic polymer than the cationic group-containing cellulose ether.

<137> Use of a composition that contains the cationic group-containing cellulose ether of any of the above <1> to <14>, a surfactant and water as a skin cleanser composition.

<138> Use of a composition that contains the cationic group-containing cellulose ether of any of the above <1> to <14>, a surfactant, an oily agent and water as a hair conditioner composition.

<139> Use of a composition that contains the cationic group-containing cellulose ether of any of the above <1> to <14>, as well as at least one treatment agent selected from a hair-coloring dye, an oxidizing agent, an alkali agent and a keratin-reducing agent, as a hair treatment composition.

EXAMPLES

In the following Production Examples, Examples and Comparative Examples, "%" means "% by mass". The group represented by the above-mentioned general formula (6) and the group represented by the above-mentioned general formula (7), where $R^{10}$ and $R^{11}$ are methyl groups, respectively, are collectively referred to as "oxypropylene group" in the following Examples, the groups where $R^{10}$ and $R^{11}$ are ethyl groups in the above-mentioned formulae (6) and (7) are collectively referred to as "oxybutylene group" and the groups where $R^{10}$ and $R^{11}$ are butyl groups in the above-mentioned formulae (6) and (7) are collectively referred to as "oxyhexylene group". Physical properties and others were measured according to the methods mentioned below.

(1) Measurement of Viscosity-Average Degree of Polymerization of Cellulose (cuprammonium process)

(1-1) Viscosity-Average Degree of Polymerization of Cellulose and CCE (i) Preparation of Solution for Measurement 0.5 g of cuprous chloride, and 20 to 30 mL of 25% aqueous ammonia were added in a measuring flask (100 mL) and completely dissolved therein, and then 1.0 g of cupric hydroxide and 25% aqueous ammonium were added thereto up to the gauge line of the flask, and then this was stirred for 3 hours until complete dissolution.

(ii) Sample Preparation 25 mg of the sample for measurement was added in a measuring flask (25 mL), and the solution prepared in the above was added thereto until the meniscus thereof could be the same as the gauge line of the flask. This was stirred for 6 hours until complete dissolution.

(iii) Measurement of Viscosity-Average Degree of Polymerization

The obtained aqueous cuprammonium solution was put into an Ubbelohde viscometer and statically left in a constant-temperature bath (20±0.1° C.) for 1 minute, and thereafter the liquid flow speed was measured. From the flow time (t (sec)) of the cuprammonium solution having a different sample concentration (g/L) and the flow time ($t_0$ (sec)) of the aqueous cuprammonium solution with no sample, the relative viscosity $\eta_r$ was calculated according to the following formula:

$$\eta_r = t/t_0$$

Next, the reduced viscosity ($\eta_{sp}/c$) at each concentration was calculated according to the following formula:

$$\eta_{sp}/c = (\eta_r - 1)/c$$

(c: sample concentration (g/dL))

Further, by extrapolating the reduced viscosity with c=0, the intrinsic viscosity [η] was calculated, and the viscosity-average degree of polymerization (n) was calculated according to the following formula:

$$n = 2000 \times [\eta]$$

In Examples, the mean degree of polymerization of CCE was considered to be the same as the mean degree of polymerization of the starting cellulose used in production.

(1-2) Viscosity-Average Degree of Polymerization of C-HPC

A sample solution was prepared in the same manner as that for preparation of the sample solution in the above (i) except that precisely-weighed C-HPC was used in place of the precisely-weighed cellulose.

The viscosity-average degree of polymerization was measured in the same manner as that in the above (ii) except that the cellulose-equivalent concentration (g/dL) was employed here as the concentration of the sample solution.

Here, the cellulose-equivalent concentration (Ccell) means the mass (g) of the cellulose skeleton moiety contained in 1 dL of the sample solution, and is defined by the following math formula:

$$C\text{cell} = u \times 162/(162 + k \times K + m \times 58)$$

[In the formula, u means the mass (g) of the precisely-weighed C-HPC used in preparing the sample solution; k and K each mean the degree of substitution and the formula weight of the cationized ethyleneoxy group in C-HPC, and m means the degree of substitution with the propylene oxy group in C-HPC.]

(2) Calculation of Degree of Substitution with Substituent, MS in CCE

The degree of substitution with a glycerol group (MS (Gly)), the degree of substitution with a cationized oxyalkylene group (MS(N+)) and the degree of substitution with a hydrocarbon group-containing group (MS(HC)) in CCE were calculated according to a system of equations of the following math formulae (1) to (3), except for the case where the hydrocarbon group-containing group is an oxypropylene group:

$$-a \times (\text{content of glycerol group (\%)}) \times MS(HC) + (74.1 - 74.1 \times (\text{content of glycerol group (\%)})) \times MS(Gly) - b \times (\text{content of glycerol group (\%)}) \times MS(N+) = 162.1 \times (\text{content of glycerol group (\%)}) \quad (1)$$

$$-a \times (\text{nitrogen content (\%)}) \times MS(HC) - 74.1 \times (\text{nitrogen content (\%)}) \times MS(Gly) + (b - b \times \text{nitrogen content (mass \%)}) \times MS(N+) = 162.1 \times (\text{nitrogen content (\%)}) \quad (2)$$

$$(a - a \times (\text{content of hydrocarbon group-containing group (\%)})) \times MS(HC) - 74.1 \times (\text{content of hydrocarbon group-containing group (\%)}) \times MS(Gly) - b \times (\text{content of hydrocarbon group-containing group (\%)}) \times MS(N+) = 162.1 \times (\text{content of hydrocarbon group-containing group (\%)}) \quad (3)$$

(In the formulae, a indicates the molecular weight of the hydrocarbon group-containing group and b indicates the molecular weight of the cationized oxyalkylene group.)

In the above-mentioned system of equations, the content of the glycerol group, the nitrogen content and the content of the hydrocarbon group-containing group each are in terms of % by mass of the glycerol group, the nitrogen that constitutes the cationized oxyalkylene group and the hydrocarbon group-containing group, which each are contained in CCE and were calculated according to the methods mentioned below.

[Measurement of Content of Glycerol Group and Hydrocarbon Group-Containing Group (% by Mass)]

The content % (by mass) of the glycerol group contained in CCE was calculated according to the Zeisel method that is known as a method of determining the mean addition molar number of the alkoxy group in a cellulose ether as described in Analytical Chemistry Vol. 51, No. 13, 2172

(1979), "15th Revised Japanese Pharmacopoeia (section of analysis method for hydroxypropyl cellulose)", etc. The procedure is shown below.

(i) One ml of n-tetradecane was added in a 25-mL measuring flask, then o-xylene was added thereto until the lower face of the liquid meniscus thereof could reach the upper edge of the gauge line of the measuring flask, and stirred to prepare an internal standard solution.

(ii) 65 mg of purified and dried CCE, and 65 mg of adipic acid were accurately metered in a 10 mL vial container, and 2 mL of the internal standard solution prepared in (i) and 2 mL of hydroiodic acid solution were added thereto and sealed up.

(iii) While stirred with a stirrer chip, the mixture in the vial container was heated with a block heater at 150° C. for 1 hour.

(iv) The upper layer (o-xylene layer) of the mixture that had been separated in two phases in the vial container was analyzed through gas chromatography to thereby quantitatively determine the glycerol group-derived isopropyl iodide, and the hydrocarbon group-containing group-derived iodide of the hydrocarbon group (for example, in case where the hydrocarbon group-containing group is an oxybutylene group, 2-butyl iodide); and from the found data, the content of the glycerol group (% by mass) in CCE and the content of the hydrocarbon group-containing group (% by mass) were calculated.

The conditions for analysis were as follows:
Column: Agilent's HP-1 (length: 30 m, inner diameter: 0.32 mm, membrane
thickness: 0.25 mm, fixed phase: 100% methylsiloxane)
Column temperature: 40° C. (5 min)→10° C./min→230° C. (5 min)
Injector temperature: 210° C.
Detector: hydrogen flame ion detector (FID)
Detector temperature: 230° C.
Amount of implantation: 1 μL
Carrier gas flow rate: helium 3.0 mL/min
[Measurement of Nitrogen Content (% by mass)] (Kjeldahl method)

100 mg of purified and dried CCE was accurately metered, to which added were 10 mL of sulfuric acid and one tablet of a decomposition promoter "KJELTABS" (by Nakayama Rika Seisakusho); and using a Kjeldahl decomposition apparatus "K-432" (by "BUCHI"), this was completely dissolved by heating at 250° C. for 30 minutes, at 300° C. for 30 minutes and at 420° C. for 80 minutes in that order. After the decomposition reaction, 30 mL of ion-exchanged water was added to the sample; and using an automatic Kjeldahl distillation/titration apparatus "K-370" (by BUCHI), this was alkalized with 40 mL of aqueous 30% sodium hydroxide solution added thereto, and then ammonia that had been liberated through distillation was collected in an aqueous 1% boric acid solution, which was then titered with 0.01 N sulfuric acid (by Wako Pure Chemicals, for quantitative analysis) to thereby determine the nitrogen content (% by mass) in CCE.

In the case where the hydrocarbon group-containing group is an oxypropylene group, not only the glycerol group but also the oxypropylene group would be converted into isopropyl iodide in the pretreatment according to the above-mentioned Zeisel method, and therefore in this case, the content of the glycerol group and that of the oxypropylene group could not be independently determined. Accordingly, in the case where the hydrocarbon group-containing group is such an oxypropylene group, the content of the oxypropylene group is first determined according to the NMR method mentioned below, and thereafter according to the method described in the above-mentioned section of "[Measurement of Content of Glycerol Group and Hydrocarbon Group-Containing Group (% by mass)], the total content of the oxypropylene group and the glycerol group is determined. From the total content, the content of the oxypropylene group determined according to the above-mentioned NMR method is subtracted to give the content of the glycerol group. For measurement of the nitrogen content (% by mass), the content of each substituent determined according to the above-mentioned method is assigned to the above-mentioned math formulae (1) to (3), and the system of equations is solved to give MS(PO), MS(Gly) and MS(N+).
[Calculation of Content (% by Mass) of Oxypropylene Group According to NMR Method]

The degree of substitution with oxypropylene group (MS (HC)) in the resultant CEE was calculated through $^1$H-NMR. The measurement method is as follows.
Apparatus: Mercury 400 (by Varian)
Observational Range: 6410.3 Hz
Data Point: 65536
Pulse Width: 45°
Pulse Delay Time: 5 sec
Integration: 128 times
Spin: No spin
Internal Standard: Sodium 3-(trimethylsilyl)propionate-d4 (TSP)
Sample for Calibration Curve: Hydroxypropyl cellulose (trade name: KLUCEL, by
Hercules, its oxypropylene group content is known: 76.15% by mass)

10 mg of purified and dried CCE was dissolved in 1 g of D20 containing the above-mentioned internal standard, and analyzed through $^1$H-NMR according to the above-mentioned measurement condition. From the signal (1.23 ppm) of the methyl group in the oxypropylene group, the content of the oxypropylene group in CCE was calculated.
(3) Evaluation of Solubility of CCE in Water 0.5 g of purified and dried CCE and 49.5 g of ion-exchanged water were put into a 50 mL columnar vial having a diameter of 32 mm, and stirred for 6 hours to give an aqueous 1% solution or 1% dispersion. The obtained aqueous 1% solution or 1% dispersion was visually evaluated for the solubility.
A: High solubility (transparent)
B: Low solubility (slightly cloudy)
C: Insoluble (cloudy)
(4) Measurement of Water Content The water content of pulp, floc cellulose and powdery cellulose was measured at a measurement temperature of 120° C., using an electronic moisture meter "MOC-120H" (by Shimadzu). About 1 g of the sample to be analyzed was analyzed with the tester, and the point at which the weight change in 30 seconds could be at most 0.1% was read as the end point of the measurement.
(5) Calculation of Degree of Crystallinity of Pulp and Powdery Cellulose Using "Rigaku R$^1$NT 2500VC X-Ray Diffractometer" (by Rigaku), the degree of crystallinity was calculated from the peak strength read on the diffraction spectrum, as measured under the condition mentioned below, according to the following math formula:

$$\text{Degree of Crystallinity } (\%) = [(I_{22.6} - I_{18.5})/I_{22.6}] \times 100$$

(In the formula, $I_{22.6}$ indicates the diffraction intensity of the lattice plane (002 plane) (diffraction angle 2θ=22.6°) of the cellulose I-type crystal in X-ray diffractiometry; and 118.5 indicates the diffraction intensity of the amorphous moiety (diffraction angle 2θ=18.5°).)
X-ray Source: Cu/Kα-radiation
Bulb Voltage: 40 kV
Bulb Current: 120 mA
Range for Measurement: 2θ=5 to 45°
Sample for Measurement: Prepared by compressing a pellet having an area of 320 mm²×thickness of 1 mm
X-ray Scan Speed: 10° s/min In case where the calculated degree of crystallinity was a negative value, the degree of crystallinity of all the samples having such a negative value was considered to be 0%.

(6) Measurement of Mean Particle Size of Cellulose

The mean particle size of powdery cellulose was measured using a laser diffraction/scattering particle sizer "LA-920" (by Horiba). As the sample to be analyzed, used was a sample dispersion prepared by adding 0.1 g of powdery cellulose to 5 mL of water followed by ultrasonic treatment for 1 minute. The volumetric basis median diameter of the sample was measured at a temperature of 25° C., and this is the mean particle size of the sample.

The mean particle size of cellulose was measured using the same measurement apparatus. Briefly, ethanol was added to cellulose and its concentration was so controlled that the transmittance thereof could fall within a range of from 70 to 95%, and then this was ultrasonically processed for 1 minute and NaOH was dissolved therein to prepare a sample dispersion.

(7) Calculation of Degree of Substitution in C-HPC

C-HPC obtained in Production Example was purified through a dialytic membrane (molecular weight cutoff: 1000), and then the aqueous solution was freeze-dried to give a purified C-HPC. The chlorine content (%) in the thus-obtained pure C-HPC was determined through elementary analysis. Assuming that the number of the cationic groups in C-HPC and the number of the counter ions, chloride ions were approximated to be the same number, from the following math formula (4), the amount of the cationized ethyleneoxy group ($-CH(Y^1)-CH(Y^2)O-$) contained in the unit mass of C-HPC (a (mol/g)) was calculated.

$$a \text{ (mol/g) (chlorine content (\%) obtained through elementary analysis)}/(35.5\times100) \quad (4)$$

According to the "Analysis Method for Hydroxypropyl Cellulose" described in Japanese Pharmacopoeia but except that the subject to be analyzed is pure C-HPC and not hydroxypropyl cellulose, the hydroxypropoxy group content (%) was determined. According to the following math formula (5), the hydroxypropoxy group content [formula weight ($OC_3H_6OH$)=75.09] (b (mol/g)) was obtained.

$$b \text{ (mol/g)=(hydroxypropoxy group content (\%) obtained through gas chromatography)}/(75.09\times100) \quad (5)$$

From the thus-obtained a and b and according to the math formulae (6) and (7) mentioned below, the degree of substitution with cationized ethyleneoxy group (k) and the degree of substitution with propyleneoxy group (m) were calculated.

$$a=k/(162+k\times K+m\times58) \quad (6)$$

$$b=m/(162+k\times K+m\times58) \quad (7)$$

[In the formulae, k and K indicate the degree of substitution with cationized ethyleneoxy group and the weight formula of the group, respectively; and m indicates the degree of substitution with propyleneoxy group.]

(8) Determination of Double Bond Position in Starting Internal Olefin

The position of the double bond in the starting internal olefin was determined through gas chromatography (hereinafter referred to as "GC"). Concretely, the internal olefin was reacted with dimethyl disulfide to provide a dithioated derivative, and then separated into the constitutive components through GC. From each peak area, the position of the double bond in the internal olefin was determined.

The apparatus and the condition for analysis were as follows:
GC apparatus: "HP6890" (by Hewlett Packard)
Column: "Ultra-Alloy-1 HT Capillary Column" 30 m×250 μm×0.15 μm (by Frontier Laboratories Ltd.)
Detector: hydrogen flame ion detector (FID)
Injection temperature: 300° C.
Detector temperature: 350° C.
He flow rate: 4.6 mL/min (9) Measurement of Mass Ratio of Hydroxy Form/Olefin Form of Internal Olefinsulfonate Salt The ratio by mass of the hydroxy form/olefin form of internal olefinsulfonate salt was measured through HPLC-MS. Concretely, the internal olefinsulfonate salt to be analyzed was separated into the hydroxy form and the olefin form though HPLC, and each form was identified through MS. From the HPLC-MS peak area of each component, the proportion of each component was determined.

The apparatus and the condition for analysis were as follows: HPLC apparatus: "Agilent Technology 1100" (by Agilent Technologies) Column: "L-Column ODS" 4.6×150 mm (by Chemicals Evaluation and Research Institute, Japan)
Sample preparation: 1/1000 dilution with methanol
Eluent A: 10 mM ammonium acetate-added water
Eluent B: 10 mM ammonium acetate-added methanol
Gradient: 0 min (A/B=30/70%)→10 min (30/70%)→55 min (0/100%)→65 min
(0/100%)→66 min (30/70%)→75 min (30/70%)
MS apparatus: "Agilent Technology 1100MS SL(G1946D)"
MS Detector: anion detector m/z 60-1600, UV 240 nm

(10) Measurement of Content of Starting Internal Olefin in Internal Olefinsulfonate Salt The content of the starting internal olefin in internal olefinsulfonate salt was measured through GC. Concretely, ethanol and petroleum ether were added to an aqueous solution of the internal olefinsulfonate salt to be analyzed, and then extracted to separate the starting internal olefin in the petroleum ether phase. From the GC peak area thereof, the olefin amount was quantified.

The apparatus and the condition for analysis were as follows:
GC apparatus: "Agilent Technology 6850" (by Agilent Technologies)
Column: "Ultra-Alloy-1HT Capillary Column" 15 m×250 μm×0.15 μm (by
Frontier Laboratories Ltd.)
Detector: hydrogen flame ion detector (FID)
Injection temperature: 300° C.
Detector temperature: 350° C.
He flow rate: 3.8 mL/min

(11) Measurement of Content of Inorganic Compound in Internal Olefinsulfonate Salt The content of the inorganic compound in internal olefinsulfonate salt was measured through potentiometric titration and neutralization titration. The content of $Na_2SO_4$ was quantified through potentiometric titration for the sulfate radical ($SO_4^{2-}$). The content of NaOH was quantified through neutralization titration with diluted hydrochloric acid.

(12) Measurement of Content of Internal Olefinsulfonate Salt with Sulfonate Group at 2-Position The bonding position of the sulfonate group in internal olefinsulfonate salt was determined through GC. Concretely, the obtained internal olefinsulfonate was reacted with trimethylsilyldiazomethane to give a methyl-esterified derivative, which was then separated into the constitutive components through GC. Based on the peak area ratio by mass of each component, the content of the internal olefinsulfonate salt with the sulfonate group positioned at the 2-position was calculated.

The apparatus and the condition for analysis were as follows:
GC apparatus: "Agilent Technology 6850" (by Agilent Technologies)
Column: "HP-1 Capillary Column" 30 m×320 μm×0.25 μm (by Agilent Technologies)
Detector: hydrogen flame ion detector (FID)
Injection temperature: 300° C.
Detector temperature: 300° C.
He flow rate: 1.0 mL/min
Oven: 60° C. (0 min)→10° C./min→300° C. (10 min)

(13) Measurement of Viscosity

A formulated composition was put into a 50-mL columnar vial having a diameter of 32 mm, and conditioned at 25° C. in a constant-temperature water tank, and then using a B-type viscometer "TVB-10M" (by Toki Sangyo), the viscosity of the sample was measured at a temperature of 25° C. and at a rotation speed of 30 rpm with Rotor No. 1, 2, 3 or 4.

The rotor to be used was so selected that the measurement results could fall within a range of from 20 to 90% of the upper limit of the viscosity detection range with the rotor used.

(14) Measurement of pH 5 g of a formulated composition and 45 g of ion-exchanged water were put into a 50-mL columnar vial having a diameter of 32 mm, stirred and uniformly dispersed, and then using a pH meter "PH METER HM-30G" (by DKK-TOA Corporation), the pH of the sample was measured.

Production Example A

Production of Starting Internal Olefin A 7000 g (28.9 mol) of 1-hexadecanol (Kalcol 6098, by Kao) and 700 g (10% by mass relative to the starting alcohol) of γ-alumina (by STREM Chemicals, Inc.) serving as a solid acid catalyst were put into a flask equipped with a stirrer, and while nitrogen (7000 mL/min) was circulated inside the system at 280° C. with stirring, this was reacted for 3 hours. After the reaction, the alcohol conversion was 100%, and the C16 internal olefin purity was 99.6%. The obtained, crude internal olefin was transferred into a distillation flask and distilled therein at 136 to 160° C./4.0 mmHg to give an internal olefin having a carbon number of 16 and having an olefin purity of 100%. The double bond distribution of the thus-obtained internal olefin was: 1.8% by mass at C1, 30.4% by mass at C2, 23.9% by mass at C3, 16.8% by mass at C4, 12.0% by mass at C5, 7.4% by mass at C6, and 7.8% by mass at C7 and C8 in total.

Production Example B

Production of Starting Internal Olefin B 7000 g (25.9 mol) of 1-octadecanol (Kalcol 8098, by Kao) and 700 g (10% by mass relative to the starting alcohol) of γ-alumina (by STREM Chemicals, Inc.) serving as a solid acid catalyst were put into a flask equipped with a stirrer, and while nitrogen (7000 mL/min) was circulated inside the system at 280° C. with stirring, this was reacted for 10 hours. After the reaction, the alcohol conversion was 100%, and the C18 internal olefin purity was 98.2%. The obtained, crude internal olefin was transferred into a distillation flask and distilled therein at an internal temperature of 148 to 158° C./0.5 mmHg to give an internal olefin having a carbon number of 18 and having an olefin purity of 100%. The double bond distribution of the thus-obtained internal olefin was: 0.8% by mass at C1, 31.3% by mass at C2, 22.9% by mass at C3, 15.5% by mass at C4, 10.8% by mass at C5, 7.2% by mass at C6, 5.3% by mass at C7, and 6.2% by mass at C8 and C9 in total.

Production Example C

Production of Starting Internal Olefin C 7000 g (28.9 mol) of 1-hexadecanol (Kalcol 6098, by Kao) and 700 g (10% by mass relative to the starting alcohol) of γ-alumina (by STREM Chemicals, Inc.) serving as a solid acid catalyst were put into a flask equipped with a stirrer, and while nitrogen (7000 mL/min) was circulated inside the system at 280° C. with stirring, this was reacted for 5 hours. After the reaction, the alcohol conversion was 100%, and the C16 internal olefin purity was 99.7%. The obtained, crude internal olefin was transferred into a distillation flask and distilled therein at 136 to 160° C./4.0 mmHg to give an internal olefin having a carbon number of 16 and having an olefin purity of 100%. The double bond distribution of the thus-obtained internal olefin was: 0.5% by mass at C1, 16.5% by mass at C2, 15.4% by mass at C3, 16.4% by mass at C4, 17.2% by mass at C5, 14.2% by mass at C6, and 19.8% by mass at C7 and C8 in total.

Production Example D

Production of Starting Internal Olefin D 7000 g (25.9 mol) of 1-octadecanol (Kalcol 8098, by Kao) and 1050 g (15% by mass relative to the starting alcohol) of γ-alumina (by STREM Chemicals, Inc.) serving as a solid acid catalyst were put into a flask equipped with a stirrer, and while nitrogen (7000 mL/min) was circulated inside the system at 285° C. with stirring, this was reacted for 13 hours. After the reaction, the alcohol conversion was 100%, and the C18 internal olefin purity was 98.5%. The obtained, crude internal olefin was transferred into a distillation flask and distilled therein at 148 to 158° C./0.5 mmHg to give an internal olefin having an olefin purity of 100% and having a carbon number of 18. The double bond distribution of the thus-obtained internal olefin was: 0.7% by mass at C1, 16.9% by mass at C2, 15.9% by mass at C3, 16.0% by mass at C4, 14.7% by mass at C5, 11.2% by mass at C6, 10.2% by mass at C7, and 14.6% by mass at C8 and C9 in total.

Production Example E

Production of Starting Internal Olefin E 6000 g (35.6 mol) of 1-dodecene (Linealene 12, by Idemitsu Kosan) and 180 g (3.0% by mass relative to the starting 1-dodecene) of β-zeolite (by Zeolyst) serving as a solid acid catalyst were put into a flask equipped with a stirrer, and while nitrogen (200 mL/min) was circulated inside the system at 120° C. with stirring, this was reacted for 12.5 hours. After the reaction, the internal isomerization of α-olefin was 98.4%, and the C12 internal olefin purity was 92.1%. The obtained, crude internal olefin was transferred into a distillation flask and distilled therein at 134 to 138° C./75.0 to 78.8 mmHg to give an internal olefin having a carbon number of 12 and having an olefin purity of 100%. The double bond distribution of the thus-obtained internal olefin was: 0.5% by mass at C1, 33.1% by mass at C2, 23.7% by mass at C3, 21.2% by mass at C4, 15.0% by mass at C5, and 6.8% by mass at C6.

Production Example 1

Production of Internal Olefinsulfonate Salt (1)

Using a thin-film sulfonation reactor (inner diameter 14 mind), length 4 m), the internal olefin having a carbon number of 16 obtained in Production Example A was sulfonated with sulfur trioxide gas having an $SO_3$ concentration of 2.8% by volume, while cooling water at 20° C. was kept circulated through the outer jacket. The reaction molar ratio of $SO_3$/internal olefin was set at 1.09.

Thus obtained, the sulfonated product was added to an aqueous alkali solution to which sodium hydroxide had been added in an amount to be 1.2 molar times the theoretical acid value (AV), and neutralized therein with stirring at 30° C. for 1 hour. The neutralized product was heated for one hour in an autoclave at 160° C. for hydrolysis, thereby giving a crude product of sodium internal olefinsulfonate having a carbon number of 16.

300 g of the obtained crude product was transferred into a separating funnel, 300 mL of ethanol was added thereto, and petroleum ether was added thereto in an amount of 300 mL every time for extraction to remove the oil-soluble impurities. During this, the inorganic compound (the main component is salt cake) that had been precipitated in the oil/water interface through ethanol addition was also separated and removed from the aqueous phase through the oil/water separation operation. This operation was repeated three times. The aqueous phase was evaporated into dryness to give a sodium internal olefinsulfonate having a carbon number of 16 (internal olefinsulfonate salt (1)). The ratio by mass of hydroxy form/olefin form, and the content of the internal olefinsulfonate salt with the sulfonate radical at the 2-position are shown in Table A-1. The content of the starting internal olefin was less than 100 ppm (less than the detection limit in GC) and the content of the inorganic compound was 1.9% by mass.

Production Example 2

Production of Internal Olefinsulfonate (2)

A sodium internal olefinsulfonate having a carbon number of 18 (internal olefinsulfonate (2)) was obtained under the same condition as that in Production Example 1 except that the internal olefin having a carbon number of 18 obtained in Production Example B was used. The ratio by mass of hydroxy form/olefin form, and the content of the internal olefinsulfonate salt with the sulfonate radical at the 2-position are shown in Table A-1. The content of the starting internal olefin was less than 100 ppm (less than the detection limit in GC) and the content of the inorganic compound was 0.9% by mass.

Production Example 3

Production of Internal Olefinsulfonate (3)

A sodium internal olefinsulfonate having a carbon number of 16 (internal olefinsulfonate (3)) was obtained under the same condition as that in Production Example 1 except that the internal olefin having a carbon number of 16 obtained in Production Example C was used. The ratio by mass of hydroxy form/olefin form, and the content of the internal olefinsulfonate salt with the sulfonate radical at the 2-position are shown in Table A-1. The content of the starting internal olefin was less than 100 ppm (less than the detection limit in GC) and the content of the inorganic compound was 1.3% by mass.

Production Example 4

Production of Internal Olefinsulfonate (4)

A sodium internal olefinsulfonate having a carbon number of 18 (internal olefinsulfonate (4)) was obtained under the same condition as that in Production Example 1 except that the internal olefin having a carbon number of 18 obtained in Production Example D was used. The ratio by mass of hydroxy form/olefin form, and the content of the internal olefinsulfonate salt with the sulfonate radical at the 2-position are shown in Table A-1. The content of the starting internal olefin was less than 100 ppm (less than the detection limit in GC) and the content of the inorganic compound was 1.7% by mass.

Production Example 5

Production of Internal Olefinsulfonate (5)

A sodium internal olefinsulfonate having a carbon number of 12 (internal olefinsulfonate (5)) was obtained under the same condition as that in Production Example 1 except that the internal olefin having a carbon number of 12 obtained in Production Example E was used. The ratio by mass of hydroxy form/olefin form, and the content of the internal olefinsulfonate salt with the sulfonate radical at the 2-position are shown in Table A-1. The content of the starting internal olefin was less than 100 ppm (less than the detection limit in GC) and the content of the inorganic compound was 0.2% by mass.

TABLE A-1

| | | Starting internal olefin | | | Internal olefinsulfonate salt | |
|---|---|---|---|---|---|---|
| | Production example | Carbon number | 2-positioned double bond (%) | HAS/IOS (by mass) | Content of internal olefinsulfonate salt with sulfonate radical at 2-position | |
| Production Example 1 | Internal olefinsulfonate (1) | A | C16 | 30.4 | 80/20 | 20.3 |
| Production Example 2 | Internal olefinsulfonate (2) | B | C18 | 31.3 | 80/20 | 21.4 |
| Production Example 3 | Internal olefinsulfonate (3) | C | C16 | 16.5 | 80/20 | 9.3 |
| Production Example 4 | Internal olefinsulfonate (4) | D | C18 | 16.9 | 80/20 | 9.6 |
| Production Example 5 | Internal olefinsulfonate (5) | E | C12 | 33.1 | 80/20 | 21.0 |

Production Example 6

Production of C-HPC (1)

(1) Chipping Step

A sheet-like wood pulp (Tembec's Biofloc HV+, mean degree of polymerization 1770, degree of crystallization 74%, water content 7.0%) was pelletized into chips of from 3 to 5 mm square, using a sheet pelletizer "SGG-220" (by Horai).

(2) Cationization Step 100 g of the chip-like pulp obtained in the above (1) was mixed with 60.8 g (0.65 mol/AGU 1 mol) of an aqueous glycidyl trimethylammonium chloride solution (by Sakamoto Yakuhin Kogyo, water content 20%, purity at least 90%) (hereinafter referred to as "GMAC") in a mortar, and then put into a batch-type shaking mill "MB-1" (by Chuo Kakohki: container total volume 3.5 L, 13 SUS304 rods of ϕ30 mm and length 218 mm each having a circular cross section, packing ratio 57%). This was ground for 12 minutes (frequency 20 Hz, amplitude 8 mm, temperature 30 to 70° C.) to give a powdery mixture of cellulose and GMAC.

The obtained powdery mixture was further mixed with 14.8 g (0.2 mol/AGU 1 mol) of an aqueous 48% sodium hydroxide solution in a mortar, and then put into the above-mentioned batch-type shaking mill. Under the same condition as above, this was ground for 120 minutes to give 175.6 g of a cationized cellulose.

(4) Hydroxypropylation Step

A kneader containing therein 100 g of the cationized cellulose obtained after ripening (unneutralized/unpurified product) was heated up to 70° C., and 40.8 g of propylene oxide (2.0 mol/AGU 1 mol, Kanto Chemical's special grade chemical) was dropwise added thereto with stirring, and reacted for 8 hours until propylene oxide was consumed and the reflux stopped.

After the reaction, the mixture was taken out of the kneader to be 140.8 g of a pale brown, crude C-HPC powder. 10.0 g of the crude C-HPC powder was sampled and neutralized with acetic acid. For the purpose of determining the degree of substitution with propyleneoxy group and that with cationized ethyleneoxy group, the neutralized product was purified through a dialytic membrane (molecular weight cutoff: 1000), and then the aqueous solution was freeze-dried to give a purified C-HPC (1).

The chlorine content in the thus-obtained pure C-HPC (1) was 3.0%, as determined through elementary analysis. The hydroxypropoxy group content, as determined according to the above-mentioned "Analysis Method for Hydroxypropyl Cellulose", was 32.5%. The degree of substitution with cationized ethyleneoxy group and that with propyleneoxy group were 0.22 and 1.1, respectively. The mean degree of polymerization of the pure C-HPC (1) was 539.

The results are shown in Table A-2.

Production Example 7

Production of C-HPC (2)

(1) Production Step for Low-Crystalline Powdery Cellulose

A sheet-like wood pulp (Tembec's Biofloc HV+, mean degree of polymerization 1770, degree of crystallization 74%, water content 7.0%) was pelletized into chips of from 3 to 5 mm square, using a shredder "MSX2000-IVP440F" (by Meiko Shokai). Subsequently, this was dried under reduced pressure at 50° C. for 12 hours to give chips of dry pulp (water content 0.4%).

Next, 100 g of the resultant chip-like dry pulp put into the same batch-type shaking mill as that used in Production Example 1. This was ground at a frequency of 20 Hz, at an amplitude of 8 mm, and at a temperature of from 30 to 70° C. for 35 minutes to give a powdery cellulose (degree of crystallinity 0%, mean degree of polymerization 836, mean particle size 52 water content 1.0%).

(2) Cationization Step 46.9 g of GMAC (0.4 mol/AGU 1 mol) was added to 100 g of the powdery cellulose obtained in the above (1), and mixed in a mortar. Subsequently, 5.14 g of aqueous 48% sodium hydroxide solution (0.1 mol/AGU 1 mol) and 18 g of ion-exchanged water were added thereto and mixed. The resultant mixture was put into the same kneader as that used in Production Example 1, and stirred at 50° C. for 4 hours to give 170 g of a cationized cellulose.

(3) Hydroxypropylation Step

The cationized cellulose obtained in the above (2) was heated at 70° C., and with stirring, 4.7 g of aqueous 48% sodium hydroxide solution (0.1 mol/AGU 1 mol) and 16.4 g of ion-exchanged water were added thereto. Further, 101 g of propylene oxide (3.0 mol/AGU 1 mol) was dropwise added thereto with stirring, and reacted for 24 hours until propylene oxide was consumed and the reflux stopped. After the reaction, the cellulose kept a flowable powdery state. 10.0 g of the reaction product was sampled and neutralized with acetic acid to give a pale brown solid. The neutralized product was purified through a dialytic membrane (molecular weight cutoff: 1000), and then the aqueous solution was freeze-dried to give a purified C-HPC (2).

The chlorine content in the thus-obtained pure C-HPC (2) was 2.1%, as determined through elementary analysis. The hydroxypropoxy group content was 49.2%. The degree of substitution with cationized ethyleneoxy group and that with propyleneoxy group were calculated to be 0.18 and 2.0, respectively. The mean degree of polymerization of the pure C-HPC (2) was 832. The results are shown in Table A-2.

TABLE A-2

| | | Mean degree of polymerization | Degree of substitution with cationized EO*1 | Degree of substitution with PO*2 |
|---|---|---|---|---|
| Production Example 6 | C-HPC (1) | 539 | 0.22 | 1.1 |
| Production Example 7 | C-HPC (2) | 832 | 0.18 | 2.0 |

*1Degree of substitution with cationized ethyleneoxy group
*2Degree of substitution with propyleneoxy group Example A1

Production of CCE (1)

(1) Step of Cutting Treatment, Drying Treatment and Grinding Treatment of Cellulose A sheet-like wood pulp (Tembec's Biofloc XV18, mean degree of polymerization, 1977) was pelletized into chips with a sheet pelletizer "SGG-220" (by Horai). Subsequently, this was dried at 80° C. for 12 hours to give a chip-like dry pulp having a water content of 0.18%. The obtained chip-like cellulose was put into an extreme mill "MX-1200XTM Model" (by Waring, total volume 150 mL), and ground at a rotation speed of 24000 rpm and at 20° C. for 30 seconds to give a floc cellulose (mean degree of polymerization 1977).

(2) Glycerolation Step 584 g of dimethyl sulfoxide (by Wako Pure Chemicals) and 116 g of tetra(n-butyl)ammonium fluoride trihydrate (TBAF, by Kanto Chemical) were put into a three-neck round-bottomed flask, and uniformly dissolved. To this, added was 7.0 g of the floc cellulose obtained in the above, and stirred at room temperature for 1 hour and dissolved. Further, 2.4 g of finely-powdered potassium hydroxide (1.0 mol/AGU 1 mol) was added thereto and well dispersed. After this was heated up to 70° C. and while the reaction liquid was kept stirred in a nitrogen stream atmosphere, 248 g of a 50% dimethyl sulfoxide solution of 124 g of glycidol (38.8 mol/AGU 1 mol) was added thereto, taking 5 hours. After the addition, this was further kept stirred for 1 hour at 70° C., and the reaction was then stopped.

Subsequently, the reaction solution as cooled to room temperature, centrifuged, and the resultant supernatant liquid was put into a mixed solvent (10 L, 25° C.) of ion-exchanged water/acetone/methanol=2/4/4 (by volume), and the precipitated polymer was taken out through filtration, washed with 1 L of the above-mentioned mixed solvent of ion-exchanged water/acetone/methanol, and then dried under reduced pressure (80° C., 0.03 kPa, 12 hours) to give 13 g of a glycerolated cellulose as a white solid.

(3) Step of Cationization, and Hydrocarbon Group-Containing Group Addition Reaction 1089 g of an aqueous 70% dimethyl sulfoxide solution was put into a three-neck round-bottomed flask, 11 g of the glycerolated cellulose obtained in the above was added thereto, stirred at room temperature and uniformly dissolved. Subsequently, 1.8 g of an aqueous 20% sodium hydroxide solution (0.25 mol/AGU 1 mol) was added thereto and stirred at room temperature. Subsequently, 24 g (3.51 mol/AGU 1 mol) of glycidyltrimethylammonium chloride (by Sakamoto Yakuhin Kogyo, water content 20% by mass, purity of the residual component after water removal, 90% or more) serving as a cationizing agent and 4.2 g (1.63 mol/AGU 1 mol) of 1,2-butylene oxide (by Tokyo Chemical Industry) serving as a hydrocarbon group-containing group-introducing agent were added to the glycerolated cellulose solution with stirring, then heated up to 50° C. and reacted for 5 hours. Subsequently, the reaction liquid was neutralized with acetic acid, then put into 10 L of ethanol/isopropanol (7/3 by volume), and the precipitated polymer was collected through filtration, washed with 1 L of the above-mentioned ethanol/isopropanol mixed solvent, and dried under reduced pressure (80° C., 0.03 kPa, 12 hours) to give 1.7 g of CCE (1) as a white solid.

The amounts added of the glycerolating agent, the cationizing agent and the hydrocarbon group-containing group-introducing agent are shown in Table A-3. In addition, the evaluation results of the resultant CCE (1) are shown in Table A-4.

Example A2

Production of CCE (2)

CCE (2) was produced in the same manner as in Example A1, except that the starting cellulose of the sheet-like wood pulp was changed to Tembec's Biofloc XV having a mean degree of polymerization 1694 and that the amounts added of the glycerolating agent, the cationizing agent and the hydrocarbon group-containing group-introducing agent were changed to those shown in Table A-3. The evaluation results are shown in Table A-4.

Example A3

Production of CCE (3)

In Example A1, the starting cellulose of the sheet-like wood pulp was changed to Tembec's Biofloc HV+ having a mean degree of polymerization 1550, and further, the step of chipping and flocculating cellulose of the step (1) was changed to the following cellulose powdering step.

(1) Step of Cutting Treatment, Drying Treatment and Grinding Treatment of Cellulose A sheet-like wood pulp (Tembec's Biofloc HV+, mean degree of polymerization, 1550) was processed into chips with a shredder "MSX2000-IVP440F" (by Meiko Shokai). Subsequently, this was dried at 80° C. for 12 hours to give chips of dry pulp having a water content 0.18%.

Next, 920 g of the resultant chip-like dry pulp put into a batch-type shaking mill (by Chuo Kakohki, FV-10: container total volume 33 L, 63 SUS304 rods of ϕ30 mm and length 510 mm each having a circular cross section, packing ratio 70% by volume). This was ground for 10 minutes at a frequency 20 Hz at an amplitude 8 mm and at a temperature 10 to 40° C. to give 890 g of a cellulose powder (mean degree of polymerization 1233).

CCE (3) was produced in the same manner as in Example A1 except that the resultant cellulose powder was used and the amounts added of the glycerolating agent, the cationizing agent and the hydrocarbon group-containing group-introducing agent were changed to those shown in Table A-3. The evaluation results are shown in Table A-4.

Examples A4 to A8

Production of CCE (4) to (8)

CCE (4) to CCE (8) were produced in the same manner as in Example A3, except that the amount added of the glycerolating agent, that of the cationizing agent and that of the hydrocarbon group-containing group-introducing agent were changed as in Table A-3. The evaluation results are shown in Table A-4.

Example A9

Production of CCE (9)

CCE (9) was produced in the same manner as in Example A2, except that the amount added of the glycerolating agent, that of the cationizing agent and that of the hydrocarbon group-containing group-introducing agent were changed as in Table A-3. The evaluation results are shown in Table A-4.

Examples A10 to A18

Production of CCE (10) to (18)

CCE (10) to CCE (18) were produced in the same manner as in Example A3, except that the amount added of the glycerolating agent, that of the cationizing agent and that of the hydrocarbon group-containing group-introducing agent were changed as in Table A-3. The evaluation results are shown in Table A-4.

Examples A19 to A20

Production of CCE (19) to (20)

CCE (19) to CCE (20) were produced in the same manner as in Example A1, except that the starting cellulose of the sheet-like wood pulp was changed to cotton linter pulp (by Shandong High-Density Chemical Fiber Co., Ltd., PCS2400, mean degree of polymerization 2005) and that the amounts added of the glycerolating agent, the cationizing agent and the hydrocarbon group-containing group-introducing agent were changed to those shown in Table A-3. The evaluation results are shown in Table A-4.

Examples A21 to A22

Production of CCE (21) to (22)

CCE (21) to CCE (22) were produced in the same manner as in Example A3, except that the amounts added of the glycerolating agent, the cationizing agent and the hydrocarbon group-containing group-introducing agent were changed to those shown in Table A-3. The evaluation results are shown in Table A-4.

Example A23

Production of CCE (23)

(1) Step of Cutting Treatment, Drying Treatment and Grinding Treatment of Cellulose As a starting cellulose, a sheet-like wood pulp (Tembec's Biofloc HV+, mean degree of polymerization, 1550) was used, and this was shredded into chips with a shredder "MSX2000-IVP440F" (by Meiko Shokai). Subsequently, this was dried at 80° C. for 12 hours to give a chip-like dry pulp having a water content of 0.18%.

Next, 920 g of the obtained, chip-like dry pulp was put into a batch-type shaking mill "FV-10" (by Chuo Kakohki: container total volume 33 L, 63 SUS304 rods of $\phi$30 mm and length 510 mm each having a circular cross section, packing ratio 70 vol %). At a frequency of 20 Hz, a total amplitude of 8 mm and a temperature of from 10 to 40° C., this was ground for 10 minutes to give 890 g of a cellulose powder (mean degree of polymerization 1233).

(2) Glycerolation reaction 167 g of dimethyl sulfoxide (by Wako Pure Chemicals) and 33 g of tetra(n-butyl)ammonium fluoride trihydrate (TBAF, by Kanto Chemical) were put into a three-neck round-bottomed flask, and uniformly dissolved. To this, added was 3.0 g of the powdery cellulose obtained in the above, and stirred at room temperature for 1 hour and dissolved. Further, 1.0 g of finely-powdered potassium hydroxide (1.0 mol/AGU 1 mol) was added thereto and well dispersed. After this was heated up to 70° C. and while the reaction liquid was kept stirred in a nitrogen stream atmosphere, 15 g of a 50% dimethyl sulfoxide solution of 7.3 g (5.3 mol/AGU 1 mol) of glycidol was added thereto, taking 5 hours. After the addition, this was further kept stirred for 1 hour at 70° C., and the reaction was then stopped.

Subsequently, the reaction solution was cooled down to room temperature, and centrifuged, and then the resulting supernatant was put into a mixed solvent of ion-exchanged water/acetone/methanol=2/4/4 (by volume) (5 L, 25° C.). The precipitated polymer was collected through filtration, then washed with 0.5 L of the above-mentioned ion-exchanged water/acetone/methanol mixed solvent, and thereafter dried under reduced pressure to give 3.5 g of a glycerolated cellulose as a white solid.

(3) Cationization reaction 67 g of an aqueous 70% dimethyl sulfoxide solution was put into a three-neck round-bottomed flask, and 1 g of the glycerolated cellulose obtained in the above was added thereto, stirred at room temperature and dissolved uniformly. Subsequently, 0.070 g of an aqueous 48% sodium hydroxide solution (0.20 mol/AGU 1 mol) was added thereto and stirred at room temperature. Subsequently, 0.47 g (0.59 mol/AGU 1 mol) of glycidyltrimethylammonium chloride (by Sakamoto Yakuhin Kogyo, water content 20% by mass, purity of the residual component after water removal, 90% or more) serving as a cationizing agent was added thereto with stirring, heated up to 50° C., and reacted for 5 hours. Subsequently, the reaction liquid was neutralized with acetic acid, put into 1 L of ethanol/isopropanol (7/3 by volume, 25° C.), and the precipitated polymer was collected through filtration, washed with 0.1 L of the above-mentioned ethanol/isopropanol mixed solvent, and dried under reduced pressure to give 1.0 g of a cellulose ether containing a glycerol group and a cationic group, as a white solid. MS(N+) and MS(Gly) of the resultant cellulose ether containing a glycerol group and a cationic group were calculated according to the above-mentioned method for calculation of substitution degree, and MS(Gly)=0.64, and MS(N+)=0.10.

(4) Reaction for Introduction of Hydrocarbon Group-Containing Group 67 g of an aqueous 70% dimethyl sulfoxide solution was put into a three-neck round-bottomed flask, and 1.0 g of the cellulose ether containing a glycerol group and a cationic group that had been obtained in the above was added thereto, stirred at room temperature and uniformly dissolved. Subsequently, 0.070 g (0.20 mol/AGU 1 mol) of an aqueous 48% sodium hydroxide solution was added thereto and stirred at room temperature. Subsequently, as a hydrocarbon group-containing group-introducing agent, 0.060 g (0.25 mol/AGU 1 mol) of propylene oxide was added thereto with stirring, heated up to 50° C. and reacted for 5 hours. The reaction liquid was neutralized with acetic acid, put into 1 L of ethanol/isopropanol (7/3 by volume, 25° C.), and the precipitated polymer was collected through filtration, washed with 0.1 L of the above-mentioned ethanol/isopropanol mixed solvent, and dried under reduced pressure to give 0.90 g of CCE (23) as a white solid.

Examples A24 to A27

Production of CCE (24) to (27)

CCE (24) to (27) were produced in the same manner as in Example A23, except that the amounts added of the glycerolating agent, the cationizing agent and the hydrocarbon group-containing group-introducing agent were changed to those shown in Table A-3. The evaluation results are shown in Table A-4.

Example A28

Production of CCE (28)

CCE (28) was produced in the same manner as in Example A1, except that the amounts added of the glycerolating agent, the cationizing agent and the hydrocarbon group-containing group-introducing agent were changed to those shown in Table A-3. The evaluation results are shown in Table A-4.

Examples A29 to A31

Production of CCE (29) to (31)

CCE (29) to (31) were produced in the same manner as in Example A2, except that the amounts added of the glycerolating agent, the cationizing agent and the hydrocarbon group-containing group-introducing agent were changed to those shown in Table A-3. The evaluation results are shown in Table A-4.

Examples A32 to A45, A59

Production of CCE (32) to (45), (59)

CCE (32) to (45) and (59) were produced in the same manner as in Example A2, except that the amounts added of the glycerolating agent, the cationizing agent and the hydrocarbon group-containing group-introducing agent were changed to those shown in Table A-3. The evaluation results are shown in Table A-4.

Examples A46 to A48, A58

Production of CCE (46) to (48), (58)

CCE (46) to (48) and (58) were produced in the same manner as in Example A1, except that the compound shown in Table A-3 was used as the hydrocarbon group-containing group-introducing agent and that the amounts added of the glycerolating agent, the cationizing agent and the hydrocarbon group-containing group-introducing agent were changed to those shown in Table A-3. The evaluation results are shown in Table A-4.

Examples A49 to A57

Production of CCE (49) to (57)

CCE (49) to (57) were produced in the same manner as in Example A3, except that the amounts added of the glycerolating agent, the cationizing agent and the hydrocarbon group-containing group-introducing agent were changed to those shown in Table A-3. The evaluation results are shown in Table A-4.

Comparative Examples A1, A2 A7

Production of Cationized Polysaccharides (1), (2), (7)

Cationized polysaccharides (1), (2) and (7) were produced in the same manner as in Example A3, except that 1,2-butylene oxide was not added and that the amounts added of the glycerolating agent and the cationizing agents were changed to those shown in Table A-3. The evaluation results are shown in Table A-4.

Comparative Examples A3 to A6

Production of Cationized Polysaccharides (3) to (6)

Cationized polysaccharides (3) to (6) were produced in the same manner as in Example A3, except that the compound shown in Table A-3 was used as the hydrocarbon group-containing group-introducing agent and that the amounts added of the glycerolating agent, the cationizing agent and the hydrocarbon group-containing group-introducing agent were changed to those shown in Table A-3. The evaluation results are shown in Table A-4.

TABLE A-3

| | | Added amount of glycerolating agent (mol/AGU*[1]) | Added amount of cationizing agent (mol/AGU*[1]) | Added amount of hydrocarbon group-containing group-introducing agent (mol/AGU*[1]) | Hydrocarbon group-containing group-introducing agent |
|---|---|---|---|---|---|
| Example A1 | CCE(1) | 38.8 | 3.51 | 1.63 | 1,2-butylene oxide |
| Example A2 | CCE(2) | 38.8 | 3.51 | 1.63 | 1,2-butylene oxide |
| Example A3 | CCE(3) | 23.0 | 0.40 | 0.21 | 1,2-butylene oxide |
| Example A4 | CCE(4) | 31.3 | 1.82 | 0.44 | 1,2-butylene oxide |

TABLE A-3-continued

| | | Added amount of glycerolating agent (mol/AGU*1) | Added amount of cationizing agent (mol/AGU*1) | Added amount of hydrocarbon group-containing group-introducing agent (mol/AGU*1) | Hydrocarbon group-containing group-introducing agent |
|---|---|---|---|---|---|
| Example A5 | CCE(5) | 25.0 | 1.77 | 0.50 | 1,2-butylene oxide |
| Example A6 | CCE(6) | 7.7 | 0.59 | 0.76 | 1,2-butylene oxide |
| Example A7 | CCE(7) | 8.5 | 0.88 | 0.83 | 1,2-butylene oxide |
| Example A8 | CCE(8) | 5.3 | 0.59 | 0.50 | 1,2-butylene oxide |
| Example A9 | CCE(9) | 8.5 | 0.88 | 0.83 | 1,2-butylene oxide |
| Example A10 | CCE(10) | 7.7 | 0.59 | 0.38 | 1,2-butylene oxide |
| Example A11 | CCE(11) | 4.4 | 0.59 | 0.50 | 1,2-butylene oxide |
| Example A12 | CCE(12) | 16.6 | 1.20 | 0.47 | 1,2-butylene oxide |
| Example A13 | CCE(13) | 41.7 | 2.18 | 0.44 | 1,2-butylene oxide |
| Example A14 | CCE(14) | 25.0 | 1.30 | 0.44 | 1,2-butylene oxide |
| Example A15 | CCE(15) | 41.7 | 1.30 | 0.44 | 1,2-butylene oxide |
| Example A16 | CCE(16) | 25.0 | 2.17 | 0.44 | 1,2-butylene oxide |
| Example A17 | CCE(17) | 41.7 | 0.59 | 0.83 | 1,2-butylene oxide |
| Example A18 | CCE(18) | 5.3 | 0.59 | 0.17 | 1,2-butylene oxide |
| Example A19 | CCE(19) | 14.2 | 0.88 | 0.50 | 1,2-butylene oxide |
| Example A20 | CCE(20) | 14.2 | 0.88 | 0.83 | 1,2-butylene oxide |
| Example A21 | CCE(21) | 41.7 | 2.72 | 0.44 | 1,2-butylene oxide |
| Example A22 | CCE(22) | 16.6 | 0.80 | 0.47 | 1,2-butylene oxide |
| Example A23 | CCE(23) | 5.3 | 0.59 | 0.25 | propylene oxide |
| Example A24 | CCE(24) | 5.3 | 0.59 | 0.15 | propylene oxide |
| Example A25 | CCE(25) | 7.7 | 0.59 | 0.17 | propylene oxide |
| Example A26 | CCE(26) | 7.7 | 0.59 | 0.25 | propylene oxide |
| Example A27 | CCE(27) | 7.7 | 0.59 | 0.38 | propylene oxide |
| Example A28 | CCE(28) | 38.8 | 3.17 | 1.60 | 1,2-epoxyhexane |
| Example A29 | CCE(29) | 40.0 | 5.71 | 0.83 | 1,2-butylene oxide |
| Example A30 | CCE(30) | 40.0 | 7.14 | 0.83 | 1,2-butylene oxide |
| Example A31 | CCE(31) | 40.0 | 35.00 | 0.83 | 1,2-butylene oxide |
| Example A32 | CCE(32) | 40.0 | 45.50 | 1.25 | 1,2-butylene oxide |
| Example A33 | CCE(33) | 40.0 | 60.00 | 2.08 | 1,2-butylene oxide |
| Example A34 | CCE(34) | 12.5 | 19.67 | 1.25 | 1,2-butylene oxide |
| Example A35 | CCE(35) | 12.5 | 28.33 | 1.25 | 1,2-butylene oxide |
| Example A36 | CCE(36) | 12.5 | 33.67 | 1.25 | 1,2-butylene oxide |
| Example A37 | CCE(37) | 50.0 | 40.00 | 1.25 | 1,2-butylene oxide |
| Example A38 | CCE(38) | 50.0 | 45.50 | 1.25 | 1,2-butylene oxide |
| Example A39 | CCE(39) | 50.0 | 52.50 | 1.25 | 1,2-butylene oxide |
| Example A40 | CCE(40) | 25.0 | 40.67 | 1.25 | 1,2-butylene oxide |
| Example A41 | CCE(41) | 12.5 | 20.04 | 0.83 | 1,2-butylene oxide |
| Example A42 | CCE(42) | 40.0 | 4.71 | 0.83 | 1,2-butylene oxide |
| Example A43 | CCE(43) | 40.0 | 6.42 | 0.83 | 1,2-butylene oxide |
| Example A44 | CCE(44) | 12.5 | 6.00 | 1.67 | 1,2-butylene oxide |
| Example A45 | CCE(45) | 12.5 | 20.00 | 1.67 | 1,2-butylene oxide |
| Example A46 | CCE(46) | 40.0 | 2.00 | 1.50 | 1,2-epoxypentane |
| Example A47 | CCE(47) | 40.0 | 2.00 | 1.50 | n-butyl glycidyl ether |
| Example A48 | CCE(48) | 38.8 | 0.40 | 3.17 | 1-bromoheptane |
| Example A49 | CCE(49) | 7.7 | 0.59 | 1.50 | 1,2-butylene oxide |
| Example A50 | CCE(50) | 25.0 | 0.59 | 0.83 | 1,2-butylene oxide |
| Example A51 | CCE(51) | 19.3 | 0.59 | 0.50 | 1,2-butylene oxide |
| Example A52 | CCE(52) | 6.2 | 0.59 | 0.50 | 1,2-butylene oxide |
| Example A53 | CCE(53) | 41.7 | 1.77 | 0.50 | 1,2-butylene oxide |
| Example A54 | CCE(54) | 19.3 | 1.50 | 0.50 | 1,2-butylene oxide |
| Example A55 | CCE(55) | 31.3 | 2.72 | 0.44 | 1,2-butylene oxide |
| Example A56 | CCE(56) | 31.3 | 3.55 | 0.44 | 1,2-butylene oxide |
| Example A57 | CCE(57) | 7.7 | 1.50 | 0.50 | 1,2-butylene oxide |
| Example A58 | CCE(58) | 4.0 | 1.44 | 0.13 | 1,2-butylene oxide |
| Example A59 | CCE(59) | 12.5 | 18.71 | 0.83 | 1,2-butylene oxide |
| Comparative Example A1 | Cationized polysaccharide (1) | 8.0 | 0.80 | 0.00 | — |
| Comparative Example A2 | Cationized polysaccharide (2) | 8.0 | 1.60 | 0.00 | — |
| Comparative Example A3 | Cationized polysaccharide (3) | 7.7 | 0.59 | 3.80 | 1,2-butylene oxide |
| Comparative Example A4 | Cationized polysaccharide (4) | 7.7 | 0.59 | 0.23 | dodecyl chloride |
| Comparative Example A5 | Cationized polysaccharide (5) | 7.7 | 0.59 | 0.12 | n-octyl chloride |
| Comparative Example A6 | Cationized polysaccharide (6) | 7.7 | 0.59 | 0.12 | C18-GE *2 |
| Comparative Example A7 | Cationized polysaccharide (7) | 8.0 | 0.40 | 0.00 | — |

*1 molar number relative to 1 mol of anhydrous glucose unit (anhydroglucose unit)
*2 stearyl glycidyl ether

TABLE A-4

| | | Degree of substitution with glycerol group [MS(Gly)] | Degree of substitution with cationized alkyleneoxy group [MS(N+)] | Degree of substitution with hydrocarbon group-containing group MS(HC)] | Hydrocarbon group-containing group | Cation charge density [mmol/g] | Mean degree of polymerization [n] | Solubility in water |
|---|---|---|---|---|---|---|---|---|
| Example A1 | CCE(1) | 2.22 | 0.20 | 0.03 | oxybutylene group | 0.54 | 1977 | A |
| Example A2 | CCE(2) | 2.20 | 0.19 | 0.03 | oxybutylene group | 0.54 | 1694 | A |
| Example A3 | CCE(3) | 2.00 | 0.20 | 0.03 | oxybutylene group | 0.58 | 1233 | A |
| Example A4 | CCE(4) | 2.47 | 0.19 | 0.05 | oxybutylene group | 0.50 | 1233 | A |
| Example A5 | CCE(5) | 1.92 | 0.18 | 0.04 | oxybutylene group | 0.54 | 1233 | A |
| Example A6 | CCE(6) | 1.24 | 0.15 | 0.04 | oxybutylene group | 0.54 | 1233 | A |
| Example A7 | CCE(7) | 1.00 | 0.12 | 0.05 | oxybutylene group | 0.47 | 1233 | A |
| Example A8 | CCE(8) | 0.64 | 0.10 | 0.03 | oxybutylene group | 0.44 | 1233 | A |
| Example A9 | CCE(9) | 0.88 | 0.13 | 0.04 | oxybutylene group | 0.52 | 1694 | A |
| Example A10 | CCE(10) | 1.24 | 0.14 | 0.02 | oxybutylene group | 0.51 | 1233 | A |
| Example A11 | CCE(11) | 0.79 | 0.13 | 0.02 | oxybutylene group | 0.54 | 1233 | A |
| Example A12 | CCE(12) | 1.54 | 0.16 | 0.02 | oxybutylene group | 0.53 | 1233 | A |
| Example A13 | CCE(13) | 3.74 | 0.26 | 0.06 | oxybutylene group | 0.53 | 1233 | A |
| Example A14 | CCE(14) | 1.98 | 0.16 | 0.03 | oxybutylene group | 0.48 | 1233 | A |
| Example A15 | CCE(15) | 2.18 | 0.14 | 0.04 | oxybutylene group | 0.40 | 1233 | A |
| Example A16 | CCE(16) | 1.99 | 0.22 | 0.03 | oxybutylene group | 0.64 | 1233 | A |
| Example A17 | CCE(17) | 2.17 | 0.06 | 0.05 | oxybutylene group | 0.18 | 1233 | A |
| Example A18 | CCE(18) | 0.73 | 0.21 | 0.03 | oxybutylene group | 0.84 | 1233 | A |
| Example A19 | CCE(19) | 1.12 | 0.10 | 0.07 | oxybutylene group | 0.38 | 2005 | A |
| Example A20 | CCE(20) | 1.04 | 0.11 | 0.10 | oxybutylene group | 0.42 | 2005 | A |
| Example A21 | CCE(21) | 3.40 | 0.28 | 0.06 | oxybutylene group | 0.60 | 1233 | A |
| Example A22 | CCE(22) | 1.53 | 0.11 | 0.03 | oxybutylene group | 0.37 | 1233 | A |
| Example A23 | CCE(23) | 0.64 | 0.10 | 0.06 | oxyxpropylene group | 0.44 | 1233 | A |
| Example A24 | CCE(24) | 0.64 | 0.09 | 0.08 | oxyxpropylene group | 0.40 | 1233 | A |
| Example A25 | CCE(25) | 1.12 | 0.09 | 0.04 | oxyxpropylene group | 0.34 | 1233 | A |
| Example A26 | CCE(26) | 1.12 | 0.10 | 0.02 | oxyxpropylene group | 0.38 | 1233 | A |
| Example A27 | CCE(27) | 1.24 | 0.12 | 0.01 | oxyxpropylene group | 0.44 | 1233 | A |
| Example A28 | CCE(28) | 1.85 | 0.27 | 0.03 | oxyhexylene group | 0.79 | 1977 | A |
| Example A29 | CCE(29) | 1.73 | 0.36 | 0.03 | oxybutylene group | 1.03 | 1694 | A |
| Example A30 | CCE(30) | 1.82 | 0.44 | 0.03 | oxybutylene group | 1.21 | 1694 | A |
| Example A31 | CCE(31) | 1.23 | 0.46 | 0.03 | oxybutylene group | 1.42 | 1694 | A |
| Example A32 | CCE(32) | 2.18 | 0.53 | 0.03 | oxybutylene group | 1.31 | 1694 | A |
| Example A33 | CCE(33) | 2.22 | 0.57 | 0.03 | oxybutylene group | 1.37 | 1694 | A |
| Example A34 | CCE(34) | 1.04 | 0.59 | 0.04 | oxybutylene group | 1.78 | 1694 | A |
| Example A35 | CCE(35) | 1.18 | 0.60 | 0.03 | oxybutylene group | 1.75 | 1694 | A |
| Example A36 | CCE(36) | 1.12 | 0.46 | 0.03 | oxybutylene group | 1.45 | 1694 | A |
| Example A37 | CCE(37) | 1.82 | 0.56 | 0.04 | oxybutylene group | 1.46 | 1694 | A |
| Example A38 | CCE(38) | 1.89 | 0.62 | 0.04 | oxybutylene group | 1.55 | 1694 | A |
| Example A39 | CCE(39) | 1.66 | 0.68 | 0.03 | oxybutylene group | 1.74 | 1694 | A |
| Example A40 | CCE(40) | 1.32 | 0.71 | 0.03 | oxybutylene group | 1.92 | 1694 | A |
| Example A41 | CCE(41) | 0.89 | 0.55 | 0.02 | oxybutylene group | 1.76 | 1694 | A |
| Example A42 | CCE(42) | 1.94 | 0.32 | 0.03 | oxybutylene group | 0.90 | 1694 | A |
| Example A43 | CCE(43) | 1.78 | 0.40 | 0.03 | oxybutylene group | 1.12 | 1694 | A |
| Example A44 | CCE(44) | 1.06 | 0.18 | 0.02 | oxybutylene group | 0.67 | 1694 | A |
| Example A45 | CCE(45) | 1.20 | 0.29 | 0.03 | oxybutylene group | 0.98 | 1694 | A |
| Example A46 | CCE(46) | 1.68 | 0.24 | 0.10 | oxypentylene group | 0.73 | 1977 | A |
| Example A47 | CCE(47) | 1.39 | 0.24 | 0.05 | n-butyl group | 0.79 | 1977 | A |
| Example A48 | CCE(48) | 1.08 | 0.24 | 0.09 | n-heptyl group | 0.84 | 1977 | A |
| Example A49 | CCE(49) | 1.24 | 0.13 | 0.07 | oxybutylene group | 0.47 | 1233 | A |
| Example A50 | CCE(50) | 1.92 | 0.06 | 0.05 | oxybutylene group | 0.19 | 1233 | A |
| Example A51 | CCE(51) | 1.37 | 0.06 | 0.05 | oxybutylene group | 0.22 | 1233 | A |
| Example A52 | CCE(52) | 1.11 | 0.11 | 0.03 | oxybutylene group | 0.42 | 1233 | A |
| Example A53 | CCE(53) | 2.17 | 0.17 | 0.04 | oxybutylene group | 0.48 | 1233 | A |
| Example A54 | CCE(54) | 1.37 | 0.15 | 0.04 | oxybutylene group | 0.52 | 1233 | A |
| Example A55 | CCE(55) | 1.87 | 0.23 | 0.03 | oxybutylene group | 0.68 | 1233 | A |
| Example A56 | CCE(56) | 2.38 | 0.31 | 0.04 | oxybutylene group | 0.80 | 1233 | A |
| Example A57 | CCE(57) | 0.79 | 0.26 | 0.05 | oxybutylene group | 0.99 | 1233 | A |
| Example A58 | CCE(58) | 2.07 | 0.16 | 0.05 | oxybutylene group | 0.47 | 1977 | A |
| Example A59 | CCE(59) | 0.90 | 0.46 | 0.03 | oxybutylene group | 1.53 | 1694 | A |
| Comparative Example A1 | Cationized polysaccharide (1) | 1.31 | 0.14 | — | — | 0.50 | 1233 | A |
| Comparative Example A2 | Cationized polysaccharide (2) | 1.31 | 0.24 | — | — | 0.81 | 1233 | A |
| Comparative Example A3 | Cationized polysaccharide (3) | 1.24 | 0.11 | 0.21 | oxybutylene group | 0.39 | 1233 | C |
| Comparative Example A4 | Cationized polysaccharide (4) | 0.78 | 0.11 | 0.01 | n-dodecyl group | 0.46 | 1233 | A |

TABLE A-4-continued

|  |  | Degree of substitution with glycerol group [MS(Gly)] | Degree of substitution with cationized alkyleneoxy group [MS(N+)] | Degree of substitution with hydrocarbon group-containing group MS(HC)] | Hydrocarbon group-containing group | Cation charge density [mmol/g] | Mean degree of polymerization [n] | Solubility in water |
|---|---|---|---|---|---|---|---|---|
| Comparative Example A5 | Cationized polysaccharide (5) | 1.00 | 0.12 | 0.04 | n-octyl group | 0.47 | 1233 | A |
| Comparative Example A6 | Cationized polysaccharide (6) | 0.92 | 0.15 | 0.03 | stearyl group | 0.57 | 1233 | C |
| Comparative Example A7 | Cationized polysaccharide (7) | 1.31 | 0.07 | — | — | 0.26 | 1233 | A |

Evaluation of Hair Wash Composition

Examples A60 to A90

Production and Evaluation of Hair Shampoo (Production)

Using any of CCE (1) to (31), and as surfactants, sodium polyoxyethylene alkylsulfate (Kao's trade name "Emal 170J" (aqueous 70% solution, mean addition molar number of oxyethylene groups: 1, alkyl chain length: C10-16), coconut oil fatty acid amide propylcarbobetaine (Kao's trade bane "Amphitol 55AB" (aqueous 30% solution)) and coconut oil fatty acid monoethanolamide (Kawaken Fine Chemical's trade name "Amizol CME") and according to an ordinary method, hair shampoos were prepared so that the effective content of each component therein could be as in Table A-5. Concretely, CCE was dissolved in water to prepare a 2% polymer solution. Separately, the other components than the polymer were taken in a beaker, heated at 80° C., then stirred and uniformly dissolved, and the polymer solution was added thereto, uniformly mixed, cooled, and finally water that had been evaporated away by heating was replenished to give a hair shampoo.

(Evaluation)

A composition comprising the components mentioned below was taken in a beaker, heated at 80° C., mixed, and after its uniform dissolution was confirmed, this was cooled to give a plain shampoo. Hair tresses (20 g) were washed with the obtained plain shampoo. The washed hair tresses were well wetted with warm water at 35 to 40° C., then again washed with the hair shampoo (0.5 g) having the composition shown in Table A-5, and rinsed with warm water (35 to 40° C.). The thus-treated hair tresses were used as those for evaluation. Five panelists evaluated the smoothness property and its sustained feeling (smootheness and the long-lasting smoothness) and the coated feeling in rinsing the hair tresses, according to the evaluation criteria and the evaluation methods mentioned below.

(Composition of Plain Shampoo)

| (Components) | (%) |
|---|---|
| Sodium polyoxyethylene laurylether sulfate (Emal E-27C) (42.0% as Emal E-27C (by Kao, active ingredient 27%)) | 11.3 |
| Coconut oil fatty acid N-methylethanolamide (Aminone C-11S (by Kao)) | 3.0 |
| Citric acid | 0.2 |
| Methylparaben | 0.3 |
| Pure water | balance |
| Total | 100.0 |

(Evaluation Criteria)

Smoothness:

7: Excellent smoothness with no friction.

6: Good smoothness with extremely little friction.

5: Good smoothness with little friction.

4: Relatively good smoothness with relatively little friction.

3: Average (based on the smoothness in Comparative Example A14).

2: Poor smoothness with feeling of squeakiness.

1: No smoothness at all with feeling of serious squeakiness.

Long-Lasting Smoothness:

7: smoothness was long-lasting for 50 seconds or more.

6: smoothness was long-lasting for 30 seconds or more but less than 50 seconds.

5: smoothness was long-lasting for 20 seconds or more but less than 30 seconds.

4: smoothness was long-lasting for 10 seconds or more but less than 20 seconds.

3: smoothness was long-lasting for 5 seconds or more but less than 10 seconds.

2: smoothness was long-lasting for 1 second or more but less than 5 seconds.

1: smoothness was long-lasting for less than 1 second.

Coated Feeling:

7: Extremely excellent coated feeling.

6: Excellent coated feeling.

5: Good coated feeling.

4: Relatively good coated feeling.
3: Average (based on the coated feeling in Comparative Example A8).
2: Poor coated feeling.
1: No coated feeling at all.
(Evaluation Method)

The scores of the evaluation results made by the five panelists were averaged to give the score point of each sample.

Comparative Examples A8 to A14

Production and Evaluation of Hair Shampoo

Using any of the cationized polysaccharides (1) to (6), and cationized hydroxyethyl cellulose (Kao's POIZ C-80M) and in the same manner as in Example A60, hair shampoos as in Table A-5 were prepared and evaluated. The results are shown in Table A-5.

TABLE A-5

| Hair wash composition | Type of polymer | Polymer | Sodium polyoxyethylene (1) alkyl ether sulfate*2 | Coconut oil fatty acid monoethanol-amide*3 | Coconut oil fatty acid amide propylbetaine*4 | Sodium chloride | pH regulator | Pure water |
|---|---|---|---|---|---|---|---|---|
| Example A60 | CCE(1) | 0.3 | 13.0 | 0.3 | 1.5 | 0.8 | adequate dose | balance |
| Example A61 | CCE(2) | 0.3 | 13.0 | 0.3 | 1.5 | 0.8 | | |
| Example A62 | CCE(3) | 0.3 | 13.0 | 0.3 | 1.5 | 0.8 | | |
| Example A63 | CCE(4) | 0.3 | 13.0 | 0.3 | 1.5 | 0.8 | | |
| Example A64 | CCE(5) | 0.3 | 13.0 | 0.3 | 1.5 | 0.8 | | |
| Example A65 | CCE(6) | 0.3 | 13.0 | 0.3 | 1.5 | 0.8 | | |
| Example A66 | CCE(7) | 0.3 | 13.0 | 0.3 | 1.5 | 0.8 | | |
| Example A67 | CCE(8) | 0.3 | 13.0 | 0.3 | 1.5 | 0.8 | | |
| Example A68 | CCE(9) | 0.3 | 13.0 | 0.3 | 1.5 | 0.8 | | |
| Example A69 | CCE(10) | 0.3 | 13.0 | 0.3 | 1.5 | 0.8 | | |
| Example A70 | CCE(11) | 0.3 | 13.0 | 0.3 | 1.5 | 0.8 | | |
| Example A71 | CCE(12) | 0.3 | 13.0 | 0.3 | 1.5 | 0.8 | | |
| Example A72 | CCE(13) | 0.3 | 13.0 | 0.3 | 1.5 | 0.8 | | |
| Example A73 | CCE(14) | 0.3 | 13.0 | 0.3 | 1.5 | 0.8 | | |
| Example A74 | CCE(15) | 0.3 | 13.0 | 0.3 | 1.5 | 0.8 | | |
| Example A75 | CCE(16) | 0.3 | 13.0 | 0.3 | 1.5 | 0.8 | | |
| Example A76 | CCE(17) | 0.3 | 13.0 | 0.3 | 1.5 | 0.8 | | |
| Example A77 | CCE(18) | 0.3 | 13.0 | 0.3 | 1.5 | 0.8 | | |
| Example A78 | CCE(19) | 0.3 | 13.0 | 0.3 | 1.5 | 0.8 | | |
| Example A79 | CCE(20) | 0.3 | 13.0 | 0.3 | 1.5 | 0.8 | | |
| Example A80 | CCE(21) | 0.3 | 13.0 | 0.3 | 1.5 | 0.8 | | |
| Example A81 | CCE(22) | 0.3 | 13.0 | 0.3 | 1.5 | 0.8 | | |
| Example A82 | CCE(23) | 0.3 | 13.0 | 0.3 | 1.5 | 0.8 | | |
| Example A83 | CCE(24) | 0.3 | 13.0 | 0.3 | 1.5 | 0.8 | | |
| Example A84 | CCE(25) | 0.3 | 13.0 | 0.3 | 1.5 | 0.8 | | |
| Example A85 | CCE(26) | 0.3 | 13.0 | 0.3 | 1.5 | 0.8 | | |
| Example A86 | CCE(27) | 0.3 | 13.0 | 0.3 | 1.5 | 0.8 | | |
| Example A87 | CCE(28) | 0.3 | 13.0 | 0.3 | 1.5 | 0.8 | | |
| Example A88 | CCE(29) | 0.3 | 13.0 | 0.3 | 1.5 | 0.8 | | |
| Example A89 | CCE(30) | 0.3 | 13.0 | 0.3 | 1.5 | 0.8 | | |
| Example A90 | CCE(31) | 0.3 | 13.0 | 0.3 | 1.5 | 0.8 | | |
| Comparative Example A8 | Cationized polysaccharide (1) | 0.3 | 13.0 | 0.3 | 1.5 | 0.8 | adequate dose | balance |
| Comparative Example A9 | Cationized polysaccharide (2) | 0.3 | 13.0 | 0.3 | 1.5 | 0.8 | | |
| Comparative Example A10 | Cationized polysaccharide (3) | 0.3 | 13.0 | 0.3 | 1.5 | 0.8 | | |
| Comparative Example A11 | Cationized polysaccharide (4) | 0.3 | 13.0 | 0.3 | 1.5 | 0.8 | | |
| Comparative Example A12 | Cationized polysaccharide (5) | 0.3 | 13.0 | 0.3 | 1.5 | 0.8 | | |
| Comparative Example A13 | Cationized polysaccharide (6) | 0.3 | 13.0 | 0.3 | 1.5 | 0.8 | | |
| Comparative Example A14 | C-HEC*1 | 0.3 | 13.0 | 0.3 | 1.5 | 0.8 | | |

| Hair wash composition | Evaluation results | | |
|---|---|---|---|
| | Smoothness | Long-lasting smoothness | Coated feeling |
| Example A60 | 6.6 | 7 | 7 |
| Example A61 | 6.6 | 6.6 | 6.4 |
| Example A62 | 6 | 6 | 6 |
| Example A63 | 5.4 | 5.4 | 6 |

TABLE A-5-continued

|  |  |  |  |
|---|---|---|---|
| Example A64 | 6 | 6 | 6 |
| Example A65 | 5.6 | 5.6 | 6 |
| Example A66 | 5.6 | 5.6 | 6 |
| Example A67 | 5.6 | 5.6 | 6 |
| Example A68 | 5.6 | 5.6 | 6 |
| Example A69 | 5.6 | 5.6 | 6 |
| Example A70 | 5 | 5 | 5 |
| Example A71 | 5 | 5.2 | 5.4 |
| Example A72 | 5 | 5 | 5 |
| Example A73 | 5 | 5.6 | 5.4 |
| Example A74 | 5 | 5 | 5.2 |
| Example A75 | 5 | 5 | 5 |
| Example A76 | 4 | 4.6 | 4.2 |
| Example A77 | 5 | 5 | 5 |
| Example A78 | 5 | 5 | 5 |
| Example A79 | 5 | 5 | 5 |
| Example A80 | 5.2 | 5.2 | 5.4 |
| Example A81 | 5 | 5.6 | 5 |
| Example A82 | 5 | 5 | 4.6 |
| Example A83 | 5 | 5 | 4.6 |
| Example A84 | 5 | 5 | 4.6 |
| Example A85 | 5 | 4.6 | 4.6 |
| Example A86 | 5.2 | 4.2 | 5 |
| Example A87 | 5 | 5.4 | 5 |
| Example A88 | 4 | 4 | 5 |
| Example A89 | 4 | 4 | 5.4 |
| Example A90 | 4 | 4 | 6 |
| Comparative Example A8 | 4.2 | 4.4 | 3 |
| Comparative Example A9 | 3.4 | 3.4 | 2.6 |
| Comparative Example A10 | 2.4 | 2.4 | 2 |
| Comparative Example A11 | 5 | 4.6 | 3.6 |
| Comparative Example A12 | 5 | 4.6 | 3.6 |
| Comparative Example A13 | 2.6 | 3 | 2 |
| Comparative Example A14 | 3 | 3 | 2 |

*1Cationized hydroxyethyl cellulose: Kao's trade name: POIZ C-80M, degree of substitution with cationized alkyleneoxy group: 0.23
*2Kao's Emal 170S (active ingredient 70%), 18.6% added
*3Kawaken Fine Chemical's Amizol CME
*4Kao's Amphitol 55AB (active ingredient 30%), 5.0% added From Table A-5, it is known that the hair wash composition using any of CCE (1) to (31) of the present invention can give an excellent smoothness and its long-lasting smoothness and a good coated feeling in rinsing.

Examples A91 to A106, Comparative Example A14

Production and Evaluation of Hair Shampoo (Production)

In the same manner as in Example A60 and using any of CCE (29), (30) and (32) to (45), prepared here were hair shampoos each comprising the active ingredients shown in Table A-6.

(Evaluation)

The hair shampoos were evaluated in the same manner as in Example A60. The finger combability and the softness in rinsing were evaluated according to the following evaluation criteria.

(Evaluation Criteria)

Finger Combability

7: Extremely excellent finger combability.

6: Extremely good finger combability.

5: Good finger combability.

4: Relatively good finger combability.

3: Average (based on the finger combability in Comparative Example A14).

2: Poor finger combability.

1: Extremely bad finger combability.

Softness:

7: excellently soft.

6: extremely soft.

5: soft.

4: relatively soft.

3: Average (based on the softness in Comparative Example A14).

2: hard.

1: Extremely hard.

TABLE A-6

| Hair Wash Composition | Type of Polymer | Polymer | Sodium polyoxy-ethylene (1) alkyl ether sulfate*1 | Coconut oil fatty acid mono-ethanol-amide *2 | Coconut oil fatty acid amide propyl-betaine *3 | Sodium chloride | pH regulator | Pure water | Smooth-ness | Long-lasting smooth-ness | Finger comb-ability | Soft-ness |
|---|---|---|---|---|---|---|---|---|---|---|---|---|
| Example A91 | CCE(32) | 0.21 | 13.0 | 0.3 | 1.5 | 0.8 | adequate dose | balance | 4 | 4 | 3.6 | 5.6 |
| Example A92 | CCE(33) | 0.21 | 13.0 | 0.3 | 1.5 | 0.8 | | | 4.6 | 5 | 4 | 6 |
| Example A93 | CCE(34) | 0.21 | 13.0 | 0.3 | 1.5 | 0.8 | | | 3.6 | 3.6 | 3.6 | 4.6 |
| Example A94 | CCE(35) | 0.21 | 13.0 | 0.3 | 1.5 | 0.8 | | | 3.6 | 3.6 | 3.6 | 5.6 |
| Example A95 | CCE(36) | 0.21 | 13.0 | 0.3 | 1.5 | 0.8 | | | 4.6 | 4.6 | 4 | 5.6 |
| Example A96 | CCE(37) | 0.21 | 13.0 | 0.3 | 1.5 | 0.8 | | | 4 | 4 | 4 | 6 |
| Example A97 | CCE(38) | 0.21 | 13.0 | 0.3 | 1.5 | 0.8 | | | 3.6 | 3.6 | 4 | 6 |
| Example A98 | CCE(39) | 0.21 | 13.0 | 0.3 | 1.5 | 0.8 | | | 3.6 | 3.6 | 3.6 | 4.6 |
| Example A99 | CCE(40) | 0.21 | 13.0 | 0.3 | 1.5 | 0.8 | | | 3.6 | 3.6 | 3.6 | 5 |
| Example A100 | CCE(41) | 0.21 | 13.0 | 0.3 | 1.5 | 0.8 | | | 3.6 | 4 | 3.6 | 4 |
| Example A101 | CCE(42) | 0.21 | 13.0 | 0.3 | 1.5 | 0.8 | | | 4 | 4.6 | 3.6 | 4.6 |
| Example A102 | CCE(43) | 0.21 | 13.0 | 0.3 | 1.5 | 0.8 | | | 4 | 4 | 4 | 5.6 |
| Example A103 | CCE(44) | 0.21 | 13.0 | 0.3 | 1.5 | 0.8 | | | 5 | 5 | 4 | 5 |
| Example A104 | CCE(45) | 0.21 | 13.0 | 0.3 | 1.5 | 0.8 | | | 3.6 | 4 | 4 | 4 |
| Example A105 | CCE(29) | 0.21 | 13.0 | 0.3 | 1.5 | 0.8 | | | 3.6 | 4 | 4 | 5 |
| Example A106 | CCE(30) | 0.21 | 13.0 | 0.3 | 1.5 | 0.8 | | | 3.6 | 4 | 4 | 6 |

*1 Kao's Emal 170S (active ingredient 70%), 18.6% added
*2 Kawaken Fine Chemical's Amizol CME
*3 Kao's Amphitol 55AB (active ingredient 30%), 5.0% added From Table A-6, it is known that the hair shampoo (hair wash composition) using any of CCE (29), (30) and (32) to (45) of the present invention can give an excellent smoothness property and its long-lasting smoothness, and finger combability and softness in rinsing.

Example A107

Body Shampoo

A body shampoo having the composition mentioned below was produced according to an ordinary method.

Both hands were wetted, 0.5 mL of the produced body shampoo was applied to the flats of both hands, bubbled, then the both hands were rinsed with running water for 10 seconds, the droplets were wiped away from the hands with a towel, and after dried, the skin touch was evaluated.

As a result, the skin washed with the body shampoo and dried had an excellent moisturizing feeling.

| (Components) | (%) |
|---|---|
| Lauric acid | 8.6 |
| Myristic acid | 8.4 |
| Palmitic acid | 2.5 |
| Sodium polyoxyethylene alkyl ether sulfate *1 | 2.9 |
| Glycerin | 1.9 |

| (Components) | (%) |
|---|---|
| Propylene glycol | 1.2 |
| Coconut oil fatty acid amide propylbetaine *2 | 0.9 |
| CCE (4) | 0.3 |
| Potassium hydroxide (to make pH 9.6) | adequate dose |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: Kao's "Amphitol 55AB" (active ingredient 30%) (In the above composition, the content is in terms of coconut oil fatty acid amide propylbetaine.)

Example A108

Body Shampoo

A body shampoo having the composition mentioned below was produced according to an ordinary method, and evaluated in the same manner as in Example A107. As a result, the skin washed with the body shampoo and dried had an excellent moisturizing feeling.

| (Components) | (%) |
| --- | --- |
| Sodium polyoxyethylene alkyl ether sulfate *1 | 10.0 |
| Coconut oil fatty acid amide propylbetaine *2 | 1.5 |
| Coconut oil fatty acid monoethanolamide | 1.0 |
| Glycerin | 2.0 |
| Sodium chloride | 1.0 |
| CCE (4) | 0.3 |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: Kao's "Amphitol 55AB" (active ingredient 30%) (In the above composition, the content is in terms of coconut oil fatty acid amide propylbetaine.)

Example A109

Body Shampoo

A body shampoo having the composition mentioned below was produced according to an ordinary method, and evaluated in the same manner as in Example A107. As a result, the skin washed with the body shampoo and dried had an excellent moisturizing feeling.

| (Components) | (%) |
| --- | --- |
| Potassium lauroylsarcosine *1 | 6.0 |
| Sodium polyoxyethylene alkyl ether sulfate *2 | 3.3 |
| Propylene glycol | 3.2 |
| Coconut oil fatty acid amide propylbetaine *3 | 2.8 |
| Glycol distearate | 1.0 |
| Coconut oil fatty acid diethanolamide | 0.7 |
| CCE (4) | 0.3 |
| Fragrance, Preservative | adequate dose |
| pH regulator (to make pH 6.0) | adequate dose |
| Pure water | balance |
| Total | 100.0 |

*1: Nikko Chemicals' NIKKOL Sarcosinate LK-30 (active ingredient 30%) (In the above composition, the content is in terms of potassium lauroylsarcosine.)
*2: Kao's Emal 270J (active ingredient 70%) (In the above composition, the content is in terms of sodium polyoxyethylene alkyl ether sulfate.)
*3: Kao's Amphitol 55AB (active ingredient 30%) (In the above composition, the content is in terms of coconut oil fatty acid amide propylbetaine.)

Example A110

Face Wash

A face wash having the composition mentioned below was produced, and evaluated in the same manner as in Example A107. As a result, the skin washed with the face wash and dried had an excellent moisturizing feeling.

| (Components) | (%) |
| --- | --- |
| Sodium cocoylmethyltaurine *1 | 1.4 |
| Lauric acid | 28.2 |
| Myristic acid | 2.8 |
| Palmitic acid | 3.1 |
| Polyethylene glycol-32 *2 | 2.0 |
| Glycerin | 16.0 |
| CCE (4) | 0.3 |
| Fragrance, Preservative | adequate dose |
| pH regulator (to make pH 9.0) | adequate dose |
| Pure water | balance |
| Total | 100.0 |

*1: Nikko Chemical's NIKKOL CMT-30 (active ingredient 30%) (In the above composition, the content is in terms of sodium cocoylmethyltaurine.)
*2: NOF's PEG #1500

Examples B1 to B100

Production and Evaluation of Hair Shampoo

Using any of CCE (1) to (3), (5), (6), (8), (10), (13), (15), (27) to (30), (41), (43) and (45) to (59) as the component (A), a hair shampoo was prepared to have the composition shown in Tables B-1 to B-9, according to an ordinary method.

Concretely, the component (A) was dissolved or uniformly dispersed in water, adequate amounts of water and the surfactant (B) were taken in a beaker, and uniformly mixed under heat at 60° C., and then cooled down to 50° C. The oily agent (C) was added thereto, uniformly mixed, and cooled down to 40° C. The pearl agent was added thereto, stirred and emulsified for 30 minutes and cooled. Finally, water that had been evaporated away by heating was replenished, and the pH of the composition was measured. Using a pH regulator (aqueous 50% citric acid solution), the pH was controlled to be 5.

The compositions of Examples B60 to B91 were prepared as follows: The component (A) was dissolved or uniformly dispersed in water, then adequate amount of water and the surfactant (B) were put into a beaker, heated up to 60° C. and uniformly mixed, and the oily agent (C) was added thereto, uniformly mixed and cooled down to 40° C. The pearl agent was added thereto, emulsified with stirring for 30 minutes, and cooled. Finally, water that had been evaporated away by heating was replenished, and the pH of the composition was measured. Using a pH regulator (aqueous 50% citric acid solution), the pH was controlled to be 5.

Hair tresses were washed with the plain shampoo shown below, then fully wetted with warm water at 35 to 40° C., 0.5 g of the shampoo of Examples B1 to B100 was applied thereto, and the hair tresses were thus shampooed therewith for 1 minute. Subsequently, the hair tresses were rinsed with warm water for 30 seconds, water was wiped away with a towel, the hair tresses were then combed and dried with warm air from a hair drier, and combed for final finish to give the hair tresses for evaluation.

Five panelists evaluated the hair tresses in point of the finger-combability in hair washing, the smoothness and the long lasting smoothness in rinsing, and the moist feeling and the uniformity after drying, according to the evaluation criteria and the evaluation methods mentioned below. The evaluation results are shown in Tables B-1 to B-9. The uniformity after drying means that the feeling from the hair root to the hair tip of hair tresses is uniform.

The composition of Comparative Example B1 is given a standard score 3, and the compositions given a mean score of at least 3.4 by the five panelists can be said to have obviously excellent performance in point of the evaluation item.

(Composition of Plain Shampoo)

| Components) | (%) |
| --- | --- |
| Na polyoxyethylene laurylether sulfate (42% as Kao's Emal E-27C (active ingredient 27%)) | 11.3 |

-continued

| Components) | (%) |
|---|---|
| Coconut oil fatty acid N-methylethanolamide (Kao's Aminone C-11S) | 3.0 |
| Citric acid | 0.2 |
| Methylparaben | 0.3 |
| Pure water | balance |
| Total | 100.0 |

(Production of Plain Shampoo)

The components were put into a beaker, heated up to 80° C., mixed and uniformly dissolved. After the dissolution was confirmed, this was cooled to give a plain shampoo.

(Evaluation Criteria, Evaluation Methods)

Finger Combability in Washing
  5: Extremely good finger combability.
  4: Good finger combability.
  3: Average (based on the finger combability in Comparative Example B1).
  2: Bad finger combability.
  1: Extremely bad finger combability.

Smoothness in Rinsing
  5: Extremely good smoothness.
  4: Good smoothness.
  3: Average (based on the smoothness in Comparative Example B1).
  2: Bad smoothness.
  1: Extremely bad smoothness.

Long-Lasting Smoothness:
  5: Extremely good long-lasting smoothness.
  4: Good long-lasting smoothness.
  3: Average (based on the long-lasting smoothness in Comparative Example B1).
  2: Bad long-lasting smoothness.
  1: Extremely bad long-lasting smoothness.

Moist Feeling after Drying
  5: Extremely good moist feeling.
  4: Good moist feeling.
  3: Average (based on the moist feeling in Comparative Example B1).
  2: Bad moist feeling.
  1: Extremely bad moist.

Uniformity after Drying
  5: Extremely good uniformity.
  4: Good uniformity.
  3: Average (based on the uniformity in Comparative Example B1).
  2: Hair tips scattering.
  1: Noticeable hair tips scattering.

Comparative Examples B1 to B3

Production and Evaluation of Hair Shampoo

Hair shampoos were prepared in the same manner as in Example B1 but using a different polymer as in Table B-1 in place of the component (A) in Example B1, and evaluated in the same manner as in Example B1. The hair shampoos of Comparative Examples B1 to B3 were also controlled to have pH of 5.

The results of evaluation of the hair shampoos of Comparative Examples B1 to B3 are shown in Table B-1.

TABLE B-1

| | | Hair Wash Composition (hair shampoo) | Example | | | | | | Comparative Example | | |
|---|---|---|---|---|---|---|---|---|---|---|---|
| | | | B1 | B2 | B3 | B4 | B5 | B6 | B1 | B2 | B3 |
| Composition (part by mass) | Component (A) | CCE(46) | 0.3 | | | | | | | | |
| | | CCE(47) | | 0.3 | | | | | | | |
| | | CCE(28) | | | 0.3 | | | | | | |
| | | CCE(48) | | | | 0.3 | | | | | |
| | | CCE(27) | | | | | 0.3 | | | | |
| | | CCE(6) | | | | | | 0.3 | | | |
| | Polymer except component (A) | cationized polysaccharide 7 | | | | | | | 0.3 | | |
| | | cationized hydroxyethyl cellulose*1 | | | | | | | | 0.3 | |
| | | hydrophobically modified cationized hydroxyethyl cellulose *2 | | | | | | | | | 0.3 |
| | Component (B) | sodium laureth(1) sulfate *3 | 13.0 | 13.0 | 13.0 | 13.0 | 13.0 | 13.0 | 13.0 | 13.0 | 13.0 |
| | | coconut oil fatty acid amide propylbetaine *4 | 1.5 | 1.5 | 1.5 | 1.5 | 1.5 | 1.5 | 1.5 | 1.5 | 1.5 |
| | | coconut oil fatty acid monoethanolamide *5 | 0.3 | 0.3 | 0.3 | 0.3 | 0.3 | 0.3 | 0.3 | 0.3 | 0.3 |

TABLE B-1-continued

| Hair Wash Composition (hair shampoo) | | | Example B1 | B2 | B3 | B4 | B5 | B6 | Comparative Example B1 | B2 | B3 |
|---|---|---|---|---|---|---|---|---|---|---|---|
| Component (C) | high-polymerized dimethyl-polysiloxane *6 | | 2.0 | 2.0 | 2.0 | 2.0 | 2.0 | 2.0 | 2.0 | 2.0 | 2.0 |
| Others | pearl agent *7 | | | | | | adequate dose | | | | |
| | pH regulator | | | | | | adequate dose | | | | |
| | pure water | | | | | | balance | | | | |
| Evaluation | Finger-Combability in rinsing | | 4.0 | 4.0 | 3.6 | 4.0 | 4.4 | 4.4 | 3.0 | 3.0 | 2.6 |
| | Smoothness in rinsing | | 4.0 | 3.6 | 4.2 | 4.0 | 4.0 | 4.6 | 3.0 | 2.0 | 2.6 |
| | Long-lasting smoothness in rinsing | | 3.6 | 3.8 | 4.2 | 4.2 | 4.0 | 4.4 | 3.0 | 1.8 | 2.8 |
| | Moist Feeling after drying | | 3.8 | 4.4 | 4.4 | 4.4 | 4.0 | 4.4 | 3.0 | 2.0 | 4.0 |
| | Uniformity after drying | | 4.4 | 3.8 | 4.0 | 4.2 | 4.2 | 4.6 | 3.0 | 2.4 | 3.8 |

*1 Kao's POIZ C-80M
*2: Dow Corning Toray's SOFTCAT
*3: Kao's Emal 170J (active ingredient 70%)
*4: Kao's Amphitol 55AB (active ingredient 30%)
*5: Kawaken Fine Chemical's Amizol CME
*6: Dow Corning Toray's BY22-029 (active ingredient 50%)
*7: Kao's Pearl Concentrate SA-M2 (active ingredient 20%)

TABLE B-2

| Hair Wash Composition (hair shampoo) | | | Example B7 | B8 |
|---|---|---|---|---|
| Composition (part by mass) | Component (A) | CCE(10) | 0.3 | |
| | | CCE(49) | | 0.3 |
| | Component (B) | sodium laureth(1) sulfate *1 | 13.0 | 13.0 |
| | | coconut oil fatty acid amide propylbetaine *2 | 1.5 | 1.5 |
| | | coconut oil fatty acid monoethanolamide *3 | 0.3 | 0.3 |
| | Component (C) | high-polymerized dimethylpolysiloxane *4 | 2.0 | 2.0 |
| | Others | pearl agent *5 | adequate dose | |
| | | pH regulator | adequate dose | |
| | | pure water | balance | |
| Evaluation | Finger-Combability in rinsing | | 4.6 | 3.4 |
| | Smoothness in rinsing | | 4.8 | 3.4 |
| | Long-lasting smoothness in rinsing | | 4.6 | 3.4 |
| | Moist Feeling after drying | | 4.6 | 3.4 |
| | Uniformity after drying | | 4.4 | 4.0 |

*1: Kao's Emal 170J (active ingredient 70%)
*2: Kao's Amphitol 55AB (active ingredient 30%)
*3: Kawaken Fine Chemical's Amizol CME
*4: Dow Corning Toray's BY22-029 (active ingredient 50%)
*5 Kao's Pearl Concentrate SA-M2 (active ingredient 20%)

TABLE B-3

| Hair Wash Composition (hair shampoos) | | | Example | | | | | | | | | | | |
|---|---|---|---|---|---|---|---|---|---|---|---|---|---|---|
| | | | B9 | B10 | B11 | B12 | B13 | B14 | B15 | B16 | B17 | B18 | B19 | B20 |
| Composition (part by mass) | Component (A) | CCE(50) | 0.3 | | | | | | | | | | | |
| | | CCE(51) | | 0.3 | | | | | | | | | | |
| | | CCE(15) | | | 0.3 | | | | | | | | | |
| | | CCE(52) | | | | 0.3 | | | | | | | | |
| | | CCE(8) | | | | | 0.3 | | | | | | | |
| | | CCE(53) | | | | | | 0.3 | | | | | | |
| | | CCE(54) | | | | | | | 0.3 | | | | | |
| | | CCE(5) | | | | | | | | 0.3 | | | | |
| | | CCE(13) | | | | | | | | | 0.3 | | | |
| | | CCE(3) | | | | | | | | | | 0.3 | | |
| | | CCE(55) | | | | | | | | | | | 0.3 | |
| | | CCE(56) | | | | | | | | | | | | 0.3 |
| | | CCE(57) | | | | | | | | | | | | |

TABLE B-3-continued

|  |  |  |  |  |  |  |  |  |  |  |  |  |  |
|---|---|---|---|---|---|---|---|---|---|---|---|---|---|
|  |  | CCE(2) |  |  |  |  |  |  |  |  |  |  |  |
|  |  | CCE(1) |  |  |  |  |  |  |  |  |  |  |  |
|  |  | CCE(58) |  |  |  |  |  |  |  |  |  |  |  |
|  |  | CCE(29) |  |  |  |  |  |  |  |  |  |  |  |
|  |  | CCE(43) |  |  |  |  |  |  |  |  |  |  |  |
|  |  | CCE(30) |  |  |  |  |  |  |  |  |  |  |  |
|  |  | CCE(45) |  |  |  |  |  |  |  |  |  |  |  |
|  |  | CCE(59) |  |  |  |  |  |  |  |  |  |  |  |
|  |  | CCE(41) |  |  |  |  |  |  |  |  |  |  |  |
|  | Component (B) | sodium laureth(1) sulfate*1 | 13.0 | 13.0 | 13.0 | 13.0 | 13.0 | 13.0 | 13.0 | 13.0 | 13.0 | 13.0 | 13.0 | 13.0 |
|  |  | coconut oil fatty acid amide propylbetaine *2 | 1.5 | 1.5 | 1.5 | 1.5 | 1.5 | 1.5 | 1.5 | 1.5 | 1.5 | 1.5 | 1.5 | 1.5 |
|  |  | coconut oil fatty acid monoethanolamide *3 | 0.3 | 0.3 | 0.3 | 0.3 | 0.3 | 0.3 | 0.3 | 0.3 | 0.3 | 0.3 | 0.3 | 0.3 |
|  | Component (C) | high-polymerized dimethyl-polysiloxane *4 | 1.0 | 1.0 | 1.0 | 1.0 | 1.0 | 1.0 | 1.0 | 1.0 | 1.0 | 1.0 | 1.0 | 1.0 |
|  | Others | pearl agent *5 |  |  |  |  |  | adequate dose |  |  |  |  |  |  |
|  |  | pH regulator |  |  |  |  |  | adequate dose |  |  |  |  |  |  |
|  |  | pure water |  |  |  |  |  | balance |  |  |  |  |  |  |
| Evaluation | Finger-Combability in rinsing |  | 4.0 | 4.4 | 4.8 | 4.4 | 4.4 | 4.8 | 4.8 | 4.6 | 4.4 | 4.8 | 4.4 | 4.6 |
|  | Smoothness in rinsing |  | 4.0 | 4.2 | 4.8 | 4.8 | 4.4 | 4.8 | 4.8 | 4.8 | 4.6 | 4.8 | 4.0 | 4.2 |
|  | Long-lasting smoothness in rinsing |  | 3.8 | 4.0 | 4.6 | 4.4 | 4.2 | 4.4 | 4.8 | 4.8 | 4.4 | 4.8 | 4.0 | 4.4 |
|  | Moist Feeling after drying |  | 3.8 | 4.0 | 4.6 | 4.4 | 4.6 | 4.6 | 4.8 | 4.8 | 4.6 | 4.6 | 4.0 | 4.6 |
|  | Uniformity after drying |  | 3.8 | 4.2 | 4.6 | 4.4 | 4.8 | 4.8 | 4.8 | 4.8 | 4.6 | 4.6 | 4.0 | 4.6 |

| | | Hair Wash Composition (hair shampoos) | Example | | | | | | | | | |
|---|---|---|---|---|---|---|---|---|---|---|---|---|
| | | | B21 | B22 | B23 | B24 | B25 | B26 | B27 | B28 | B29 | B30 |
| Composition (part by mass) | Component (A) | CCE(50) | | | | | | | | | | |
| | | CCE(51) | | | | | | | | | | |
| | | CCE(15) | | | | | | | | | | |
| | | CCE(52) | | | | | | | | | | |
| | | CCE(8) | | | | | | | | | | |
| | | CCE(53) | | | | | | | | | | |
| | | CCE(54) | | | | | | | | | | |
| | | CCE(5) | | | | | | | | | | |
| | | CCE(13) | | | | | | | | | | |
| | | CCE(3) | | | | | | | | | | |
| | | CCE(55) | | | | | | | | | | |
| | | CCE(56) | | | | | | | | | | |
| | | CCE(57) | 0.3 | | | | | | | | | |
| | | CCE(2) | | 0.3 | | | | | | | | |
| | | CCE(1) | | | 0.3 | | | | | | | |
| | | CCE(58) | | | | 0.3 | | | | | | |
| | | CCE(29) | | | | | 0.3 | | | | | |
| | | CCE(43) | | | | | | 0.3 | | | | |
| | | CCE(30) | | | | | | | 0.3 | | | |
| | | CCE(45) | | | | | | | | 0.3 | | |
| | | CCE(59) | | | | | | | | | 0.3 | |
| | | CCE(41) | | | | | | | | | | 0.3 |
| | Component (B) | sodium laureth(1) sulfate*1 | 13.0 | 13.0 | 13.0 | 13.0 | 13.0 | 13.0 | 13.0 | 13.0 | 13.0 | 13.0 |
| | | coconut oil fatty acid amide propylbetaine *2 | 1.5 | 1.5 | 1.5 | 1.5 | 1.5 | 1.5 | 1.5 | 1.5 | 1.5 | 1.5 |
| | | coconut oil fatty acid monoethanolamide *3 | 0.3 | 0.3 | 0.3 | 0.3 | 0.3 | 0.3 | 0.3 | 0.3 | 0.3 | 0.3 |
| | Component (C) | high-polymerized dimethyl-polysiloxane *4 | 1.0 | 1.0 | 1.0 | 1.0 | 1.0 | 1.0 | 1.0 | 1.0 | 1.0 | 1.0 |
| | Others | pearl agent *5 | | | | | adequate dose | | | | | |
| | | pH regulator | | | | | adequate dose | | | | | |
| | | pure water | | | | | balance | | | | | |

TABLE B-3-continued

| | | | | | | | | | | |
|---|---|---|---|---|---|---|---|---|---|---|
| Evaluation | Finger-Combability in rinsing | 4.8 | 5.0 | 4.8 | 4.6 | 4.6 | 4.0 | 5.0 | 4.8 | 5.0 | 4.0 |
| | Smoothness in rinsing | 3.8 | 5.0 | 5.0 | 4.6 | 4.2 | 4.0 | 4.4 | 4.2 | 4.0 | 3.4 |
| | Long-lasting smoothness in rinsing | 3.8 | 5.0 | 5.0 | 4.8 | 4.8 | 5.0 | 5.0 | 5.0 | 4.0 | 4.0 |
| | Moist Feeling after drying | 4.6 | 5.0 | 5.0 | 4.8 | 4.0 | 4.4 | 4.6 | 4.8 | 5.0 | 5.0 |
| | Uniformity after drying | 4.8 | 5.0 | 4.8 | 4.6 | 4.0 | 4.4 | 4.0 | 4.2 | 5.0 | 4.4 |

*1 Kao's Emal 170J (active ingredient 70%)
*2: Kao's Amphitol 55AB (active ingredient 30%)
*3: Kawaken Fine Chemical's Amizol CME
*4: Dow Corning Toray's BY22-029 (active ingredient 50%)
*5: Kao's Pearl Concentrate SA-M2 (active ingredient 20%)

TABLE B-4

| | | Hair Wash Composition | Example | | | |
|---|---|---|---|---|---|---|
| | | (hair shampoo) | B31 | B32 | B33 | B34 |
| Composition (part by mass) | Component (A) | CCE(58) | 0.1 | 0.3 | 0.5 | 1.0 |
| | Component (B) | sodium laureth(1) sulfate *1 | 13.0 | 13.0 | 13.0 | 13.0 |
| | | coconut oil fatty acid amide propylbetaine *2 | 1.5 | 1.5 | 1.5 | 1.5 |
| | | coconut oil fatty acid monoethanolamide *3 | 0.3 | 0.3 | 0.3 | 0.3 |
| | Component (C) | high-polymerized dimethyl-polysiloxane *4 | 1.0 | 1.0 | 1.0 | 1.0 |
| | Others | pearl agent*5 | | adequate dose | | |
| | | pH regulator | | adequate dose | | |
| | | pure water | | balance | | |
| Blending Ratio (by mass) | | (A)/(B) | 0.0068 | 0.0203 | 0.0338 | 0.0676 |
| | | (A)/(C) | 0.1 | 0.3 | 0.5 | 1.0 |
| Evaluation | Finger-Combability in rinsing | | 4.0 | 4.6 | 4.8 | 5.0 |
| | Smoothness in rinsing | | 3.6 | 4.6 | 5.0 | 5.0 |
| | Long-lasting smoothness in rinsing | | 3.6 | 4.8 | 5.0 | 5.0 |
| | Moist Feeling after drying | | 3.6 | 4.8 | 5.0 | 5.0 |
| | Uniformity after drying | | 4.0 | 4.6 | 4.0 | 4.4 |

*1: Kao's Emal 170J (active ingredient 70%)
*2: Kao's Amphitol 55AB (active ingredient 30%)
*3: Kawaken Fine Chemical's Amizol CME
*4: Dow Corning Toray's BY22-029 (active ingredient 50%)
*5 Kao's Pearl Concentrate SA-M2 (active ingredient 20%)

TABLE B-5

| | | Hair Wash Composition | Example | | | | | | | |
|---|---|---|---|---|---|---|---|---|---|---|
| | | (hair shampoo) | B35 | B36 | B37 | B38 | B39 | B40 | B41 | B42 |
| Composition (part by mass) | Component (A) | CCE(58) | 0.3 | 0.3 | 0.3 | 0.3 | 0.3 | 0.3 | 0.3 | 0.3 |
| | Component (B) | sodium lauryl sulfate *1 | 13.0 | | | | | | | |
| | | ammonium laureth-(1) sulfate *2 | | 13.0 | | | | | | |

TABLE B-5-continued

| | | | | | | | | | | |
|---|---|---|---|---|---|---|---|---|---|---|
| | | sodium laureth-(2) sulfate *3 | | 13.0 | 13.0 | 13.0 | 13.0 | 13.0 | | |
| | | sodium laureth-(3) sulfate *4 | | | | | | | | 13.0 |
| | | sodium laureth-(4,5) acetate *5 | | | | | | | | |
| | | sodium laureth-(10) acetate *6 | | | | | | | | |
| | | sodium laureth-(2) sulfosuccinate *7 | | | | | | | | |
| | | sodium olefin (C14-16) sulfonate *8 | | | | | | | | |
| | | sodium lauroylmethyl-sarcosine *9 | | | | | | | | |
| | | sodium alkylglutamate *10 | | | | | | | | |
| | | coconut oil fatty acid monoethanolamide *11 | 0.3 | 0.3 | 0.3 | 0.3 | 0.3 | 0.3 | 0.3 | 0.3 |
| | | coconut oil fatty acid methylethanolamide *12 | | | | | | | | |
| | | coconut oil fatty acid amide propylbetaine *13 | 1.5 | 1.5 | 1.5 | 1.5 | 1.5 | 1.5 | 1.5 | 1.5 |
| | | lauramide monoiso-propanolamide *14 | | | | | | | | |
| | | laurylcarboxymethyl-hydroxyimidazolium betaine *15 | | | | | | | | |
| | | laurylhydroxy-sulfobetaine *16 | | | | | | | | |
| | | laurylbetaine *17 | | | | | | | | |
| | | laureth-3 *18 | | | | | | | | |
| | | alkylglucoside *19 | | | | | | | | |
| | | behentrimonium chloride *20 | | | | 0.5 | | | | |
| | | cetyltrimonium chloride *21 | | | | | | 0.5 | | |
| | | lauric acid *22 | | | | | | | 0.5 | |
| | | myristic acid *23 | | | | | | | 0.5 | |
| | Component (C) | high-polymerized dimethyl-polysiloxane *24 | 2.0 | 2.0 | 2.0 | 2.0 | 2.0 | 2.0 | 2.0 | 2.0 |
| | Others | pearl agent *25 | | | | adequate dose | | | | |
| | | pH regulator | | | | adequate dose | | | | |
| | | pure water | | | | balance | | | | |
| Blending Ratio (by mass) | | (A)/(B) | 0.0203 | 0.0203 | 0.0203 | 0.0196 | 0.0196 | 0.0196 | 0.0196 | 0.0203 |
| | | (A)/(C) | | | | 0.15 | | | | |
| Evaluation | | Finger-Combability in rinsing | 4.6 | 4.0 | 4.4 | 4.0 | 4.8 | 3.8 | 4.0 | 4.0 |
| | | Smoothness in rinsing | 3.8 | 4.2 | 4.6 | 4.6 | 4.8 | 4.6 | 4.8 | 4.4 |
| | | Long-lasting smoothness in rinsing | 3.8 | 4.2 | 4.8 | 4.8 | 4.8 | 4.8 | 4.8 | 4.4 |
| | | Moist Feeling after drying | 3.6 | 5.0 | 4.6 | 4.8 | 5.0 | 4.8 | 4.8 | 4.6 |
| | | Uniformity after drying | 3.4 | 4.0 | 4.4 | 4.8 | 5.0 | 4.8 | 4.4 | 4.4 |

| | | Hair Wash Composition | Example | | | | | | | |
|---|---|---|---|---|---|---|---|---|---|---|
| | | (hair shampoo) | B43 | B44 | B45 | B46 | B47 | B48 | B49 | B50 |
| Composition (part by mass) | Component (A) | CCE(58) | 0.3 | 0.3 | 0.3 | 0.3 | 0.3 | 0.3 | 0.3 | 0.3 |
| | Component (B) | sodium lauryl sulfate *1 | | | | | | | | |
| | | ammonium laureth-(1) sulfate *2 | | | | | | | | |
| | | sodium laureth-(2) sulfate *3 | | | | | | | | |
| | | sodium laureth-(3) sulfate *4 | | | | | | | | |
| | | sodium laureth-(4,5) acetate *5 | 13.0 | | | | | | | |

TABLE B-5-continued

|  |  |  |  |  |  |  |  |  |  |
|---|---|---|---|---|---|---|---|---|---|
| | acetate *5 | | | | | | | | |
| | sodium laureth-(10) acetate *6 | 13.0 | | | | | | | |
| | sodium laureth-(2) sulfosuccinate *7 | | 13.0 | | | | | | |
| | sodium olefin (C14-16) sulfonate *8 | | | 13.0 | | | | | |
| | sodium lauroylmethyl-sarcosine *9 | | | | 13.0 | | | | |
| | sodium alkylglutamate *10 | | | | | 13.0 | | | |
| | coconut oil fatty acid monoethanolamide *11 | 0.3 | 0.3 | 0.3 | 0.3 | 0.3 | 0.3 | 0.3 | 0.3 |
| | coconut oil fatty acid methylethanolamide *12 | | | | | | | | |
| | coconut oil fatty acid amide propylbetaine *13 | 1.5 | 1.5 | 1.5 | 1.5 | 1.5 | 1.5 | 1.5 | 1.5 |
| | lauramide monoiso-propanolamide *14 | | | | | | | | |
| | laurylcarboxymethyl-hydroxyimidazolium betaine *15 | | | | | | | 13.0 | |
| | laurylhydroxy-sulfobetaine *16 | | | | | | | | |
| | laurylbetaine *17 | | | | | | | | |
| | laureth-3 *18 | | | | | | | | |
| | alkylglucoside *19 | | | | | | | | 13.0 |
| | behentrimonium chloride *20 | | | | | | | | |
| | cetyltrimonium chloride *21 | | | | | | | | |
| | lauric acid *22 | | | | | | | | |
| | myristic acid *23 | | | | | | | | |
| Component (C) | high-polymerized dimethyl-polysiloxane *24 | 2.0 | 2.0 | 2.0 | 2.0 | 2.0 | 2.0 | 2.0 | 2.0 |
| Others | pearl agent *25 | | | | adequate dose | | | | |
| | pH regulator | | | | adequate dose | | | | |
| | pure water | | | | balance | | | | |
| Blending Ratio (by mass) | (A)/(B) | 0.0203 | 0.0203 | 0.0203 | 0.0203 | 0.0203 | 0.0203 | 0.0203 | 0.0203 |
| | (A)/(C) | | | | 0.15 | | | | |
| Evaluation | Finger-Combability in rinsing | 4.0 | 3.6 | 3.6 | 5.0 | 4.0 | 3.6 | 3.4 | 3.4 |
| | Smoothness in rinsing | 4.6 | 4.4 | 4.8 | 5.0 | 4.4 | 4.0 | 5.0 | 4.4 |
| | Long-lasting smoothness in rinsing | 5.0 | 5.0 | 5.0 | 5.0 | 4.4 | 4.0 | 5.0 | 5.0 |
| | Moist Feeling after drying | 4.6 | 5.0 | 5.0 | 4.4 | 4.2 | 4.0 | 4.0 | 4.8 |
| | Uniformity after drying | 3.8 | 3.6 | 4.0 | 4.6 | 4.4 | 4.8 | 4.0 | 4.8 |

| | | Hair Wash Composition (hair shampoo) | Example | | | | |
|---|---|---|---|---|---|---|---|
| | | | B51 | B52 | B53 | B54 | B55 |
| Composition (part by mass) | Component (A) | CCE(58) | 0.3 | 0.3 | 0.3 | 0.3 | 0.3 |
| | Component (B) | sodium lauryl sulfate *1 | | | | | |
| | | ammonium laureth-(1) sulfate *2 | | | | | |
| | | sodium laureth-(2) sulfate *3 | 13.0 | 13.0 | 13.0 | 13.0 | 13.0 |
| | | sodium laureth-(3) sulfate *4 | | | | | |
| | | sodium laureth-(4,5) acetate *5 | | | | | |
| | | sodium laureth-(10) acetate *6 | | | | | |
| | | sodium laureth-(2) sulfosuccinate *7 | | | | | |

TABLE B-5-continued

| | | | | | | | |
|---|---|---|---|---|---|---|---|
| | | sodium olefin (C14-16) sulfonate *8 | | | | | |
| | | sodium lauroylmethylsarcosine *9 | | | | | |
| | | sodium alkylglutamate *10 | | | | | |
| | | coconut oil fatty acid monoethanolamide *11 | | | | | |
| | | coconut oil fatty acid methylethanolamide *12 | 1.0 | | | | |
| | | coconut oil fatty acid amide propylbetaine *13 | | | | | |
| | | lauramide monoisopropanolamide *14 | | 1.0 | | | |
| | | laurylcarboxymethyl-hydroxyimidazolium betaine *15 | | | | | |
| | | laurylhydroxysulfobetaine *16 | | | 2.0 | | |
| | | laurylbetaine *17 | | | | 2.0 | |
| | | laureth-3 *18 | | | | | 2.0 |
| | | alkylglucoside *19 | | | | | |
| | | behentrimonium chloride *20 | | | | | |
| | | cetyltrimonium chloride *21 | | | | | |
| | | lauric acid *22 | | | | | |
| | | myristic acid *23 | | | | | |
| | Component (C) | high-polymerized dimethylpolysiloxane *24 | 2.0 | 2.0 | 2.0 | 2.0 | 2.0 |
| | Others | pearl agent *25 | adequate dose | | | | |
| | | pH regulator | adequate dose | | | | |
| | | pure water | balance | | | | |
| Blending Ratio (by mass) | | (A)/(B) | 0.0214 | 0.0214 | 0.02 | 0.02 | 0.02 |
| | | (A)/(C) | | | 0.15 | | |
| Evaluation | | Finger-Combability in rinsing | 3.6 | 3.8 | 4.0 | 4.4 | 4.0 |
| | | Smoothness in rinsing | 4.0 | 3.8 | 4.2 | 4.0 | 4.0 |
| | | Long-lasting smoothness in rinsing | 4.0 | 3.8 | 4.2 | 4.8 | 3.8 |
| | | Moist Feeling after drying | 4.4 | 3.8 | 4.0 | 4.0 | 3.8 |
| | | Uniformity after drying | 3.6 | 3.6 | 4.4 | 4.6 | 4.0 |

*1: Kao's Emal 0
*2: Kao's Emal 170S-A (active ingredient 70%)
*3: Kao's Emal 270S (active ingredient 70%)
*4: Kao's Emal 327 (active ingredient 27%)
*5: Kao's KAO AKYPO RMN45NV (active ingredient 23.5%)
*6: Kao's KAO AKYPO RMN100NV (active ingredient 23.5%)
*7: New Japan Chemical's Rika-Mild ES-100 (active ingredient 30%)
*8: Nikko Chemical's NIKKOL OS-14
*9: Innospec's Iselux TM LQ-CLR-PE
*10: Ajinomoto's Amisoft CS-11
*11: Kawaken Fine Chemical's Amizol CME
*12: Kao's Aminone C-11S
*13: Kao's Amphitol 55AB (active ingredient 30%)
*14: Kawaken Fine Chemical's Amizol PLME-A
*15: Kao's Amphitol 20YB (active ingredient 30%)
*16: Kao's Amphitol 20HD (active ingredient 30%)
*17: Kao's Amphitol 20BS (active ingredient 30%)
*18: Kao's Emulgen 103
*19: Kao's Midol 12 (active ingredient 40%)
*20: Kao's Cortamine 2285E-E (active ingredient 58%)
*21: Kao's Cortamine 60W (active ingredient 30%)
*22: Kao's Lunac L-98
*23: Kao's Lunac M-98
*24: Dow Corning Torav's BY22-029 (active ingredient 50%)
*25: Kao's Pearl Concentrate SA-M2 (active ingredient 20%)

TABLE B-6

| | Hair Wash Composition | | Example | | | |
|---|---|---|---|---|---|---|
| | | (hair shampoo) | B56 | B57 | B58 | B59 |
| Composition (part by mass) | Component (A) | CCE(58) | 0.3 | 0.3 | 0.3 | 0.3 |
| | Component (B) | sodium laureth(1) sulfate *1 | 13 | 13 | 13 | 13 |
| | | coconut oil fatty acid amide propylbetaine *2 | 1.5 | 1.5 | 1.5 | 1.5 |
| | | coconut oil fatty acid monoethanolamide *3 | 0.3 | 0.3 | 0.3 | 0.3 |
| | Component (C) | high-polymerized dimethyl-polysiloxane *4 | 0.5 | 1.0 | 5.0 | 10 |
| | Others | pearl agent*5 | | adequate dose | | |
| | | pH regulator | | adequate dose | | |
| | | pure water | | balance | | |
| Blending Ratio (by mass) | | (A)/(B) | | 0.0203 | | |
| | | (A)/(C) | 0.6 | 0.3 | 0.06 | 0.03 |
| Evaluation | Finger-Combability in rinsing | | 4.4 | 4.6 | 4.0 | 3.4 |
| | Smoothness in rinsing | | 4.6 | 4.6 | 4.8 | 4.4 |
| | Long-lasting smoothness in rinsing | | 4.6 | 4.8 | 4.4 | 4.4 |
| | Moist Feeling after drying | | 4.2 | 4.8 | 5.0 | 5.0 |
| | Uniformity after drying | | 4.4 | 4.6 | 5.0 | 5.0 |

*1: Kao's Emal 170J (active ingredient 70%)
*2: Kao's Amphitol 55AB (active ingredient 30%)
*3: Kawaken Fine Chemical's Amizol CME
*4: Dow Corning Toray's BY22-029 (active ingredient 50%)
*5 Kao's Pearl Concentrate SA-M2 (active ingredient 20%)

TABLE B-7

| | Hair Wash Composition | | Example | | | | | | | | | | | | |
|---|---|---|---|---|---|---|---|---|---|---|---|---|---|---|---|
| | | (hair shampoo) | B60 | B61 | B62 | B63 | B64 | B65 | B66 | B67 | B68 | B69 | B70 | B71 | B72 |
| Composition (part by mass) | Component (A) | CCE(58) | 0.3 | 0.3 | 0.3 | 0.3 | 0.3 | 0.3 | 0.3 | 0.3 | 0.3 | 0.3 | 0.3 | 0.3 | 0.3 |
| | Component (B) | Sodium laureth(1) sulfate *1 | 13 | 13 | 13 | 13 | 13 | 13 | 13 | 13 | 13 | 13 | 13 | 13 | 13 |
| | | coconut oil fatty acid amide propylbetaine *2 | 1.5 | 1.5 | 1.5 | 1.5 | 1.5 | 1.5 | 1.5 | 1.5 | 1.5 | 1.5 | 1.5 | 1.5 | 1.5 |
| | | coconut oil fatty acid monoethanolamide *3 | 0.3 | 0.3 | 0.3 | 0.3 | 0.3 | 0.3 | 0.3 | 0.3 | 0.3 | 0.3 | 0.3 | 0.3 | 0.3 |
| | Component (C) | oleic acid *4 | 1 | | | | | | | | | | | | |
| | | isostearic acid *5 | | 1 | | | | | | | | | | | |
| | | macadamia nut oil *6 | | | 1 | | | | | | | | | | |
| | | avocado oil *7 | | | | 1 | | | | | | | | | |
| | | sunflower oil *8 | | | | | 1 | | | | | | | | |
| | | dipentaerythrityl (hydroxystearate/stearate/rosin ester) *9 | | | | | | 1 | | | | | | | |
| | | myristyl myristate *10 | | | | | | | 1 | | | | | | |
| | | isopropyl palmitate *11 | | | | | | | | 1 | | | | | |
| | | cetyl palmitate *12 | | | | | | | | | 1 | | | | |
| | | stearyl stearate *13 | | | | | | | | | | 1 | | | |
| | | squalane *14 | | | | | | | | | | | 1 | | |
| | | liquid paraffin *15 | | | | | | | | | | | | 1 | |
| | | paraffin wax *16 | | | | | | | | | | | | | 1 |

TABLE B-7-continued

| | Hair Wash Composition (hair shampoo) | | B60 | B61 | B62 | B63 | B64 | B65 | B66 | B67 | B68 | B69 | B70 | B71 | B72 |
|---|---|---|---|---|---|---|---|---|---|---|---|---|---|---|---|
| | Others | pearl agent *17 | | | | | | adequate dose | | | | | | | |
| | | pH regulator | | | | | | adequate dose | | | | | | | |
| | | pure water | | | | | | balance | | | | | | | |
| Evaluation | Finger-Combability in rinsing | | 4.8 | 3.6 | 4.0 | 3.8 | 3.6 | 3.6 | 4.6 | 3.8 | 3.6 | 4.4 | 3.8 | 4.0 | 3.6 |
| | Smoothness in rinsing | | 4.4 | 4.0 | 5.0 | 4.6 | 4.6 | 4.4 | 4.6 | 4.0 | 3.8 | 4.0 | 4.4 | 4.4 | 4.4 |
| | Long-lasting smoothness in rinsing | | 4.8 | 4.0 | 4.8 | 4.4 | 4.4 | 4.2 | 4.6 | 4.0 | 3.8 | 4.2 | 4.6 | 4.4 | 4.6 |
| | Moist Feeling after drying | | 4.8 | 4.4 | 4.6 | 4.2 | 4.2 | 4.8 | 4.6 | 4.4 | 4.0 | 4.2 | 4.6 | 4.6 | 4.8 |
| | Uniformity after drying | | 4.4 | 4.6 | 4.0 | 4.0 | 4.0 | 4.6 | 4.0 | 3.8 | 3.6 | 3.8 | 4.0 | 4.6 | 4.4 |

*1: Kao's Emal 170J (active ingredient 70%)
*2: Kao's Amphitol 55AB (active ingredient 30%)
*3: Kawaken Fine Chemical's Amizol CME
*4: Kao's Lunac LO-V
*5: Kokyu Alcohol Kogyo's Isostearic Acid EX
*6: Nikko Chemicals' Macadamia nuts oil
*7: Nikko Chemicals' pure avocado oil
*8: Nihon Ryutsu Sangyo's edible sunflower oil
*9: Nisshin Oillio's Cosmol 168ARV
*10: Kao's Exeparl MYM
*11: Kao's Exeparl IPP
*12: Cognis' CUTINA CP
*13: Kao's Exeparl SS
*14: Nikko Chemicals' squalane
*15: Kaneda's Hi-call K-230
*16: Nippon Serio's PARAFFIN WAX 125
*17: Kao's Pearl Concentrate SA-M2 (active ingredient 20%)

TABLE B-8

| | Hair Wash Composition (hair shampoo) | | B73 | B74 | B75 | B76 | B77 | B78 | B79 | B80 | B81 | B82 |
|---|---|---|---|---|---|---|---|---|---|---|---|---|
| Composition (part by mass) | Component (A) | CCE(58) | 0.3 | 0.3 | 0.3 | 0.3 | 0.3 | 0.3 | 0.3 | 0.3 | 0.3 | 0.3 |
| | Component (B) | sodium laureth(1) sulfate *1 | 13 | 13 | 13 | 13 | 13 | 13 | 13 | 13 | 13 | 13 |
| | | coconut oil fatty acid amide propylbetaine*2 | 1.5 | 1.5 | 1.5 | 1.5 | 1.5 | 1.5 | 1.5 | 1.5 | 1.5 | 1.5 |
| | | coconut oil fatty acid monoethanolamino*3 | 0.3 | 0.3 | 0.3 | 0.3 | 0.3 | 0.3 | 0.3 | 0.3 | 0.3 | 0.3 |
| | Component (C) | laurylalcohol*4 | 1 | | | | | | | | | |
| | | myristylalcohol*5 | | 1 | | | | | | | | |
| | | cetylalcohol*6 | | | 1 | | | | | | | |
| | | stearylalcohol*7 | | | | 1 | | | | | | |
| | | behenylalcohol*8 | | | | | 1 | | | | | |
| | | dioctylether*9 | | | | | | 1 | | | | |
| | | dioctylcarbonate*10 | | | | | | | 1 | | | |
| | | PPG-3benzyl-ethermyristate*11 | | | | | | | | 1 | | |
| | | isostearyl-glycerylether*12 | | | | | | | | | 1 | |
| | | isostearyl-cholesterylester*13 | | | | | | | | | | 1 |
| | | PPG-3caprylether | | | | | | | | | | |
| | | PPG-4caprylether | | | | | | | | | | |
| | | PPG-5caprylether | | | | | | | | | | |
| | | PPG-6caprylether | | | | | | | | | | |
| | | PPG-10caprylether | | | | | | | | | | |
| | | PPG-3decylether | | | | | | | | | | |
| | | PPG-10decylether | | | | | | | | | | |
| | | PPG-3laurylether | | | | | | | | | | |
| | | PPG-10laurylether | | | | | | | | | | |

TABLE B-8-continued

|  |  |  |  |  |  |  |  |  |  |  |
|---|---|---|---|---|---|---|---|---|---|---|
| Others | pearl agent*14 |  |  |  |  | adequate dose |  |  |  |  |
|  | pH regulator |  |  |  |  | adequate dose |  |  |  |  |
|  | pure water |  |  |  |  | balance |  |  |  |  |
| Evaluation | Finger-Combability in rinsing | 4.8 | 5.0 | 4.6 | 4.6 | 4.4 | 3.8 | 3.8 | 4.0 | 5.0 | 5.0 |
|  | Smoothness in rinsing | 4.4 | 4.4 | 4.2 | 4.8 | 4.4 | 3.8 | 3.8 | 4.0 | 4.4 | 4.2 |
|  | Long-lasting smoothness in rinsing | 4.2 | 4.8 | 4.8 | 5.0 | 4.4 | 4.6 | 4.2 | 4.6 | 5.0 | 4.6 |
|  | Moist Feeling after drying | 4.8 | 4.6 | 4.6 | 4.6 | 4.0 | 4.8 | 4.0 | 4.8 | 5.0 | 4.0 |
|  | Uniformity after drying | 4.8 | 4.6 | 4.6 | 5.0 | 3.6 | 3.8 | 4.0 | 4.8 | 4.6 | 3.6 |

| | | Hair Wash Composition (hair shampoo) | Example |||||||||
|---|---|---|---|---|---|---|---|---|---|---|---|
| | | | B83 | B84 | B85 | B86 | B87 | B88 | B89 | B90 | B91 |
| Composition (part by mass) | Component (A) | CCE(58) | 0.3 | 0.3 | 0.3 | 0.3 | 0.3 | 0.3 | 0.3 | 0.3 | 0.3 |
| | Component (B) | sodium laureth(1) sulfate *1 | 13 | 13 | 13 | 13 | 13 | 13 | 13 | 13 | 13 |
| | | coconut oil fatty acid amide propylbetaine*2 | 1.5 | 1.5 | 1.5 | 1.5 | 1.5 | 1.5 | 1.5 | 1.5 | 1.5 |
| | | coconut oil fatty acid monoethanolamino*3 | 0.3 | 0.3 | 0.3 | 0.3 | 0.3 | 0.3 | 0.3 | 0.3 | 0.3 |
| | Component (C) | laurylalcohol*4 | | | | | | | | | |
| | | myristylalcohol*5 | | | | | | | | | |
| | | cetylalcohol*6 | | | | | | | | | |
| | | stearylalcohol*7 | | | | | | | | | |
| | | behenylalcohol*8 | | | | | | | | | |
| | | dioctylether*9 | | | | | | | | | |
| | | dioctylcarbonate*10 | | | | | | | | | |
| | | PPG-3benzyl-ethermyristate*11 | | | | | | | | | |
| | | isostearyl-glycerylether*12 | | | | | | | | | |
| | | isostearyl-cholesterylester*13 | | | | | | | | | |
| | | PPG-3caprylether | 1 | | | | | | | | |
| | | PPG-4caprylether | | 1 | | | | | | | |
| | | PPG-5caprylether | | | 1 | | | | | | |
| | | PPG-6caprylether | | | | 1 | | | | | |
| | | PPG-10caprylether | | | | | 1 | | | | |
| | | PPG-3decylether | | | | | | 1 | | | |
| | | PPG-10decylether | | | | | | | 1 | | |
| | | PPG-3laurylether | | | | | | | | 1 | |
| | | PPG-10laurylether | | | | | | | | | 1 |
| | Others | pearl agent*14 | | | | | adequate dose | | | | |
| | | pH regulator | | | | | adequate dose | | | | |
| | | pure water | | | | | balance | | | | |
| Evaluation | | Finger-Combability in rinsing | 4.6 | 4.0 | 4.4 | 4.4 | 4.8 | 4.8 | 4.8 | 4.6 | 5.0 |
| | | Smoothness in rinsing | 3.8 | 4.2 | 4.4 | 4.4 | 4.6 | 5.0 | 4.4 | 4.6 | 4.8 |
| | | Long-lasting smoothness in rinsing | 3.8 | 4.2 | 4.4 | 4.6 | 4.8 | 5.0 | 4.8 | 4.6 | 5.0 |
| | | Moist Feeling after drying | 4.4 | 4.0 | 4.4 | 4.4 | 4.6 | 5.0 | 4.6 | 4.8 | 4.8 |
| | | Uniformity after drying | 4.6 | 4.0 | 4.0 | 4.0 | 4.4 | 4.4 | 4.0 | 4.6 | 4.4 |

*1: Kao's Emal 170J (active ingredient 70%)
*2Kao's Amphitol 55AB (active ingredient 30%)
*3Kawaken Fine Chemical's Amizol CME
*4Kao's Kalcol 2098
*5Kao's Kalcol 4098
*6Kao's Kalcol 6098
*7Kao's Kalcol 8093
*8Kao's Kalcol 220-80
*9Cognis' Cetiol OE
*10Cognis' Cetiol CC
*11Croda's Crodamol STS
*12Kao's Penetol CE-IS

*13 Kao's Exeparl IS-CE-A
*14 Kao's Pearl Concentrate SA-M2 (active ingredient 20%)

TABLE B-9

|  |  | Hair Wash Composition (hair shampoo) | Example | | | | | | | | |
|---|---|---|---|---|---|---|---|---|---|---|---|
|  |  |  | B92 | B93 | B94 | B95 | B96 | B97 | B98 | B99 | B100 |
| Composition (part by mass) | Component (A) | CCE(58) | 0.3 | 0.3 | 0.3 | 0.3 | 0.3 | 0.3 | 0.3 | 0.3 | 0.3 |
|  | Component (B) | sodium laureth(1) sulfate *1 | 13 | 13 | 13 | 13 | 13 | 13 | 13 | 13 | 13 |
|  |  | coconut oil fatty acid amide propylbetaine *2 | 1.5 | 1.5 | 1.5 | 1.5 | 1.5 | 1.5 | 1.5 | 1.5 | 1.5 |
|  |  | coconut oil fatty acid monoethanolamide *9 | 0.3 | 0.3 | 0.3 | 0.3 | 0.3 | 0.3 | 0.3 | 0.3 | 0.3 |
|  | Component (C) | dimethiconol *4 | 1 |  |  |  |  |  |  |  |  |
|  |  | polyether-modified silicone *5 |  | 1 |  |  |  |  |  |  |  |
|  |  | polyether-modified silicone *6 |  |  | 1 |  |  |  |  |  |  |
|  |  | high-polymerized dimethylsiloxane *7 |  |  |  | 1 |  |  |  |  |  |
|  |  | high-polymerized dimethylsiloxane *8 |  |  |  |  | 1 |  |  |  |  |
|  |  | high-polymerized dimethylsiloxane *9 |  |  |  |  |  | 1 |  |  |  |
|  |  | amino-modified high-polymerized dimethyl-polysiloxane *10 |  |  |  |  |  |  | 1 |  |  |
|  |  | amino-modified high-polymerized dimethyl-polysiloxane *11 |  |  |  |  |  |  |  | 1 |  |
|  |  | amino-modified high-polymerized dimethyl-polysiloxane *12 |  |  |  |  |  |  |  |  | 1 |
|  | Others | pearl agent *13 |  |  |  |  | adequate dose | | | | |
|  |  | pH regulator |  |  |  |  | adequate dose | | | | |
|  |  | pure water |  |  |  |  | balance | | | | |
| Evaluation | Finger-Combability in rinsing |  | 4.0 | 4.4 | 3.6 | 4.0 | 4.4 | 4.4 | 4.8 | 4.6 | 4.6 |
|  | Smoothness in rinsing |  | 4.4 | 5.0 | 4.0 | 4.8 | 4.2 | 4.6 | 4.0 | 4.8 | 4.8 |
|  | Long-lasting smoothness in rinsing |  | 4.8 | 5.0 | 4.0 | 4.8 | 4.4 | 4.8 | 4.8 | 5.0 | 4.6 |
|  | Moist Feeling after drying |  | 4.4 | 4.0 | 3.6 | 4.0 | 4.8 | 4.4 | 4.0 | 4.6 | 3.8 |
|  | Uniformity after drying |  | 4.0 | 4.0 | 4.4 | 4.4 | 4.4 | 4.6 | 4.0 | 4.8 | 4.2 |

*1: Kao's Emal 170J (active ingredient 70%)
*2: Kao's Amphitol 55AB (active ingredient 30%)
*3: Kawaken Fine Chemical's Amizol CME
*4: Dow Corning Toray's 1785EMULSION (active ingredient 60%)
*5: Shin-etsu Chemical Industry's KF6011
*6: Kao's Sofcare GS-G
*7: Dow Corning Toray's BY22-007 (active ingredient 50%)
*8: Dow Corning Toray's BY22-050A (active ingredient 50%)
*9: Dow Corning Toray's BY22-060 (active ingredient 60%)
*10: Dow Corning Toray's BY22-079 (active ingredient 14%)
*11: Dow Corning Toray's SM8904 (active ingredient 40%)
*12: Shin-etsu Chemical Industry's KF8020
*13: Kao's Pearl Concentrate SA-M2 (active ingredient 20%)

From Tables B-1 to B-9, it is known that the hair shampoos (hair wash compositions) of Examples B1 to B100 are excellent hair shampoos capable of giving finger combability in hair washing, smoothness and long-lasting smoothness in rinsing, and moist feeling and uniformity after drying.

Examples B101 to B106

Evaluation of Dimethicone Persistence in Hair Shampoo

Using any of CCE (2), (29), (30), (41), (43) or (59) as the component (A), hair shampoos each having the composition as shown in Table B-10 were prepared in the same manner as in Example B1.

With the plain shampoo mentioned above, 1 g of hair tresses "BS-B-A" (by View Lux: 10 cm) were washed, well wetted with warm water at 35 to 40° C., and 0.1 g of the hair shampoo of Examples B101 to B106 was applied thereto, and the hair tresses were thus washed for 1 minutes. Afterwards, these were rinsed with warm water for 30 seconds, then toweled for water removal, well combed, and further dried with hot air from a drier to prepare hair tresses for evaluation. The tresses were immersed in 10 mL of chloroform for 10 minutes and stirred to extract out the dimethicone having adsorbed to the tresses. This extraction operation was carried out three times, and the extracts were collected, and the solvent was evaporated away. Heavy chloroform was added to the residue to dissolve it, and dimethicone was quantified through $^1$H-NMR. The results are shown in Table B-10.

Examples B107 to B119, Comparative Example B4

Evaluation of Dimethicone Persistence in Hair Shampoo

In Examples B107 to B119, hair shampoos each having the composition shown in Table B-11 were prepared in the same manner as in Example B1 and evaluated in the same manner as in Example B101 and using any of CCE (29), (30), (32) to (41) and (43) as the component (A).

In Comparative Example B4, a hair shampoo was prepared in the same manner as in Example B107 but using the polymer shown in Table B-11 in place of the component (A) in Example B107 and evaluated in the same manner as in Example B101.

The results of evaluation of the hair shampoos of Examples B107 to B119 and Comparative Example B4 are shown in Table B-11.

TABLE B-10

| Hair Wash Composition (hair shampoo) | | | Example | | | | | |
|---|---|---|---|---|---|---|---|---|
| | | | B101 | B102 | B103 | B104 | B105 | B106 |
| Composition (part by mass) | Component (A) | CCE(2) cation charge density 0.53 mmol/g | 0.3 | | | | | |
| | | CCE(29) cation charge density 1.04 mmol/g | | 0.3 | | | | |
| | | CCE(43) cation charge density 1.12 mmol/g | | | 0.3 | | | |
| | | CCE(30) cation charge density 1.20 mmol/g | | | | 0.3 | | |
| | | CCE(59) cation charge density 1.53 mmol/g | | | | | 0.3 | |
| | | CCE(41) cation charge density 1.76 mmol/g | | | | | | 0.3 |
| | Component (B) | sodium laureth(1) sulfate *1 | 13.0 | 13.0 | 13.0 | 13.0 | 13.0 | 13.0 |
| | | coconut oil fatty acid amide propylbetaine *2 | 1.5 | 1.5 | 1.5 | 1.5 | 1.5 | 1.5 |
| | | coconut oil fatty acid monoethanolamide *3 | 0.3 | 0.3 | 0.3 | 0.3 | 0.3 | 0.3 |
| | Component (C) | high-polymerized dimethylpolysiloxane *4 | 1.0 | 1.0 | 1.0 | 1.0 | 1.0 | 1.0 |
| | Others | pearl agent *5 | adequate dose | | | | | |
| | | pH regulator | adequate dose | | | | | |
| | | pure water | balance | | | | | |
| Evaluation | | high-polymerized dimethylpolysiloxane adsorption (mg/hair 1 g) | 0.11 | 0.44 | 0.39 | 0.33 | 0.44 | 0.82 |

*1: Kao's Emal 170J (active ingredient 70%)
*2: Kao's Amphitol 55AB (active ingredient 30%)
*3: Kawaken Fine Chemical's Amizol CME
*4: Dow Corning Toray's BY22-029 (active ingredient 50%)
*5: Kao's Pearl Concentrate SA-M2 (active ingredient 20%)

TABLE B-11

| Hair Wash Composition | | | Example | | | | | | | |
|---|---|---|---|---|---|---|---|---|---|---|
| | | (hair shampoo) | B107 | B108 | B109 | B110 | B111 | B112 | B113 | B114 |
| Composition (part by mass) | Component (A) | CCE(32) cation charge density 1.31 mmol/g | 0.21 | | | | | | | |
| | | CCE(33) cation charge density 1.37 mmol/g | | 0.21 | | | | | | |
| | | CCE(34) cation charge density 1.78 mmol/g | | | 0.21 | | | | | |
| | | CCE(35) cation charge density 1.75 mmol/g | | | | 0.21 | | | | |
| | | CCE(36) cation charge density 1.45 mmol/g | | | | | 0.21 | | | |
| | | CCE(37) cation charge density 1.46 mmol/g | | | | | | 0.21 | | |
| | | CCE(38) cation charge density 1.55 mmol/g | | | | | | | 0.21 | |
| | | CCE(39) cation charge density 1.74 mmol/g | | | | | | | | 0.21 |
| | | CCE(40) cation charge density 1.92 mmol/g | | | | | | | | |
| | | CCE(41) cation charge density 1.76 mmol/g | | | | | | | | |
| | | CCE(29) cation charge density 1.04 mmol/g | | | | | | | | |
| | | CCE(43) cation charge density 1.12 mmol/g | | | | | | | | |
| | | CCE(30) cation charge density 1.20 mmol/g | | | | | | | | |
| | Polymer except Component (A) | cationized guar gum *1 | | | | | | | | |
| | Component (B) | sodium polyoxyethylene(1) alkyl ether sulfate *2 | 13.0 | 13.0 | 13.0 | 13.0 | 13.0 | 13.0 | 13.0 | 13.0 |
| | | coconut oil fatty acid monoethanolamide *3 | 0.3 | 0.3 | 0.3 | 0.3 | 0.3 | 0.3 | 0.3 | 0.3 |
| | | coconut oil fatty acid amide propylbetaine *4 | 1.5 | 1.5 | 1.5 | 1.5 | 1.5 | 1.5 | 1.5 | 1.5 |
| | Component (C) | high-polymerized dimethylpolysiloxane *5 | 2.0 | 2.0 | 2.0 | 2.0 | 2.0 | 2.0 | 2.0 | 2.0 |
| | Others | pearl agent *6 | 1.0 | 1.0 | 1.0 | 1.0 | 1.0 | 1.0 | 1.0 | 1.0 |
| | | sodium chloride | 0.8 | 0.8 | 0.8 | 0.8 | 0.8 | 0.8 | 0.8 | 0.8 |
| | | pH regulator | | | | adequate amount | | | | |
| | | pure water | | | | balance | | | | |

TABLE B-11-continued

| | | | | | | | | | |
|---|---|---|---|---|---|---|---|---|---|
| Evaluation | high-polymerized dimethyl-polysiloxane adsorption (mg/hair 1 g) | 0.59 | 0.57 | 0.61 | 0.62 | 0.56 | 0.57 | 0.58 | 0.75 |

| | | Hair Wash Composition (hair shampoo) | Example | | | | | Comparative Example |
|---|---|---|---|---|---|---|---|---|
| | | | B115 | B116 | B117 | B118 | B119 | B4 |
| Composition (part by mass) | Component (A) | CCE(32) cation charge density 1.31 mmol/g | | | | | | |
| | | CCE(33) cation charge density 1.37 mmol/g | | | | | | |
| | | CCE(34) cation charge density 1.78 mmol/g | | | | | | |
| | | CCE(35) cation charge density 1.75 mmol/g | | | | | | |
| | | CCE(36) cation charge density 1.45 mmol/g | | | | | | |
| | | CCE(37) cation charge density 1.46 mmol/g | | | | | | |
| | | CCE(38) cation charge density 1.55 mmol/g | | | | | | |
| | | CCE(39) cation charge density 1.74 mmol/g | | | | | | |
| | | CCE(40) cation charge density 1.92 mmol/g | 0.21 | | | | | |
| | | CCE(41) cation charge density 1.76 mmol/g | | 0.21 | | | | |
| | | CCE(29) cation charge density 1.04 mmol/g | | | 0.21 | | | |
| | | CCE(43) cation charge density 1.12 mmol/g | | | | 0.21 | | |
| | | CCE(30) cation charge density 1.20 mmol/g | | | | | 0.21 | |
| | Polymer except Component (A) | cationized guar gum *1 | | | | | | 0.30 |
| | Component (B) | sodium polyoxyethylene(1) alkyl ether sulfate *2 | 13.0 | 13.0 | 13.0 | 13.0 | 13.0 | 13.0 |
| | | coconut oil fatty acid monoethanolamide *3 | 0.3 | 0.3 | 0.3 | 0.3 | 0.3 | 0.3 |
| | | coconut oil fatty acid amide propylbetaine *4 | 1.5 | 1.5 | 1.5 | 1.5 | 1.5 | 1.5 |
| | Component (C) | high-polymerized dimethyl-polysiloxane *5 | 2.0 | 2.0 | 2.0 | 2.0 | 2.0 | 2.0 |
| | Others | pearl agent *6 | 1.0 | 1.0 | 1.0 | 1.0 | 1.0 | 1.0 |
| | | sodium chloride | 0.8 | 0.8 | 0.8 | 0.8 | 0.8 | 0.8 |
| | | pH regulator | adequate amount | | | | | |
| | | pure water | balance | | | | | |

TABLE B-11-continued

| Evaluation | high-polymerized dimethyl-polysiloxane adsorption (mg/hair 1 g) | 0.62 | 0.57 | 0.29 | 0.29 | 0.34 | 0.24 |
|---|---|---|---|---|---|---|---|

*1: Rhodia's Jaguar C-13S
*2: Kao's Emal 170S (active ingredient 70%), 18.6% added
*3: Kawaken Fine Chemical's Amizol CME
*4: Kao's Amphitol 55AB (active ingredient 30%), 5.0% added
*5: Kao's Amphitol 55AB (active ingredient 30%), 5.0% added
*6: Kao's Pearl Concentrate SA-M2 (active ingredient 20%)

From Table B-10, it is known that the samples having a higher cation charge density are more excellent in dimethicone persistence therein. In addition, from Table B-11, it is known that the hair shampoos of Examples B107 to B119 are excellent in dimethicone persistence therein though the amount of the polymer added thereto is smaller than that in the hair shampoo of Comparative Example B4.

Example B120

Body Shampoo

A body shampoo having the composition mentioned below was produced according to an ordinary method.

Both hands were wetted, 0.5 mL of the produced body shampoo was applied to both hands, bubbled, then both hands were rinsed with running water for 10 seconds, the droplets were wiped away from the hands with a towel, and after dried, the skin touch was evaluated.

As a result, the skin washed with the body shampoo and dried had an excellent moisturizing feeling.

| (Components) | (%) |
|---|---|
| Sodium polyoxyethylene alkyl ether sulfate *1 | 6.2 |
| Sodium cocoylisethionate *2 | 5.8 |
| Coconut oil fatty acid amide propylbetaine *3 | 3.7 |
| Glycerin | 3.2 |
| Lauric acid | 4.0 |
| Myristic acid | 0.5 |
| Palmitic acid | 1.5 |
| Stearic acid | 1.5 |
| Sunflower oil | 13.2 |
| CCE (58) | 0.2 |
| Potassium hydroxide (to make pH 7.3) | adequate dose |
| Fragrance, Preservative | adequate dose |
| Pure water | balance |
| Total | 100.0 |

*1: Kao's Emal 270J (active ingredient 70%) (In the above composition, the content is in terms of sodium polyoxyethylene alkyl ether sulfate.)
*2: NOF's Diapon CI (active ingredient 100%)
*3: Kao's Amphitol 55AB (active ingredient 30%) (In the above composition, the content is in terms of coconut oil fatty acid amide propylbetaine.)

Example B121

Face Wash

A face wash having the composition mentioned below was produced, and evaluated in the same manner as in Example B120. As a result, the skin washed with the face wash and dried had an excellent moisturizing feeling.

| (Components) | (%) |
|---|---|
| Sodium cocoylglycinate *1 | 9.4 |
| Sodium cocoamphoacetate *2 | 2.5 |
| Coconut oil fatty acid amide propylbetaine *3 | 1.7 |
| Lauric acid | 2.0 |
| Glycerin | 6.0 |
| Vaseline | 9.0 |
| CCE (58) | 0.3 |
| Fragrance, Preservative | adequate dose |
| pH regulator (to make pH 7.9) | adequate dose |
| Pure water | balance |
| Total | 100.0 |

*1: Ajinomoto's AMILITE GCS-11 (active ingredient 100%)
*2: Nikko Chemical's NIKKOL AM-101 (active ingredient 40%) (In the above composition, the content is in terms of sodium cocoamphoacetate.)
*3: Kao's Amphitol 55AB (active ingredient 30%) (In the above composition, the content is in terms of coconut oil fatty acid amide propylbetaine.)

Example B122

Face Wash

A face wash having the composition mentioned below was produced and evaluated in the same manner as in Example B120. As a result, the skin washed with the face wash and dried had an excellent moisturizing feeling.

| (Components) | (%) |
|---|---|
| Sodium cocoylmethyltaurate *1 | 1.4 |
| Lauric acid | 28.2 |
| Myristic acid | 2.8 |
| Palmitic acid | 3.1 |
| PEG-32 *2 | 2.0 |
| Glycerin | 16.0 |
| Vaseline | 5.0 |
| CCE (58) | 0.3 |
| Fragrance, Preservative | adequate dose |
| pH regulator (to make pH 9.0) | adequate dose |
| Pure water | balance |
| Total | 100.0 |

*1: Nikko Chemical's NIKKOL CMT-30 (active ingredient 30%)
(In the above composition, the content is in terms of sodium cocoylmethyltaurate.)
*2: NOF's PEG#1500

Examples B123 to B130

Production and Evaluation of Hair Shampoo

Using CCE (3) as the component (A), a hair shampoo having the composition shown in Table B-12 was prepared in the same manner as in Example B1.

Hair tresses were washed with the above-mentioned plain shampoo, then fully wetted with warm water at 35 to 40° C., 0.5 g of the hair shampoo of Examples B123 to B130 was applied thereto, and the hair tresses were thus shampooed therewith for 1 minute. Subsequently, the hair tresses were rinsed with warm water for 30 seconds, water was wiped away with a towel, the hair tresses were then combed and dried with warm air from a hair drier, and combed for final finish, thereby providing tresses for evaluation.

Five panelists evaluated the hair tresses in point of the finger combability in hair washing, the smoothness and the long lasting smoothness in rinsing, and the moist feeling and the uniformity after drying, according to the evaluation criteria and the evaluation methods mentioned below. The evaluation results are shown in Table B-12.

The composition of Comparative Example B5 is given a standard score 3, and the compositions given a mean score of at least 3.4 by the five panelists can be said to have obviously excellent performance in point of the evaluation item.

(Evaluation Criteria, Evaluation Methods)
Finger-Combability in Washing
 5: Extremely good finger combability.
 4: Good finger combability.
 3: Average (based on the finger combability in Comparative Example B5).
 2: Bad finger combability.
 1: Extremely bad finger combability.
Smoothness in Rinsing
 5: Extremely good smoothness.
 4: Good smoothness.
 3: Average (based on the smoothness in Comparative Example B5).
 2: Bad smoothness.
 1: Extremely bad smoothness.
Long-Lasting Smoothness:
 5: Extremely good long-lasting smoothness.
 4: Good long-lasting smoothness.
 3: Average (based on the long-lasting smoothness in Comparative Example B5).
 2: Bad long-lasting smoothness.
 1: Extremely bad long-lasting smoothness.
Moist Feeling after Drying
 5: Extremely good moist feeling.
 4: Good moist feeling.
 3: Average (based on the moist feeling in Comparative Example B5).
 2: Bad moist feeling.
 1: Extremely bad moist.
Uniformity after Drying
 5: Extremely good uniformity.
 4: Good uniformity.
 3: Average (based on the uniformity in Comparative Example B5).
 2: Hair tips scattering.
 1: Noticeable hair tips scattering.

Comparative Example B5

Production and Evaluation of Hair Shampoo

In the same manner as in Example B1, a hair shampoo of Comparative Example B5 was prepared but using the composition shown in Table B-12 in place of the component (A) in Example B1, and evaluated in the same manner as above. The hair shampoo of Comparative Example B5 was also controlled to have a pH of 5.

TABLE B-12

| Hair Wash Composition (hair shampoo) | | | Example | | | | | | | | Comparative Example |
|---|---|---|---|---|---|---|---|---|---|---|---|
| | | | B123 | B124 | B125 | B126 | B127 | B128 | B129 | B130 | B5 |
| Composition (part by mass) | Component (A) | CCE(3) | 0.3 | 0.3 | 0.3 | 0.3 | 0.3 | 0.3 | 0.3 | 0.3 | |
| | | cationized guar gum *1 | | | | | | | | | 0.3 |
| | Component (B) | internal olefinsulfonate salt (1) | 10.0 | | 8.0 | 8.0 | 12.0 | | | | |
| | | internal olefinsulfonate salt (2) | | 10.0 | 2.0 | 2.0 | 3.0 | | | | |
| | | internal olefinsulfonate salt (3) | | | | | | 10.0 | | | |
| | | internal olefinsulfonate salt (4) | | | | | | | 10.0 | | |
| | | internal olefinsulfonate salt (5) | | | | | | | | 10.0 | |
| | | sodium laureth(2) sulfate *2 | | | | | | | | | 10.0 |
| | | coconut oil fatty acid amide propylbetaine *3 | 2.0 | 2.0 | 2.0 | | 2.0 | 2.0 | 2.0 | 2.0 | 2.0 |
| | | betaine lauryldimethyl-aminoacetate *4 | | | | 2.0 | | | | | |
| | | coconut oil fatty acid monoethanolamide *5 | 0.3 | 0.3 | 0.3 | 0.3 | 0.3 | 0.3 | 0.3 | 0.3 | 0.3 |

TABLE B-12-continued

| | Hair Wash Composition (hair shampoo) | | Example | | | | | | | | Comparative Example |
|---|---|---|---|---|---|---|---|---|---|---|---|
| | | | B123 | B124 | B125 | B126 | B127 | B128 | B129 | B130 | B5 |
| | Component (C) | high-polymerized dimethyl-polysiloxane *6 | 2.0 | 2.0 | 2.0 | 2.0 | 2.0 | 2.0 | 2.0 | 2.0 | 2.0 |
| | Others | pearl agent *7 | | | | | moderate dose | | | | |
| | | pH regulator | | | | | moderate dose | | | | |
| | | pure water | | | | | balance | | | | |
| Evaluation | Finger-Combability in rinsing | | 4.6 | 4.0 | 4.4 | 5.0 | 4.8 | 4.0 | 3.6 | 4.4 | 3.0 |
| | Smoothness in rinsing | | 4.8 | 4.6 | 4.8 | 4.8 | 4.8 | 4.0 | 3.4 | 4.6 | 3.0 |
| | Long-lasting smoothness in rinsing | | 4.6 | 4.4 | 4.8 | 4.8 | 4.8 | 4.0 | 3.6 | 4.6 | 3.0 |
| | Moist Feeling after drying | | 4.0 | 3.4 | 3.6 | 4.8 | 5.0 | 4.0 | 3.6 | 4.0 | 3.0 |
| | Uniformity after drying | | 4.0 | 3.8 | 3.8 | 4.8 | 4.6 | 4.0 | 3.4 | 3.6 | 3.0 |

*1: Rhodia's Jaguar C-13S
*2: Kao's Emal 270J (active ingredient 70%)
*3: Kao's Amphitol 55AB (active ingredient 30%)
*4: Kao's Amphitol 20BS (active ingredient 30%)
*5: Kawaken Fine Chemical's Amizol CME
*6: Dow Corning Torav's BY22-029 (active ingredient 50%)
*7: Kao's Pearl Concentrate SA-M2 (active ingredient 20%)

Examples C1 to C83

Production and Evaluation of Hair Shampoo

Using any of CCE (1) to (3), (6), (8), (10), (13), (27), (28), (30), (41), (46) to (50), (57) and (58) as CCE (A), a hair shampoo was prepared to have the composition shown in Tables C-1 to C-10, according to an ordinary method.

Concretely, CCE (A) and the other cationic polymer (D) than CCE (A) were dissolved or uniformly dispersed in water, an adequate amount the surfactant (B) was taken in a beaker, and uniformly mixed under heat at 60° C., and then cooled down to 50° C. Finally, water that had been evaporated away by heating was replenished, and the pH of the composition was measured. Using a pH regulator (aqueous 50% citric acid solution), the pH was controlled to be 5.

Hair tresses were washed with the plain shampoo shown below, then fully wetted with warm water at 35 to 40° C., 0.5 g of hair shampoo of Examples C1 to C83 was applied thereto, and the hair tresses were thus shampooed therewith for 1 minute. Subsequently, the hair tresses were rinsed with warm water for 30 seconds, water was wiped away with a towel, the hair tresses were then combed and dried with warm air from a hair drier, and combed for final finish to give the hair tresses for evaluation.

Five panelists evaluated the hair tresses in point of the foam softness, the finger-combability and the softness of the hair in hair washing, as well as the smoothness, the softness, the long lasting smoothness and the coated feeling in rinsing, according to the evaluation criteria and the evaluation methods mentioned below. The evaluation results are shown in Tables C-1 to C-10.

The coated feeling means that the surface of the hair has a feeling that is likely coated with a gel-like lubricant substance, and when the washed hair could have an excellent coated feeling, then the hair could enjoy more strongly the effects of the present invention, smoothness property and its sustained feeling.

The composition of Comparative Example C1 is given a standard score 3, and the compositions given a mean score of at least 3.4 by the five panelists can be said to have obviously excellent performance in point of the evaluation item.

(Composition of Plain Shampoo)

| Components) | (%) |
|---|---|
| Na polyoxyethylene laurylether sulfate (42% as Kao's Emal E-27C (active ingredient 27%)) | 11.3 |
| Coconut oil fatty acid N-methylethanolamide (Kao's Aminone C-11S) | 3.0 |
| Citric acid | 0.2 |
| Methylparaben | 0.3 |
| Pure water | balance |
| Total | 100.0 |

(Production of Plain Shampoo)

The components were put into a beaker, heated up to 80° C., mixed and uniformly dissolved. After the dissolution was confirmed, this was cooled to give a plain shampoo.

(Evaluation Criteria, Evaluation Methods)

Foam Softness in Washing
  5: Extremely soft.
  4: Soft.
  3: Average (based on the softness in Comparative Example C1).
  2: Hard.
  1: Extremely hard.

Finger Combability in Washing
  5: Extremely good finger combability.
  4: Good finger combability.
  3: Average (based on the finger combability in Comparative Example C1).
  2: Bad finger combability.
  1: Extremely bad finger combability.

Hair Softness in Washing
 5: Extremely soft.
 4: Soft.
 3: Average (based on the softness in Comparative Example C1).
 2: Hard.
 1: Extremely hard.
Smoothness in Rinsing
 5: Extremely good smoothness.
 4: Good smoothness.
 3: Average (based on the smoothness in Comparative Example C1).
 2: Bad smoothness.
 1: Extremely bad smoothness.
Softness in Rinsing
 5: Extremely soft.
 4: Soft.
 3: Average (based on the softness in Comparative Example C1).
 2: Hard.
 1: Extremely hard.
Long-Lasting Smoothness:
 5: Extremely good long-lasting smoothness.
 4: Good long-lasting smoothness.
 3: Average (based on the long-lasting smoothness in Comparative Example C1).
 2: Bad long-lasting smoothness.
 1: Extremely bad long-lasting smoothness.
Coated Feeling in Rinsing
 5: Extremely good coated feeling.
 4: Good coated feeling.
 3: Average (based on the coated feeling in Comparative Example C1).
 2: Bad coated feeling.
 1: Extremely bad coated feeling.

Comparative Examples C1 to C3

In the same manner as in Example C1, hair shampoos of Comparative Examples C1 to C3 were prepared to have the composition shown in Table C-1. The hair shampoos of Comparative Examples C1 to C3 were also controlled to have a pH of 5. The results are shown in Table C-1.

TABLE C-1

| Hair Wash Composition (hair shampoo) | | | Example | | | | | | Comparative Example | | |
|---|---|---|---|---|---|---|---|---|---|---|---|
| | | | C1 | C2 | C3 | C4 | C5 | C6 | C1 | C2 | C3 |
| Composition (part by mass) | Component (A) | CCE(46) | 0.3 | | | | | | | | |
| | | CCE(47) | | 0.3 | | | | | | | |
| | | CCE(28) | | | 0.3 | | | | | | |
| | | CCE(48) | | | | 0.3 | | | | | |
| | | CCE(27) | | | | | 0.3 | | | | |
| | | CCE(6) | | | | | | 0.3 | | | |
| | Component (D) | cationized guar gum *1 | 0.1 | 0.1 | 0.1 | 0.1 | 0.1 | 0.1 | 0.3 | | |
| | | polyquaternium-69 *2 | | | | | | | | 0.3 | |
| | | polyquaternium-7 *3 | | | | | | | | | 0.3 |
| | Component (B) | sodium laureth(2) sulfate *4 | 13.0 | 13.0 | 13.0 | 13.0 | 13.0 | 13.0 | 13.0 | 13.0 | 13.0 |
| | | coconut oil fatty acid amide propylbetaine *5 | 1.5 | 1.5 | 1.5 | 1.5 | 1.5 | 1.5 | 1.5 | 1.5 | 1.5 |
| | | coconut oil fatty acid monoethanolamide *6 | 0.3 | 0.3 | 0.3 | 0.3 | 0.3 | 0.3 | 0.3 | 0.3 | 0.3 |
| | Others | pH regulator | moderate dose | | | | | | | | |
| | | pure water | balance | | | | | | | | |
| Evaluation Results | | Foam softness in washing | 3.4 | 3.2 | 3.0 | 3.0 | 3.4 | 3.6 | 3.0 | 2.0 | 1.4 |
| | | Finger-combability in washing | 4.6 | 4.6 | 5.0 | 4.6 | 5.0 | 5.0 | 3.0 | 3.6 | 2.6 |
| | | Hair softness in washing | 4.0 | 3.6 | 4.4 | 3.8 | 4.0 | 4.2 | 3.0 | 2.6 | 2.6 |
| | | Smoothness in rinsing | 4.2 | 4.6 | 5.0 | 4.2 | 4.8 | 5.0 | 3.0 | 2.6 | 2.6 |
| | | Hair softness in rinsing | 4.4 | 4.4 | 5.0 | 4.2 | 5.0 | 5.0 | 3.0 | 3.4 | 2.4 |
| | | Long-lasting smoothness | 4.0 | 4.6 | 5.0 | 4.2 | 5.0 | 5.0 | 3.0 | 2.6 | 2.6 |
| | | Coated feeling in rinsing | 4.0 | 4.0 | 4.8 | 3.8 | 4.6 | 4.8 | 3.0 | 3.0 | 2.0 |

*1: Rhodia's Jaguar C-13S
*2: Dow Chemical's SOFTCAT SL-60
*3: Lubrizol's Marcoat 550 (active ingredient 9%)
*4: Kao's Emal 270S (active ingredient 70%)
*5: Kao's Amphitol 55AB (active ingredient 30%)
*6: Kawaken Fine Chemical's Amizol CME The details of the components used in Table C-1 are shown below.

*1: Rhodia's Jaguar C-13S
*2: Dow Chemical's SOFTCAT SL-60 (polyquaternium-69)
  Polymer of quaternary ammonium salt obtained from vinylcaprolactam, vinylpyrrolidone, dimethylaminopropyl-methacrylamide (DMAPA) and methacryloylaminopropyl-lauryldimonium chloride.
*3: Lubrizol's Marcoat 550 (active ingredient 9%) (polyquaternium-7)
  Polymer of quaternary ammonium obtained from acrylic acid amide and dimethyldiallylammonium chloride.
*4: Kao's Emal 270S (active ingredient 70%)
*5: Kao's Amphitol 55AB (active ingredient 30%)
*6: Kawaken Fine Chemical's Amizol CME

TABLE C-2

| | Hair Wash Composition | | Example | |
|---|---|---|---|---|
| | (hair shampoo) | | C7 | C8 |
| Composition (part by mass) | Component (A) | CCE(10) | 0.3 | |
| | | CCE(49) | | 0.3 |
| | Component (D) | cationized guar gum *1 | 0.1 | 0.1 |
| | Component (B) | sodium laureth-2 sulfate *2 | 13.0 | 13.0 |
| | | coconut oil fatty acid amide propylbetaine *3 | 1.5 | 1.5 |
| | | coconut oil fatty acid monoethanolamide *4 | 0.3 | 0.3 |
| | Others | pH regulator | adequate dose | |
| | | pure water | balance | |
| Evaluation Results | | Foam softness in washing | 3.4 | 3.4 |
| | | Finger-combability in washing | 4.6 | 4.6 |
| | | Hair softness in washing | 3.2 | 3.6 |
| | | Smoothness in rinsing | 4.6 | 4.6 |
| | | Hair softness in rinsing | 4.8 | 4.4 |
| | | Long-lasting smoothness | 4.8 | 4.6 |
| | | Coated feeling in rinsing | 4.6 | 3.8 |

*1: Rhodia's Jaguar C-13S
*2: Kao's Emal 270S (active ingredient 70%)
*3: Kao's Amphitol 55AB (active ingredient 30%)
*4: Kawaken Fine Chemical's Amizol CME

TABLE C-3

| | | Hair Wash Composition | Example | | | | | | | | |
|---|---|---|---|---|---|---|---|---|---|---|---|
| | | (hair shampoo) | C9 | C10 | C11 | C12 | C13 | C14 | C15 | C16 | C17 |
| Composition (part by mass) | Component (A) | CCE(50) | 0.3 | | | | | | | | |
| | | CCE(8) | | 0.3 | | | | | | | |
| | | CCE(13) | | | 0.3 | | | | | | |
| | | CCE(3) | | | | 0.3 | | | | | |
| | | CCE(57) | | | | | 0.3 | | | | |
| | | CCE(2) | | | | | | 0.3 | | | |
| | | CCE(1) | | | | | | | 0.3 | | |
| | | CCE(30) | | | | | | | | 0.3 | |
| | | CCE(41) | | | | | | | | | 0.3 |
| | Component (D) | cationized guar gum *1 | 0.1 | 0.1 | 0.1 | 0.1 | 0.1 | 0.1 | 0.1 | 0.1 | 0.1 |
| | Component (B) | sodium laureth-2 sulfate *2 | 13.0 | 13.0 | 13.0 | 13.0 | 13.0 | 13.0 | 13.0 | 13.0 | 13.0 |
| | | coconut oil fatty acid amide propylbetaine *3 | 1.5 | 1.5 | 1.5 | 1.5 | 1.5 | 1.5 | 1.5 | 1.5 | 1.5 |
| | | coconut oil fatty acid monoethanolamide *4 | 0.3 | 0.3 | 0.3 | 0.3 | 0.3 | 0.3 | 0.3 | 0.3 | 0.3 |
| | Others | pH regulator | adequate dose | | | | | | | | |
| | | pure water | balance | | | | | | | | |
| Evaluation Results | | Foam softness in washing | 3.4 | 3.4 | 3.6 | 4.0 | 3.6 | 4.0 | 4.2 | 3.4 | 3.4 |
| | | Finger-combability in washing | 4.6 | 5.0 | 4.8 | 5.0 | 4.8 | 5.0 | 5.0 | 5.0 | 4.6 |
| | | Hair softness in washing | 3.2 | 3.8 | 3.6 | 3.8 | 3.6 | 4.6 | 4.6 | 4.6 | 3.6 |
| | | Smoothness in rinsing | 4.2 | 5.0 | 5.0 | 5.0 | 4.8 | 5.0 | 5.0 | 4.6 | 4.6 |
| | | Hair softness in rinsing | 4.4 | 4.6 | 5.0 | 5.0 | 4.8 | 5.0 | 5.0 | 5.0 | 4.6 |
| | | Long-lasting smoothness | 4.2 | 5.0 | 5.0 | 5.0 | 5.0 | 5.0 | 5.0 | 5.0 | 4.6 |
| | | Coated feeling in rinsing | 4.0 | 4.6 | 4.8 | 4.8 | 4.4 | 5.0 | 5.0 | 5.0 | 4.6 |

*1: Rhodia's Jaguar C-13S
*2: Kao's Emal 270S (active ingredient 70%)
*3: Kao's Amphitol 55AB (active ingredient 30%)
*4: Kawaken Fine Chemical's Amizol CME

TABLE C-4

| | | Hair Wash Composition (hair shampoo) | Example | | | | | |
|---|---|---|---|---|---|---|---|---|
| | | | C18 | C19 | C20 | C21 | C22 | C23 |
| Composition (part by mass) | Component (A) | CCE(58) | 0.3 | 0.3 | 0.3 | 0.05 | 0.1 | 0.5 |
| | Component (D) | cationized guar gum *1 | 0.05 | 0.1 | 0.5 | 0.3 | 0.3 | 0.3 |
| | Component (B) | sodium laureth-2 sulfate *2 | 13.0 | 13.0 | 13.0 | 13.0 | 13.0 | 13.0 |
| | | coconut oil fatty acid amide propylbetaine *3 | 1.5 | 1.5 | 1.5 | 1.5 | 1.5 | 1.5 |
| | | coconut oil fatty acid monoethanolamide *4 | 0.3 | 0.3 | 0.3 | 0.3 | 0.3 | 0.3 |
| | Others | pH regulator | adequate dose | | | | | |
| | | pure water | balance | | | | | |
| Blending Ratio | | (A)/(D) | 6.000 | 3.000 | 0.600 | 0.167 | 0.333 | 1.667 |
| | | (A)/(B) | 0.0203 | 0.0203 | 0.0203 | 0.0034 | 0.0068 | 0.0338 |
| Evaluation Results | | Foam softness in washing | 3.4 | 3.8 | 4.4 | 4.0 | 4.0 | 3.4 |
| | | Finger-combability in washing | 4.6 | 4.6 | 5.0 | 4.6 | 5.0 | 5.0 |
| | | Hair softness in washing | 3.2 | 3.4 | 4.6 | 3.2 | 3.6 | 4.2 |
| | | Smoothness in rinsing | 4.6 | 5.0 | 5.0 | 4.4 | 5.0 | 5.0 |
| | | Hair softness in rinsing | 4.4 | 4.6 | 5.0 | 5.0 | 5.0 | 5.0 |
| | | Long-lasting smoothness | 4.6 | 4.6 | 5.0 | 4.6 | 5.0 | 5.0 |
| | | Coated feeling in rinsing | 4.0 | 4.4 | 5.0 | 5.0 | 5.0 | 5.0 |

*1: Rhodia's Jaguar C-13S
*2: Kao's Emal 270S (active ingredient 70%)
*3: Kao's Amphitol 55AB (active ingredient 30%)
*4: Kawaken Fine Chemical's Amizol CME

TABLE C-5

| | | Hair Wash Composition (hair shampoo) | Example | |
|---|---|---|---|---|
| | | | C24 | C25 |
| Composition (part by mass) | Component (A) | CCE(58) | 0.3 | 0.3 |
| | Component (D) | C-HPC(1) | 0.2 | |
| | | C-HPC(2) | | 0.2 |
| | Component (B) | sodium laureth-2 sulfate *1 | 13.0 | 13.0 |
| | | coconut oil fatty acid amide propylbetaine *2 | 1.5 | 1.5 |
| | | coconut oil fatty acid monoethanolamide *3 | 0.3 | 0.3 |
| | Others | pH regulator | adequate dose | |
| | | pure water | balance | |
| Evaluation Results | | Foam softness in washing | 3.4 | 4.0 |
| | | Finger-combability in washing | 5.0 | 5.0 |
| | | Hair softness in washing | 4.2 | 4.6 |
| | | Smoothness in rinsing | 5.0 | 5.0 |
| | | Hair softness in rinsing | 5.0 | 5.0 |
| | | Long-lasting smoothness | 5.0 | 5.0 |
| | | Coated feeling in rinsing | 4.8 | 4.4 |

*1: Kao's Emal 270S (active ingredient 70%)
*2: Kao's Amphitol 55AB (active ingredient 30%)
*3: Kawaken Fine Chemical's Amizol CME

TABLE C-6

| | | Hair Wash Composition (hair shampoo) | Example | | | | |
|---|---|---|---|---|---|---|---|
| | | | C26 | C27 | C28 | C29 | C30 |
| Composition (part by mas) | Component (A) | CCE(58) | 0.3 | 0.3 | 0.3 | 0.3 | 0.3 |
| | Component (D) | cationized guar gum *1 | 0.2 | | | | |
| | | cationized guar gum *2 | | 0.2 | | | |
| | | cationized guar gum *3 | | | 0.2 | | |
| | | cationized guar gum *4 | | | | 0.2 | |
| | | cationized | | | | | 0.2 |

TABLE C-6-continued

| | | Hair Wash Composition | Example | | | | |
|---|---|---|---|---|---|---|---|
| | | (hair shampoo) | C26 | C27 | C28 | C29 | C30 |
| | Component (B) | guar gum *4 | | | | | |
| | | cationized guar gum *5 | | | | | 0.2 |
| | | sodium laureth-2 sulfate *6 | 13.0 | 13.0 | 13.0 | 13.0 | 13.0 |
| | | coconut oil fatty acid amide propylbetaine *7 | 1.5 | 1.5 | 1.5 | 1.5 | 1.5 |
| | | coconut oil fatty acid monoethanolamide *8 | 0.3 | 0.3 | 0.3 | 0.3 | 0.3 |
| | Others | pH regulator | adequate amount | | | | |
| | | pure water | balance | | | | |
| Evaluation Results | | Foam softness in washing | 4.4 | 4.4 | 3.4 | 3.4 | 3.4 |
| | | Finger-combability in washing | 5.0 | 4.6 | 5.0 | 4.6 | 4.6 |
| | | Hair softness in washing | 4.0 | 4.0 | 4.2 | 3.6 | 4.0 |
| | | Smoothness in rinsing | 4.6 | 5.0 | 4.6 | 4.2 | 4.6 |
| | | Hair softness in rinsing | 5.0 | 5.0 | 5.0 | 4.6 | 5.0 |
| | | Long-lasting smoothness | 4.6 | 4.8 | 4.8 | 4.8 | 5.0 |
| | | Coated feeling in rinsing | 5.0 | 5.0 | 5.0 | 4.4 | 4.2 |

*1: Rhodia's Jaguar C-13S
*2: Rhodia's Jaguar C-17
*3: Rhodia's Jaguar C-162
*4: Rhodia's Jaguar C-500
*5: Rhodia's Jaguar C-EXCEL
*6: Kao's Emal 270S (active ingredient 70%)
*7: Kao's Amphitol 55AB (active ingredient 30%)
*8: Kawaken Fine Chemical's Amizol CME

TABLE C-7

| | | Hair Wash Composition | Example | | |
|---|---|---|---|---|---|
| | | (hair shampoo) | C31 | C32 | C33 |
| Composition (part by mass) | Component (A) | CCE(58) | 0.3 | 0.3 | 0.3 |
| | Component (D) | caesalpinia spinosa hydroxypropyltrimonium chloride *1 | 0.2 | | |
| | | locust bean hydroxypropyltrimonium chloride *2 | | 0.2 | |
| | | trigonella foenum-graecum hydroxypropyltrimonium chloride *3 | | | 0.2 |
| | Component (B) | sodium laureth-2 sulfate *4 | 13.0 | 13.0 | 13.0 |
| | | coconut oil fatty acid amide propylbetaine *5 | 1.5 | 1.5 | 1.5 |
| | | coconut oil fatty acid monoethanolamide *6 | 0.3 | 0.3 | 0.3 |
| | Others | pH regulator | adequate amount | | |
| | | pure water | balance | | |
| Evaluation Results | | Foam softness in washing | 3.6 | 4.0 | 4.0 |
| | | Finger-combability in washing | 3.4 | 4.0 | 4.8 |
| | | Hair softness in washing | 3.4 | 4.8 | 4.8 |
| | | Smoothness in rinsing | 3.6 | 4.6 | 4.8 |
| | | Hair softness in rinsing | 4.0 | 5.0 | 4.0 |
| | | Long-lasting smoothness | 4.2 | 4.8 | 4.0 |
| | | Coated feeling in rinsing | 4.4 | 5.0 | 3.8 |

*1: Toho Chemical Industry's Catinal CTR100
*2: Toho Chemical Industry's Catinal CLB100
*3: Toho Chemical Industry's Catinal CG-100
*4: Kao's Emal 270S (active ingredient 70%)
*5: Kao's Amphitol 55AB (active ingredient 30%)
*6: Kawaken Fine Chemical's Amizol CME

TABLE C-8

| | | Hair Wash Composition (hair shampoo) | Example | | | | | | | | | | | | | |
|---|---|---|---|---|---|---|---|---|---|---|---|---|---|---|---|---|
| | | | C34 | C35 | C36 | C37 | C38 | C39 | C40 | C41 | C42 | C43 | C44 | C45 | C46 | C47 |
| Composition (part by mass) | Component (A) | CCE(58) | 0.3 | 0.3 | 0.3 | 0.3 | 0.3 | 0.3 | 0.3 | 0.3 | 0.3 | 0.3 | 0.3 | 0.3 | 0.3 | 0.3 |
| | Component (D) | polyquaternium-10 *1 | 0.2 | | | | | | | | | | | | | |
| | | polyquaternium-10 *2 | | 0.2 | | | | | | | | | | | | |
| | | polyquaternium-10 *3 | | | 0.2 | | | | | | | | | | | |
| | | polyquaternium-10 *4 | | | | 0.2 | | | | | | | | | | |
| | | polyquaternium-10 *5 | | | | | 0.2 | | | | | | | | | |
| | | polyquaternium-67 *6 | | | | | | 0.2 | | | | | | | | |
| | | polyquaternium-68 *7 | | | | | | | 0.2 | | | | | | | |
| | | polyquaternium-69 *8 | | | | | | | | 0.2 | | | | | | |
| | | polyquaternium-70 *9 | | | | | | | | | 0.2 | | | | | |
| | | polyquaternium-71 *10 | | | | | | | | | | 0.2 | | | | |
| | | polyquaternium-72 *11 | | | | | | | | | | | 0.2 | | | |
| | | polyquaternium-73 *12 | | | | | | | | | | | | 0.2 | | |
| | | polyquaternium-74 *13 | | | | | | | | | | | | | 0.2 | |
| | | polyquaternium-75 *14 | | | | | | | | | | | | | | 0.2 |
| | Component (B) | sodium laureth-2 sulfate *15 | 13.0 | 13.0 | 13.0 | 13.0 | 13.0 | 13.0 | 13.0 | 13.0 | 13.0 | 13.0 | 13.0 | 13.0 | 13.0 | 13.0 |
| | | coconut oil fatty acid amide propylbetaine *16 | 1.5 | 1.5 | 1.5 | 1.5 | 1.5 | 1.5 | 1.5 | 1.5 | 1.5 | 1.5 | 1.5 | 1.5 | 1.5 | 1.5 |
| | | coconut oil fatty acid monoethanolamide *17 | 0.3 | 0.3 | 0.3 | 0.3 | 0.3 | 0.3 | 0.3 | 0.3 | 0.3 | 0.3 | 0.3 | 0.3 | 0.3 | 0.3 |
| | Others | pearl agent | | | | | | | adequate dose | | | | | | | |
| | | pH regulator | | | | | | | adequate dose | | | | | | | |
| | | pure water | | | | | | | balance | | | | | | | |
| Evaluation Results | | Foam softness in washing | 3.0 | 3.2 | 4.0 | 3.8 | 3.4 | 4.2 | 3.8 | 3.4 | 3.6 | 3.4 | 3.0 | 3.0 | 4.0 | 4.2 |
| | | Finger-combability in washing | 4.6 | 4.6 | 5.0 | 4.6 | 4.6 | 5.0 | 5.0 | 4.2 | 4.6 | 4.6 | 4.6 | 5.0 | 5.0 | 4.8 |
| | | Hair softness in washing | 3.0 | 3.2 | 4.0 | 4.2 | 3.2 | 4.0 | 4.2 | 3.6 | 3.6 | 3.6 | 3.2 | 4.6 | 4.6 | 3.8 |
| | | Smoothness in rinsing | 4.2 | 4.6 | 5.0 | 5.0 | 4.6 | 5.0 | 5.0 | 4.6 | 4.4 | 4.6 | 4.6 | 5.0 | 4.6 | 4.6 |
| | | Hair softness in rinsing | 3.8 | 4.4 | 4.8 | 5.0 | 4.4 | 5.0 | 5.0 | 4.8 | 5.0 | 5.0 | 5.0 | 5.0 | 5.0 | 5.0 |
| | | Long-lasting smoothness | 4.6 | 4.6 | 4.8 | 5.0 | 4.6 | 5.0 | 5.0 | 4.6 | 4.6 | 4.6 | 5.0 | 5.0 | 4.6 | 4.6 |
| | | Coated feeling in rinsing | 4.0 | 4.0 | 4.4 | 4.6 | 4.0 | 5.0 | 5.0 | 5.0 | 4.4 | 4.6 | 5.0 | 5.0 | 5.0 | 4.2 |

*1 Dow Chemical's UCARE JR125
*2 Dow Chemical's UCARE JR400
*3 Dow Chemical's UCARE JR30M
*4 Dow Chemical's UCARE LR400
*5 Dow Chemical's UCARE LR30M
*6 Dow Chemical's SOFTCAT SL-5
*7 Dow Chemical's SOFTCAT SL-30
*8 Dow Chemical's SOFTCAT SL-60
*9 Dow Chemical's SOFTCAT SL-100
*10 Dow Chemical's SOFTCAT SX-400X
*11 Dow Chemical's SOFTCAT SX-1300H
*12 Dow Chemical's SOFTCAT SX-1300X
*13 Dow Chemical's SOFTCAT SK-H
*14 Dow Chemical's SOFTCAT SK-MH
*15 Kao's Emal 270S (active ingredient 70%)
*16 Kao's Amphitol 55AB (active ingredient 30%)
*17 Kawaken Fine Chemical's Amizol CME

TABLE C-9

| | | Hair Wash Composition (hair shampoo) | Example | | | | | | | | |
|---|---|---|---|---|---|---|---|---|---|---|---|
| | | | C48 | C49 | C50 | C51 | C52 | C53 | C54 | C55 | C56 |
| Composition (part by mass) | Component (A) | CCE(58) | 0.3 | 0.3 | 0.3 | 0.3 | 0.3 | 0.3 | 0.3 | 0.3 | 0.3 |
| | Component (D) | starch hydroxypropyl-trimonium | 0.2 | | | | | | | | |

TABLE C-9-continued

|  |  |  |  |  |  |  |  |  |  |  |
|---|---|---|---|---|---|---|---|---|---|---|
|  | chloride *1 |  |  |  |  |  |  |  |  |  |
|  | Cassia hydroxypropyl-trimonium chloride *2 | 0.2 |  |  |  |  |  |  |  |  |
|  | Cassia hydroxypropyl-trimonium chloride *3 |  | 0.2 |  |  |  |  |  |  |  |
|  | polyquaternium-5 *4 |  |  | 0.2 |  |  |  |  |  |  |
|  | polyquaternium-7 *5 |  |  |  | 0.2 |  |  |  |  |  |
|  | polyquaternium-7 *6 |  |  |  |  | 0.2 |  |  |  |  |
|  | polyquaternium-7 *7 |  |  |  |  |  | 0.2 |  |  |  |
|  | polyquaternium-7 *8 |  |  |  |  |  |  | 0.2 |  |  |
|  | polyquaternium-22 *9 |  |  |  |  |  |  |  | 0.2 |  |
|  | polyquaternium-22 *10 |  |  |  |  |  |  |  |  |  |
|  | polyquaternium-39 *11 |  |  |  |  |  |  |  |  |  |
|  | polyquaternium-47 *12 |  |  |  |  |  |  |  |  |  |
|  | polyquaternium-53 *13 |  |  |  |  |  |  |  |  |  |
|  | polyquaternium-87 *14 |  |  |  |  |  |  |  |  |  |
|  | polyquaternium-52 *15 |  |  |  |  |  |  |  |  |  |
|  | polyquaternium-52 *16 |  |  |  |  |  |  |  |  |  |
| Component (B) | sodium laureth-2 sulfate *17 | 13.0 | 13.0 | 13.0 | 13.0 | 13.0 | 13.0 | 13.0 | 13.0 | 13.0 |
|  | coconut oil fatty acid amide propylbetaine *18 | 1.5 | 1.5 | 1.5 | 1.5 | 1.5 | 1.5 | 1.5 | 1.5 | 1.5 |
|  | coconut oil fatty acid monoethanolamide *19 | 0.3 | 0.3 | 0.3 | 0.3 | 0.3 | 0.3 | 0.3 | 0.3 | 0.3 |
| Others | pearl agent |  |  |  | adequate dose |  |  |  |  |  |
|  | pH regulator |  |  |  | adequate dose |  |  |  |  |  |
|  | pure water |  |  |  | balance |  |  |  |  |  |
| Evaluation Results | Foam softness in washing | 3.0 | 3.0 | 3.4 | 3.4 | 3.4 | 3.8 | 4.0 | 3.6 | 3.2 |
|  | Finger-combability in washing | 4.0 | 5.0 | 4.6 | 5.0 | 4.2 | 4.6 | 4.6 | 5.0 | 4.6 |
|  | Hair softness in washing | 3.2 | 3.8 | 4.6 | 4.4 | 3.6 | 4.6 | 4.2 | 4.6 | 4.0 |
|  | Smoothness in rinsing | 4.2 | 5.0 | 4.8 | 4.6 | 4.6 | 4.8 | 5.0 | 5.0 | 5.0 |
|  | Hair softness in rinsing | 4.0 | 5.0 | 4.8 | 4.0 | 4.4 | 5.0 | 5.0 | 5.0 | 4.4 |
|  | Long-lasting smoothness | 4.2 | 4.8 | 5.0 | 4.0 | 4.6 | 4.4 | 5.0 | 5.0 | 4.6 |
|  | Coated feeling in rinsing | 3.8 | 5.0 | 4.4 | 3.6 | 4.0 | 4.4 | 5.0 | 5.0 | 4.8 |

|  |  | Hair Wash Composition (hair shampoo) | Example |  |  |  |  |  |  |
|---|---|---|---|---|---|---|---|---|---|
|  |  |  | C57 | C58 | C59 | C60 | C61 | C62 | C63 |
| Composition (part by mass) | Component (A) | CCE(58) | 0.3 | 0.3 | 0.3 | 0.3 | 0.3 | 0.3 | 0.3 |
|  | Component (D) | starch hydroxypropyl-trimonium chloride *1 |  |  |  |  |  |  |  |
|  |  | Cassia hydroxypropyl-trimonium chloride *2 |  |  |  |  |  |  |  |
|  |  | Cassia hydroxypropyl-trimonium chloride *3 |  |  |  |  |  |  |  |
|  |  | polyquaternium-5 *4 |  |  |  |  |  |  |  |
|  |  | polyquaternium-7 *5 |  |  |  |  |  |  |  |
|  |  | polyquaternium-7 *6 |  |  |  |  |  |  |  |
|  |  | polyquaternium-7 *7 |  |  |  |  |  |  |  |
|  |  | polyquaternium-7 *8 |  |  |  |  |  |  |  |
|  |  | polyquaternium-22 *9 |  |  |  |  |  |  |  |
|  |  | polyquaternium-22 *10 | 0.2 |  |  |  |  |  |  |
|  |  | polyquaternium-39 *11 |  | 0.2 |  |  |  |  |  |
|  |  | polyquaternium-47 *12 |  |  | 0.2 |  |  |  |  |
|  |  | polyquaternium-53 *13 |  |  |  | 0.2 |  |  |  |
|  |  | polyquaternium-87 *14 |  |  |  |  | 0.2 |  |  |

TABLE C-9-continued

| | | | | | | | | | |
|---|---|---|---|---|---|---|---|---|---|
| | Component (B) | polyquaternium-52 *15 | | | | | | 0.2 | |
| | | polyquaternium-52 *16 | | | | | | | 0.2 |
| | | sodium laureth-2 sulfate *17 | 13.0 | 13.0 | 13.0 | 13.0 | 13.0 | 13.0 | 13.0 |
| | | coconut oil fatty acid amide propylbetaine *18 | 1.5 | 1.5 | 1.5 | 1.5 | 1.5 | 1.5 | 1.5 |
| | | coconut oil fatty acid monoethanolamide *19 | 0.3 | 0.3 | 0.3 | 0.3 | 0.3 | 0.3 | 0.3 |
| | Others | pearl agent | | | adequate dose | | | | |
| | | pH regulator | | | adequate dose | | | | |
| | | pure water | | | balance | | | | |
| Evaluation Results | | Foam softness in washing | 3.0 | 3.4 | 4.4 | 4.4 | 3.4 | 3.4 | 3.8 |
| | | Finger-combability in washing | 4.2 | 4.6 | 5.0 | 5.0 | 5.0 | 5.0 | 5.0 |
| | | Hair softness in washing | 4.6 | 4.4 | 4.6 | 4.6 | 4.6 | 4.6 | 4.6 |
| | | Smoothness in rinsing | 4.6 | 4.6 | 5.0 | 4.6 | 4.8 | 4.2 | 5.0 |
| | | Hair softness in rinsing | 5.0 | 5.0 | 5.0 | 5.0 | 5.0 | 5.0 | 5.0 |
| | | Long-lasting smoothness | 4.6 | 4.6 | 5.0 | 5.0 | 4.6 | 5.0 | 5.0 |
| | | Coated feeling in rinsing | 5.0 | 5.0 | 5.0 | 5.0 | 5.0 | 4.0 | 5.0 |

*1 Lubrizol's Sensomer-C150 polymer
*2 Lubrizol's Sensomer-CT250 polymer
*3 Lubrizol's Sensomer-CT400 polymer
*4 Lubrizol's Merquat 5
*5 Lubrizol's Merquat 550
*6 Lubrizol's Merquat 740
*7 Lubrizol's Merquat 2200
*8 Lubrizol's Merquat S
*9 Lubrizol's Merquat 280
*10 Lubrizol's Merquat 295
*11 Lubrizol's Merquat 3330DRY
*12 Lubrizol's Merquat 2001
*13 Lubrizol's Merquat 2003PR
*14 BASF's Luviquat Sensation
*15 Kao's Sofcare KG-301W
*16 Kao's Sofcare KG-101W-E
*17 Kao's Emal 270S (active ingredient 70%)
*18 Kao's Amphitol 55AB (active ingredient 30%)
*19 Kawaken Fine Chemical's Amizol CME

TABLE C-10

| Hair Wash Composition (hair shampoo) | | | Example | | | | | | |
|---|---|---|---|---|---|---|---|---|---|
| | | | C64 | C65 | C66 | C67 | C68 | C69 | C70 |
| Composition (part by mass) | Component (A) | CCE(58) | 0.3 | 0.3 | 0.3 | 0.3 | 0.3 | 0.3 | 0.3 |
| | Component (D) | cationized guar gum *1 | 0.1 | 0.1 | 0.1 | 0.1 | 0.1 | 0.1 | 0.1 |
| | Component (B) | sodium lauryl sulfate *2 | 13.0 | | | | | | |
| | | ammonium laureth-(1) sulfate *3 | | 13.0 | | | | | |
| | | sodium laureth-(1) sulfate *4 | | | 13.0 | 13.0 | 13.0 | 13.0 | 13.0 |
| | | sodium laureth-(3) sulfate *5 | | | | | | | |
| | | sodium laureth-(4.5) acetate *6 | | | | | | | |
| | | sodium laureth-(10) acetate *7 | | | | | | | |
| | | α-olefin sulfonate *8 | | | | | | | |
| | | sodium lauroylmethyl sarcosine *9 | | | | | | | |
| | | sodium | | | | | | | |

TABLE C-10-continued

|  |  |  |  |  |  |  |  |  |  |
|---|---|---|---|---|---|---|---|---|---|
|  |  | alkylglutamate *10 |  |  |  |  |  |  |  |
|  |  | coconut oil fatty acid monoethanolamide *11 | 0.3 | 0.3 | 0.3 | 0.3 | 0.3 | 0.3 | 0.3 |
|  |  | coconut oil fatty acid methylethanolamide *12 |  |  |  |  |  |  |  |
|  |  | coconut oil fatty acid amide propylbetaine *13 | 1.5 | 1.5 | 1.5 | 1.5 | 1.5 | 1.5 | 1.5 |
|  |  | lauramide monoiso-propanolamide *14 |  |  |  |  |  |  |  |
|  |  | laurylcarboxymethyl-hydroxyimidazolium betaine *15 |  |  |  |  |  |  |  |
|  |  | laurylhydroxysulfo-betaine *16 |  |  |  |  |  |  |  |
|  |  | laurylbetaine *17 |  |  |  |  |  |  |  |
|  |  | laureth-3 *18 |  |  |  |  |  |  |  |
|  |  | alkylglucoside *19 |  |  |  |  |  |  |  |
|  |  | behenetrimonium chloride *20 |  |  |  |  | 0.5 |  |  |
|  |  | cetyltrimonium chloride *21 |  |  |  |  |  | 0.5 |  |
|  |  | lauric acid *22 |  |  |  |  |  |  | 0.5 |
|  |  | myristic acid *23 |  |  |  |  |  |  |  | 0.5 |
|  | Others | pH regulator pure water | adequate dose balance |  |  |  |  |  |  |
| Blending Ratio |  | (A)/(D) |  |  |  | 3.00 |  |  |  |
|  |  | (A)/(B) | 0.02027 | 0.02027 | 0.02027 | 0.01961 | 0.01961 | 0.01961 | 0.01961 |
| Evaluation Results |  | Foam softness in washing | 3.0 | 3.4 | 3.4 | 3.4 | 3.8 | 3.8 | 3.4 |
|  |  | Finger-combability in washing | 5.0 | 5.0 | 5.0 | 5.0 | 5.0 | 4.6 | 4.6 |
|  |  | Hair softness in washing | 4.0 | 4.4 | 4.4 | 3.8 | 3.8 | 3.4 | 3.6 |
|  |  | Smoothness in rinsing | 4.2 | 4.6 | 4.6 | 5.0 | 4.6 | 4.6 | 4.2 |
|  |  | Hair softness in rinsing | 4.4 | 4.6 | 4.4 | 5.0 | 5.0 | 4.8 | 4.2 |
|  |  | Long-lasting smoothness | 4.2 | 4.6 | 4.6 | 5.0 | 5.0 | 4.6 | 4.2 |
|  |  | Coated feeling in rinsing | 4.0 | 4.4 | 4.0 | 4.8 | 4.6 | 4.4 | 3.6 |

|  |  | Hair Wash Composition (hair shampoo) | Example |  |  |  |  |  |  |
|---|---|---|---|---|---|---|---|---|---|
|  |  |  | C71 | C72 | C73 | C74 | C75 | C76 | C77 |
| Composition (part by mass) | Component (A) | CCE(58) | 0.3 | 0.3 | 0.3 | 0.3 | 0.3 | 0.3 | 0.3 |
|  | Component (D) | cationized guar gum *1 | 0.1 | 0.1 | 0.1 | 0.1 | 0.1 | 0.1 | 0.1 |
|  | Component (B) | sodium lauryl sulfate *2 |  |  |  |  |  |  |  |
|  |  | ammonium laureth-(1) sulfate *3 |  |  |  |  |  |  |  |
|  |  | sodium laureth-(1) sulfate *4 |  |  |  |  |  |  |  |
|  |  | sodium laureth-(3) sulfate *5 | 13.0 |  |  |  |  |  |  |
|  |  | sodium laureth-(4.5) acetate *6 |  | 13.0 |  |  |  |  |  |
|  |  | sodium laureth-(10) acetate *7 |  |  | 13.0 |  |  |  |  |
|  |  | α-olefin sulfonate *8 |  |  |  | 13.0 |  |  |  |
|  |  | sodium lauroylmethyl sarcosine *9 |  |  |  |  | 13.0 |  |  |
|  |  | sodium alkylglutamate *10 |  |  |  |  |  | 13.0 |  |
|  |  | coconut oil fatty acid monoethanolamide *11 | 0.3 | 0.3 | 0.3 | 0.3 | 0.3 | 0.3 | 0.3 |
|  |  | coconut oil |  |  |  |  |  |  |  |

TABLE C-10-continued

|  |  |  |  |  |  |  |  |  |
|---|---|---|---|---|---|---|---|---|
|  | fatty acid methylethanolamide *12 |  |  |  |  |  |  |  |
|  | coconut oil fatty acid amide propylbetaine *13 | 1.5 | 1.5 | 1.5 | 1.5 | 1.5 | 1.5 | 1.5 |
|  | lauramide monoiso-propanolamide *14 |  |  |  |  |  |  |  |
|  | laurylcarboxymethyl-hydroxyimidazolium betaine *15 |  |  |  |  |  |  | 13.0 |
|  | laurylhydroxysulfo-betaine*16 |  |  |  |  |  |  |  |
|  | laurylbetaine *17 |  |  |  |  |  |  |  |
|  | laureth-3 *18 |  |  |  |  |  |  |  |
|  | alkylglucoside *19 |  |  |  |  |  |  |  |
|  | behenetrimonium chloride *20 |  |  |  |  |  |  |  |
|  | cetyltrimonium chloride *21 |  |  |  |  |  |  |  |
|  | lauric acid *22 |  |  |  |  |  |  |  |
|  | myristic acid *23 |  |  |  |  |  |  |  |
| Others | pH regulator |  |  |  | adequate dose |  |  |  |
|  | pure water |  |  |  | balance |  |  |  |
| Blending Ratio | (A)/(D) |  |  |  | 3.00 |  |  |  |
|  | (A)/(B) | 0.02027 | 0.02027 | 0.02027 | 0.02027 | 0.02027 | 0.02027 | 0.02027 |
| Evaluation Results | Foam softness in washing | 3.0 | 3.0 | 1.8 | 3.4 | 4.0 | 4.4 | 4.4 |
|  | Finger-combability in washing | 4.6 | 4.2 | 3.2 | 5.0 | 4.6 | 4.2 | 5.0 |
|  | Hair softness in washing | 3.2 | 3.2 | 2.2 | 4.4 | 3.6 | 4.6 | 4.6 |
|  | Smoothness in rinsing | 4.2 | 5.0 | 4.6 | 5.0 | 5.0 | 5.0 | 5.0 |
|  | Hair softness in rinsing | 4.0 | 5.0 | 3.6 | 5.0 | 4.8 | 5.0 | 5.0 |
|  | Long-lasting smoothness | 4.0 | 5.0 | 3.6 | 5.0 | 4.8 | 5.0 | 5.0 |
|  | Coated feeling in rinsing | 3.6 | 5.0 | 3.0 | 4.8 | 4.4 | 4.8 | 4.8 |

|  |  | Hair Wash Composition | Example |  |  |  |  |  |
|---|---|---|---|---|---|---|---|---|
|  |  | (hair shampoo) | C78 | C79 | C80 | C81 | C82 | C83 |
| Composition (part by mass) | Component (A) | CCE(58) | 0.3 | 0.3 | 0.3 | 0.3 | 0.3 | 0.3 |
|  | Component (D) | cationized guar gum *1 | 0.1 | 0.1 | 0.1 | 0.1 | 0.1 | 0.1 |
|  | Component (B) | sodium lauryl sulfate *2 |  |  |  |  |  |  |
|  |  | ammonium laureth-(1) sulfate *3 |  |  |  |  |  |  |
|  |  | sodium laureth-(1) sulfate *4 |  | 13.0 | 13.0 | 13.0 | 13.0 | 13.0 |
|  |  | sodium laureth-(3) sulfate *5 |  |  |  |  |  |  |
|  |  | sodium laureth-(4.5) acetate *6 |  |  |  |  |  |  |
|  |  | sodium laureth-(10) acetate *7 |  |  |  |  |  |  |
|  |  | α-olefin sulfonate *8 |  |  |  |  |  |  |
|  |  | sodium lauroylmethyl sarcosine *9 |  |  |  |  |  |  |
|  |  | sodium alkylglutamate *10 |  |  |  |  |  |  |
|  |  | coconut oil fatty acid monoethanolamide *11 | 0.3 |  |  |  |  |  |
|  |  | coconut oil fatty acid methylethanolamide *12 |  | 1.0 |  |  |  |  |
|  |  | coconut oil fatty acid amide propylbetaine *13 | 1.5 |  |  |  |  |  |

TABLE C-10-continued

|  | Component | | | | | | |
|---|---|---|---|---|---|---|---|
| | lauramide monoisopropanolamide *14 | | | 1.0 | | | |
| | laurylcarboxymethylhydroxyimidazolium betaine *15 | | | | | | |
| | laurylhydroxysulfobetaine*16 | | | | 2.0 | | |
| | laurylbetaine *17 | | | | | 2.0 | |
| | laureth-3 *18 | | | | | | 2.0 |
| | alkylglucoside *19 | 13.0 | | | | | |
| | behenetrimonium chloride *20 | | | | | | |
| | cetyltrimonium chloride *21 | | | | | | |
| | lauric acid *22 | | | | | | |
| | myristic acid *23 | | | | | | |
| Others | pH regulator | | | adequate dose | | | |
| | pure water | | | balance | | | |
| Blending Ratio | (A)/(D) | | | 3.00 | | | |
| | (A)/(B) | 0.02027 | 0.02143 | 0.02143 | 0.02000 | 0.02000 | 0.02000 |
| Evaluation Results | Foam softness in washing | 3.8 | 4.0 | 4.0 | 3.4 | 3.8 | 3.4 |
| | Finger-combability in washing | 4.2 | 5.0 | 5.0 | 4.6 | 5.0 | 5.0 |
| | Hair softness in washing | 3.2 | 3.6 | 4.0 | 3.6 | 4.0 | 4.0 |
| | Smoothness in rinsing | 5.0 | 4.6 | 4.6 | 4.2 | 4.6 | 4.6 |
| | Hair softness in rinsing | 5.0 | 4.4 | 4.2 | 3.8 | 4.6 | 4.8 |
| | Long-lasting smoothness | 5.0 | 4.6 | 4.4 | 4.2 | 4.8 | 4.6 |
| | Coated feeling in rinsing | 5.0 | 4.0 | 4.0 | 3.6 | 4.0 | 4.4 |

*1 Rhodia's Jaguar C-13S
*2: Kao's Emal 0
*3: Kao's Emal 170S-A (active ingredient 70%)
*4: Kao's Emal 170J (active ingredient 70%)
*5: Kao's Emal 327 (active ingredient 27%)
*6: Kao's KAO AKYPO RMN45NV (active ingredient 23.5%)
*7: Kao's KAO AKYPO RMN100NV (active ingredient 23.5%)
*8: Nikko Chemical's NIKKOL OS-14
*9: Innospec's Iselux TM LQ-CLR-PE
*10: Ajinomoto's Amisoft CS-11
*11: Kawaken Fine Chemical's Amizol CME
*12: Kao's Aminone C-11S
*13: Kao's Amphitol 55AB (active ingredient 30%)
*14: Kawaken Fine Chemical's Amizol PLME-A
*15: Kao's Amphitol 20YB (active ingredient 30%)
*16: Kao's Amphitol 20HD (active ingredient 30%)
*17: Kao's Amphitol 20BS (active ingredient 30%)
*18: Kao's Emulgen 103
*19: Kao's Midol 12 (active ingredient 40%)
*20: Kao's Cortamine 2285E-E (active ingredient 58%)
*21: Kao's Cortamine 60W (active ingredient 30%)
*22: Kao's Lunac L-98
*23: Kao's Lunac M-98

From Tables C-1 to C-10, it is known that the hair shampoos of Examples C1 to C83 are excellent in the foam softness, the finger-combability and the hair softness in washing, and in the smoothness, the softness, the long-lasting smoothness and the coated feeling in rinsing.

Example C84

Hair Shampoo

A hair shampoo comprising the components mentioned below was produced in the same manner as in Example C1. As a result, the hair washed with the hair shampoo had an excellent moist feeling after drying.

| (Components) | (%) |
|---|---|
| Sodium laureth-1 sulfate *1 | 13.0 |
| Coconut oil fatty acid amide propylbetaine *2 | 2.0 |
| Coconut oil fatty acid monoethanolamide *3 | 1.0 |
| CCE (58) | 0.3 |
| Cationized hydroxyethyl cellulose *4 | 0.1 |
| Dimethyldiallylammonium chloride-acrylamide copolymer *5 | 0.1 |
| High-polymerized dimethylpolysiloxane *6 | 2.0 |
| Amino-modified high-polymerized dimethylpolysiloxane *7 | 1.0 |

| (Components) | (%) |
|---|---|
| PPG-3 caprylyl ether *8 | 0.5 |
| Pearl agent *9 | 1.0 |
| Fragrance, Preservative | adequate dose |
| Pure water | balance |
| Total | 100.0 |

*1: Kao's Emal 170J (active ingredient 70%)
*2: Kao's Amphitol 55AB (active ingredient 30%)
*3: Kao's Aminone C-11S
*4: Kao's POIZ C-80M
*5: Lubrizol's Merquat 550 (active ingredient 9%)
*6: Dow Corning Toray's BY22-029 (active ingredient 50%)
*7: Dow Corning Toray's SM8904 (active ingredient 40%)
*8: Kao's Kao Sofcare GP-1
*9: Kao's Pearl Concentrate SA-M2

Example C85

Hair Shampoo

A hair shampoo having the composition mentioned below was produced and evaluated in the same manner as in Example C1. As a result, the hair washed with the hair shampoo and dried had an excellent moist feeling.

| (Components) | (%) |
|---|---|
| Sodium laureth-1 sulfate *1 | 13.0 |
| Coconut oil fatty acid amide propylbetaine *2 | 1.5 |
| Coconut oil fatty acid monoethanolamide *3 | 1.0 |
| CCE (58) | 0.3 |
| C-HPC (1) | 0.1 |
| High-polymerized dimethylpolysiloxane *4 | 2.0 |
| PPG-3 caprylyl ether *5 | 1.0 |
| Pearl agent *6 | 1.0 |
| Fragrance, Preservative | adequate dose |
| Pure water | balance |
| Total | 100.0 |

*1: Kao's Emal 170J (active ingredient 70%)
*2: Kao's Amphitol 55AB (active ingredient 30%)
*3: Kao's Aminone C-11S
*4: Dow Corning Toray's BY22-029 (active ingredient 50%)
*5: Kao's Kao Sofcare GP-1
*6: Kao's Pearl Concentrate SA-M2

Example C86

Body Shampoo

A body shampoo having the composition mentioned below was produced according to an ordinary method.
Both hands were wetted, 0.5 mL of the produced body shampoo was applied to both hands, bubbled, then both hands were rinsed with running water for 10 seconds, the droplets were wiped away from the hands with a towel, and after dried, the skin touch was evaluated.
As a result, the skin washed with the body shampoo and dried had an excellent moist feeling.

| (Components) | (%) |
|---|---|
| Lauric acid | 8.6 |
| Myristic acid | 8.4 |
| Palmitic acid | 2.5 |
| Sodium polyoxyethylene alkyl ether sulfate *1 | 2.9 |
| Glycerin | 1.9 |
| Propylene glycol | 1.2 |
| Coconut oil fatty acid amide propylbetaine *2 | 0.9 |
| CCE (48) | 0.2 |
| Cationized guar gum *3 | 0.1 |
| Potassium hydroxide (to make pH 9.6) | adequate dose |
| Fragrance, Preservative | adequate dose |
| Pure water | balance |
| Total | 100.0 |

*1: Kao's "Emal 270J" (active ingredient 70%) (In the above composition, the content is in terms of sodium polyoxyethylene alkyl ether sulfate.)
*2: Kao's "Amphitol 55AB" (active ingredient 30%) (In the above composition, the content is in terms of coconut oil fatty acid amide propylbetaine.)
*3: Rhodia's (Jaguar C-13S" (active ingredient 100%)

Example C87

Body Shampoo

A body shampoo having the composition mentioned below was produced according to an ordinary method, and evaluated in the same manner as in Example C86. As a result, the skin washed with the body shampoo and dried had an excellent moist feeling.

| (Components) | (%) |
|---|---|
| Sodium polyoxyethylene alkyl ether sulfate *1 | 10.0 |
| Coconut oil fatty acid amide propylbetaine *2 | 1.5 |
| Coconut oil fatty acid monoethanolamide | 1.0 |
| Glycerin | 2.0 |
| Sodium chloride | 1.0 |
| CCE (48) | 0.2 |
| Polyquaternium-10 *3 | 0.1 |
| Fragrance, Preservative | adequate dose |
| Pure water | balance |
| Total | 100.0 |

*1: Kao's Emal 270J (active ingredient 70%) (In the above composition, the content is in terms of sodium polyoxyethylene alkyl ether sulfate.)
*2: Kao's Amphitol 55AB (active ingredient 30%) (In the above composition, the content is in terms of coconut oil fatty acid amide propylbetaine.)
*3: Kao's POIZ C-80M (active ingredient 100%)

Example C88

Body Shampoo

A body shampoo having the composition mentioned below was produced according to an ordinary method, and evaluated in the same manner as in Example C86. As a result, the skin washed with the body shampoo and dried had an excellent moist feeling.

| (Components) | (%) |
|---|---|
| Potassium lauroylsarcosinate *1 | 6.0 |
| Sodium polyoxyethylene alkyl ether sulfate *2 | 3.3 |
| Propylene glycol | 3.2 |
| Coconut oil fatty acid amide propylbetaine *3 | 2.8 |
| Glycol distearate | 1.0 |
| Coconut oil fatty acid diethanolamide | 0.7 |
| CCE (48) | 0.2 |
| Polyquaternium-10 *4 | 0.1 |

-continued

| (Components) | (%) |
|---|---|
| Fragrance, Preservative | adequate dose |
| pH regulator (to make pH 6.0) | adequate dose |
| Pure water | balance |
| Total | 100.0 |

*1: Nikko Chemical's NIKKOL SARCOSINATE LK-30 (active ingredient 30%) (In the above composition, the content is in terms of potassium lauroylsarcosinate.)
*2: Kao's Emal 270J (active ingredient 70%) (In the above composition, the content is in terms of sodium polyoxyethylene alkyl ether sulfate.)
*3: Kao's Amphitol 55AB (active ingredient 30%) (In the above composition, the content is in terms of coconut oil fatty acid amide propylbetaine.)
*4: Kao's POIZ C-80M (active ingredient 100%)

Example C89

Face Wash

A face wash having the composition mentioned below was produced and evaluated in the same manner as in Example C86. As a result, the skin washed with the body shampoo and dried had an excellent moist feeling.

| (Components) | (%) |
|---|---|
| Na cocoylmethyltaurate *1 | 1.4 |
| Lauric acid | 28.2 |
| Myristic acid | 2.8 |
| Palmitic acid | 3.1 |
| PEG-32 *2 | 2.0 |
| Glycerin | 16.0 |
| CCE (48) | 0.2 |
| Polyquaternium-10*3 | 0.1 |
| Fragrance, Preservative | adequate dose |
| pH regulator (to make pH 9.0) | adequate dose |
| Pure water | balance |
| Total | 100.0 |

*1: Nikko Chemical's NIKKOL CMT-30 (active ingredient 30%) (In the above composition, the content is in terms of sodium cocoylmethyltaurate.)
*2: NOF's PEG#1500 (active ingredient 100%)
*3Kao's POIZ C-80M (active ingredient 100%)

Examples C90 to C98

Production and Evaluation of Hair Shampoo

Using CCE (58) as the component (A) and in the same manner as in Example C1, a hair shampoo was prepared to have the composition shown in Table C-11.

Hair tresses were washed with the above-mentioned plain shampoo, then fully wetted with warm water at 35 to 40° C., 0.5 g of the shampoo of Examples C90 to C98 was applied thereto, and the hair tresses were thus shampooed therewith for 1 minute. Subsequently, the hair tresses were rinsed with warm water for 30 seconds, water was wiped away with a towel, the hair tresses were then combed and dried with warm air from a hair drier, and combed for final finish to give the hair tresses for evaluation.

Five panelists evaluated the hair tresses in point of the foam softness, the finger-combability and the softness of the hair in hair washing, as well as the smoothness, the softness, the long lasting smoothness ad the coated feeling in rinsing, according to the evaluation criteria and the evaluation methods mentioned below. The results are shown in Table C-11.

The composition of Comparative Example C4 is given a standard score 3, and the compositions given a mean score of at least 3.4 by the five panelists can be said to have obviously excellent performance in point of the evaluation item.

(Evaluation Criteria, Evaluation Methods)
Foam Softness in Washing
    5: Extremely soft.
    4: Soft.
    3: Average (based on the softness in Comparative Example C4).
    2: Hard.
    1: Extremely hard.
Finger Combability in Washing
    5: Extremely good finger combability.
    4: Good finger combability.
    3: Average (based on the finger combability in Comparative Example C4).
    2: Bad finger combability.
    1: Extremely bad finger combability.
Hair Softness in Washing
    5: Extremely soft.
    4: Soft.
    3: Average (based on the softness in Comparative Example C4).
    2: Hard.
    1: Extremely hard.
Smoothness in Rinsing
    5: Extremely good smoothness.
    4: Good smoothness.
    3: Average (based on the smoothness in Comparative Example C4).
    2: Bad smoothness.
    1: Extremely bad smoothness.
Softness in Rinsing
    5: Extremely soft.
    4: Soft.
    3: Average (based on the softness in Comparative Example C4).
    2: Hard.
    1: Extremely hard.
Long-Lasting Smoothness:
    5: Extremely good long-lasting smoothness.
    4: Good long-lasting smoothness.
    3: Average (based on the long-lasting smoothness in Comparative Example C4).
    2: Bad long-lasting smoothness.
    1: Extremely bad long-lasting smoothness.
Coated Feeling in Rinsing
    5: Extremely good coated feeling.
    4: Good coated feeling.
    3: Average (based on the coated feeling in Comparative Example C4).
    2: Bad coated feeling.
    1: Extremely bad coated feeling.

Comparative Example C4

Production and Evaluation of Hair Shampoo

In the same manner as in Example C1 but a different component was used in place of the component (A) in Example C1, a hair shampoo having the composition shown in the column of Comparative Example C4 in Table C-11 was prepared, and evaluated in the same manner as above. The hair shampoo of Comparative Example C4 was also controlled to have a pH of 5.

TABLE C-11

| | | Hair Wash Composition (hair shampoo) | C90 | C91 | C92 | C93 | C94 | C95 | C96 | C97 | C98 | Comparative Example C4 |
|---|---|---|---|---|---|---|---|---|---|---|---|---|
| Composition (part by mass) | Component (A) | CCE(58) | 0.3 | 0.3 | 0.3 | 0.3 | 0.3 | 0.3 | 0.3 | 0.3 | 0.3 | |
| | Component (D) | cationized guar gum *1 | 0.1 | 0.1 | 0.1 | 0.1 | 0.1 | 0.1 | 0.1 | 0.1 | | 0.3 |
| | | C-HPC(1) | | | | | | | | | 0.2 | |
| | Component (B) | internal olefinsulfonate salt (1) | 10.0 | | 8.0 | 8.0 | 12.0 | | | | 8.0 | |
| | | internal olefinsulfonate salt (2) | | 10.0 | 2.0 | 2.0 | 3.0 | | | | 2.0 | |
| | | internal olefinsulfonate salt (3) | | | | | | 10.0 | | | | |
| | | internal olefinsulfonate salt (4) | | | | | | | 10.0 | | | |
| | | internal olefinsulfonate salt (5) | | | | | | | | 10.0 | | |
| | | sodium laureth(2) sulfate *2 | | | | | | | | | | 10.0 |
| | | coconut oil fatty acid amide propylbetaine *3 | 2.0 | 2.0 | 2.0 | | 2.0 | 2.0 | 2.0 | 2.0 | 2.0 | 2.0 |
| | | betaine lauryl-dimethyl-aminoacetate *4 | | | | 2.0 | | | | | | |
| | | coconut oil fatty acid monoethanolamide *5 | 0.3 | 0.3 | 0.3 | 0.3 | 0.3 | 0.3 | 0.3 | 0.3 | 0.3 | 0.3 |
| | Others | high-polymerized dimethylpolysiloxane *6 | | | | | | | | | 2.0 | |
| | | pearl agent *7 | | | | | | adequate dose | | | | |
| | | pH regulator | | | | | | adequate dose | | | | |
| | | pure water | | | | | | balance | | | | |
| Evaluation Results | | Foam softness in washing | 4.4 | 4.0 | 4.6 | 4.6 | 5.0 | 3.6 | 3.6 | 3.6 | 5.0 | 3.0 |
| | | Finger-combability in washing | 4.8 | 4.2 | 4.8 | 5.0 | 5.0 | 4.2 | 3.6 | 3.4 | 4.8 | 3.0 |
| | | Hair softness in washing | 4.8 | 4.2 | 5.0 | 5.0 | 5.0 | 4.0 | 3.8 | 3.4 | 4.8 | 3.0 |
| | | Smoothness in rinsing | 5.0 | 3.6 | 5.0 | 5.0 | 4.8 | 4.2 | 4.0 | 3.8 | 4.2 | 3.0 |
| | | Hair softness in rinsing | 5.0 | 5.0 | 5.0 | 5.0 | 5.0 | 4.6 | 4.2 | 5.0 | 5.0 | 3.0 |
| | | Long-lasting smoothness | 5.0 | 3.6 | 5.0 | 5.0 | 4.8 | 5.0 | 4.4 | 5.0 | 4.6 | 3.0 |
| | | Coated feeling in rinsing | 5.0 | 5.0 | 5.0 | 5.0 | 5.0 | 5.0 | 5.0 | 5.0 | 5.0 | 3.0 |

*1: Rhodia's Jaguar C-13S
*2: Kao's Emal 270J (active ingredient 70%)
*3: Kao's Amphitol 55AB (active ingredient 30%)
*4: Kao's Amphitol 20BS (active ingredient 30%)
*5: Kawaken Fine Chemical's Amizol CME
*6: Dow Corning Toray's BY22-029 (active ingredient 50%)
*7: Kao's Pearl Concentrate SA-M2 (active ingredient 20%)

Examples D1 to D68

Production and Evaluation of Conditioner

Using any of CCE (1) to (3), (6), (8), (10), (13), (27), (28), (30), (41), (46) to (50), (57) and (58) as the component (A), conditioners having the composition shown in Tables D-1 to D-9 were prepared according to an ordinary method.

Concretely, the component (A), an adequate amount of water and an adequate amount of the pH regulator were taken in a beaker, and dissolved under heat at 80° C. The component (B) that had been melted at 80° C. was added thereto and emulsified with stirring for 1 hour. This was cooled down to 50° C., and the component (C) was added thereto and uniformly mixed. Finally, water that had been evaporated away by heating was replenished, and the pH of the composition was measured. If desired, the pH of the composition was controlled to be 5, using a pH regulator (aqueous 50% citric acid solution and aqueous 48% sodium hydroxide solution).

In Examples D42 to D59, the component (A), an adequate amount of water and an adequate amount of the pH regulator were taken in a beaker, and dissolved under heat at 80° C.

A mixture of the component (B) and the component (C) that had been melted at 80° C. was added thereto and emulsified with stirring for 1 hour. Finally, water that had been evaporated away by heating was replenished, and the pH of the composition was measured. If desired, the pH of the composition was controlled to be 5, using a pH regulator (aqueous 50% citric acid solution and aqueous 48% sodium hydroxide solution).

Hair tresses that had been washed with plain shampoo were well wetted with warm water at 35 to 40° C., 1 g of the conditioner of Examples D1 to D68 was applied thereto and left as such for 1 minute, then rinsed with warm water for 30 seconds, toweled to remove water, and then combed. Subsequently, the hair was dried with warm air from a drier, and finally combed to provide hair tresses for evaluation. Five panelists evaluated the hair in point of the presence in application of the conditioner to the hair, and in point of the softness and the smoothness in rinsing, and the coated feeling after drying. The results are shown in Tables D-1 to D-9.

The composition of Comparative Example D1 is given a standard score 3, and the compositions given a mean score of at least 3.4 by the five panelists can be said to have obviously excellent performance in point of the evaluation item.

(Composition of Plain Shampoo)

| (Components) | (%) |
|---|---|
| Na polyoxyethylene laurylether sulfate (42% as Kao's Emal E-27C (active ingredient 27%)) | 11.3 |
| Coconut oil fatty acid N-methylethanolamide (Kao's Aminone C-11S) | 3.0 |
| Citric acid | 0.2 |
| Methylparaben | 0.3 |
| Pure water | balance |
| Total | 100.0 |

(Production of Plain Shampoo)

The components were put into a beaker, heated up to 80° C., mixed and uniformly dissolved. After the dissolution was confirmed, this was cooled to give a plain shampoo.

(Evaluation Criteria, Evaluation Methods)
Presence in Application
   5: Excellent presence feeling.
   4: Good presence feeling.
   3: Average (based on the presence feeling in Comparative Example D1).
   2: Poor presence feeling.
   1: No presence feeling.
Softness in Rinsing
   5: Extremely soft.
   4: Soft.
   3: Average (based on the softness in Comparative Example D1).
   2: Hard.
   1: Extremely hard.
Smoothness in Rinsing
   5: Excellent smoothness
   4: Good smoothness.
   3: Average (based on the smoothness in Comparative Example D1).
   2: Bad smoothness.
   1: Extremely bad smoothness.
Coated Feeling after Drying
   5: Extremely good coated feeling.
   4: Good coated feeling.
   3: Average (based on the coated feeling in Comparative Example D1).
   2: Bad coated feeling.
   1: No coated feeling.

Comparative Examples D1 to D2

Production and Evaluation of Conditioner

In the same manner as in Example D1 but various polymers shown in Table D-1 were used in place of the component (A) in Example D1, conditioners were prepared, and evaluated. The results are shown in Table D-1.

The conditioners of Comparative Examples D1 and D2 were also controlled to have a pH of 5.

TABLE D-1

| Hair Conditioner Composition | | | Example | | | | | | Comparative Example | |
|---|---|---|---|---|---|---|---|---|---|---|
| | | | D1 | D2 | D3 | D4 | D5 | D6 | D1 | D2 |
| Composition (part by mass) | Component (A) | CCE(46) | 0.3 | | | | | | | |
| | | CCE(47) | | 0.3 | | | | | | |
| | | CCE(28) | | | 0.3 | | | | | |
| | | CCE(48) | | | | 0.3 | | | | |
| | | CCE(27) | | | | | 0.3 | | | |
| | | CCE(6) | | | | | | 0.3 | | |
| | Polymer except Component (A) | cationized polysaccharide (7) | | | | | | | 0.3 | |
| | | cationized hydroxyethyl cellulose *1 | | | | | | | | 0.3 |
| | Component (B) | behenyltrimethyl-ammonium chloride *2 | 1.5 | 1.5 | 1.5 | 1.5 | 1.5 | 1.5 | 1.5 | 1.5 |
| | Component (C) | cetyl alcohol *3 | 1.3 | 1.3 | 1.3 | 1.3 | 1.3 | 1.3 | 1.3 | 1.3 |
| | | stearyl alcohol *4 | 2.6 | 2.6 | 2.6 | 2.6 | 2.6 | 2.6 | 2.6 | 2.6 |
| | | high-polymerized dimethyl-polysiloxane *5 | 2.0 | 2.0 | 2.0 | 2.0 | 2.0 | 2.0 | 2.0 | 2.0 |
| | Others | pH regulator | | | | | adequate dose | | | |
| | | solvent | | | | | adequate dose | | | |
| | | pure water | | | | | balance | | | |

TABLE D-1-continued

| Hair Conditioner | | Example | | | | | | Comparative Example | |
|---|---|---|---|---|---|---|---|---|---|
| Composition | | D1 | D2 | D3 | D4 | D5 | D6 | D1 | D2 |
| Evaluation Results | Presence feeling in application | 3.6 | 4.2 | 3.6 | 3.6 | 4.4 | 4.0 | 3.0 | 2.0 |
| | Softness in rinsing | 3.6 | 4.4 | 4.2 | 4.4 | 4.6 | 4.2 | 3.0 | 2.0 |
| | Smoothness in rinsing | 3.6 | 4.4 | 4.0 | 4.4 | 4.6 | 4.0 | 3.0 | 2.0 |
| | Coated feeling after drying | 4.6 | 4.4 | 4.4 | 4.6 | 4.0 | 4.2 | 3.0 | 2.6 |

*1 Kao's POIZ C-80M
*2 Kao's Cortamine 2285E-E
*3 Kao's Kalcol 6098
*4 Kao's Kalcol 8098
*5 Dow Corning Toray's BY22-029 (active ingredient 50%)

TABLE D-2

| Hair Conditioner Composition | | | Example | |
|---|---|---|---|---|
| | | | D7 | D8 |
| Composition (part by mass) | Component (A) | CCE(10) | 0.3 | |
| | | CCE(49) | | 0.3 |
| | Component (B) | behenyltrimethylammonium chloride *1 | 1.5 | 1.5 |
| | Component (C) | cetyl alcohol *2 | 1.3 | 1.3 |
| | | stearyl alcohol *3 | 2.6 | 2.6 |
| | | high-polymerized dimethylpolysiloxane *4 | 2.0 | 2.0 |
| | Others | pH regulator | adequate dose | |
| | | solvent | adequate dose | |
| | | pure water | balance | |
| Evaluation Results | | Presence feeling in application | 4.0 | 3.8 |
| | | Softness in rinsing | 4.2 | 4.0 |
| | | Smoothness in rinsing | 4.4 | 3.8 |
| | | Coated feeling after drying | 4.0 | 4.0 |

*1 Kao's Cortamine 2285E-E
*2 Kao's Kalcol 6098
*3 Kao's Kalcol 8098
*4 Dow Corning Toray's BY22-029 (active ingredient 50%)

TABLE D-3

| Hair Conditioner Composition | | | Example | | | | | | | | |
|---|---|---|---|---|---|---|---|---|---|---|---|
| | | | D10 | D11 | D12 | D13 | D14 | D15 | D16 | D17 | D18 |
| Composition (part by mass) | Component (A) | CCE(50) | 0.3 | | | | | | | | |
| | | CCE(8) | | 0.3 | | | | | | | |
| | | CCE(13) | | | 0.3 | | | | | | |
| | | CCE(3) | | | | 0.3 | | | | | |
| | | CCE(57) | | | | | 0.3 | | | | |
| | | CCE(2) | | | | | | 0.3 | | | |
| | | CCE(1) | | | | | | | 0.3 | | |
| | | CCE(30) | | | | | | | | 0.3 | |
| | | CCE(41) | | | | | | | | | 0.3 |
| | Component (B) | behenyltrimethylammonium chloride *1 | 1.5 | 1.5 | 1.5 | 1.5 | 1.5 | 1.5 | 1.5 | 1.5 | 1.5 |
| | Component (C) | cetyl alcohol *2 | 1.3 | 1.3 | 1.3 | 1.3 | 1.3 | 1.3 | 1.3 | 1.3 | 1.3 |
| | | stearyl alcohol *3 | 2.6 | 2.6 | 2.6 | 2.6 | 2.6 | 2.6 | 2.6 | 2.6 | 2.6 |
| | | high-polymerized dimethyl-polysiloxane *4 | 2.0 | 2.0 | 2.0 | 2.0 | 2.0 | 2.0 | 2.0 | 2.0 | 2.0 |
| | Others | pH regulator | | | | | adequate dose | | | | |
| | | solvent | | | | | adequate dose | | | | |
| | | pure water | | | | | balance | | | | |
| Evaluation Results | | Presence feeling in application | 4.2 | 4.4 | 4.6 | 4.8 | 4.2 | 4.4 | 4.6 | 3.8 | 4.0 |
| | | Softness in rinsing | 4.4 | 4.4 | 4.6 | 4.8 | 4.4 | 5.0 | 5.0 | 4.8 | 4.4 |
| | | Smoothness in rinsing | 3.6 | 4.0 | 4.8 | 4.8 | 4.0 | 5.0 | 5.0 | 4.8 | 4.8 |

TABLE D-3-continued

| Hair Conditioner Composition | Example | | | | | | | | |
|---|---|---|---|---|---|---|---|---|---|
| | D10 | D11 | D12 | D13 | D14 | D15 | D16 | D17 | D18 |
| Coated feeling after drying | 4.2 | 4.0 | 4.6 | 4.6 | 3.6 | 4.8 | 5.0 | 5.0 | 5.0 |

*1 Kao's Cortamine 2285E-E
*2 Kao's Kalcol 6098
*3 Kao's Kalcol 8098
*4 Dow Corning Toray's BY22-029 (active ingredient 50%)

TABLE D-4

| Hair Conditioner Composition | | | Example | | | |
|---|---|---|---|---|---|---|
| | | | D19 | D20 | D21 | D22 |
| Composition (part by mass) | Component (A) | CCE(58) | 0.1 | 0.5 | 1 | 2 |
| | Component (B) | behenyltrimethyl-ammonium chloride *1 | 1.5 | 1.5 | 1.5 | 1.5 |
| | Component (C) | cetyl alcohol *2 | 1.3 | 1.3 | 1.3 | 1.3 |
| | | stearyl alcohol *3 | 2.6 | 2.6 | 2.6 | 2.6 |
| | | high-polymerized dimethyl-polysiloxane *4 | 2.0 | 2.0 | 2.0 | 2.0 |
| | Others | pH regulator | adequate dose | | | |
| | | solvent | adequate dose | | | |
| | | pure water | balance | | | |
| Blending Ratio | | (A)/(B) | 0.067 | 0.333 | 0.667 | 1.333 |
| | | (A)/(C) | 0.017 | 0.085 | 0.169 | 0.339 |
| Evaluation Results | | Presence feeling in application | 4.2 | 5.0 | 5.0 | 5.0 |
| | | Softness in rinsing | 4.6 | 4.8 | 4.6 | 4.4 |
| | | Smoothness in rinsing | 4.6 | 4.4 | 4.6 | 4.6 |
| | | Coated feeling after drying | 4.6 | 5.0 | 5.0 | 5.0 |

*1 Kao's Cortamine 2285E-E
*2 Kao's Kalcol 6098
*3 Kao's Kalcol 8098
*4 Dow Corning Toray's BY22-029 (active ingredient 50%)

TABLE D-5

| Hair Conditioner Composition | | | Example | | | | | | | | | | | |
|---|---|---|---|---|---|---|---|---|---|---|---|---|---|---|
| | | | D23 | D24 | D25 | D26 | D27 | D28 | D29 | D30 | D31 | D32 | D33 | D34 |
| Composition (part by mass) | Component (A) | CCE(58) | 0.3 | 0.3 | 0.3 | 0.3 | 0.3 | 0.3 | 0.3 | 0.3 | 0.3 | 0.3 | 0.3 | 0.3 |
| | Component (B) | stearyltrimethyl-ammonium chloride *1 | 1.5 | | | | | | | | | | | |
| | | behenyltrimethyl-ammonium chloride *2 | | | | | | 1.5 | 1.5 | 1.5 | 1.5 | 1.5 | 1.5 | 1.5 | 1.5 |
| | | stearoxypropyl-trimethyl ammonium chloride *3 | | 1.5 | | | | | | | | | | | |
| | | stearamidopropyl-dimethylamine *4 | | | 1.5 | | | | | | | | | | |
| | | behenamidopropyl-dimethylamine *5 | | | | 1.5 | | | | | | | | | |
| | | distearyldimethyl-ammonium chloride *6 | | | | | 0.5 | | | | | | | | |
| | | dialkyldimethyl-ammonium chloride *7 | | | | | | 0.5 | | | | | | | |
| | | lauryl glucoside *8 | | | | | | | 0.5 | | | | | | |
| | | polyoxyethylene(3) lauryl ether *9 | | | | | | | | 0.5 | | | | | |
| | | polyoxyethylene (20) lauryl ether *10 | | | | | | | | | 0.5 | | | | |
| | | coconut oil fatty acid monoethanolamide *11 | | | | | | | | | | 0.5 | | | |

TABLE D-5-continued

| Hair Conditioner Composition | | | D23 | D24 | D25 | D26 | D27 | D28 | D29 | D30 | D31 | D32 | D33 | D34 |
|---|---|---|---|---|---|---|---|---|---|---|---|---|---|---|
| | | lauramidomonoiso-propanolamide *12 | | | | | | | | | | | 0.5 | |
| | | coconut oil fatty acid methylethanolamide *13 | | | | | | | | | | | | 0.5 |
| | Component (C) | cetyl alcohol *14 | 1.3 | 1.3 | 1.3 | 1.3 | 1.3 | 1.3 | 1.3 | 1.3 | 1.3 | 1.3 | 1.3 | 1.3 |
| | | stearyl alcohol *15 | 2.6 | 2.6 | 2.6 | 2.6 | 2.6 | 2.6 | 2.6 | 2.6 | 2.6 | 2.6 | 2.6 | 2.6 |
| | | high-polymerized dimethyl-polysiloxane *16 | 2.0 | 2.0 | 2.0 | 2.0 | 2.0 | 2.0 | 2.0 | 2.0 | 2.0 | 2.0 | 2.0 | 2.0 |
| | Others | pH regulator | | | | | | adequate dose | | | | | | |
| | | solvent | | | | | | adequate dose | | | | | | |
| | | pure water | | | | | | balance | | | | | | |
| Evaluation Results | | Presence feeling in application | 4.6 | 4.0 | 3.8 | 3.6 | 3.6 | 4.2 | 3.8 | 4.2 | 3.6 | 4.4 | 4.0 | 4.8 |
| | | Softness in rinsing | 4.6 | 4.0 | 4.4 | 4.2 | 4.4 | 4.2 | 4.0 | 4.6 | 4.2 | 4.4 | 4.6 | 4.4 |
| | | Smoothness in rinsing | 4.0 | 4.4 | 4.0 | 4.6 | 4.4 | 4.0 | 4.6 | 4.2 | 4.0 | 4.4 | 4.6 | 4.0 |
| | | Coated feeling after drying | 4.0 | 4.8 | 4.0 | 4.6 | 4.6 | 4.0 | 4.2 | 4.6 | 4.6 | 4.0 | 4.4 | 4.8 |

*1 Kao's Cortamine 86W (active ingredient 28%)
*2 Kao's Cortamine 2285E-E (active ingredient 58%)
*3 Kao's Cortamine E-80K (active ingredient 45%)
*4 Toho Chemical Industry's Catinal MPAS
*5 Toho Chemical Industry's Catinal BMPA
*6 Kao's Cortamine D86P (active ingredient 75%)
*7 Kao's Cortamine D2345P (active ingredient 75%)
*8 Kao's Midol 12 (active ingredient 40%)
*9 Kao's Emulgen 103
*10 Kao's Emulgen 130
*11 Kawaken Fine Chemical's Amizol CME
*12 Kawaken Fine Chemical's Amizol PLME-A
*13 Kao's Aminone C-11S
*14 Kao's Kalcol 6098
*15 Kao's Kalcol 8098
*16 Dow Corning Toray's BY22-029 (active ingredient 50%)

TABLE D-6

| Hair Conditioner Composition | | | D35 | D36 | D37 | D38 | D39 | D40 | D41 |
|---|---|---|---|---|---|---|---|---|---|
| Composition (part by mass) | Component (A) | CCE(58) | 0.3 | 0.3 | 0.3 | 0.3 | 0.3 | 0.3 | 0.3 |
| | Component (B) | behenyltrimethyl-ammonium chloride *1 | 0.5 | 2.0 | 4.0 | 1.5 | 1.5 | 1.5 | 1.5 |
| | Component (C) | cetyl alcohol *2 | 1.3 | 1.3 | 1.3 | 1.0 | 3.0 | 5.0 | 1.3 |
| | | stearyl alcohol *3 | 2.6 | 2.6 | 2.6 | 1.0 | 3.0 | 5.0 | 2.6 |
| | | high-polymerized dimethyl-polysiloxane *4 | 2.0 | 2.0 | 2.0 | 2.0 | 2.0 | 2.0 | 10.0 |
| | Others | pH regulator | | | | adequate dose | | | |
| | | solvent | | | | adequate dose | | | |
| | | pure water | | | | balance | | | |
| Blending Ratio | | (A)/(B) | 0.6 | 0.15 | 0.075 | 0.2 | 0.2 | 0.2 | 0.2 |
| | | (A)/(C) | 0.051 | 0.051 | 0.051 | 0.075 | 0.038 | 0.025 | 0.022 |
| Evaluation Results | | Presence feeling in application | 3.8 | 5.0 | 3.6 | 3.6 | 5.0 | 5.0 | 3.6 |
| | | Softness in rinsing | 4.4 | 5.0 | 5.0 | 4.4 | 4.6 | 5.0 | 5.0 |
| | | Smoothness in rinsing | 4.0 | 4.8 | 3.8 | 4.4 | 4.2 | 4.0 | 4.0 |
| | | Coated feeling after drying | 4.6 | 4.8 | 4.6 | 4.6 | 4.6 | 5.0 | 5.0 |

*1 Kao's Cortamine 2285E-E
*2 Kao's Kalcol 6098
*3 Kao's Kalcol 8098
*4 Dow Corning Toray's BY22-029 (active ingredient 50%)

TABLE D-7

| Hair Conditioner | | | Example | | | | |
|---|---|---|---|---|---|---|---|
| Composition | | | D42 | D43 | D44 | D45 | D46 |
| Composition (part by mass) | Component (A) | CCE(58) | 0.3 | 0.3 | 0.3 | 0.3 | 0.3 |
| | Component (B) | behenyltrimethyl-ammonium chloride *1 | 1.5 | 1.5 | 1.5 | 1.5 | 1.5 |
| | Component (C) | cetyl alcohol *2 | 1.3 | 1.3 | 1.3 | 1.3 | 1.3 |
| | | stearyl alcohol *3 | 2.6 | 2.6 | 2.6 | 2.6 | 2.6 |
| | | isostearic acid *4 | 1 | | | | |
| | | macadamia nut oil *5 | | 1 | | | |
| | | myristyl myristate *6 | | | 1 | | |
| | | squalane *7 | | | | 1 | |
| | | liquid paraffin *8 | | | | | 1 |
| | Others | pH regulator | adequate dose | | | | |
| | | solvent | adequate dose | | | | |
| | | pure water | balance | | | | |
| Evaluation Results | | Presence feeling in application | 4.2 | 4.0 | 4.6 | 4.8 | 5.0 |
| | | Softness in rinsing | 4.8 | 4.8 | 4.8 | 4.8 | 4.6 |
| | | Smoothness in rinsing | 4.6 | 4.4 | 4.6 | 5.0 | 5.0 |
| | | Coated feeling after drying | 4.4 | 4.8 | 5.0 | 4.8 | 4.6 |

*1 Kao's Cortamine 2285E-E
*2 Kao's Kalcol 6098
*3 Kao's Kalcol 8098
*4 Kokyu Alcohol Kogyo's Isostearic Acid EX
*5 Nikko Chemicals' Macadamia Nut Oil
*6 Kao's Exeparl MYM
*7: Nikko Chemicals' squalane
*8: Kaneda's Hi-call K-230

TABLE D-8

| Hair Conditioner | | | Example | | | | | | | | | | | | |
|---|---|---|---|---|---|---|---|---|---|---|---|---|---|---|---|
| Composition | | | D47 | D48 | D49 | D50 | D51 | D52 | D53 | D54 | D55 | D56 | D57 | D58 | D59 |
| Composition (part by mass) | Component (A) | CCE(58) | 0.3 | 0.3 | 0.3 | 0.3 | 0.3 | 0.3 | 0.3 | 0.3 | 0.3 | 0.3 | 0.3 | 0.3 | 0.3 |
| | Component (B) | behenyltrimethyl-ammonium chloride *1 | 1.5 | 1.5 | 1.5 | 1.5 | 1.5 | 1.5 | 1.5 | 1.5 | 1.5 | 1.5 | 1.5 | 1.5 | 1.5 |
| | Component (C) | cetyl alcohol *2 | 1.3 | 1.3 | 1.3 | 1.3 | 1.3 | 1.3 | 1.3 | 1.3 | 1.3 | 1.3 | 1.3 | 1.3 | 1.3 |
| | | stearyl alcohol *3 | 2.6 | 2.6 | 2.6 | 2.6 | 2.6 | 2.6 | 2.6 | 2.6 | 2.6 | 2.6 | 2.6 | 2.6 | 2.6 |
| | | dioctyl ether *4 | 1 | | | | | | | | | | | | |
| | | dioctyl carbonate *5 | | 1 | | | | | | | | | | | |
| | | PPG-3 benzyl ether myristate *6 | | | 1 | | | | | | | | | | |
| | | isostearyl glyceryl ether *7 | | | | 1 | | | | | | | | | |
| | | PPG-3 caprylyl ether *8 | | | | | 1 | | | | | | | | |
| | | PPG-4 caprylyl ether | | | | | | 1 | | | | | | | |
| | | PPG-5 caprylyl ether | | | | | | | 1 | | | | | | |
| | | PPG-6 caprylyl ether | | | | | | | | 1 | | | | | |
| | | PPG-10 caprylyl ether | | | | | | | | | 1 | | | | |
| | | PPG-3 decyl ether | | | | | | | | | | 1 | | | |
| | | PPG-10 decyl ether | | | | | | | | | | | 1 | | |
| | | PPG-3 lauryl ether | | | | | | | | | | | | 1 | |
| | | PPG-10 lauryl ether | | | | | | | | | | | | | 1 |
| | Others | pH regulator | adequate dose | | | | | | | | | | | | |
| | | solvent | adequate dose | | | | | | | | | | | | |
| | | pure water | balance | | | | | | | | | | | | |
| Evaluation Results | | Presence feeling in application | 4.6 | 4.4 | 4.6 | 5.0 | 3.6 | 4.0 | 3.8 | 3.8 | 4.2 | 4.4 | 4.6 | 4.0 | 4.0 |
| | | Softness in rinsing | 4.4 | 4.4 | 4.4 | 5.0 | 4.8 | 4.8 | 5.0 | 4.8 | 5.0 | 5.0 | 5.0 | 5.0 | 5.0 |
| | | Smoothness in rinsing | 4.8 | 4.2 | 4.4 | 5.0 | 4.8 | 4.6 | 4.4 | 4.2 | 4.4 | 5.0 | 4.8 | 5.0 | 5.0 |

TABLE D-8-continued

| Hair Conditioner Composition | | | D47 | D48 | D49 | D50 | D51 | D52 | D53 | D54 | D55 | D56 | D57 | D58 | D59 |
|---|---|---|---|---|---|---|---|---|---|---|---|---|---|---|---|
| | Coated feeling after drying | | 4.8 | 4.0 | 4.2 | 4.8 | 4.6 | 4.6 | 4.8 | 4,8 | 5.0 | 4.8 | 4.6 | 5.0 | 4.6 |

*1 Kao's Cortamine 2285E-E
*2 Kao's Kalcol 6098
*3 Kao's Kalcol 8098
*4 Cognis' Cetiol OE
*5 Cognis' Cetiol CC
*6 Croda's Crodamol STS
*7: Kao's Penetol GE-IS
*8: Kao's Sofcare GP-1

TABLE D-9

| Hair Conditioner Composition | | | D60 | D61 | D62 | D63 | D64 | D65 | D66 | D67 | D68 |
|---|---|---|---|---|---|---|---|---|---|---|---|
| Composition (part by mass) | Component (A) | CCE(58) | 0.3 | 0.3 | 0.3 | 0.3 | 0.3 | 0.3 | 0.3 | 0.3 | 0.3 |
| | Component (B) | behenyltrimethyl-ammonium chloride*1 | 1.5 | 1.5 | 1.5 | 1.5 | 1.5 | 1.5 | 1.5 | 1.5 | 1.5 |
| | Component (C) | cetyl alcohol *2 | 1.3 | 1.3 | 1.3 | 1.3 | 1.3 | 1.3 | 1.3 | 1.3 | 1.3 |
| | | stearyl alcohol *3 | 2.6 | 2.6 | 2.6 | 2.6 | 2.6 | 2.6 | 2.6 | 2.6 | 2.6 |
| | | dimethiconol *4 | 1 | | | | | | | | |
| | | polyether-modified silicone *5 | | 1 | | | | | | | |
| | | polyether-modified silicone *6 | | | 1 | | | | | | |
| | | high-polymerized dimethylsiloxane *7 | | | | 1 | | | | | |
| | | high-polymerized dimethylsiloxane *8 | | | | | 1 | | | | |
| | | high-polymerized dimethylsiloxane *9 | | | | | | 1 | | | |
| | | amino-modified high-polymerized dimethyl-polysiloxane *10 | | | | | | | 1 | | |
| | | amino-modified high-polymerized dimethyl-polysiloxane *11 | | | | | | | | 1 | |
| | | amino-modified high-polymerized dimethyl-polysiloxane *12 | | | | | | | | | 1 |
| | | pH regulator | adequate dose | | | | | | | | |
| | | solvent | adequate dose | | | | | | | | |
| | | pure water | balance | | | | | | | | |
| Evaluation Results | | Presence feeling in application | 4.4 | 4.0 | 4.2 | 4.4 | 4.8 | 4.0 | 4.4 | 4.0 | 4.6 |
| | | Softness in rinsing | 5.0 | 4.8 | 4.8 | 5.0 | 5.0 | 4.6 | 5.0 | 5.0 | 5.0 |
| | | Smoothness in rinsing | 4.4 | 4.2 | 4.4 | 4.6 | 5.0 | 4.6 | 4.0 | 4.6 | 4.8 |
| | | Coated feeling after drying | 4.8 | 4.6 | 4.8 | 4.6 | 5.0 | 5.0 | 4.8 | 4.8 | 4.8 |

*1 Kao's Cortamine 2285E-E
*2 Kao's Kalcol 6098
*3 Kao's Kalcol 8098
*4 Dow Corning Toray's 1785 EMULSION (active ingredient 60%)
*5 Shin-etsu Chemical Industry's KF6011
*6 Kao's Sofcare GS-G
*7 Dow Corning Toray's BY22-007 (active ingredient 50%)
*8 Dow Corning Toray's BY22-050A (active ingredient 50%)
*9 Dow Corning Toray's BY22-060 (active ingredient 60%)
*10 Dow Corning Toray's BY22-079 (active ingredient 14%)
*11 Dow Corning Toray's SM8904 (active ingredient 40%)
*12 Shin-etsu Chemical Industry's KF8020

From Tables D-1 to D-9, it is known that the conditioners of Examples D1 to D68 are excellent conditioners capable of giving presence feeling in application, softness in rinsing, smoothness in rinsing, and coated feeling after drying.

Example D69

In the same manner as in Example D1, a leave-in hair conditioner having the composition mentioned below was prepared.

| (Components) | (%) |
| --- | --- |
| CCE (30) | 0.05 |
| Stearyl alcohol | 0.4 |
| High-polymerized dimethylsiloxane *1 | 0.1 |
| Behenyltrimethylammonium chloride | 0.2 |
| pH regulator | adequate dose |
| Pure water | balance |
| Total | 100.0 |

*1: Dow Corning Toray's BY22-060 (active ingredient 60%)

Hair tresses that had been washed with the plain shampoo used in Example D1 were well wetted with warm water at 35 to 40° C., water was removed from the hair tresses, which were then dried with warm air from a drier, and then combed. One g of the hair conditioner of Example D69 was applied to the hair tresses and left as such for adjustment. After dried at room temperature, the hair tresses were organoleptically evaluated.

The hair conditioner gave a good coated feeling to the dried hair.

Example D70

In the same manner as in Example D1, a leave-in hair conditioner having the composition mentioned below was prepared.

| (Components) | (%) |
| --- | --- |
| CCE (30) | 0.5 |
| Stearyl alcohol | 4.0 |
| High-polymerized dimethylsiloxane *1 | 4.0 |
| Cetyltrimethylammonium chloride | 5.0 |
| pH regulator | adequate dose |
| Pure water | balance |
| Total | 100.0 |

*1: Dow Corning Toray's BY22-060 (active ingredient 60%), 6.7% added.

Hair tresses that had been washed with the plain shampoo used in Example D1 were well wetted with warm water at 35 to 40° C., water was removed from the hair tresses, which were then dried with warm air from a drier, and then combed. 0.1 g of the hair conditioner of Example D70 was applied to the hair tips and left as such for adjustment. After dried at room temperature, the hair tresses were organoleptically evaluated.

The hair conditioner gave a good coated feeling to the dried hair.

Examples E1 to E17 and Comparative Examples E1 to E2

Production and Evaluation of Two-Pack Hair Bleach Composition (1) Preparation of First Pack The other components than the higher alcohol, aqueous 28% ammonia solution and propylene glycol shown in Tables E-1 to E-2 were mixed with an adequate amount of water and stirred. This was heated at 60° C. and completely dissolved. To this was added a mixture prepared by previously mixing cetyl alcohol and propylene glycol and heated at 70° C., and emulsified for 30 minutes. After this was cooled down to 40° C., aqueous 28% ammonia solution and the remaining water were added and uniformly mixed to prepare a first pack.

The details of the components except the component (A) and the cationized polysaccharide (7) shown in Tables E-1 to E-2 are as follows.

Cationized hydroxyethyl cellulose (Amerchol's UCARE POLYMER LR30M)

Ceteareth-13 (Kao's Emulgen 220)

Sodium laureth-1 sulfate (Kao's Emal 170J, active ingredient 70%)

(2) Preparation of Second Pack

As shown in Tables E-1 and E-2, the surfactants (ceteareth-13 and sodium laureth-1 sulfate), the other components (EDTA-2-sodium, phosphoric acid, disodium hydrogenphosphate), and an adequate amount of water were mixed with stirring, and completely dissolved by heating up to 60° C. To this was added the higher alcohol that had been heated at 70° C., and emulsified. After this was cooled down to 40° C., aqueous 35% hydrogen peroxide solution and the remaining water were added thereto and uniformly mixed to prepare a second pack. The pH was 4.

(3) Evaluation of Two-Pack Hair Bleach Composition

Hair (artificial black hair, BS-B3A) with no chemical treatment history, which is commercially sold by Beaulax and which has a length of 30 cm and a mass of 10 g, was used. 3 g of the hair sample was dressed in a width of 2 cm so as to have a uniform thickness. One end of the hair was fixed to a plastic plate having a width of 2 cm with an adhesive, thereby preparing a test piece of hair tresses.

The hair tresses were washed with a plain shampoo having the composition mentioned below, and dried with warm air from a drier. The first pack and the second pack obtained in the above (1) and (2) were mixed in a ratio by mass of ⅔, and 3 g of the resulting blend was applied to the hair tresses. Subsequently, the hair tresses were left at 30° C. for 30 minutes to thereby obtain hair tresses for evaluation.

Five panelists rinsed the evaluation tresses with warm water for 1 minute, and then evaluated for the smoothness, the coat feeling and the softness in rinsing, according to the following evaluation criteria.

The results are shown in Tables E-1 to E-2.

[Composition of Plain Shampoo]

| Components) | (%) |
| --- | --- |
| Na polyoxyethylene (2 mol) laurylether sulfate (Kao's Emal E-27C (active ingredient 27%), 40.7% added) | 11.0 |
| Coconut oil fatty acid N-methylethanolamide (Kao's Aminone C-11S) | 3.0 |
| Citric acid | 0.2 |
| Methylparaben | 0.3 |
| Pure water | balance |
| Total | 100.0 |

[Production of Plain Shampoo]

Na polyoxyethylene (2 mol) laurylether sulfate and coconut oil fatty acid N-methylethanolamide and an adequate amount of water were mixed and dissolved uniformly.

Further, methylparaben was added thereto and uniformly dissolved. Finally, citric acid and the remaining water were added and uniformly dissolved.
(Evaluation Criteria: Based on Standard Score 3 in Comparative Example E1)
The evaluation results of the five panelists were averaged to be a score of the sample.

Smoothness
5: Extremely good smoothness.
4: Good smoothness.
3: Average.
2: Bad smoothness.
1: Extremely bad smoothness.

Coated Feeling
5: Extremely good coated feeling.
4: Good coated feeling.
3: Average.
2: Bad coated feeling.
1: No coated feeling at all.

Softness
5: Extremely good softness.
4: Good softness.
3: Average.
2: Bad softness.
1: No softness.

TABLE E-1

| | | | Example | | | | | Comparative Example | |
|---|---|---|---|---|---|---|---|---|---|
| | | | E1 | E2 | E3 | E4 | E5 | E1 | E2 |
| | | Two-Pack Hair Bleach Composition: 1st pack | | | | | | | |
| Composition (part by mass) | Component (A) | CCE(46) | 0.1 | | | | | | |
| | | CCE(28) | | 0.1 | | | | | |
| | | CCE(27) | | | 0.1 | | | | |
| | | CCE(6) | | | | 0.1 | | | |
| | | CCE(49) | | | | | 0.1 | | |
| | Polymer except Component (A) | cationized polysaccharide (7) | | | | | | 0.1 | |
| | | cationized hydroxyethyl cellulose | | | | | | | 0.1 |
| | Component (E) | aqueous 28% ammonia solution | 6.5 | 6.5 | 6.5 | 6.5 | 6.5 | 6.5 | 6.5 |
| | | monoethanolamine | 0.5 | 0.5 | 0.5 | 0.5 | 0.5 | 0.5 | 0.5 |
| | Component (B) | ceteareth-13 | 1.0 | 1.0 | 1.0 | 1.0 | 1.0 | 1.0 | 1.0 |
| | | sodium laureth-1 sulfate | 2.0 | 2.0 | 2.0 | 2.0 | 2.0 | 2.0 | 2.0 |
| | Component (C) | cetyl alcohol | 5.0 | 5.0 | 5.0 | 5.0 | 5.0 | 5.0 | 5.0 |
| | Others | propylene glycol | 4.0 | 4.0 | 4.0 | 4.0 | 4.0 | 4.0 | 4.0 |
| | | sodium sulfite | 0.3 | 0.3 | 0.3 | 0.3 | 0.3 | 0.3 | 0.3 |
| | | sodium ascorbate | 0.3 | 0.3 | 0.3 | 0.3 | 0.3 | 0.3 | 0.3 |
| | | EDTA-2-sodium | 0.3 | 0.3 | 0.3 | 0.3 | 0.3 | 0.3 | 0.3 |
| | | pure water | | | | | balance | | |
| Property | | viscosity (25° C., mPa·s) | 15710 | 6170 | 6630 | 2930 | — | 4100 | 6650 |
| | | pH | 10.9 | 10.8 | 10.8 | 10.7 | 10.3 | 10.8 | 10.9 |
| | | Two-Pack Hair Bleach Composition: 2nd pack | | | | | | | |
| Composition (part by mass) | Component (E) | aqueous 35% hydrogen peroxide solution | 16.9 | 16.9 | 16.9 | 16.9 | 16.9 | 16.9 | 16.9 |
| | Component (B) | ceteareth-13 | 0.5 | 0.5 | 0.5 | 0.5 | 0.5 | 0.5 | 0.5 |
| | | sodium laureth-1 sulfate | 1.0 | 1.0 | 1.0 | 1.0 | 1.0 | 1.0 | 1.0 |
| | Component (C) | cetyl alcohol | 3.0 | 3.0 | 3.0 | 3.0 | 3.0 | 3.0 | 3.0 |
| | Others | EDTA-2-sodium | 0.1 | 0.1 | 0.1 | 0.1 | 0.1 | 0.1 | 0.1 |
| | | phosphoric acid | 0.1 | 0.1 | 0.1 | 0.1 | 0.1 | 0.1 | 0.1 |
| | | disodium hydrogenphosphate | 0.2 | 0.2 | 0.2 | 0.2 | 0.2 | 0.2 | 0.2 |
| | | pure water | | | | | balance | | |
| Evaluation Results | | smoothness in rinsing | 3.4 | 3.4 | 4.0 | 4.0 | 4.0 | 3.0 | 2.6 |
| | | coated feeling in rinsing | 3.6 | 3.8 | 4.0 | 4.0 | 4.0 | 3.0 | 3.0 |
| | | softness in rinsing | 3.6 | 3.8 | 3.8 | 4.0 | 4.0 | 3.0 | 3.4 |

TABLE E-2

|  |  |  | \multicolumn{12}{c}{Example} |
|---|---|---|---|---|---|---|---|---|---|---|---|---|---|---|
|  |  |  | E6 | E7 | E8 | E9 | E10 | E11 | E12 | E13 | E14 | E15 | E16 | E17 |
|  |  | Two-Pack Hair Bleach Composition: 1st pack |  |  |  |  |  |  |  |  |  |  |  |  |
| Composition (part by mass) | Component (A) | CCE(50) | 0.1 |  |  |  |  |  |  |  |  |  |  |  |
|  |  | CCE(13) |  | 0.1 |  |  |  |  |  |  |  |  |  |  |
|  |  | CCE(3) |  |  | 0.1 |  |  |  |  |  |  |  |  |  |
|  |  | CCE(57) |  |  |  | 0.1 |  |  |  |  |  |  |  |  |
|  |  | CCE(1) |  |  |  |  | 0.1 |  |  |  |  |  |  |  |
|  |  | CCE(58) |  |  |  |  |  | 0.1 |  |  | 0.05 | 0.3 | 0.5 | 1.0 |
|  |  | CCE(41) |  |  |  |  |  |  | 0.1 |  |  |  |  |  |
|  |  | CCE(33) |  |  |  |  |  |  |  | 0.1 |  |  |  |  |
|  | Component (E) | aqueous 28% ammonia solution | 6.5 | 6.5 | 6.5 | 6.5 | 6.5 | 6.5 | 6.5 | 6.5 | 6.5 | 6.5 | 6.5 | 6.5 |
|  |  | monoethanolamine | 0.5 | 0.5 | 0.5 | 0.5 | 0.5 | 0.5 | 0.5 | 0.5 | 0.5 | 0.5 | 0.5 | 0.5 |
|  | Component (B) | ceteareth-13 | 1.0 | 1.0 | 1.0 | 1.0 | 1.0 | 1.0 | 1.0 | 1.0 | 1.0 | 1.0 | 1.0 | 1.0 |
|  |  | sodium laureth-1 sulfate | 2.0 | 2.0 | 2.0 | 2.0 | 2.0 | 2.0 | 2.0 | 2.0 | 2.0 | 2.0 | 2.0 | 2.0 |
|  | Component (C) | cetyl alcohol | 5.0 | 5.0 | 5.0 | 5.0 | 5.0 | 5.0 | 5.0 | 5.0 | 5.0 | 5.0 | 5.0 | 5.0 |
|  | Others | propylene glycol | 4.0 | 4.0 | 4.0 | 4.0 | 4.0 | 4.0 | 4.0 | 4.0 | 4.0 | 4.0 | 4.0 | 4.0 |
|  |  | sodium sulfite | 0.3 | 0.3 | 0.3 | 0.3 | 0.3 | 0.3 | 0.3 | 0.3 | 0.3 | 0.3 | 0.3 | 0.3 |
|  |  | sodium ascorbate | 0.3 | 0.3 | 0.3 | 0.3 | 0.3 | 0.3 | 0.3 | 0.3 | 0.3 | 0.3 | 0.3 | 0.3 |
|  |  | EDTA-2-sodium | 0.3 | 0.3 | 0.3 | 0.3 | 0.3 | 0.3 | 0.3 | 0.3 | 0.3 | 0.3 | 0.3 | 0.3 |
|  |  | pure water |  |  |  |  |  | balance |  |  |  |  |  |  |
|  |  | viscosity (25° C., mPa · s) | 4140 | 10180 | 7800 | 2220 | 6340 | 5520 | 6650 | 8020 | — | — | — | — |
|  |  | pH | 10.8 | 10.7 | 10.8 | 10.8 | 10.8 | 10.8 | 10.7 | 10.8 | — | — | — | — |
|  |  | Two-Pack Hair Bleach Composition: 2nd pack |  |  |  |  |  |  |  |  |  |  |  |  |
| Composition (part by mass) | Component (E) | aqueous 35% hydrogen peroxide solution | 16.9 | 16.9 | 16.9 | 16.9 | 16.9 | 16.9 | 16.9 | 16.9 | 17.0 | 17.0 | 17.0 | 17.0 |
|  | Component (B) | ceteareth-13 | 0.5 | 0.5 | 0.5 | 0.5 | 0.5 | 0.5 | 0.5 | 0.5 | 0.5 | 0.5 | 0.5 | 0.5 |
|  |  | sodium laureth-1 sulfate | 1.0 | 1.0 | 1.0 | 1.0 | 1.0 | 1.0 | 1.0 | 1.0 | 1.0 | 1.0 | 1.0 | 1.0 |
|  | Component (C) | cetyl alcohol | 3.0 | 3.0 | 3.0 | 3.0 | 3.0 | 3.0 | 3.0 | 3.0 | 3.0 | 3.0 | 3.0 | 3.0 |
|  | Others | EDTA-2-sodium | 0.1 | 0.1 | 0.1 | 0.1 | 0.1 | 0.1 | 0.1 | 0.1 | 0.1 | 0.1 | 0.1 | 0.1 |
|  |  | phosphoric acid | 0.1 | 0.1 | 0.1 | 0.1 | 0.1 | 0.1 | 0.1 | 0.1 | 0.1 | 0.1 | 0.1 | 0.1 |
|  |  | disodium hydrogenphosphate | 0.2 | 0.2 | 0.2 | 0.2 | 0.2 | 0.2 | 0.2 | 0.2 | 0.2 | 0.2 | 0.2 | 0.2 |
|  |  | pure water |  |  |  |  |  | balance |  |  |  |  |  |  |
| Evaluation Results |  | smoothness in rinsing | 4.2 | 3.6 | 3.6 | 3.8 | 4.2 | 4.2 | 3.6 | 3.4 | 3.4 | 4.4 | 4.6 | 4.4 |
|  |  | coated feeling in rinsing | 4.2 | 4.4 | 4.8 | 3.8 | 4.4 | 4.6 | 4.6 | 4.4 | 3.4 | 4.6 | 4.8 | 5.0 |
|  |  | softness in rinsing | 4.2 | 4.4 | 4.2 | 3.6 | 4.4 | 4.6 | 4.6 | 4.4 | 3.4 | 4.6 | 4.8 | 5.0 |

From Tables E-1 to E-2, it is known that the hair bleaches of Examples E1 to E17 gave good smoothness, coated feeling and softness to the treated hair in treatment and rinsing.

Example E18 and Comparative Example E3

Production and Evaluation of Two-Pack Hair Color Composition

A two-pack hair color composition shown in Table E-3 was produced in the same manner as in Example E1. The pH of the first pack was 10, and the pH of the second pack was 4. Example E18 was evaluated in the same manner as in Example E1, based on the standard score 3 in Comparative Example E3. The results are shown in Table E-3.

The details of the components except the component (A) shown in Table E-3 are as follows.

Cationized hydroxyethyl cellulose (Amerchol's UCARE POLYMER LR30M)
Ceteareth-13 (Kao's Emulgen 220)
Sodium laureth-1 sulfate (Kao's Emal 170J, active ingredient 70%)

From Table E-3, it is known that the hair color composition of Example E18 gave good smoothness, coated feeling and softness to the treated hair in treatment and rinsing.

TABLE E-3

|  |  |  | Example E18 | Comparative Example E3 |
|---|---|---|---|---|
|  |  | Two-Pack Hair Color Composition: 1st pack |  |  |
| Composition (part by mass) | Component (A) | CCE(58) | 0.5 |  |
|  | Polymer except Component (A) | cationized hydroxyethyl cellulose |  | 0.5 |
|  | Component (E) | para-aminophenol | 0.3 | 0.3 |
|  |  | resorcin | 0.3 | 0.3 |
|  |  | 5-amino-orthocresol | 0.1 | 0.1 |
|  |  | toluene-2,5-diamine hydrochloride | 0.6 | 0.6 |
|  |  | monoethanolamine | 0.5 | 0.5 |
|  |  | aqueous 28% ammonia solution | 6.5 | 6.5 |
|  | Component (B) | ceteareth-13 | 1.0 | 1.0 |
|  |  | sodium laureth-1 sulfate | 2.0 | 2.0 |
|  | Component (C) | cetyl alcohol | 5.0 | 5.0 |
|  | Others | propylene glycol | 4.0 | 4.0 |
|  |  | sodium sulfite | 0.3 | 0.3 |
|  |  | sodium ascorbate | 0.3 | 0.3 |
|  |  | EDTA-2-sodium | 0.3 | 0.3 |
|  |  | pure water | balance | balance |
|  |  | Two-Pack Hair Color Composition: 2nd pack |  |  |
| Composition (part by mass) | Component (E) | aqueous 35% hydrogen peroxide solution | 17.0 | 17.0 |
|  | Component (B) | ceteareth-13 | 0.5 | 0.5 |
|  |  | sodium laureth-1 sulfate | 1.0 | 1.0 |
|  | Component (C) | cetyl alcohol | 3.0 | 3.0 |
|  | Others | EDTA-2-sodium | 0.1 | 0.1 |
|  |  | phosphoric acid | 0.1 | 0.1 |
|  |  | disodium hydrogenphosphate | 0.2 | 0.2 |
|  |  | pure water | balance | balance |
| Evaluation Results |  | smoothness in rinsing | 4.2 | 3.0 |
|  |  | coated feeling in rinsing | 4.4 | 3.0 |
|  |  | softness in rinsing | 4.0 | 3.0 |

Example E19 and Comparative Example E4

Production and Evaluation of Two-Pack Hair Color Composition

A two-pack hair color composition shown in Table E-4 was produced in the same manner as in Example E1. The pH of the first pack was 10, and the pH of the second pack was 4. Example E19 was evaluated in the same manner as in Example E1, based on the standard score 3 in Comparative Example E4. The results are shown in Table E-4.

The details of the components except the component (A) shown in Table E-4 are as follows.
Hexadimethrine bromide (by Sigma Aldrich)
Laureth-12 (Kao's Emulgen 120)
Oleth-30 (Kao's Emulgen 430)
Laureth-3 (Kao's Emulgen 103)

From Table E-4, it is known that the two-pack hair color composition of Example E19 gave good smoothness, coated feeling and softness to the treated hair in treatment and rinsing.

TABLE E-4

|  |  |  | Example E19 | Comparative Example E4 |
|---|---|---|---|---|
|  |  | Two-Pack Hair Color Composition: 1st pack |  |  |
| Composition (part by mass) | Component (A) | CCE(58) | 0.5 |  |
|  | Polymer except Component (A) | hexadimethrine bromide |  | 0.5 |
|  | Component (E) | para-aminophenol | 0.3 | 0.3 |
|  |  | resorcin | 0.3 | 0.3 |
|  |  | 5-amino-orthocresol | 0.1 | 0.1 |
|  |  | toluene-2,5-diamine hydrochloride | 0.6 | 0.6 |
|  |  | monoethanolamine | 1.4 | 1.4 |
|  |  | aqueous 28% ammonia solution | 6.5 | 6.5 |
|  | Component (B) | laureth-12 | 7.0 | 7.0 |
|  |  | oleth-30 | 4.0 | 4.0 |
|  |  | laureth-3 | 5.0 | 5.0 |
|  |  | lauric acid | 3.0 | 3.0 |
|  | Component (C) | cetyl alcohol | 5.8 | 5.8 |
|  |  | stearyl alcohol | 5.8 | 5.8 |
|  | Others | propylene glycol | 7.0 | 7.0 |
|  |  | sodium sulfite | 0.3 | 0.3 |
|  |  | sodium ascorbate | 0.3 | 0.3 |

TABLE E-4-continued

|  |  |  | Example E19 | Comparative Example E4 |
|---|---|---|---|---|
|  |  | EDTA-2-sodium | 0.1 | 0.1 |
|  |  | pure water | balance | balance |
|  |  | Two-Pack Hair Color Composition: 2nd pack |  |  |
| Composition (part by mass) | Component (E) | aqueous 35% hydrogen peroxide solution | 17.0 | 17.0 |
|  | Component (B) | ceteareth-13 | 0.5 | 0.5 |
|  |  | sodium laureth-1 sulfate | 1.0 | 1.0 |
|  | Component (C) | cetyl alcohol | 3.0 | 3.0 |
|  | Others | EDTA-2-sodium | 0.1 | 0.1 |
|  |  | phosphoric acid | 0.1 | 0.1 |
|  |  | disodium hydrogenphosphate | 0.2 | 0.2 |
|  |  | pure water | balance | balance |
| Evaluation Results |  | smoothness in rinsing | 4.6 | 3.0 |
|  |  | coated feeling in rinsing | 5.0 | 3.0 |
|  |  | softness in rinsing | 5.0 | 3.0 |

Example E20 and Comparative Examples E5 to E6

Production and Evaluation of Two-Pack Hair Color Composition

A two-pack hair color composition shown in Table E-5 was produced in the same manner as in Example E1. The pH of the first pack was 10, and the pH of the second pack was 4. Example E20 was evaluated in the same manner as in Example E1, based on the standard score 3 in Comparative Example E6. The results are shown in Table E-5.

The details of the components except the component (A) shown in Table E-5 are as follows.

Cationized hydroxyethyl cellulose (Amerchol's UCARE POLYMER LR30M)

Dimethyldiallylammonium chloride-acrylamide copolymer (Nalco's Marcoat 295)

Ceteareth-13 (Kao's Emulgen 220)

Stearyltrimethylammonium chloride (Kao's Quartamin 86W, active ingredient 28%)

From Table E-5, it is known that the two-pack hair color composition of Example E20 gave good smoothness, coated feeling and softness to the treated hair in treatment and rinsing.

TABLE E-5

|  |  |  | Example E20 | Comparative Example E5 | Comparative Example E6 |
|---|---|---|---|---|---|
|  |  | Two-Pack Hair Color Composition: 1st pack |  |  |  |
| Composition (parts by mass) | Component (A) | CCE(58) | 0.5 |  |  |
|  | Polymer except Component (A) | cationized hydroxyethyl cellulose |  | 0.5 |  |
|  |  | dimethyldiallylammonium chloride-acrylamide copolymer |  |  | 0.5 |
|  | Component (E) | para-aminophenol | 0.3 | 0.3 | 0.3 |
|  |  | resorcin | 0.3 | 0.3 | 0.3 |
|  |  | 5-amino-orthocresol | 0.1 | 0.1 | 0.1 |
|  |  | toluene-2,5-diamine hydrochloride | 0.6 | 0.6 | 0.6 |
|  |  | monoethanolamine | 0.5 | 0.5 | 0.5 |
|  |  | aqueous 28% ammonia solution | 6.5 | 6.5 | 6.5 |
|  | Component (B) | ceteareth-13 | 1.0 | 1.0 | 1.0 |
|  |  | stearyltrimethylammonium chloride | 2.0 | 2.0 | 2.0 |
|  | Component (C) | cetyl alcohol | 7.0 | 7.0 | 7.0 |
|  | Others | propylene glycol | 4.0 | 4.0 | 4.0 |
|  |  | sodium sulfite | 0.3 | 0.3 | 0.3 |
|  |  | sodium ascorbate | 0.3 | 0.3 | 0.3 |
|  |  | EDTA-2-sodium | 0.3 | 0.3 | 0.3 |
|  |  | pure water | balance | balance | balance |
|  |  | Two-Pack Hair Color Composition: 2nd pack |  |  |  |
| Composition (parts by mass) | Component (E) | aqueous 35% hydrogen peroxide solution | 17.0 | 17.0 | 17.0 |
|  | Component (B) | ceteareth-13 | 0.4 | 0.4 | 0.4 |
|  |  | stearyltrimonium chloride | 0.6 | 0.6 | 0.6 |
|  | Component (C) | cetyl alcohol | 3.0 | 3.0 | 3.0 |
|  | Others | EDTA-2-sodium | 0.1 | 0.1 | 0.1 |
|  |  | phosphoric acid | 0.1 | 0.1 | 0.1 |
|  |  | disodium hydrogenphosphate | 0.2 | 0.2 | 0.2 |
|  |  | pure water | balance | balance | balance |
| Evaluation Results |  | smoothness in rinsing | 3.6 | 2.4 | 3.0 |
|  |  | coated feeling in rinsing | 4.0 | 3.0 | 3.0 |
|  |  | softness in rinsing | 4.4 | 3.0 | 3.0 |

Example E21 and Comparative Examples E7 to E8

Production and Evaluation of Permanent Wave Composition (1) Preparation of First Pack As shown in Table E-6, the other components than 50% ammonium thioglycolate and 28% ammonia were mixed with an adequate amount of water and stirred until complete dissolution. 50% ammonium thioglycolate, 28% ammonia and the remaining water were added thereto and stirred for complete dissolution, thereby preparing a first pack. The pH was 9.

The details of the other components than the component (A) in Table E-6 are as follows.
Cationized hydroxyethyl cellulose (Amerchol's UCARE POLYMER LR30M)
Dimethyldiallylammonium chloride-acrylamide copolymer (Nalco's Marcoat 295)
Ceteareth-13 (Kao's Emulgen 220)

(2) Preparation of Second Pack

As shown in Table E-6, sodium bromate, propylene glycol, surfactants (ceteareth-13, laureth-3), keratin hydrolyzate (Seiwa Kasei's Promois (active ingredient 10%), 1.0% added) and an adequate amount of water were mixed and stirred until complete dissolution. Amodimethicone (Dow Corning Toray's SM8904 (active ingredient 40%), 1.25% added) was added thereto, and uniformly mixed to prepare a second pack. The pH was 7.

(3) Evaluation of Permanent Wave Composition

Hair (artificial black hair, BS-B3A) with no chemical treatment history, which is commercially sold by Beaulax and which has a length of 30 cm and a mass of 10 g, was used. 2 g of the hair sample was dressed in a width of 2 cm so as to have a uniform thickness. One end of the hair was fixed to a plastic plate having a width of 2 cm with an adhesive, thereby preparing a test piece of hair tresses.

Thus prepared, the hair tresses were washed with the same plain shampoo as in Example E1, then toweled to remove water, and combed. The hair tresses were wound around a rod having a diameter of 9 mm (Dariya's Venezel Cold Rod No. 6), then 2 g of the first pack was applied thereto, left as such at 30° C. for 15 minutes, and thereafter the hair was rinsed with warm water for 3 minutes. Further, 2 g of the second pack was applied thereto, left as such at 30° C. for 15 minutes, and the hair was removed from the rod, thereby preparing hair tresses for evaluation.

Five panelists rinsed the evaluation tresses with warm water for 1 minute, and then evaluated for the smoothness, the coated feeling and the softness in rinsing in the same manner as in Example E1. In addition, the tresses were rinsed with a plain conditioner having the composition mentioned below, and evaluated for the finger-combability, the smoothness and the long-lasting smoothness in rinsing.

The permanent wave compositions were evaluated, based on the sample of Comparative Example E7 given a standard score of 3. For the smoothness, the coated feeling and the softness in rinsing, the same standard as in Example E1 was employed here. For the finger combability, the smoothness and the long-lasting smoothness in rinsing after treatment with the conditioner, the following criteria were employed here. The results are shown in Table E-6.

From Table E-6, it is known that the permanent wave composition of Example E21 gave good smoothness, coated feeling and softness to the treated hair in treatment and rinsing. In addition, it is known that the composition also gave good finger combability, smoothness and long-lasting smoothness in hair rinsing after treatment

[Composition of Plain Conditioner]

| (Components) | (%) |
|---|---|
| Stearoxypropyltrimethylammonium chloride | 1.0 |
| Cetyl alcohol | 0.6 |
| Stearyl alcohol | 2.3 |
| Propylene glycol | 1.0 |
| Phenoxyethanol | 0.3 |
| Pure water | balance |
| Total | 100.0 |

[Production of Plain Conditioner]

Phenoxyethanol and an adequate amount of water were mixed and heated up to 80° C. To this, added was a mixture prepared by previously mixing stearoxypropyltrimethylammonium chloride, cetyl alcohol, stearyl alcohol and propylene glycol and heating up to 70° C., and emulsified, and then cooled down to room temperature.

(Evaluation Criteria: Based on Comparative Example E7 Given a Standard Score of 3)

The evaluation results made by the five panelists were averaged to be the score of each sample.

Finger Combability after Treatment with Conditioner
  5: Extremely good finger combability.
  4: Good finger combability.
  3: Average.
  2: Bad finger combability.
  1: Extremely bad finger combability.

Smoothness after Conditioner Treatment
  5: Extremely good smoothness.
  4: Good smoothness.
  3: Average.
  2: Bad smoothness.
  1: Extremely bad smoothness.

Long-Lasting Smoothness after Conditioner Treatment
  5: Extremely good long-lasting smoothness.
  4: Good long-lasting smoothness.
  3: Average.
  2: Bad long-lasting smoothness.
  1: No long-lasting smoothness at all.

TABLE E-6

| | | | Example | Comparative Example | |
|---|---|---|---|---|---|
| | | | E21 | E7 | E8 |
| Permanent Wave Composition: 1st pack | | | | | |
| Composition (parts by mass) | Component (A) | CCE(58) | 0.5 | | |
| | Polymer except Component (A) | cationized hydroxyethyl cellulose | | 0.5 | |
| | | dimethyldiallylammonium chloride-acrylamide copolymer | | | 0.5 |

TABLE E-6-continued

|  |  |  | Example | Comparative Example | |
| --- | --- | --- | --- | --- | --- |
|  |  |  | E21 | E7 | E8 |
|  | Component (E) | 50% ammonium thioglycolate | 12 | 12 | 12 |
|  |  | ammonium hydrogencarbonate | 2.5 | 2.5 | 2.5 |
|  |  | 28% ammonia | 1.5 | 1.5 | 1.5 |
|  |  | monoethanolamine | 1 | 1 | 1 |
|  | Component (B) | ceteareth-13 | 1 | 1 | 1 |
|  | Others | ethanol | 5 | 5 | 5 |
|  |  | propylene glycol | 5 | 5 | 5 |
|  |  | EDTA-2-sodium | 0.5 | 0.5 | 0.5 |
|  |  | pure water | balance | balance | balance |
|  |  | Permanent Wave Composition: 2nd pack |  |  |  |
| Composition | Component (E) | sodium bromate | 7.5 | 7.5 | 7.5 |
| (parts by mass) | Component (B) | ceteareth-13 | 0.75 | 0.75 | 0.75 |
|  |  | laureth-3 | 0.25 | 0.25 | 0.25 |
|  | Others | amodimethicone | 0.5 | 0.5 | 0.5 |
|  |  | propylene glycol | 5 | 5 | 5 |
|  |  | keratin hydrolyzate | 0.1 | 0.1 | 0.1 |
|  |  | pure water | balance | balance | balance |
| Evaluation | during | smoothness | 5.0 | 3.0 | 2.0 |
| Results | rinsing | coated feeling | 5.0 | 3.0 | 1.0 |
|  |  | softness | 5.0 | 3.0 | 1.0 |
|  | during | finger combability | 4.0 | 3.0 | 2.0 |
|  | rinsing after | smoothness | 5.0 | 3.0 | 1.0 |
|  | conditioner | long-lasting smoothness | 5.0 | 3.0 | 1.0 |
|  | treatment |  |  |  |  |

Example E22 and Comparative Examples E9 to E10

Production and Evaluation of Hair Relaxer (1) Preparation of First Pack

As shown in Table E-7, the other components than 50% ammonium thioglycolate were mixed with an adequate amount of water and stirred until complete dissolution. 50% ammonium thioglycolate and the remaining water were added thereto and stirred for complete dissolution, thereby preparing a first pack. The pH was 9.

The details of the components except the component (A) in Table E-7 are as follows.
Cationized hydroxyethyl cellulose (Amerchol's UCARE POLYMER LR30M)
Dimethyldiallylammonium chloride-acrylamide copolymer (Nalco's Marcoat 295)
Ceteareth-13 (Kao's Emulgen 220)

(2) Preparation of Second Pack

As shown in Table E-7, lactic acid, β-naphthalenesulfonic acid, benzyloxyethanol, ethanol, ceteareth-13 and an adequate amount of water were mixed and stirred until complete dissolution. Next, an aqueous 48% sodium hydroxide solution was added thereto, stirred and mixed. Further, aqueous 35% hydrogen peroxide and the remaining water were added and stirred until complete dissolution to prepare a second pack. The pH was 3.

(3) Evaluation of Hair Relaxer

Unruly hair tresses provided by a Japanese adult woman, having a length of 26 cm and a mass of 10 g, were tested here as a sample. This was treated with the same plain shampoo as in Example E1, rinsed with running water and air-dried. 2 g of the sample hair tresses were trimmed to have a uniform thickness and a width of 2 cm. One end of the sample was fixed to a plastic board having a width of 2 cm with an adhesive, thereby preparing test hair tresses.

Thus prepared, the hair tresses were treated with the same plain shampoo as in Example E1, towel-dried and combed. 1.5 g of the first pack was applied to the hair tresses, then left as such at 25° C. for 15 minutes, thereafter rinsed with warm water for 30 seconds, and towel-dried. Subsequently, the hair tresses were treated with a high-temperature hair iron set at 130° C. Next, 1.5 g of the second pack was applied thereto and left as such at 25° C. for 5 minutes, thereby preparing hair tresses for evaluation.

Five panelists rinsed the resultant hair tresses for evaluation with warm water for 1 minute, and evaluated them in the same manner as in Example E1. In addition, in the same manner as in Example E21, the hair tresses were evaluated in point of the finger combability, the smoothness and the long-lasting smoothness in rinsing after conditioner treatment. The hair relaxer was evaluated, based on the sample of Comparative Example E9 given a standard score of 3. The results are shown in Table E-7.

From Table E-7, it is known that the hair relaxer of Example E22 gave good smoothness, coated feeling and softness to the hair during treatment and rinsing. In addition, it is also known that the hair relaxer gave good finger combability, smoothness and long-lasting smoothness in rinsing the hair after conditioner treatment.

TABLE E-7

|  |  |  | Example | Comparative Example | |
|---|---|---|---|---|---|
|  |  |  | E22 | E9 | E10 |
|  |  | Hair Relaxer: 1st pack |  |  |  |
| Composition (parts by mass) | Component (A) | CCE(58) | 1 |  |  |
|  | Polymer except Component (A) | cationized hydroxyethyl cellulose |  | 1 |  |
|  |  | dimethyldiallylammonium chloride-acrylamide copolymer |  |  | 1 |
|  | Component (E) | 50% ammonium thioglycolate | 13 | 13 | 13 |
|  |  | monoethanolamine | 2 | 2 | 2 |
|  |  | ammonium hydrogencarbonate | 2 | 2 | 2 |
|  | Others | β-naphthalenesulfonic acid | 2 | 2 | 2 |
|  |  | benzyloxyethanol | 3.5 | 3.5 | 3.5 |
|  |  | ethanol | 4 | 4 | 4 |
|  |  | propylene glycol | 5 | 5 | 5 |
|  |  | EDTA-2-sodium | 0.5 | 0.5 | 0.5 |
|  |  | pure water | balance | balance | balance |
|  |  | Hair Relaxer: 2nd pack |  |  |  |
| Composition (parts by mass) | Component (E) | 35% hydrogen peroxide | 5 | 5 | 5 |
|  |  | 48% sodium hydroxide aqueous solution | 0.1 | 0.1 | 0.1 |
|  | Component (B) | ceteareth-13 | 1 | 1 | 1 |
|  | Others | lactic acid | 4.5 | 4.5 | 4.5 |
|  |  | β-naphthalenesulfonic acid | 1.5 | 1.5 | 1.5 |
|  |  | benzyloxyethanol | 3.5 | 3.5 | 3.5 |
|  |  | ethanol | 10 | 10 | 10 |
|  |  | pure water | balance | balance | balance |
| Evaluation Results | during rinsing | smoothness | 5.0 | 3.0 | 2.0 |
|  |  | coated feeling | 5.0 | 3.0 | 1.0 |
|  |  | softness | 5.0 | 3.0 | 1.0 |
|  | during rinsing after conditioner treatment | finger combability | 5.0 | 3.0 | 3.0 |
|  |  | smoothness | 5.0 | 3.0 | 1.0 |
|  |  | long-lasting smoothness | 5.0 | 3.0 | 1.0 |

Example E23

Production and Evaluation of One-Pack Hair Color Composition

CCE (58), hydroxypropylxanthane gum (DSP Gokyo Food & Chemical's Rhaball gum EX) and an adequate amount of water were mixed and stirred, and dissolved with heating up to 60° C. Aqueous 71% glycolic acid solution, Black No. 401, Orange No. 205, ethanol, glycerin, laureth-13 (Kao's Emulgen 120) and PEG-11 methyl ether dimethicone (Shin-etsu Chemical Industry's KF-6011) were added thereto and stirred until dissolution. This was cooled down to 40° C., and an adequate amount of water was added thereto and uniformly mixed to give a one-pack hair color composition comprising the components mentioned below. The pH was 3.

3 g of hair tresses that had been washed with the same plain shampoo as in Example E1 were dried with hot air from a drier. 3 g of the one-pack hair color composition was applied to the hair tresses. Subsequently, the hair tresses were left as such at 30° C. for 30 minutes thereby providing hair tresses for evaluation.

The hair tresses for evaluation were evaluated in the same manner as in Example E1. As a result, the hair tresses were given good smoothness, coated feeling and softness during treatment and rinsing.

| (Components) | (%) |
|---|---|
| CCE (58) | 1.0 |
| Black No. 401 | 0.5 |
| Orange No. 205 | 0.3 |
| Laureth-13 | 0.3 |
| PEG-11 methyl ethyl dimethicone | 1.6 |
| 71% glycolic acid | 5.7 |
| Ethanol | 7.0 |
| Glycerin | 1.0 |
| Hydroxypropyl xanthane gum | 1.4 |
| Pure water | balance |
| Total | 100.0 |

Example E24

Production and Evaluation of One-Pack Hair Bleach Composition

A one-pack hair color composition comprising the components mentioned below was produced and evaluated.

CCE (58), oleth-30 (Kao's Emulgen 430), PEG(60)-hydrogenated castor oil (Kao's Emanone CH-60(K)), polysorbate-40 (Kao's Rheodol TW-P120), dipropylene glycol, EDTA-2-sodium, disodium hydrogenphosphate, phosphoric acid and an adequate amount of water were mixed and stirred. This was heated up to 60° C. and completely dissolved. Cetyl alcohol that had been heated up to 70° C. was added thereto, and emulsified. This was cooled down to 40° C., 35% hydrogen peroxide and the remaining water were added, and uniformly mixed to give a one-pack hair color composition mentioned below. The pH was 3.

3 g of hair tresses that had been washed with the same plain shampoo as in Example E1 were dried with hot air from a drier. 3 g of the one-pack hair bleach composition was applied to the hair tresses. Subsequently, the hair tresses were left as such at 30° C. for 30 minutes thereby providing hair tresses for evaluation.

The hair tresses for evaluation were evaluated in the same manner as in Example E1. As a result, the hair tresses were given good smoothness, coated feeling and softness during treatment and rinsing.

| (Components) | (%) |
|---|---|
| CCE (58) | 0.5 |
| 35% hydrogen peroxide | 16.8 |
| Oleth-30 | 3.0 |
| PEG(60)-hydrogenated castor oil | 0.5 |
| Polysorbate-40 | 0.5 |
| Cetyl alcohol | 10.0 |
| Dipropylene glycol | 2.0 |
| EDTA-2-sodium | 0.1 |
| Disodium hydrogenphosphate | 0.1 |
| Phosphoric acid | 0.2 |
| Pure water | balance |
| Total | 100.0 |

INDUSTRIAL APPLICABILITY

When incorporated in a hair wash composition such as hair shampoo or the like, the cationic group-containing cellulose ether of the present invention can provide foam softness, good finger-combability and hair softness in washing, excellent smoothness, long-lasting smoothness, finger combability, softness and coated feeling in hair rinsing, and moist feeling and uniformity after drying. When incorporated in a skin cleanser composition such as body wash, face wash or the like, the cationic group-containing cellulose ether can provide excellent moisturizing feeling after skin washing. When incorporated in a hair conditioner composition, the cationic group-containing cellulose ether can provide good presence in application, excellent smoothness and softness in rising, and excellent coated feeling after drying. In addition, when incorporated in a hair treatment composition, the cationic group-containing cellulose ether can provide good smoothness, coated feeling and softness to the hair in rinsing after treatment.

The invention claimed is:

1. A cationic group-containing cellulose ether, which has a main chain derived from an anhydroglucose represented by the following general formula (1), and in which the degree of substitution with a cationized oxyalkylene group per the anhydroglucose unit is from 0.01 to 1.0, the degree of substitution with a glycerol group is from 0.5 to 5.0, and the degree of substitution with a group that contains a hydrocarbon group, has from 3 to 7 carbon atoms and is represented by any of the following general formulae (6) to (7) is from 0.0001 to 0.2:

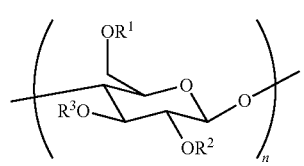
(1)

wherein $R^1$, $R^2$ and $R^3$ each independently represent a substituent comprising at least one structural unit selected from the following formulae (2) to (7), or a hydrogen atom; n indicates a mean degree of polymerization of the anhydroglucose-derived main chain, and is a number of from 100 to 12000;

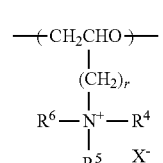
(2)

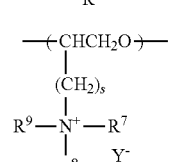
(3)

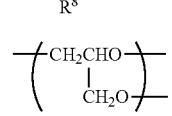
(4)

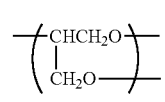
(5)

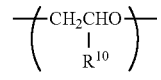
(6)

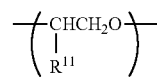
(7)

wherein the structural unit represented by the formula (2) or (3) is a cationized oxyalkylene group; the structural unit represented by the formula (4) or (5) is a glycerol group; and the structural unit represented by any of the formulae (6) to (7) is a group containing a hydrocarbon group and having from 3 to 7 carbon atoms; $R^4$ to $R^9$ each independently represent a linear or branched alkyl group having from 1 to 3 carbon atoms; $X^-$ and $Y^-$ each represent an anion; and r and s each indicate an integer of from 0 to 3; $R^{10}$ and $R^{11}$ each independently represent a linear or branched alkyl group having from 1 to 5 carbon atoms, or a linear or branched alkenyl group having from 2 to 5 carbon atoms; in the structural unit represented by any of the formulae (2) to (7), the oxygen atom bonds to a hydrogen atom or to the carbon atom of the above-mentioned structural unit.

2. The cationic group-containing cellulose ether according to claim 1, of which the cation charge density is from 0.05 mmol/g to 2.0 mmol/g.

3. A surfactant composition comprising the cationic group-containing cellulose ether of claim 1, a surfactant and water.

4. The surfactant composition according to claim 3, wherein the content of the cationic group-containing cellulose ether is from 0.01% by mass to 10% by mass.

5. The surfactant composition according to claim 3, wherein the ratio by mass of the cationic group-containing cellulose ether to the surfactant is from 0.0002 to 10.

6. The surfactant composition according to claim 3, wherein the content of the surfactant is from 1% by mass to 80% by mass.

7. The surfactant composition according to claim 3, wherein the degree of substitution with a cationized oxyalkylene group per the anhydroglucose unit in the cationic group-containing cellulose ether is from 0.04 to 0.6, the degree of substitution with a glycerol group is from 0.5 to 4.0, and the degree of substitution with a hydrocarbon group-containing group having from 3 to 7 carbon atoms is from 0.005 to 0.15.

8. A hair wash composition comprising the cationic group-containing cellulose ether of claim 1, a surfactant and water.

9. The hair wash composition according to claim 8, wherein the degree of substitution with a cationized oxyalkylene group per the anhydroglucose unit in the cationic group-containing cellulose ether is from 0.07 to 0.30, the degree of substitution with a glycerol group is from 0.5 to 3.8, and the degree of substitution with a hydrocarbon group-containing group having from 3 to 7 carbon atoms is from 0.005 to 0.10.

10. The hair wash composition according to claim 8, which further comprises an oily agent.

11. The hair wash composition according to claim 8, which further comprises any other cationic polymer than the cationic group-containing cellulose ether.

12. The hair wash composition according to claim 11, wherein the ratio by mass of the cationic group-containing cellulose ether to the other cationic polymer than the cationic group-containing cellulose ether is from 0.05 to 10.

13. A skin cleanser composition comprising the cationic group-containing cellulose ether of claim 1, a surfactant and water.

14. A hair conditioner composition comprising the cationic group-containing cellulose ether of claim 1, a surfactant, an oily agent and water.

15. The hair conditioner composition according to claim 14, wherein the degree of substitution with a cationized oxyalkylene group per the anhydroglucose unit in the cationic group-containing cellulose ether is from 0.17 to 0.60, the degree of substitution with a glycerol group is from 0.8 to 3.8, and the degree of substitution with a hydrocarbon group-containing group having from 3 to 7 carbon atoms is from 0.02 to 0.06.

16. A hair treatment composition comprising the cationic group-containing cellulose ether of claim 1, as well as at least one treatment agent selected from a hair-coloring dye, an oxidizing agent, an alkali agent, and a keratin-reducing agent.

17. A method of washing hair, comprising washing hair with the hair wash composition of claim 8, then rinsing and drying the hair.

18. A method of cleansing a skin, comprising washing a skin with the skin cleanser composition of claim 13, then rinsing and drying the skin.

19. A method of conditioning hair, comprising washing hair with a detergent, and then applying the hair conditioner composition of claim 14 to the hair.

20. A method of treating hair, comprising treating hair through contact with the hair treatment composition of claim 16, then rinsing and drying the hair.

* * * * *